(12) United States Patent
Boy et al.

(10) Patent No.: US 8,637,523 B2
(45) Date of Patent: Jan. 28, 2014

(54) COMPOUNDS FOR THE REDUCTION OF BETA-AMYLOID PRODUCTION

(75) Inventors: Kenneth M. Boy, Durham, CT (US);
Jason M. Guernon, Moodus, CT (US);
John E. Macor, Guilford, CT (US);
Lorin A. Thompson, III, Higganum, CT (US); Yong-Jin Wu, Madison, CT (US);
Yunhui Zhang, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 341 days.

(21) Appl. No.: 13/180,623

(22) Filed: Jul. 12, 2011

(65) Prior Publication Data
US 2012/0184565 A1    Jul. 19, 2012

Related U.S. Application Data

(60) Provisional application No. 61/364,425, filed on Jul. 15, 2010.

(51) Int. Cl.
*A61P 27/02*    (2006.01)
*A61P 35/00*    (2006.01)
*C07D 498/04*   (2006.01)
*A61P 25/28*    (2006.01)

(52) U.S. Cl.
USPC .......................................... 514/257; 540/469

(58) Field of Classification Search
None
See application file for complete search history.

(56) References Cited

FOREIGN PATENT DOCUMENTS

WO    WO 2009/087127    7/2009

OTHER PUBLICATIONS

Anderson, D.H. et al., "Characterization of β amyloid assemblies in drusen: the deposits associated with aging and age-related macular degeneration", Experimental Eye Research, vol. 78, pp. 243-256 (2004).
Barten, D.M. et al., "γ-Secretase Inhibitors for Alzheimer's Disease: Balancing Efficacy and Toxicity", Drugs R.D., vol. 7, No. 2, pp. 87-97 (2006).
Cleary, J.P. et al., "Natural oligomers of the amyloid-β protein specifically disrupt cognitive function", Nature Neuroscience, vol. 8, No. 1, pp. 79-84 (2005).
Conde, S., "β-Amyloid peptide as a target for treatment of Alzheimer's disease", Expert Opin. Ther. Patents, vol. 12, No. 4, pp. 503-512 (2002).
Deramecourt, V. et al., "Biochemical Staging of Synucleinopathy and Amyloid Deposition in Dementia with Lewy Bodies", J. Neuropathol. Exp. Neurol., vol. 65, No. 3, pp. 278-288 (2006).
Goldstein, L.E. et al., "Cytosolic β-amyloid deposition and supranuclear cataracts in lenses from people with Alzheimer's disease", The Lancet, vol. 361, pp. 1258-1265 (2003).
Grundman, M. et al., "Mild Cognitive Impairment Can Be Distinguished from Alzheimer Disease and Normal Aging for Clinical Trials", Arch. Neurol., vol. 61, pp. 59-66 (2004).
Hamilton, R.L. et al., "Alzheimer disease pathology in amyotrophic lateral sclerosis", Acta Neuropathol., vol. 107, pp. 515-522 (2004).
Loane, D.J. et al., "Amyloid precursor protein secretases as therapeutic targets for traumatic brain injury", Nature Medicine, vol. 15, No. 4, pp. 377-379 (2009).
Murphy, M.P. et al., "Inclusion-body myositis and Alzheimer disease: Two sides of the same coin, or different currencies altogether?", Neurology, vol. 66, Suppl. 1, pp. S65-S68 (2006).
Neumann, M. et al., "Ubiquitinated TDP-43 in Frontotemporal Lobar Degeneration and Amyotrophic Lateral Sclerosis", Science, vol. 314, pp. 130-133 (2006).
Selkoe, D.J., "Alzheimer's Disease: Genes, Proteins, and Therapy", Physiological Reviews, vol. 81, No. 2, pp. 741-766 (2001).
Thal, D.R. et al., "Two Types of Sporadic Cerebral Amyloid Angiopathy", Journal of Neuropathology and Experimental Neurology, vol. 61, No. 3, pp. 282-293 (2002).
The National Institute on Aging, and Reagan Institute Working Group on Diagnostic Criteria for the Neuropathological Assessment of Alzheimer's Disease, "Consensus Recommendations for the Postmortem Diagnosis of Alzheimer's Disease", Neurobiology of Aging, vol. 18, No. S4, pp. S1-S2 (1997).
Walsh, D.M. et al., "Deciphering the Molecular Basis of Memory Failure in Alzheimer's Disease", Neuron, vol. 44, pp. 181-193 (2004).
Watkins, T.A. et al., "Distinct Stages of Myelination Regulated by γ-Secretase and Astrocytes in a Rapidly Myelinating CNS Coculture System", Neuron, vol. 60, pp. 555-569 (2008).
Wolfe, M.S., "Secretase Targets for Alzheimer's Disease: Identification and Therapeutic Potential", Journal of Medicinal Chemistry, vol. 44, No. 13, pp. 2039-2060 (2001).
Wolfe, M.S. et al., "Intramembrane Proteolysis: Theme and Variations", Science, vol. 305, pp. 1119-1123 (2004).

(Continued)

*Primary Examiner* — Bong-Sook Baek
(74) *Attorney, Agent, or Firm* — John F. Levis

(57) ABSTRACT

Compounds of the formula (I) are provided, including pharmaceutically acceptable salts thereof:

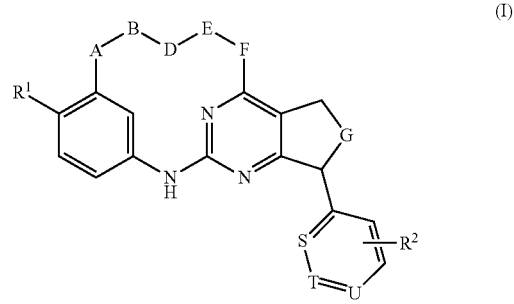

which modulate β-amyloid peptide (β-AP) production, and are useful in the treatment of Alzheimer's Disease and other conditions affected by β-amyloid peptide (β-AP) production.

12 Claims, No Drawings

(56) References Cited

OTHER PUBLICATIONS

Yokota, O. et al., "NACP/α-Synuclein, NAC, and β-amyloid pathology of familial Alzheimer's disease with the E184D presenilin-1 mutation: a clinicopathological study of two autopsy cases", Acta Neuropathol., vol. 104, pp. 637-648 (2002).

Yoshida, T. et al., "The potential role of amyloid β in the pathogenesis of age-related macular degeneration", The Journal of Clinical Investigation, vol. 115, No. 10, pp. 2793-2800 (2005).

COMPOUNDS FOR THE REDUCTION OF BETA-AMYLOID PRODUCTION

CROSS-REFERENCE TO RELATED APPLICATION

This non-provisional application claims the benefit of U.S. Provisional Application Ser. No. 61/364,425 filed Jul. 15, 2010.

FIELD OF THE INVENTION

The present invention relates to compounds which are inhibitors of β-amyloid peptide (Aβ) production, as well as to methods of treating Alzheimer's Disease (AD) and other conditions related to β-amyloid production using these compounds. The invention further relates to pharmaceutical compositions comprising these compounds.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., *Arch Neurol.* (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme (BACE), to generate the N-terminus, and γ-secretase, to generate the C-terminus (Selkoe, D. J., *Physiol Rev.* (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.*, (2001) 81: 741-766). Current evidence suggests that oligomeric, protofibrillar and intracellular Aβ42 play a significant role in the disease process (Cleary, J. P. et al., *Nat. Neurosci.* (2005) 8: 79-84). Inhibitors of the enzymes that form Aβ42, such as γ-secretase, represent potential disease-modifying therapeutics for the treatment of AD.

Evidence suggests that a reduction in brain Aβ levels by inhibition of γ-secretase may prevent the onset and progression of AD (Selkoe, D. *Physiol. Rev.* (2001) 81: 741-766; Wolfe, M., *J. Med. Chem.* (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit γ-secretase and reduce production of Aβ could be used to treat these or other Aβ-dependent diseases.

Excess production and/or reduced clearance of Aβ causes CAA (Thal, D. et al., *J. Neuropath. Exp. Neuro.* (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that reduce Aβ levels could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol (Berl)* (2002) 104: 637-648). Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB and, therefore, compounds that reduce Aβ levels could reduce or prevent DLB.

Approximately 25% of ALS patients have significant dementia or aphasia (Hamilton, R. L. et al., *Acta Neuropathol (Berl)* (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol (Berl)* (2004) 107: 515-522). These patients should be identifiable with amyloid imaging agents and potentially could be treated by compounds that reduce Aβ levels.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that reduce Aβ levels could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that reduce Aβ levels could reduce or prevent age-related macular degeneration.

Compounds which inhibit gamma secretase may also be useful in treating conditions associated with loss of myelination, for example multiple sclerosis (Watkins, T. A., et al., *Neuron* (2008) 60: 555-569).

A recent study by Georgetown University Medical Center researchers suggests that gamma-secretase inhibitors may prevent long-term damage from traumatic brain injury (Loane, D. J., et al., *Nature Medicine* (2009): 1-3).

A logical approach to reducing Aβ levels is to block the action of the secretases. A complementary approach is to selectively reduce production of Aβ1-42 by the action of certain compounds that serve to direct the γ-secretase-mediated cleavage of APP to instead produce shorter forms of Aβ.

These shorter forms appear to aggregate less easily and solutions of the shorter forms of Aβ are less neurotoxic than solutions of Aβ1-42 (See Barten, Donna M.; Meredith, Jere E., Jr.; Zaczek, Robert; Houston, John G.; Albright, Charles F. *Drugs in R&D* (2006), 7(2), 87-97). Thus, compounds that selectively reduce Aβ1-42 production and their pharmaceutical compositions are beneficial agents that will prevent damage from overproduction of Aβ and are useful in treating Alzheimer's disease, Down syndrome, CAA, and inclusion body myositis, DLB, and other disorders where Aβ is overproduced.

What is therefore needed in the art are new compounds that inhibit β-amyloid peptide (Aβ) production, as well as compositions containing these compounds, and methods of treatment which utilize these compounds.

SUMMARY OF THE INVENTION

In its first aspect the present invention provides a compound of formula (I) including pharmaceutically acceptable salts thereof:

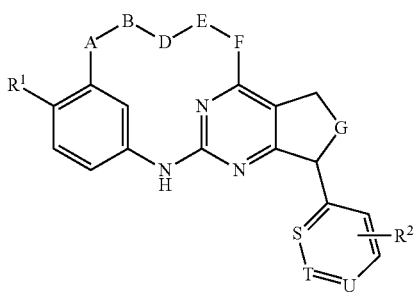

(I)

wherein $R^1$ is a nitrile group, or is a five- or six-membered heteroaromatic ring containing from one to three heteroatoms independently selected from nitrogen, oxygen, and sulfur; wherein said heteroaromatic ring is optionally substituted with one or two groups selected from halo, halo$C_{1-6}$alkyl, hydroxyl, amino, $C_{1-6}$alkoxy, and $C_{1-6}$alkyl;

A is selected from O and $CH_2$, or is a bond;
B is selected from —$(CH_2)_n$—, —CH=CH-(cis), —CH=CH-(trans), and —$(CH_2)_n$CH($R^3$)—;
D is selected from O, $NR^3$, —CH(OH)—, —CH(O$R^3$)—, and —CH(N[$R^3$]$_2$)—, or is a bond;
E is selected from —$(CH_2)_n$—, —CH=CH-(cis), —CH=CH-(trans), and —$(CH_2)_n$CH($R^3$)—;
F is selected from O and $NR^3$, or is a bond;
G is selected from —$CH_2$—, —$CH_2$—$CH_2$—, $NR^3$, and —N($R^3$)—$CH_2$—;
S, T, and U are independently selected from carbon and nitrogen, with the proviso that no more than one of S, T, and U is nitrogen;
$R^2$ is optionally one, two, or three of the following: halogen, $C_{1-4}$alkoxy, $OCF_3$, $C_{1-4}$alkyl, and CN;
$R^3$ is independently $C_{1-4}$ alkyl or hydrogen; and
n is 0-3.

In a first embodiment of the first aspect the present invention provides a compound of formula (I), including pharmaceutically acceptable salts thereof, wherein $R^1$ is a five-membered heteroaromatic ring containing two nitrogen atoms wherein the ring is substituted with a halo group.

In a second embodiment of the first aspect the present invention provides a compound of formula (I), including pharmaceutically acceptable salts thereof, wherein $R^1$ is a five-membered heteroaromatic ring containing three nitrogen atoms wherein the ring is substituted with an alkyl group.

In a third embodiment of the first aspect the present invention provides a compound of formula (I), including pharmaceutically acceptable salts thereof, wherein $R^1$ is CN.

In a fourth embodiment of the first aspect the present invention provides a compound of formula (I), including pharmaceutically acceptable salts thereof, wherein A is oxygen.

In a fifth embodiment of the first aspect the present invention provides a compound of formula (I), including pharmaceutically acceptable salts thereof, wherein B-D-E is —$CH_2$—CH=CH—$(CH_2)_n$—, where the olefin is either cis or trans.

In a sixth embodiment of the first aspect the present invention provides a compound of formula (I), including pharmaceutically acceptable salts thereof, wherein B-D-E is —$(CH_2)_n$—.

In a seventh embodiment of the first aspect the present invention provides a compound of formula (I), including pharmaceutically acceptable salts thereof, wherein F is NH, NMe, or NEt.

In a second aspect the present invention provides a pharmaceutical composition for the treatment of disorders responsive to the reduction of β-amyloid peptide production comprising a therapeutically effective amount of a compound of formula (I), including pharmaceutically acceptable salts thereof, in association with a pharmaceutically acceptable carrier or diluent.

In a third aspect the present invention provides a method for the treatment of disorders responsive to the reduction of β-amyloid peptide production in a mammal in need thereof, which comprises administering to said mammal a therapeutically effective amount of a compound of formula (I), including pharmaceutically acceptable salts thereof. In a first embodiment of the third aspect said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer. In a second embodiment of the third aspect said disorder is selected from Alzheimer's Disease and Down Syndrome. In a third embodiment of the third aspect said disorder is Alzheimer's Disease.

Other aspects of the present invention may include suitable combinations of embodiments disclosed herein.

Yet other aspects and embodiments may be found in the description provided herein.

DETAILED DESCRIPTION OF THE EMBODIMENTS

The description of the present invention herein should be construed in congruity with the laws and principals of chemical bonding. In some instances it may be necessary to remove a hydrogen atom in order accommodate a substituent at any given location.

It should be understood that the compounds encompassed by the present invention are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

In some instances, the number of carbon atoms in any particular group is denoted before the recitation of the group. For example, the term "haloC$_{1-6}$alkoxy" denotes a haloalkoxy group containing one to six carbon atoms and the term "C$_{1-4}$alkoxyC$_{1-2}$alkyl" denotes an alkoxy group containing one to four alkoxy groups attached to the parent molecular moiety through an alkyl group of one or two carbon atoms. Where these designations exist they supersede all other definitions contained herein.

As used herein, the singular forms "a", "an", and "the" include plural reference unless the context clearly dictates otherwise.

Unless otherwise expressly set forth elsewhere in the text, the following terms shall have the following meanings:

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylamino," as used herein, refers to —NHR$^x$, wherein R$^x$ is an alkyl group.

The term "alkylaminoalkoxy," as used herein, refers to an alkylamino group attached to the parent molecular moiety through an alkoxy group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "alkylsulfonylamido," as used herein refers to —C(O)NHS(O)$_2$R$^x$ wherein R$^x$ is an alkyl group.

The term "amino," as used herein, refers to —NH$_2$.

The term "cyano," as used herein, refers to —CN.

The term "cycloalkyl," as used herein, refers to a saturated monocyclic hydrocarbon ring system having three to fourteen carbon atoms and zero heteroatoms.

The term "cycloalkylamino," as used herein, refers to —NR$^x$ wherein Rx is a cycloalkyl group.

The term "dialkylamino," as used herein, refers to —NR$^x$R$^y$, wherein R$^x$ and R$^y$ are each alkyl groups.

The term "dialkylaminoalkoxy," as used herein, refers to a dialkylamino group attached to the parent molecular moiety through an alkoxy group.

The term "dimethylamino," as used herein, refers to —N(CH$_3$)$_2$.

The terms "halo" and "halogen," as used herein, refer to F, Cl, Br, and I.

The term "haloalkoxy," as used herein, refers to an alkoxy group substituted with one, two, three, or four halogen atoms.

The term "haloalkyl," as used herein, refers to an alkyl group substituted with one, two, three, or four halogen atoms.

The term "hydrogen" or "H", as used herein, refers to hydrogen, including its isotopes.

The term "hydroxy," as used herein, refers to —OH.

The term "methylamino," as used herein, refers to —NHCH$_3$.

The term "sulfonyl," as used herein, refers to —SO$_2$—.

It should be understood that the invention encompasses all stereochemical forms, or mixtures thereof, which possess the ability to reduce β-amyloid peptide production.

Certain compounds of the present invention may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present invention may exist in zwitterionic form and the present disclosure includes each zwitterionic form of these compounds and mixtures thereof.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfuric acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g., hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

Examples of such prodrug esters include

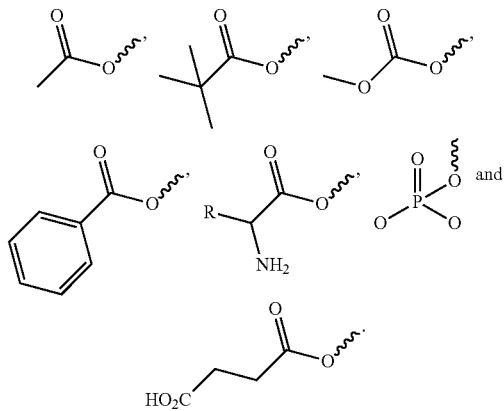

The term "prodrug ethers" include both phosphate acetals and O-glucosides.

Representative examples of such prodrug ethers include

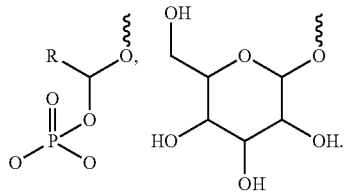

As set forth above, the present invention provides a compound of formula (I), including pharmaceutically acceptable salts thereof:

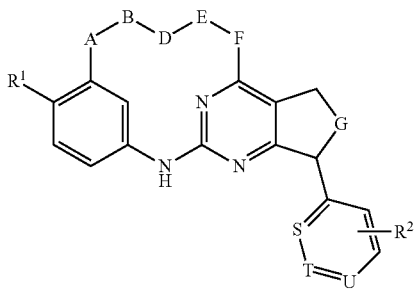

(I)

wherein $R^1$ is a nitrile group, or is a five- or six-membered heteroaromatic ring containing from one to three heteroatoms independently selected from nitrogen, oxygen, and sulfur; wherein said heteroaromatic ring is optionally substituted with one or two groups selected from halo, halo$C_{1-6}$alkyl, hydroxyl, amino, $C_{1-6}$alkoxy, and $C_{1-6}$alkyl;

A is selected from O and $CH_2$, or is a bond;
B is selected from $—(CH_2)_n—$, $—CH=CH$-(cis), $—CH=CH$-(trans), and $—(CH_2)_nCH(R^3)—$;
D is selected from O, $NR^3$, $—CH(OH)—$, $—CH(OR^3)—$, and $—CH(N[R^3]_2)—$, or is a bond;
E is selected from $—(CH_2)_n—$, $—CH=CH$-(cis), $—CH=CH$-(trans), and $—(CH_2)_nCH(R^3)—$;
F is selected from O and $NR^3$, or is a bond;
G is selected from $—CH_2—$, $—CH_2—CH_2—$, $NR^3$, and $—N(R^3)—CH_2—$; S, T, and U are independently selected from carbon and nitrogen, with the proviso that no more than one of S, T, and U is nitrogen;
$R^2$ is optionally one, two, or three of the following: halogen, $C_{1-4}$alkoxy, $OCF_3$, $C_{1-4}$alkyl, CN;
$R^3$ is independently $C_{1-4}$ alkyl or hydrogen; and
n is 0-3.

Preferably, $R^1$ is a five-membered heteroaromatic ring containing two nitrogen atoms wherein the ring is substituted with a halo group.

In a further embodiment, $R^1$ is a five-membered heteroaromatic ring containing three nitrogen atoms wherein the ring is substituted with an alkyl group, more preferably a methyl group.

It is also preferred that $R^1$ be $—CN$.

In yet a further embodiment of the compound of formula (I), A is oxygen.

In another embodiment, B-D-E is $—CH_2—CH=CH—(CH_2)_n—$, where the olefin is either cis or trans. In yet a further embodiment, B-D-E is $—(CH_2)_n—$, with n being either 3 or 4. It is also preferred that B-D-E be $—CH_2—CH(OH)—CH_2—CH_2—$, $—CH_2—CH_2—CH(OH)—CH_2—$, $—CH_2—CH_2—N(R^3)—CH_2—CH_2—$, or $—CH_2—CH_2—O—CH_2—CH_2—$.

In a further embodiment, B-D-E-F is $—(CH_2)_n—CH(R^3)—NR^3—$, or $—(CH_2)_n—NR^3—(CH_2)_n—$.

It is also preferred that F is NH, NMe, or NEt, wherein "Me" denotes methyl, and "Et" denotes ethyl.

In addition, it is preferred that G is $—CH_2—$, $—CH_2—CH_2—$, or $—N(R^3)—CH_2—$.

Some preferred compounds herein include the following:

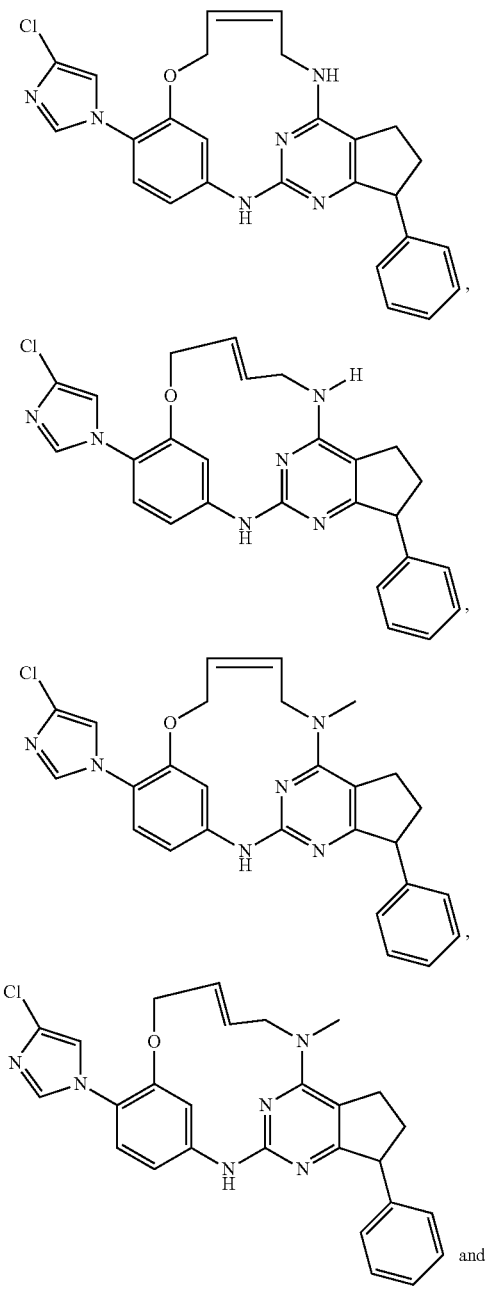

and

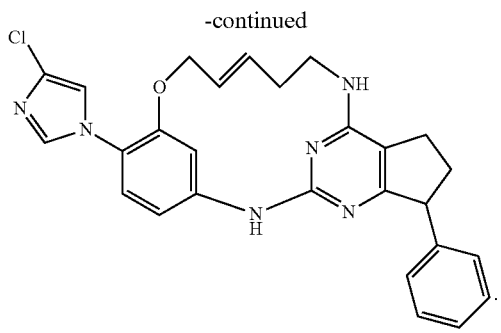

In addition, the following compounds are also preferred:
(11Z)-7-(4-chloro-1H-imidazol-1-yl)-18-phenyl-10,13,14, 16,17,18-hexahydro-15,2-(azeno)-8,4-(metheno)cyclopenta[h][1,6,10,12]oxatriazacycloheptadecine;
(11E)-7-(4-chloro-1H-imidazol-1-yl)-18-phenyl-10,13,14, 16,17,18-hexahydro-15,2-(azeno)-8,4-(metheno)cyclopenta[h][1,6,10,12]oxatriazacycloheptadecine;
(11Z)-7-(4-chloro-1H-imidazol-1-yl)-14-methyl-18-phenyl-10,13,14,16,17,18-hexahydro-15,2-(azeno)-8,4-(metheno)cyclopenta[h][1,6,10,12]oxatriazacycloheptadecine;
(11E)-7-(4-chloro-1H-imidazol-1-yl)-14-methyl-18-phenyl-10,13,14,16,17,18-hexahydro-15,2-(azeno)-8,4-(metheno)cyclopenta[h][1,6,10,12]oxatriazacycloheptadecine;
(11E)-7-(4-chloro-1H-imidazol-1-yl)-19-phenyl-3,10,13, 14,15,17,18,19-octahydro-2,16-(azeno)-8,4-(metheno)cyclopenta[j][1,7,9,13]oxatriazacyclooctadecine;
(11Z)-7-(4-chloro-1H-imidazol-1-yl)-14-methyl-19-phenyl-3,10,13,14,15,17,18,19-octahydro-2,16-(azeno)-8,4-(metheno)cyclopenta[j][1,7,9,13]oxatriazacyclooctadecine;
(11E)-7-(4-chloro-1H-imidazol-1-yl)-14-methyl-19-phenyl-3,10,13,14,15,17,18,19-octahydro-2,16-(azeno)-8,4-(metheno)cyclopenta[j][1,7,9,13]oxatriazacyclooctadecine;
7-(4-chloro-1H-imidazol-1-yl)-19-phenyl-10,11,13,14,15, 17,18,19-octahydro-16,2-(azeno)-8,4-(metheno)cyclopenta[i][1,4,7,11,13]dioxatriazacyclooctadecine;
7-(4-chloro-1H-imidazol-1-yl)-17-phenyl-11,12,13,15,16, 17-hexahydro-10H-14,2-(azeno)-8,4-(metheno)cyclopenta[g][1,5,9,11]oxatriazacyclohexadecine;
7-(4-chloro-1H-imidazol-1-yl)-13-methyl-17-phenyl-11,12, 13,15,16,17-hexahydro-10H-14,2-(azeno)-8,4-(metheno)cyclopenta[g][1,5,9,11]oxatriazacyclohexadecine;
7-(4-chloro-1H-imidazol-1-yl)-19-phenyl-3,10,11,12,13,14, 15,17,18,19-decahydro-2,16-(azeno)-8,4-(metheno)cyclopenta[j][1,7,9,13]oxatriazacyclooctadecine;
7-(4-chloro-1H-imidazol-1-yl)-18-phenyl-10,11,12,13,14, 16,17,18-octahydro-15,2-(azeno)-8,4-(metheno)cyclopenta[h][1,6,10,12]oxatriazacycloheptadecine;
7-(4-chloro-1H-imidazol-1-yl)-14-methyl-18-phenyl-10,11, 12,13,14,16,17,18-octahydro-15,2-(azeno)-8,4-(metheno)cyclopenta[h][1,6,10,12]oxatriazacycloheptadecine;
(11Z)-7-(4-chloro-1H-imidazol-1-yl)-18-(2,4-difluorophenyl)-10,13,14,16,17,18-hexahydro-15,2-(azeno)-8,4-(metheno)cyclopenta[h][1,6,10,12]oxatriazacycloheptadecine;
(11E)-7-(4-chloro-1H-imidazol-1-yl)-18-(2,4-difluorophenyl)-10,13,14,16,17,18-hexahydro-15,2-(azeno)-8,4-(metheno)cyclopenta[h][1,6,10,12]oxatriazacycloheptadecine;
(11Z)-7-(4-chloro-1H-imidazol-1-yl)-18-phenyl-10,13,14, 16,17,18-hexahydro-15,2-(azeno)-8,4-(metheno)cyclopenta[h][1,10,12]oxadiazacycloheptadecine;
(11E)-7-(4-chloro-1H-imidazol-1-yl)-18-phenyl-10,13,14, 16,17,18-hexahydro-15,2-(azeno)-8,4-(metheno)cyclopenta[h][1,10,12]oxadiazacycloheptadecine;
(11Z)-7-(4-chloro-1H-imidazol-1-yl)-18-(2,4-difluorophenyl)-14-methyl-10,13,14,16,17,18-hexahydro-15,2-(azeno)-8,4-(metheno)cyclopenta[h][1,6,10,12]oxatriazacycloheptadecine;
7-(4-chloro-1H-imidazol-1-yl)-18-(2,4-difluorophenyl)-14-methyl-10,11,12,13,14,16,17,18-octahydro-15,2-(azeno)-8,4-(metheno)cyclopenta[h][1,6,10,12]oxatriazacycloheptadecine;
7-(4-chloro-1H-imidazol-1-yl)-17-(2,4-difluorophenyl)-13-methyl-11,12,13,15,16,17-hexahydro-10H-14,2-(azeno)-8,4-(metheno)cyclopenta[g][1,5,9,11]oxatriazacyclohexadecine;
(11Z)-7-cyano-18-phenyl-10,13,14,16,17,18-hexahydro-15, 2-(azeno)-8,4-(metheno)cyclopenta[h][1,6,10,12]oxatriazacycloheptadecine;
(11E)-7-cyano-18-phenyl-10,13,14,16,17,18-hexahydro-15, 2-(azeno)-8,4-(metheno)cyclopenta[h][1,6,10,12]oxatriazacycloheptadecine;
7-cyano-18-phenyl-10,11,12,13,14,16,17,18-octahydro-15, 2-(azeno)-8,4-(metheno)cyclopenta[h][1,6,10,12]oxatriazacycloheptadecine;
(11Z)-7-cyano-18-(2,4-difluorophenyl)-10,13,14,16,17,18-hexahydro-15,2-(azeno)-8,4-(metheno)cyclopenta[h][1,6, 10,12]oxatriazacycloheptadecine;
(11E)-7-cyano-18-(2,4-difluorophenyl)-10,13,14,16,17,18-hexahydro-15,2-(azeno)-8,4-(metheno)cyclopenta[h][1,6, 10,12]oxatriazacycloheptadecine;
7-cyano-19-(4-fluorophenyl)-11,12,13,14,15,17,18,19-octahydro-10H-16,2-(azeno)-8,4-(metheno)cyclopenta[i][1, 4,7,11,13]oxatetraazacyclooctadecine;
7-cyano-19-(4-fluorophenyl)-12-methyl-11,12,13,14,15,17, 18,19-octahydro-10H-16,2-(azeno)-8,4-(metheno)cyclopenta[i][1,4,7,11,13]oxatetraazacyclooctadecine;
(11Z)-7-cyano-18-(2,4-difluorophenyl)-14-methyl-10,13, 14,16,17,18-hexahydro-15,2-(azeno)-8,4-(metheno)cyclopenta[h][1,6,10,12]oxatriazacycloheptadecine;
(11Z)-7-cyano-14-methyl-18-phenyl-10,13,14,16,17,18-hexahydro-15,2-(azeno)-8,4-(metheno)cyclopenta[h][1,6, 10,12]oxatriazacycloheptadecine;
(11E)-7-cyano-14-methyl-18-phenyl-10,13,14,16,17,18-hexahydro-15,2-(azeno)-8,4-(metheno)cyclopenta[h][1,6, 10,12]oxatriazacycloheptadecine;
7-cyano-13-methyl-17-phenyl-11,12,13,15,16,17-hexahydro-10H-14,2-(azeno)-8,4-(metheno)cyclopenta[g][1,5,9, 11]oxatriazacyclohexadecine;
7-cyano-18-(2,4-difluorophenyl)-14-methyl-10,11,12,13, 14,16,17,18-octahydro-15,2-(azeno)-8,4-(metheno)cyclopenta[h][1,6,10,12]oxatriazacycloheptadecine;
7-cyano-17-(2,4-difluorophenyl)-11,12,13,15,16,17-hexahydro-10H-14,2-(azeno)-8,4-(metheno)cyclopenta[g][1,5,9,11]oxatriazacyclohexadecine;
7-cyano-14-methyl-18-phenyl-10,11,12,13,14,16,17,18-octahydro-15,2-(azeno)-8,4-(metheno)cyclopenta[h][1,6, 10,12]oxatriazacycloheptadecine;
7-cyano-17-(2,4-difluorophenyl)-13-methyl-11,12,13,15, 16,17-hexahydro-10H-14,2-(azeno)-8,4-(metheno)cyclopenta[g][1,5,9,11]oxatriazacyclohexadecine;
(11Z)-7-cyano-18-phenyl-10,13,14,16,17,18-hexahydro-15, 2-(azeno)-8,4-(metheno)cyclopenta[h][1,10,12]oxadiazacycloheptadecine;
(11E)-7-cyano-18-phenyl-10,13,14,16,17,18-hexahydro-15, 2-(azeno)-8,4-(metheno)cyclopenta[h][1,10,12]oxadiazacycloheptadecine;

7-cyano-18-phenyl-10,11,12,13,14,16,17,18-octahydro-15,2-(azeno)-8,4-(metheno)cyclopenta[h][1,10,12]oxadiazacycloheptadecine;

(11Z)-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11E)-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11Z)-14-methyl-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11Z)-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11E)-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11Z)-14-methyl-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11Z)-18-(4-fluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11E)-18-(4-fluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

7-(5-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine;

14-methyl-7-(5-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine;

7-(3-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine;

14-methyl-7-(3-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine;

(11Z)-18-(2,4-difluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11E)-18-(2,4-difluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11Z)-18-(2,4-difluorophenyl)-7-(5-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11E)-18-(2,4-difluorophenyl)-7-(5-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

19-(4-fluorophenyl)-7-(3-methyl-1H-1,2,4-triazol-1-yl)-11,12,13,14,15,17,18,19-octahydro-10H-16,2-(azeno)-8,4-(metheno)cyclopenta[i][1,4,7,11,13]oxatetraazacyclooctadecine;

19-(4-fluorophenyl)-12-methyl-7-(3-methyl-1H-1,2,4-triazol-1-yl)-11,12,13,14,15,17,18,19-octahydro-10H-16,2-(azeno)-8,4-(metheno)cyclopenta[i][1,4,7,11,13]oxatetraazacyclooctadecine;

(11Z)-18-(2,4-difluorophenyl)-14-methyl-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11Z)-7-(3-methyl-1H-1,2,4-triazol-1-yl)-18-phenyl-10,13,14,16,17,18-hexahydro-15,2-(azeno)-8,4-(metheno)cyclopenta[h][1,10,12]oxadiazacycloheptadecine;

(11E)-7-(3-methyl-1H-1,2,4-triazol-1-yl)-18-phenyl-10,13,14,16,17,18-hexahydro-15,2-(azeno)-8,4-(metheno)cyclopenta[h][1,10,12]oxadiazacycloheptadecine;

13-methyl-7-(3-methyl-1H-1,2,4-triazol-1-yl)-17-phenyl-11,12,13,15,16,17-hexahydro-10H-14,2-(azeno)-8,4-(metheno)cyclopenta[g][1,5,9,11]oxatriazacyclohexadecine;

18-(2,4-difluorophenyl)-14-methyl-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecine;

7-(3-methyl-1H-1,2,4-triazol-1-yl)-18-phenyl-10,11,12,13,14,16,17,18-octahydro-15,2-(azeno)-8,4-(metheno)cyclopenta[h][1,10,12]oxadiazacycloheptadecine;

17-(2,4-difluorophenyl)-7-(3-methyl-1H-1,2,4-triazol-1-yl)-11,12,13,15,16,17-hexahydro-10H-14,2-(azeno)-8,4-(metheno)cyclopenta[g][1,5,9,11]oxatriazacyclohexadecine;

18-(2,4-difluorophenyl)-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecine;

13-methyl-7-(3-methyl-1H-1,2,4-triazol-1-yl)-17-(4-fluorophenyl)-11,12,13,15,16,17-hexahydro-10H-14,2-(azeno)-8,4-(metheno)cyclopenta[g][1,5,9,11]oxatriazacyclohexadecine;

18-(2,4-difluorophenyl)-13-methyl-7-(3-methyl-1H-1,2,4-triazol-1-yl)-10,11,12,13,14,16,17,18-octahydro-3H-15,2-(azeno)-4,8-(metheno)cyclopenta[h][1,6,10,12]oxatriazacycloheptadecine;

18-(4-fluorophenyl)-3,11,12,13,14,16,17,18-octahydro-10H-2,15-(azeno)-4,8-(metheno)cyclopenta[h][1,4,10,12]oxatriazacycloheptadecine-7-carbonitrile;

(11E)-7-cyano-18-(4-fluorophenyl)-18-methyl-10,13,14,16,17,18-hexahydro-15,2-(azeno)-8,4-(metheno)cyclopenta[h][1,6,10,12]oxatriazacycloheptadecine;

(11Z)-7-cyano-18-(4-fluorophenyl)-18-methyl-10,13,14,16,17,18-hexahydro-15,2-(azeno)-8,4-(metheno)cyclopenta[h][1,6,10,12]oxatriazacycloheptadecine;

19-(4-fluorophenyl)-17-methyl-7-(3-methyl-1H-1,2,4-triazol-1-yl)-11,12,13,14,16,17,18,19-octahydro-10H-15,2-(azeno)-8,4-(metheno)pyrido[3,4-h][1,6,10,12]oxatriazacycloheptadecine;

7-cyano-19-(4-fluorophenyl)-17-methyl-11,12,13,14,16,17,18,19-octahydro-10H-15,2-(azeno)-8,4-(metheno)pyrido[3,4-h][1,6,10,12]oxatriazacycloheptadecine;

18-(4-fluorophenyl)-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecin-11(3H)-ol;

7-cyano-18-(4-fluorophenyl)-10,11,12,13,14,16,17,18-octahydro-15,2-(azeno)-8,4-(metheno)cyclopenta[h][1,6,10,12]oxatriazacycloheptadecin-11(3H)-ol, and (11Z)-14,17-dimethyl-7-cyano-19-(4-fluorophenyl)-13,14,16,17,18,19-hexahydro-10H-15,2-(azeno)-8,4-(metheno)

pyrido[3,4-h][1,6,10,12]oxatriazacycloheptadecine; or a pharmaceutically acceptable salt thereof.

When it is possible that, for use in therapy, therapeutically effective amounts of a compound of formula (I), including pharmaceutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I) including pharmaceutically acceptable salts thereof, and one or more pharmaceutically acceptable carriers, diluents, or excipients. The compounds of formula (I), including pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of formula (I), including pharmaceutically acceptable salts thereof, with one or more pharmaceutically acceptable carriers, diluents, or excipients.

The dosage of the compounds of Formula I to achieve a therapeutic effect will depend not only on such factors as the age, weight and sex of the patient and mode of administration, but also on the degree of β-AP reduction desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable daily dose of a compound of Formula I or pharmaceutical composition thereof for a mammal, including man, suffering from, or likely to suffer from any condition related to β-AP production as described herein, will be from about 0.05 mg/kg to about 10 mg/kg and preferably, about 0.1 to 2 mg/kg when administered parenterally. For oral administration, the dose may be in the range from about 0.1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carriers) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), including pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) including pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The present invention will now be described in connection with certain embodiments which are not intended to limit its scope. On the contrary, the present invention covers all alternatives, modifications, and equivalents as can be included within the scope of the claims. Thus, the following examples, which include specific embodiments, will illustrate one practice of the present invention, it being understood that the examples are for the purposes of illustration of certain embodiments and are presented to provide what is believed to be the most useful and readily understood description of its procedures and conceptual aspects.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The starting materials useful to synthesize the compounds of the present invention are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present invention. The details concerning the use of protecting groups in accordance with the present disclosure are known to those skilled in the art.

The abbreviations used in the present application, including particularly in the illustrative schemes and examples which follow, are well-known to those skilled in the art. Some of the abbreviations used are as follows:

Chemical abbreviations used in the specification and Examples are defined as follows: "dba" for dibenzylideneacetone; "t-Bu" for tert-butyl; "DCM" for dichloromethane; "LDA" for lithium diisopropylamide; "Ph" for phenyl; "TFA" for trifluoracetic acid; "Et" for ethyl; "DMF" for N,N-dimethylformamide; "OAc" for acetate; "h" for hours, "min" for minutes; and "THF" for tetrahydrofuran.

General Schemes:

Examples of methods useful for the production of compounds of the invention are illustrated in Schemes 1-15. Schemes 1-3 outline different routes for the synthesis of substituted aniline fragments used in the preparation of the title compounds. As illustrated in Scheme 1, a variety of terminal alkenols can be added to either chloro- or fluoro-nitrophenols 1, to generate chloro- or fluoro-alkenoxynitrobenzenes 2. A variety of heterocycles 3, including but not limited to 1H-imidazole, 4-methyl-1H-imidazole, 4-chloro-1H-imidazole, and 4-(difluoromethyl)-1H-imidazole can be added to said intermediate 2, under basic conditions to provide heteroaryl substituted nitroarenes 4. Reduction of the compounds 4 using reagents which spare the olefin functionality, including iron in acidic medium or $SnCl_2$, or other conditions known to one skilled in the art, affords substituted anilines 5. While Scheme 1 illustrates the preparation of 4-(1H-imidazol-1-yl)anilines 4, it should be recognized to one skilled in the art that this method is widely applicable to the synthesis of other 4-heteroarylanilines, including but not limited to variously substituted 4-(1H-1,2,4-triazol-1-yl) anilines and 4-(1H-1,2,3-triazol-1-yl)anilines. In addition, substituted nitropyridinols can be used in place of the nitrophenols of formula 1 to ultimately provide amino-substituted pyridines.

Scheme 1

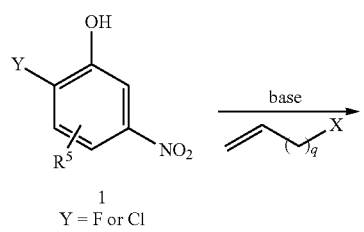

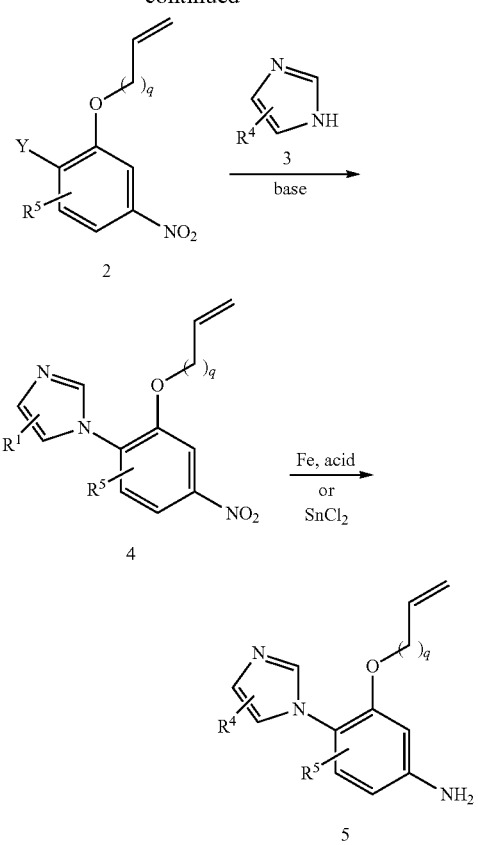

As illustrated in Scheme 2, a variety of heterocycles 3, including but not limited to 1H-imidazole, 4-methyl-1H-imidazole, 4-chloro-1H-imidazole, 4-(difluoromethyl)-1H-imidazole can be added to difluoro- or chloro-fluoro-nitroarenes 6 to generate fluoro-heteroaryl nitrobenzenes 7. Reaction of terminal alkenols under basic conditions with intermediates 7 provides heteroaryl substituted nitroarenes 4. Reduction of the compounds 4 using reagents which spare the olefin functionality, including iron in acidic medium or $SnCl_2$, or other conditions known to one skilled in the art, affords substituted anilines 5. While Scheme 1 illustrates the preparation of 4-(1H-imidazol-1-yl)anilines 4, it should be recognized to one skilled in the art that this method is widely applicable to the synthesis of other 4-heteroarylanilines, including but not limited to variously substituted 4-(1H-1,2,4-triazol-1-yl) anilines and 4-(1H-1,2,3-triazol-1-yl)anilines.

Scheme 2

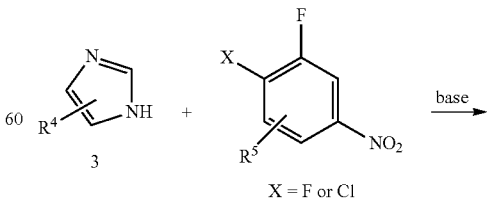

19
-continued

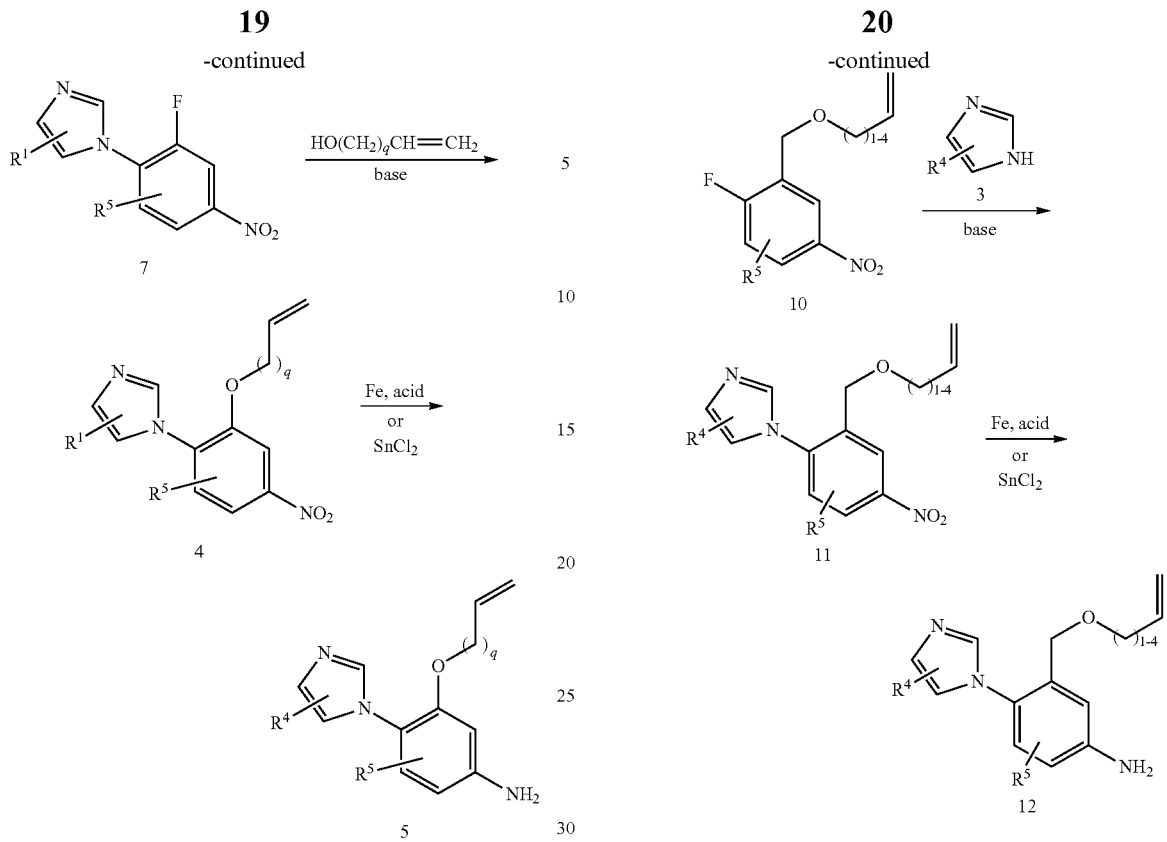

20
-continued

An additional method for the preparation of analogs of claim 1 is described in Scheme 3. The known 2-fluoro-5-nitrotoluene 8 can be brominated with NBS under photochemical conditions to afford 9. The bromide therein can be displaced with a variety of alcohols as described in WO200815569. By extension, this could be applied to the appropriate terminal alkenols described to afford the fluoronitroarenes 10. The fluoro substituent is subsequently displaced by a heterocycle under basic conditions to yield 11. As above, nitro group reduction in an orthogonal manner with respect to the olefin affords anilines 12.

The following schemes outline different routes for the synthesis of 2,4-dichloro-7-aryl-6,7-dihydro-5H-cyclopenta[d]pyrimidines used in the preparation of the title compounds. As illustrated on Scheme 4, cyclopentanone 13 can react with a variety of arylmagnesium halides to produce tertiary alcohols 14. In the presence of dehydrating agents, such as mineral acids or thionyl chloride, these tertiary alcohols can undergo elimination of water to yield olefins 15. Upon treatment with peroxidizing agents, such as performic acid, olefins 15 can be transformed to 2-arylcyclopentanones 16. Abu Thaher, B.; Koch, P.; Del Amo, V.; Knochel, P.; Laufer, S. *Synthesis* 2008, 2, 225-228.

Scheme 3

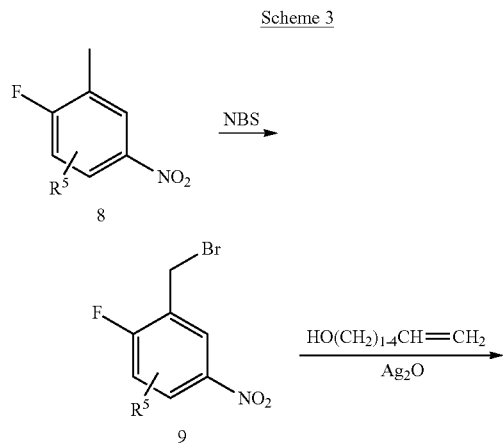

Scheme 4

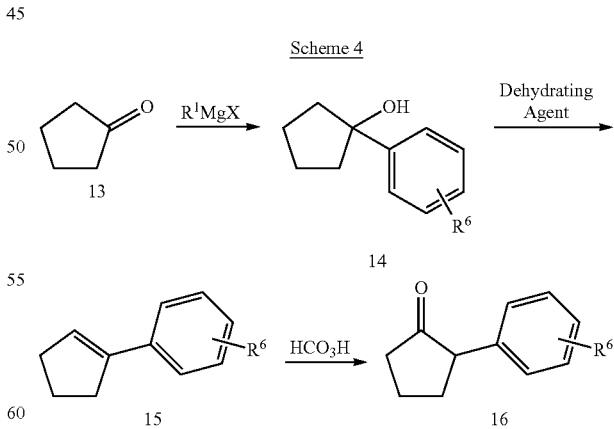

Alternatively, as indicated on Scheme 5, 2-arylcyclopentanones 16 can be prepared by treatment of cyclopenteneoxide 17 with various arylmagnesium halides, in the presence of copper salts, such as copper iodide, followed by oxidation of resulting alcohols 18. The said oxidation can be carried out by a number of oxidation agents known to those skilled in the arts, the superior results achieved by the use of Dess-Martin periodinane. Dess, D. B.; Martin, J. C. *J. Org. Chem.* 1983, 48, 4155-4156.

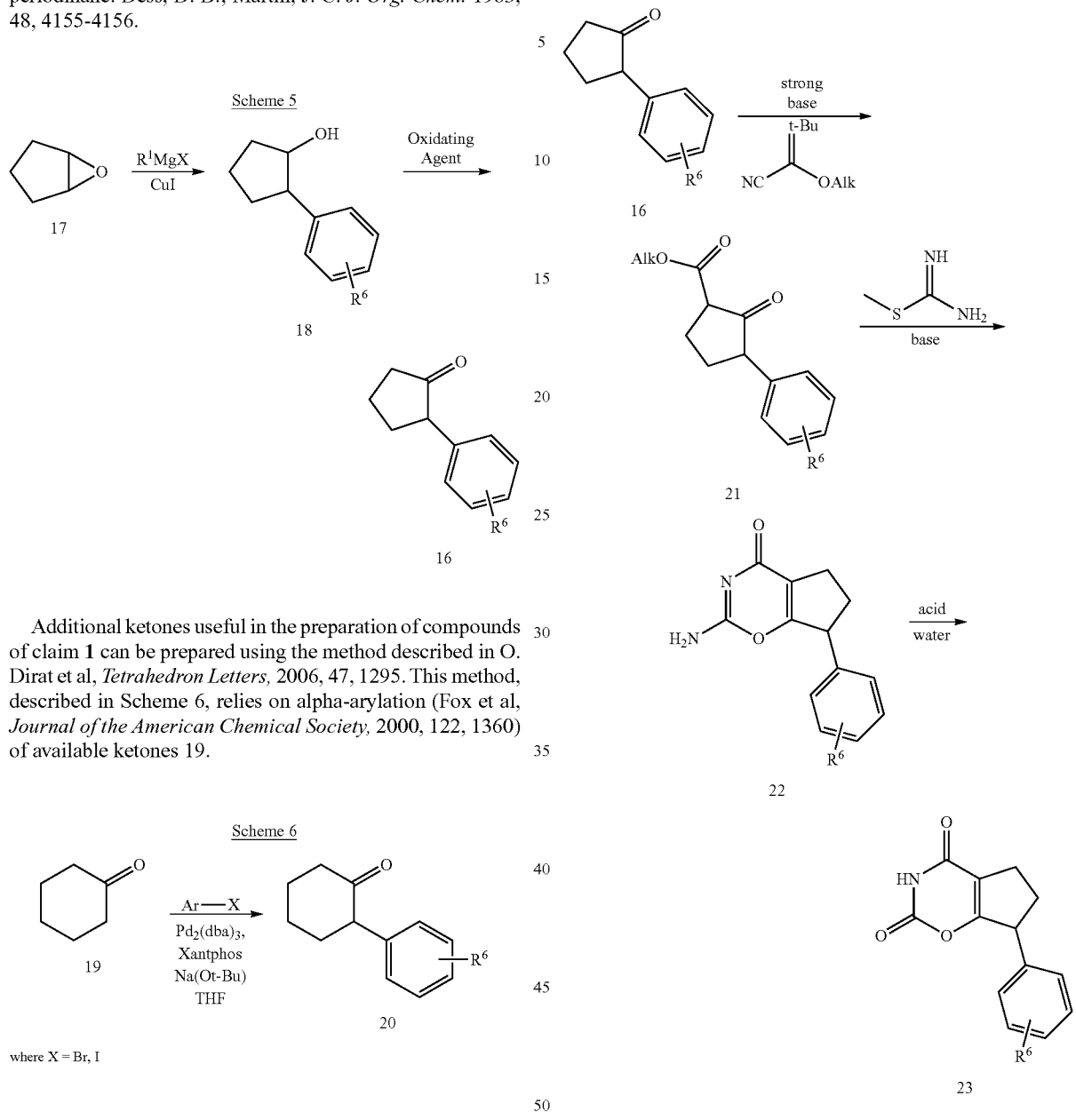

Additional ketones useful in the preparation of compounds of claim 1 can be prepared using the method described in O. Dirat et al, *Tetrahedron Letters*, 2006, 47, 1295. This method, described in Scheme 6, relies on alpha-arylation (Fox et al, *Journal of the American Chemical Society*, 2000, 122, 1360) of available ketones 19.

As indicated in Scheme 7, 2-arylcyclopentanones 23 can be deprotonated with a strong base, such as LDA and treated with alkylcyanoformate to give ketoesters 21, which upon reaction with 2-methyl-2-thiopseudourea provide 2-amino-7-aryl-6,7-dihydrocyclopenta[e][1,3]oxazin-4(5H)-ones 22. The latter compounds undergo acid-catalyzed hydrolysis to form 7-aryl-6,7-dihydrocyclopenta[e][1,3]oxazine-2,4(3H,5H)-diones 23. Larsen, J. S.; Christensen, L.; Ludvig, G.; Jorgensen, P. T.; Pedersen, E. B.; Nielsen, C. *J. Chem. Soc., Perkin Trans.* 12000, 3035-3038.

Alternatively, 7-aryl-6,7-dihydrocyclopenta[e][1,3]oxazine-2,4(3H,5H)-diones 23 are available by reaction of 2-arylcyclopentanones 16 with N-(chlorocarbonyl)isocyanate (Scheme 8). Subsequent treatment of 7-aryl-6,7-dihydrocyclopenta[e][1,3]oxazine-2,4(3H,5H)-diones 23 with ammonia in water, followed by chlorination with phosphorus oxychloride affords 2,4-dichloro-7-aryl-6,7-dihydro-5H-cyclopenta[d]pyrimidines 25.

Scheme 8

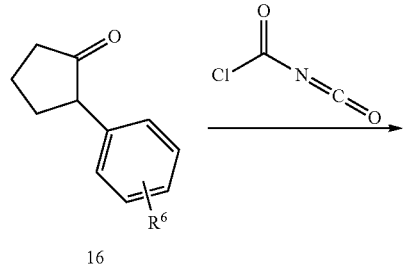

16

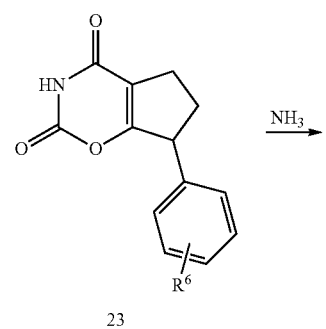

23

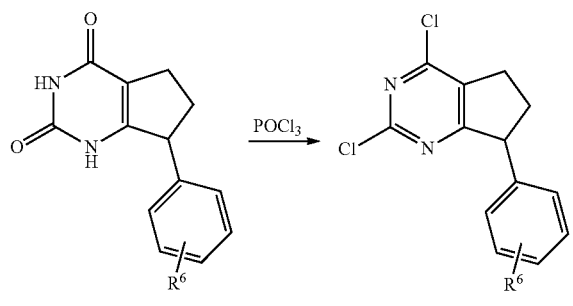

24              25

In a similar manner to the synthesis described in Scheme 8, additional ketones can be reacted with N-(chlorocarbonyl) isocyanate to provide additional oxazine diones 26 that can be reacted with ammonia to provide the pyrimidine diones 27 (Scheme 9). Chlorination then provides the intermediate dichlorides 28.

Scheme 9

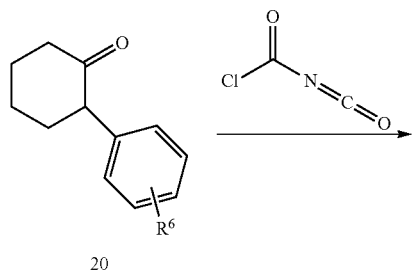

20

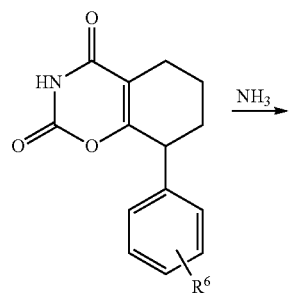

26

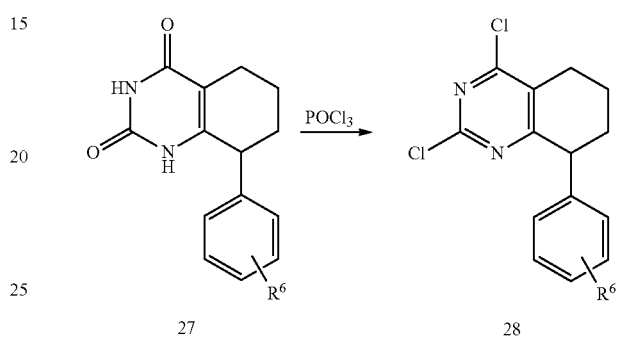

27              28

Synthesis of 2,4-dichloro-7-aryl-6,7-dihydro-5H-cyclopenta[d]pyrimidines 25 could also be performed according to the pathway described on Scheme 10. 4-Chloro-2,6-dimethoxypyrimidine 29 could be deprotonated with a strong base, such as n-butyllithium or 2,2,6,6-tetramethylpiperidine, and quenched with allyl bromide to give 5-allyl-4-chloro-2,6-dimethoxypyrimidine 30. Nencka, R.; Votruba, I.; Hřebabecký, H.; Jansa, P.; Tloušt'ová, E.; Horskà, K.; Masojídková, M.; Holý, A. *J. Med. Chem.* 2007, 50, 6016-6023. The latter compound can react with α-styrylborinic acids in the presence of a palladium catalyst, such as tetrakis(triphenylphosphine)palladium, to provide compounds of formula 31 which can undergo ring closure olefine metathesis under Grubbs conditions to form 2,4-dimethoxy-7-aryl-5H-cyclopenta[d]pyrimidines 32. Grubbs, R. H. *Handbook of Metathesis*, 2003, First Edition, Wiley-VCH. The double bond in compounds 32 can be reduced to give 2,4-dimethoxy-7-aryl-6,7-dihydro-5H-cyclopenta[d]pyrimidines 33, which upon acid-catalyzed hydrolysis, followed by chlorination with phosphorus oxychloride afford intermediates 25.

Scheme 10

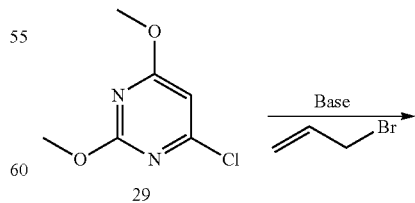

29

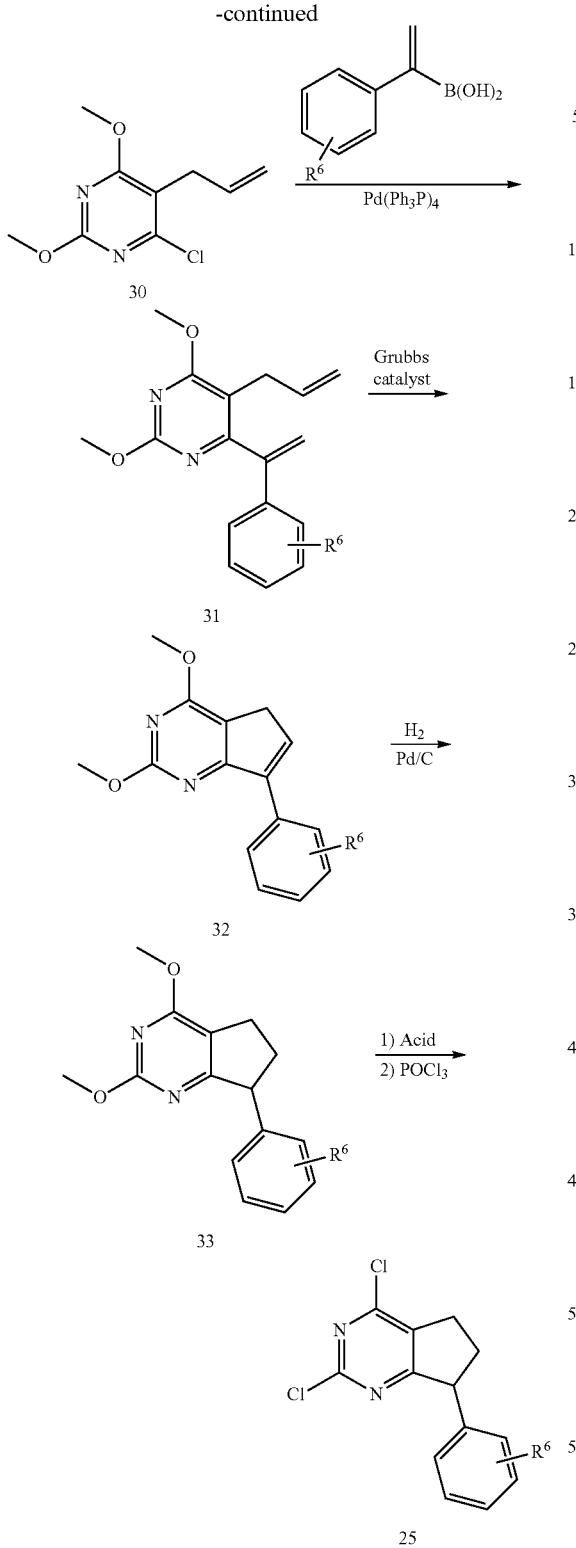

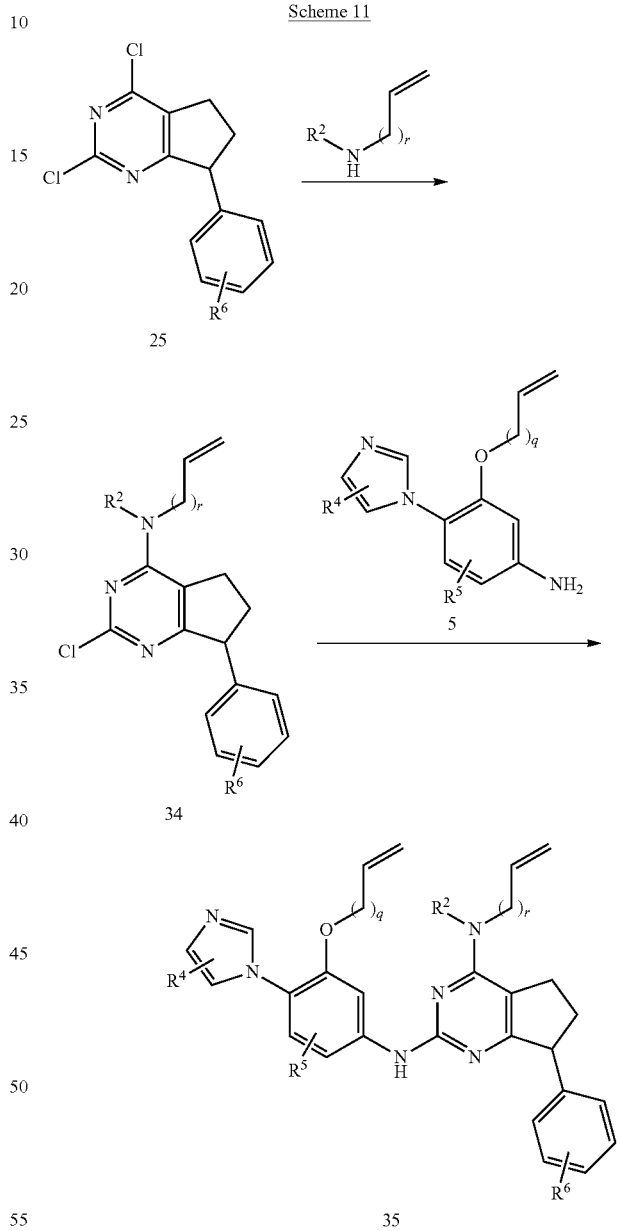

-continued ditions, (for example, using sodium hydride). Alternatively, the coupling can be completed under metal catalysis, with conditions known in the literature, for instance the use of $Pd(dba)_2$ and Xantphos catalyst in the presence of a strong base (NaOt-Bu) or $Na_2CO_3$ in an aqueous cosolvent mixture (typically THF/water or dioxane/water).

Scheme 11

2,4-Dichloro-7-aryl-6,7-dihydro-5H-cyclopenta[d]pyrimidines 25 selectively react with primary and secondary amines containing a terminal olefin to give 4-amino derivatives 34, which under heating can be coupled with anilines 5 to form ring-closing metathesis substrates 35. (Scheme 11). The said coupling can be performed either under acidic conditions (for example, using acetic acid), or under basic conditions.

As shown in Scheme 12, bis-olefins 35 can be reacted under dilute conditions via ring-closing metathesis (Grubbs, R. H. *Handbook of Metathesis,* 2003, First Edition, Wiley-VCH.) to form cis and trans olefins 36. These compounds can be further reacted to reduce the olefin using Pd/C and $H_2$ or similar conditions to afford the macrocycles 37.

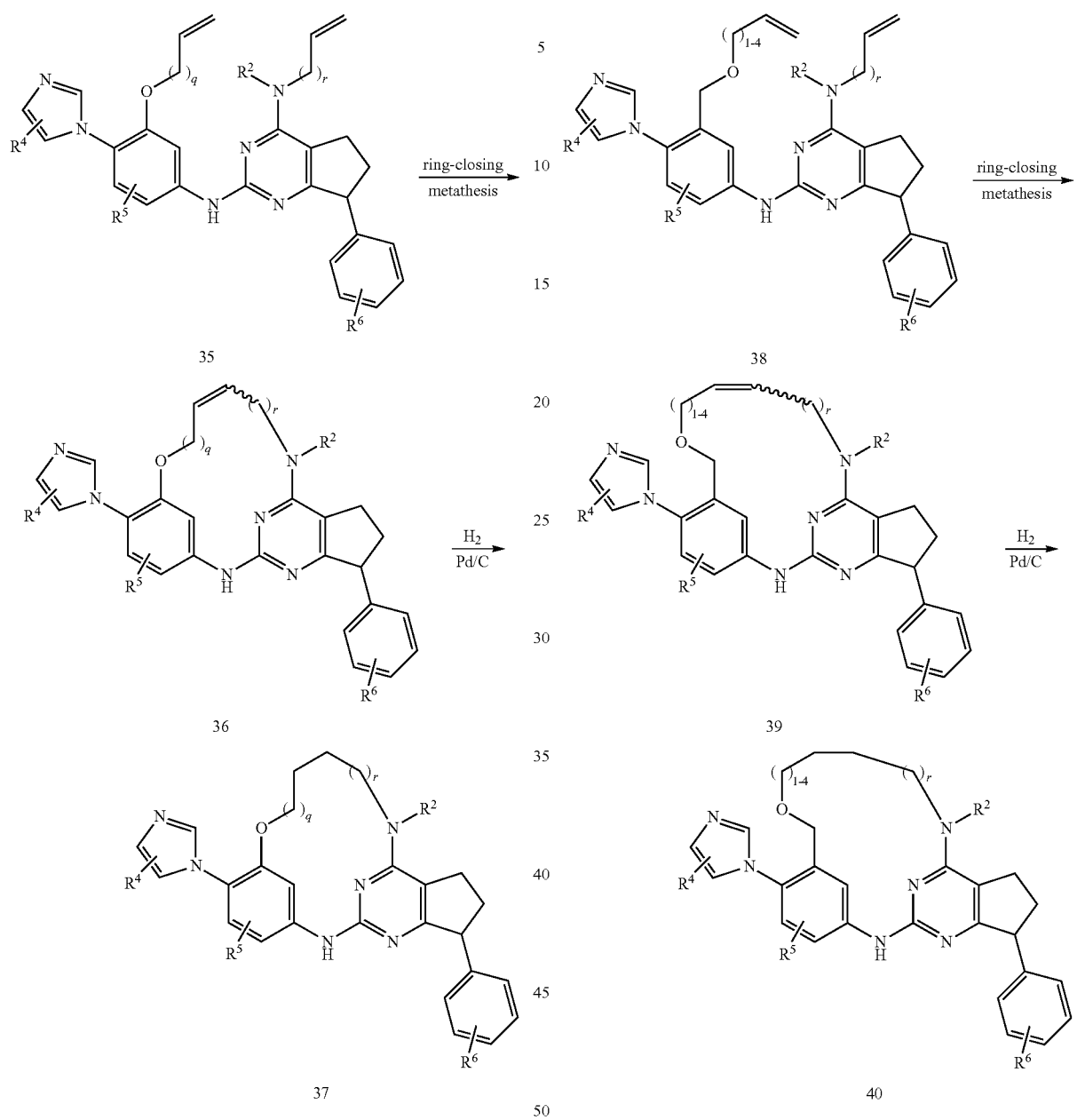

Appropriate substituted anilines may comprise the structure of the key compounds, such as 39-cis, 39-trans, and 40, utilizing analogous chemistry. The concept is described in Scheme 13. Additional variations on this general scheme are evident to one skilled in the art.

An additional method for the preparation of analogs of claim 1 is described in Scheme 14. The known 3,4-difluoronitrobenzene 41 was displaced with an appropriate heterocycle 3. The additional fluoro group is displaced under basic conditions with an appropriately functionalized and optionally protected aminoalcohol 43. Removal of any protecting group present utilizing conditions known by those skilled in the art (Green, T. W., Wuts, P. G. M. *Protective Groups in Organic Synthesis*, 1999, Third Edition, John Wiley & Sons), followed by displacement of the 4-position of an appropriate pyrimidine dichloride 45 yields compounds of the structure 46. Reduction of the nitro group under conditions orthogonal to the chloro group affords the aniline, followed by displacement of the 2-chloro substituent utilizing the conditions described in Scheme 11 to afford the title macrocycles 47.

Scheme 14

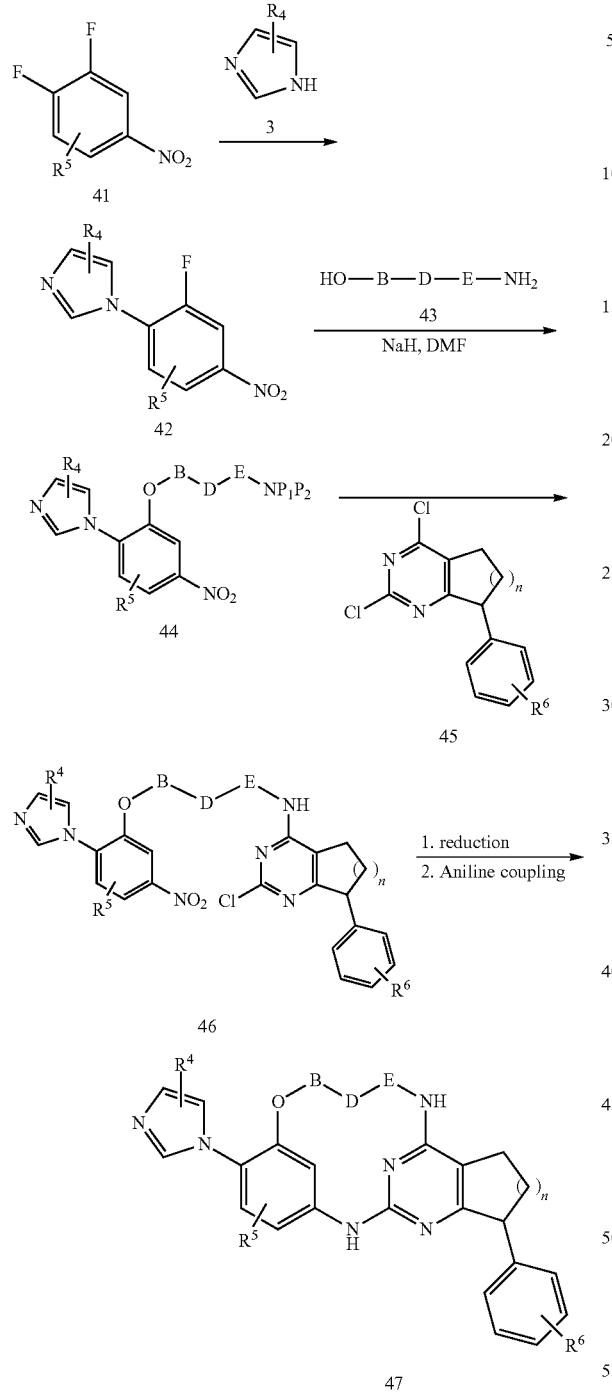

The racemic title compounds can be separated by chiral methods known to a reasonable person skilled in the arts, to provide individual enantiomers (Scheme 15). This is demonstrated below in the cyclopenta[d]pyrimidine series, but equally applies to the other racemic compounds described herein.

Scheme 15

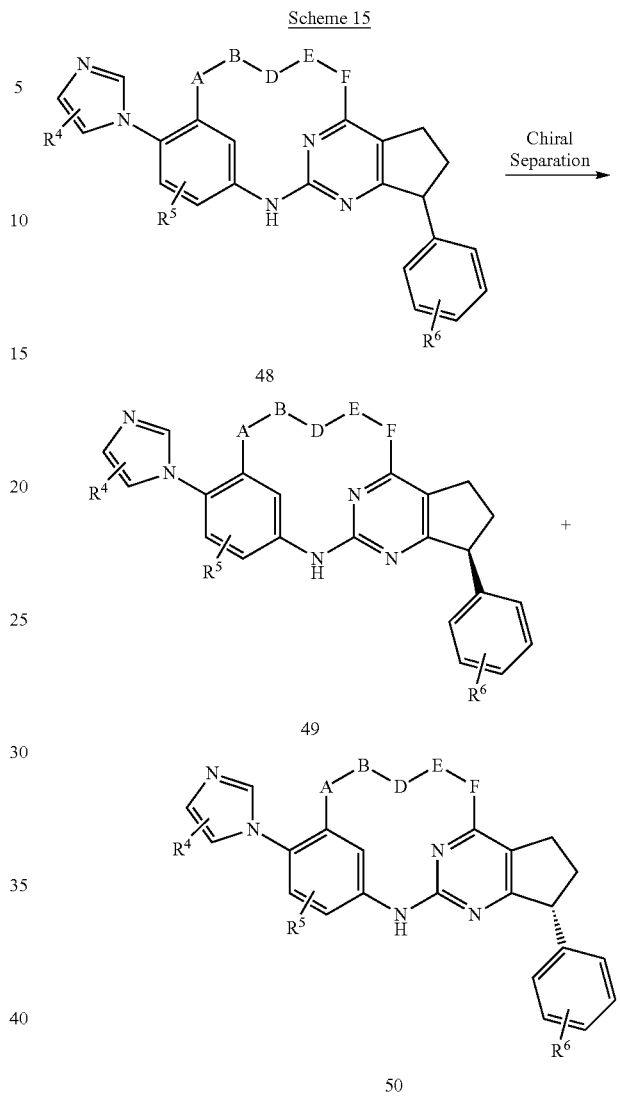

Additional members of the class of compounds of claim 1 can be prepared as is shown in Scheme 16. Carboxylation of benzonitriles followed by simple reduction using metal catalysis (Palladium on carbon or similar methods) provides the substituted beta-amino ester 53. Condensation with an acrylic ester provides intermediate 54, which can be alkylated on nitrogen to directly provide access to $R^3$ substituents. The intermediate 55 is then cyclized in the presence of base (usually KOt-Bu) to provide the beta-keto ester 56. Condensation of the beta-keto ester 56 with urea under basic conditions provides the pyrimidine dione intermediate 57, which can then be chlorinated under standard conditions to provide the dichloride 58. This dichloride can be converted into compounds of claim 1 in the usual way (vide infra).

Scheme 16

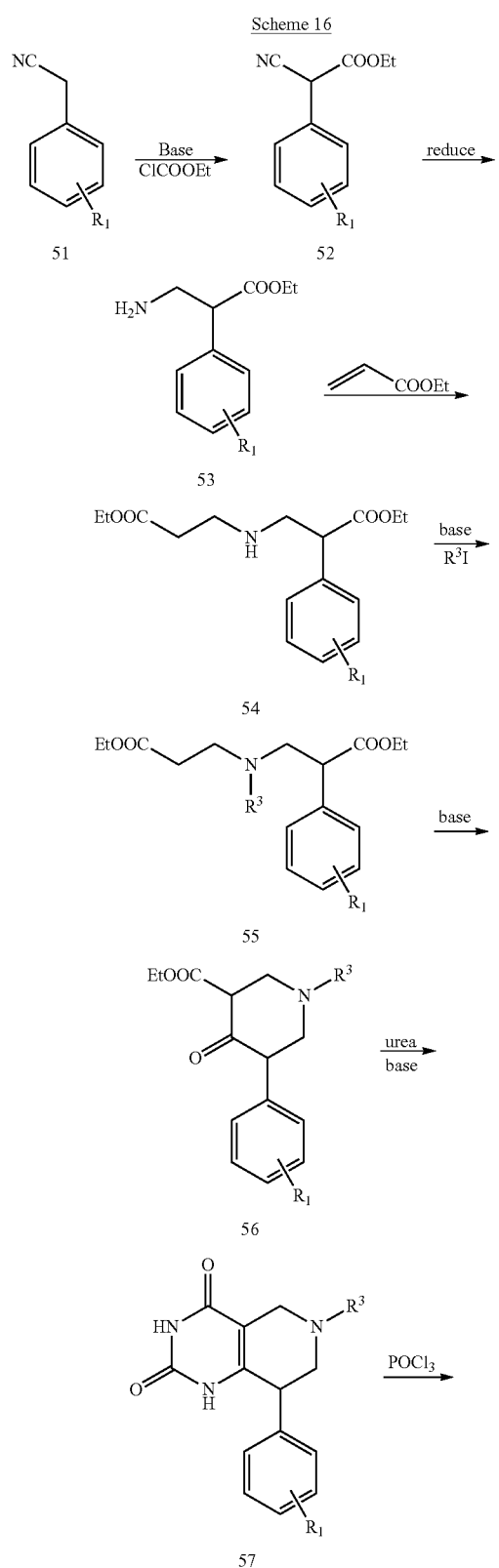

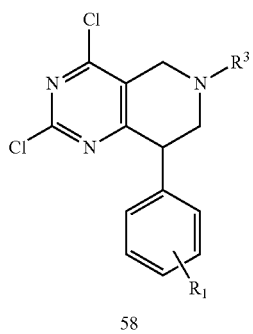

Additional members of the class of compounds of claim 1 can be prepared as is shown in Scheme 17. Esterification of an amino acid followed by alkylation with ethyl 4-bromobutyrate provides intermediate 61, which can be alkylated on nitrogen to directly provide access to $R^3$ substituents. The intermediate 62 is then cyclized in the presence of base (usually KOt-Bu) to provide the beta-keto ester 63. Condensation of the beta-keto ester 63 with urea under basic conditions provides the pyrimidine dione intermediate 64, which can then be chlorinated under standard conditions to provide the dichloride 65. This dichloride can be converted into compounds of claim 1 in the usual way (vide infra).

Scheme 17

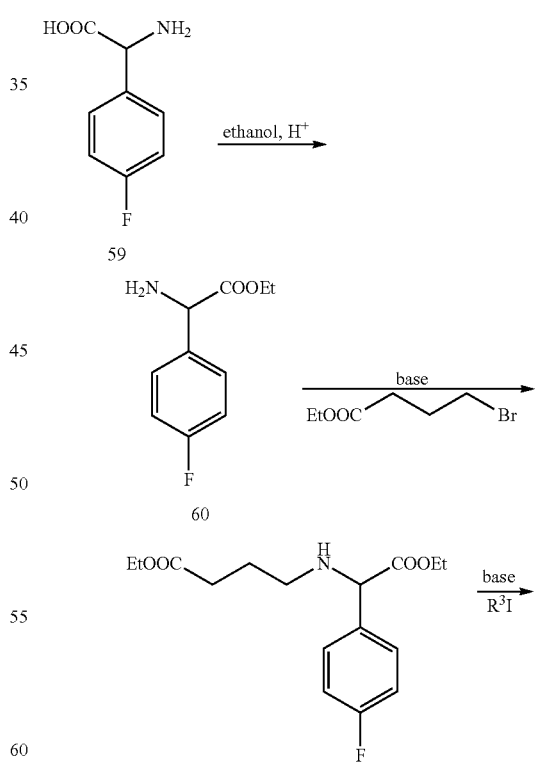

-continued

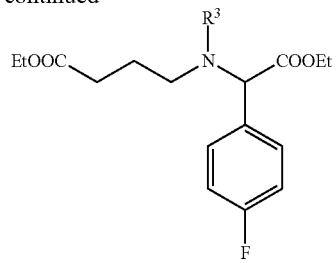

62

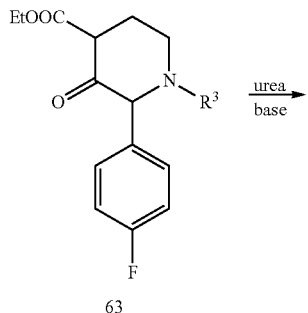

63

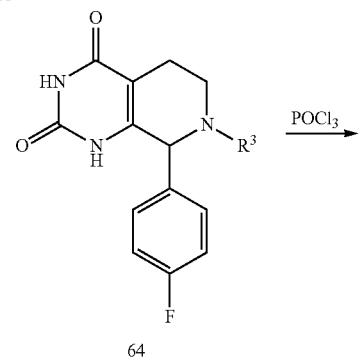

64

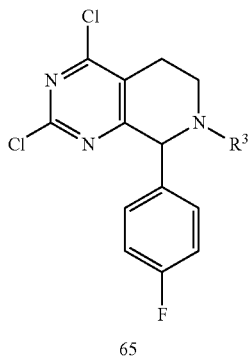

65

Additional members of the class of compounds of claim 1 can be prepared as is shown in Scheme 18. When F is a bond, the pyrimidine C(4) is directly attached to carbon. This is achieved by the cross-coupling with a Grignard reagent in the presence of a catalyst, usually Fe(acac)$_2$. 2,4-Dichloro-7-aryl-6,7-dihydro-5H-cyclopenta[d]pyrimidines 25 selectively react with the organometallic compounds to form the substituted pyrimidines 66, which under heating can be coupled with anilines 5 to form ring-closing metathesis substrates 67. The said coupling can be performed either under acidic conditions (for example, using acetic acid), or under basic conditions, (for example, using sodium hydride). Alternatively, the coupling can be completed under metal catalysis, with conditions known in the literature, for instance the use of Pd(dba)$_2$ and Xantphos catalyst in the presence of a strong base (NaOt-Bu) or Na$_2$CO$_3$ in an aqueous cosolvent mixture (typically THF/water or dioxane/water). Bis-olefins 67 can be reacted under dilute conditions via ring-closing metathesis (Grubbs, R. H. *Handbook of Metathesis,* 2003, First Edition, Wiley-VCH.) to form cis and trans olefins 68. These compounds can be further reacted to reduce the olefin using Pd/C and H$_2$ or similar conditions to afford the macrocycles 69. Alternate pyrimidine dichlorides may be used in place of dichloride 25, as would be apparent to one skilled in the art.

Scheme 18

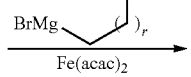

66

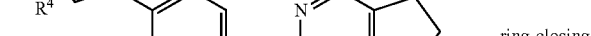

67

-continued

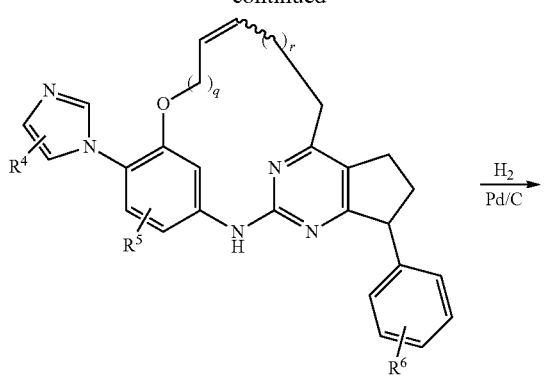

68

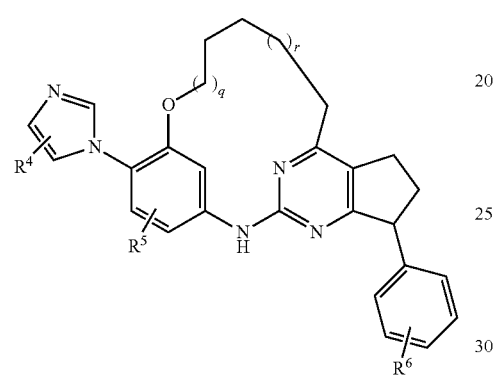

69

"HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "standard conditions", samples were dissolved in methanol (1 mg/mL) and run using a gradient program with a solvent flow rate of 1.0 mL/min. Reverse phase preparatory HPLC: When described as performed under "standard conditions", samples (approx. 20 mg) were dissolved in methanol (10 mg/mL) and purified on a 30 mm×100 mm Waters-Atlantis S5 column using a 10 minute gradient elution from 0% to 100% buffer B in buffer A (buffer A=10% $CH_3OH$/90% water/0.1% TFA and buffer B=90% MeOH/10% water/0.1% TFA). at 40 mL/minute.

Proton NMR spectra were obtained on a Bruker 400 or 500 spectrometer. Data were referred to the lock solvent.

The examples provided are intended to assist in a further understanding of the present invention. Particular materials employed, species and conditions are intended to further illustrate the specific embodiments of the invention and not limit the reasonable scope thereof.

SYNTHESIS OF COMPOUNDS

Preparation A 4-(4-chloro-1H-imidazol-1-yl)-3-allyloxyaniline

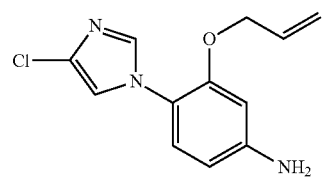

Intermediate A(1)

2-chloro-5-nitrophenol

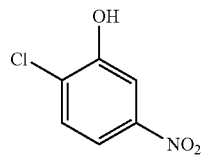 [SMILES: O=[N+]([O-])c1ccc(Cl)c(O)c1]

To a stirred solution of 1-chloro-2-methoxy-4-nitrobenzene (20 g, 106.6 mmol) in dichloromethane (500 mL) at −78° C. under a flow of Nitrogen gas, a solution of $BBr_3$ (747 mmol) in dichloromethane was added dropwise. The reaction was stirred overnight at −20° C., then for 1 h at 4° C. To the reaction, 10 mL of MeOH and 100 mL of water were added dropwise. The resulting mixture was made basic with 10% NaOH solution. The aqueous layer was then made acidic and was extracted with chloroform. The combined organic layers were dried with Na2SO4, filtered and concentrated in vacuo to afford the yellow solid 2-chloro-5-nitrophenol (12.5 g, 68%).

Intermediate A(2)

2-(allyloxy)-1-chloro-4-nitrobenzene

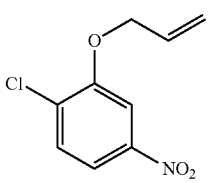

To a stirred solution of 2-chloro-5-nitrophenol (13.0 g, 75.1 mmol) in DMF (150 mL) was added $K_2CO_3$ (15.5 g, 113 mmol). The mixture was cooled to 0° C., and allyl bromide (9.60 mL, 113 mmol) was added dropwise. The reaction was then allowed to stir overnight at rt under nitrogen. The reaction was concentrated to remove DMF, then EtOAc was added to the residue. The mixture was washed with water and brine. The organic layer was dried (Na$_2$SO$_4$), and concentrated in vacuo to afford the highly yellow solid 2-(allyloxy)-1-chloro-4-nitrobenzene (11.5 g, 72% yield). LC-MS (M+H)$^+$212.2. $^1$H NMR (400 MHz, CDCl$_3$) δ ppm 7.81-7.77 (2H, m), 7.52 (1H, d, J=8.8 Hz), 6.12-6.02 (1H, m), 5.54-5.37 (2H, m), 4.72-4.70 (2H, m).

Intermediate A(3)

1-(2-(allyloxy)-4-nitrophenyl)-4-chloro-1H-imidazole

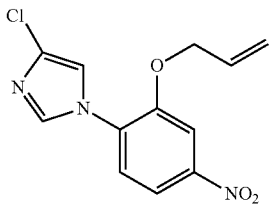 [SMILES: C=CCOc1cc([N+](=O)[O-])ccc1-n1cnc(Cl)c1]

A mixture of 4-chloro-1H-imidazole (3.31 g, 32.0 mmol), 2-(allyloxy)-1-chloro-4-nitrobenzene (6.50 g, 30.8 mmol), and potassium hydroxide flakes (1.90 g, 33.9 mmol) in anhydrous DMSO (50 mL) was heated at 90° C. for 20 h under nitrogen. The reaction mixture was allowed to cool to rt and ice-cold water was added. The resulting precipitate was collected by vacuum filtration. The product was dried, and purified by column chromatography (5% EtOAc/Hexane) to afford the yellow solid 1-(2-(allyloxy)-4-nitrophenyl)-4-chloro-1H-imidazole (3.48 g, 40% yield). LC-MS (M+H)$^+$ 280.2. $^1$H NMR (400 MHz, CDCl$_3$) δ ppm 7.97-7.93 (2H, m), 7.77 (1H, s), 7.44 (1H, d, J=8.8 Hz), 6.05-5.98 (1H, m), 5.45-5.37 (2H, m), 4.70-4.65 (2H, m).

Preparation A 4-(4-chloro-1H-imidazol-1-yl)-3-allyloxyaniline

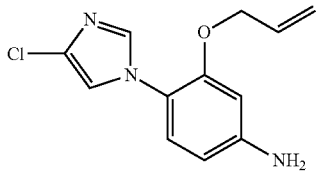 [SMILES: C=CCOc1cc(N)ccc1-n1cnc(Cl)c1]

Iron powder-325 mesh (737 mg, 12.5 mmol) was added to a round bottom flask charged with a mixture of 1-(2-(allyloxy)-4-nitrophenyl)-4-chloro-1H-imidazole (500 mg, 1.8 mmol), absolute methanol (10 mL), and ammonium chloride (768 mg, 14 mmol). A water-cooled reflux condenser was attached to the flask and the heterogeneous mixture was heated to 65° C. with vigorous stirring for 30 min. The reaction mixture was filtered, and washed with methanol. The solvent was removed in vacuo. EtOAc was added to the residue, and washed with water and brine. The organic layer was dried over MgSO4, filtered, and concentrated to afford 4-(4-chloro-1H-imidazol-1-yl)-3-allyloxyaniline (380 mg, 83% yield). LC-MS (M+H)$^+$250.0. $^1$H NMR (500 MHz, CDCl$_3$) δ ppm 7.48 (d, J=1.22 Hz, 1H), 6.97-7.02 (m, 2H), 6.26-6.32 (m, 2H), 5.87-5.98 (m, 1H), 5.20-5.34 (m, 2H), 4.48 (d, J=5.19 Hz, 2H), 3.86 (br s, 2H).

Preparation B and C

B: 3-(allyloxy)-4-(3-methyl-1H-1,2,4-triazol-1-yl) aniline

C: 3-(allyloxy)-4-(5-methyl-1H-1,2,4-triazol-1-yl) aniline

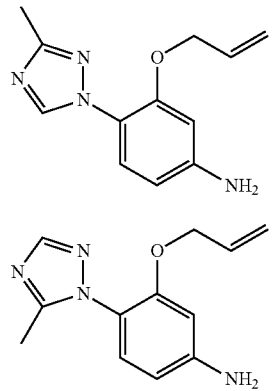

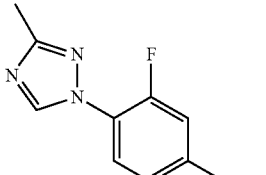

Intermediate B(1) and C(1)

B(1): 1-(2-fluoro-4-nitrophenyl)-3-methyl-1H-1,2,4-triazole

C(1): 1-(2-fluoro-4-nitrophenyl)-5-methyl-1H-1,2,4-triazole

A mixture of 3-methyl-1H-1,2,4-triazole (15.0 g, 181 mmol), 1,2-difluoro-4-nitrobenzene (28.7 g, 181 mmol), and sodium bicarbonate (15.2 g, 181 mmol) in DMSO (100 mL) was heated at 80° C. for 48 h. The reaction mixture was allowed to cool to rt and was poured into water (800 mL). The aqueous mixture was extracted with EtOAc (3×200 mL). The combined organic extracts were sequentially washed with water (500 mL) and brine solution (100 mL). The organic layer was dried over sodium sulfate, filtered, and concentrated in vacuo. The crude reaction mixture was purified using silica gel chromatography (30-80% EtOAc/hexane, linear gradient) to afford two regioisomeric products. Pure fractions of the less polar regioisomer were combined and concentrated to afford 1-(2-fluoro-4-nitrophenyl)-3-methyl-1H-1,2,4-triazole (7.2 g, 30.8 mmol, 17% yield) as an off-white solid. Data for 1-(2-fluoro-4-nitrophenyl)-3-methyl-1H-1,2,4-triazole [B1]: LC-MS (M+H)⁺=223.1. ¹H NMR (500 MHz, CDCl₃) δ ppm 8.73 (d, J=2.7 Hz, 1H), 8.15-8.26 (m, 3H), 2.53 (s, 3H). Pure fractions of the more polar regioisomer were combined and concentrated to afford 1-(2-fluoro-4-nitrophenyl)-5-methyl-1H-1,2,4-triazole (6.23 g, 15% yield) as an off-white solid. Data for 1-(2-fluoro-4-nitrophenyl)-5-methyl-1H-1,2,4-triazole [C1]: LC-MS (M+H)⁺=223.1. ¹H NMR (500 MHz, CDCl₃) δ ppm 8.18-8.24 (m, 2H), 8.04 (s, 1H), 7.69-7.78 (m, 1H), 2.47-2.53 (m, 3H).

Intermediate B(2)

1-(2-(allyloxy)-4-nitrophenyl)-3-methyl-1H-1,2,4-triazole

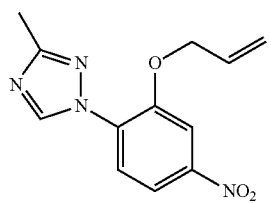

A suspension of NaH (2.295 g 57.4 mmol, 60% dispersion in mineral oil) in DMF (85 mL) was cooled at 0° C. and a solution 1-(2-fluoro-4-nitrophenyl)-3-methyl-1H-1,2,4-triazole (8.50 g 38.3 mmol) was added dropwise. Allyl alcohol (2.67 g, 49.9 mmol) was added via syringe over 10 min. The reaction mixture was allowed to warm to room temperature. After 30 min, TLC showed completion of reaction. The reaction mixture was slowly quenched with water (20 mL), treated with 200 mL of brine and extracted with EtOAc (3×200 mL). The combined organic extracts were washed with water (3×200 mL) and brine solution (100 mL). The organic layer was dried over sodium sulfate, filtered, and concentrated in vacuo. The crude reaction mixture was purified using silica gel chromatography (20-80% EtOAc/hexane, linear gradient). Pure fractions were concentrated under reduced pressure to afford 1-(2-(allyloxy)-4-nitrophenyl)-3-methyl-1H-1,2,4-triazole (5 g, 19.21 mmol 50% yield) as a yellow colored solid. LC-MS (M+H)⁺=261.0. ¹H NMR (400 MHz, CDCl₃) δ ppm 8.906 (s, 1H), 8.09 (d, 1H, J=8.8 Hz), 7.99-7.94 (m, 2H), 6.13-6.03 (m, 1H), 5.50-5.54 (m, 2H), 4.80-4.79 (m, 2H), 2.497 (s, 3H).

Intermediate C(2)

1-(2-(allyloxy)-4-nitrophenyl)-5-methyl-1H-1,2,4-triazole

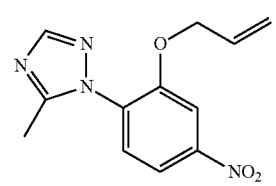

A suspension of NaH (0.675 g, 16.88 mmol, 60% dispersion in mineral oil) in DMF (25 mL) was cooled to 0° C. A solution 1-(2-fluoro-4-nitrophenyl)-5-methyl-1H-1,2,4-triazole (2.50 g, 11.25 mmol) was added dropwise. Allyl alcohol (0.784 g, 13.5 mmol) was added via syringe over 5 min. The reaction mixture was allowed to warm up to room temperature. After 30 min, TLC showed completion of reaction. It was slowly quenched with water (10 mL), diluted with brine (100 mL), and extracted with EtOAc (3×50 mL). The organic layer was dried over sodium sulfate, filtered, and concentrated in vacuo. The crude reaction mixture was purified using silica gel chromatography (20-80% EtOAc/hexane, linear gradient). Pure fractions were concentrated under reduced pressure to afford 1-(2-(allyloxy)-4-nitrophenyl)-5-methyl-1H-1,2,4-triazole (1.5 g 51% yield) as a yellow-brown colored solid. LC-MS (M+H)⁺=261.0. ¹H NMR (400 MHz, CDCl₃) δ ppm 8.02-7.94 (m, 3H), 7.58 (d, 1H, J=8.4 Hz), 5.98-5.89 (m, 1H), 5.37-5.32 (m, 2 H), 4.69-4.70 (m, 2H), 2.403 (s, 3H).

Preparation B 3-(allyloxy)-4-(3-methyl-1H-1,2,4-triazol-1-yl)aniline

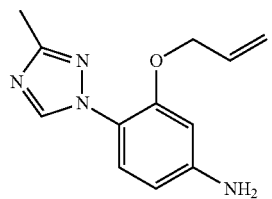

Iron powder-325 mesh (565 mg, 9.6 mmol), was taken in a round bottom flask charged with a mixture of 1-(2-(allyloxy)-4-nitrophenyl)-3-methyl-1H-1,2,4-triazole (500 mg, 1.921 mmol), absolute methanol (5 ml), water (1 mL) and ammonium chloride (517 mg, 9.61 mmol). A water-cooled reflux condenser was attached to the flask and the heterogeneous mixture was heated to 65° C. with vigorous stirring for 50 min. The reaction mixture was filtered and washed with methanol. The solvent was removed in vacuo. EtOAc was added to the residue, and washed with water and brine. The organic layer was dried over MgSO4, filtered, and concentrated to afford 3-(allyloxy)-4-(3-methyl-1H-1,2,4-triazol-1-yl)aniline. (270 mg, 61% yield). LC-MS (M+H)+=231.2 $^1$H NMR (400 MHz, DMSO-d6) δ ppm 8.434 (s, 1H), 7.11 (d, 1H, J=8.8 Hz), 6.34 (s, 1H), 6.21 (d, 1H, J=8.4 Hz), 5.99-5.93 (m, 1H), 5.42 (s, 2H), 5.29-5.18 (m, 2H), 4.50-4.48 (m, 2H), 2.28 (s, 3H).

Preparation C 3-(allyloxy)-4-(5-methyl-1H-1,2,4-triazol-1-yl)aniline

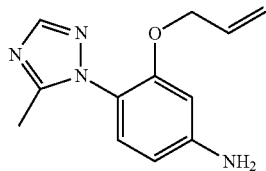

C

Iron powder-325 mesh (4.52 g, 76.86 mmol) was added to a round bottom flask charged with a mixture of 1-(2-(allyloxy)-4-nitrophenyl)-5-methyl-1H-1,2,4-triazole (4 g, 15.37 mmol), absolute methanol (40 mL), water (8 mL) and ammonium chloride (4.11 g, 76.86 mmol). A water-cooled reflux condenser was attached to the flask and the heterogeneous mixture was heated to 65° C. with vigorous stirring for 50 min. The reaction mixture was filtered and washed with methanol. The solvent was removed in vacuo. EtOAc was added to the residue, and washed with water and brine. The organic layer was dried over MgSO4, filtered, and concentrated to afford 3-(allyloxy)-4-(5-methyl-1H-1,2,4-triazol-1-yl)aniline (1.5 g, 42% yield) as a dark brown solid. LC-MS (M+H)+=231.2 $^1$H NMR (400 MHz, DMSO-d6) δ ppm 7.880 (s, 1H), 6.96 (d, 1H, J=8.4 Hz), 6.35 (s, 1H), 6.24 (d, 1H, J=8.4 Hz), 5.95-5.89 (m, 1H), 5.88 (s, 2H), 5.19-5.16 (dd, 2H, J=1.6, 13 Hz), 4.47 (d, 2H, J=4.8 Hz), 2.20 (s, 3H).

Preparation D 2-(allyloxy)-4-aminobenzonitrile

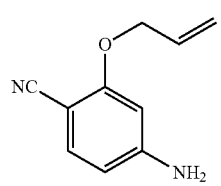

D

Intermediate D(1)

2-(allyloxy)-4-nitrobenzonitrile

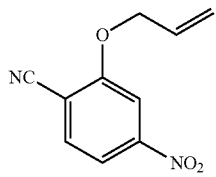

D(1)

To a stirred solution of 2-hydroxy-4-nitrobenzonitrile (5.0 g, 30.48 mmol) in DMF (50 mL) was added Cs$_2$CO$_3$ (19.9 g, 60.97 mmol). The mixture was cooled to 0° C., and allyl bromide (4.39 g, 36.58 mmol) was added dropwise. The reaction mixture was stirred for 12 h at 90° C. under nitrogen. The reaction mixture was cooled to rt and concentrated to remove DMF, then EtOAc (50 mL) was added to the residue. The mixture was washed with water (2×30 mL) and brine (30 mL). The organic layer was dried with Na$_2$SO$_4$, and concentrated in vacuo to afford the yellow solid, 2-(allyloxy)-4-nitrobenzonitrile (4 g, 65% yield). LC-MS (M+H)+=205.2 $^1$H NMR (400 MHz, CDCl$_3$) δ ppm 7.87-7.86 (m, 1H), 7.811 (s, 1H), 7.76 (d, 1H, J=8.4 Hz), 6.11-6.01 (m, 1H), 5.56-5.55 (dd, 1H, J=1.6, 3.2 Hz), 5.52 (d, 1H, J=1.6 Hz), 4.79 (d, 2H, J=4.8 Hz).

Preparation D 2-(allyloxy)-4-aminobenzonitrile

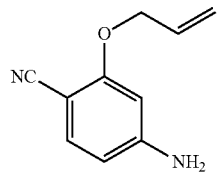

D

Iron powder-325 mesh (5.7 g, 98.0 mmol) was taken in a round bottom flask charged with a mixture of 2-(allyloxy)-4-nitrobenzonitrile (4.0 g, 19.6 mmol), absolute methanol (40 mL), water (8 mL) and ammonium chloride (5.2 g, 98 mmol). A water-cooled reflux condenser was attached to the flask and the heterogeneous mixture was heated to 65° C. with vigorous stirring for 50 min. The reaction mixture was filtered, and washed with methanol. The solvent was removed in vacuo. EtOAc was added to the residue, and the solution was washed with water and brine. The organic layer was dried over MgSO4, filtered, and concentrated to afford 2-(allyloxy)-4-aminobenzonitrile (3.2 g, 94% yield) as a light-brown solid. LC-MS (M+H)+=175.2 $^1$H NMR (400 MHz, CDCl$_3$) δ ppm 7.29 (d, 1H, J=8.4 Hz), 6.22 (dd, 1H, J=2.0, 8.4 Hz), 6.14 (s, 1H), 6.07-5.98 (m, 1H), 5.48 (dd, 1H, J=1.6, 3.2 Hz), 5.44 (dd, 1H, J=1.6, 3.2 Hz), 4.59 (d, 2H, J=1.6 Hz).

Preparation E 2-(2-(2-(4-chloro-1H-imidazol-1-yl)-5-nitrophenoxy)ethoxy)ethanamine

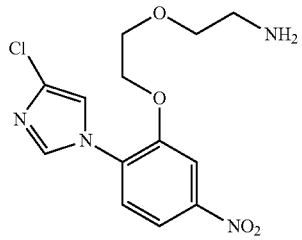 [SMILES: NCCOCCOc1cc([N+](=O)[O-])ccc1-n1cnc(Cl)c1]

Intermediate E(1)

tert-butyl (2-(2-hydroxy)ethoxy)ethylcarbamate

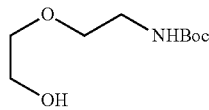

To an ice-cold solution of 2-(2-aminoethoxyethanol) (10 g, 95.23 mmol) in dichloromethane (500 mL) was added triethylamine (19.23 g, 190.47 mmol), followed by Boc-anhydride (22.62 g, 104.76 mmol) dropwise over fifteen minutes at 0° C. The reaction mixture was allowed to warm to rt and stirred for 18 h while monitoring by TLC. The solvent was removed under reduced pressure and the residue was taken up in ethyl acetate (400 mL) and washed with saturated ammonium chloride solution (2×250 mL). The organic layer was dried over anhydrous sodium sulphate and concentrated to give tert-butyl (2-(2-hydroxy)ethoxy)ethylcarbamate (10.9 g, 55.8%) as a colorless liquid. $^1$H NMR (400 MHz, DMSO-d6) δ ppm 6.76 (1H, s), 4.56 (1H, t, J=5.2 Hz), 3.50-3.46 (2H, m), 3.41-3.36 (4H, m), 3.10-3.05 (2H, m), 1.38 (9H, s).

Intermediate E(2)

tert-butyl (2-(2-bromo)ethoxy)ethylcarbamate

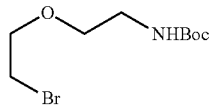

To an ice-cold solution of tert-butyl (2-(2-hydroxy)ethoxy) ethylcarbamate (5 g, 24.5 mmol) in dichloromethane (200 mL) was added triphenylphosphine (9.63 g, 36.7 mmol) followed by carbon tetrabromide (12.18 g, 36.7 mmol) at 0° C. The reaction mixture was warmed to rt and stirred for 18 h. The solvent was removed under reduced pressure and the residue was purified by silica gel column chromatography (60-120 mesh silica) using 5-10% ethyl acetate in pet-ether to give tert-butyl 3-bromopropylcarbamate (4.9 g, 70.73%) as a light-brown liquid. $^1$H NMR (400 MHz, CDCl$_3$) δ ppm 4.90 (1H, s), 3.77 (2H, t, J=6.0 Hz), 3.55 (2H, t, J=5.2 Hz), 3.46 (2H, t, J=6.0 Hz), 3.32 (2H, q, J=5.2 Hz), 1.44 (9H, s).

Intermediate E(3)

tert-butyl 2-(2-(2-chloro-5-nitrophenoxy)ethoxy) ethylcarbamate

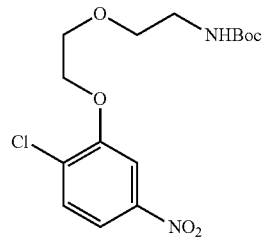 [SMILES: CC(C)(C)OC(=O)NCCOCCOc1cc([N+](=O)[O-])ccc1Cl]

To a mixture of 2-chloro-5-nitrophenol (2 g, 11.62 mmol), cesium carbonate (5.66 g, 17.44 mmol) in DMF (20 mL), intermediate E(2) (4.95 g, 17.44 mmol) was added, followed by tetrabutylammonium iodide (0.214 g, 0.581 mmol) at room temperature. The reaction mixture was stirred at rt for 18 h. The solvent was removed under reduced pressure and the residue was taken up in ethyl acetate (200 mL) and washed with brine (2×100 mL). The organic layer was dried over anhydrous sodium sulphate and concentrated to give tert-butyl 2-(2-(2-chloro-5-nitrophenoxy)ethoxy)ethylcarbamate (2.1 g, 50%) as a light-brown solid. LC-MS (M–100)$^+$ =260.7. $^1$H NMR (400 MHz, CDCl$_3$) δ ppm 7.87-7.81 (2H, m), 7.54-7.52 (1H, d, J=8.8 Hz), 4.95 (1H, s), 4.31-4.29 (2H, m), 3.92-3.90 (2H, m), 3.66-3.64 (2H, t, J=6.0 Hz), 3.37-3.33 (2H, m), 1.44 (9H, s).

Intermediate E(4)

tert-butyl 2-(2-(2-(4-chloro-1H-imidazol-1-yl)-5-nitrophenoxy)ethoxy)ethylcarbamate

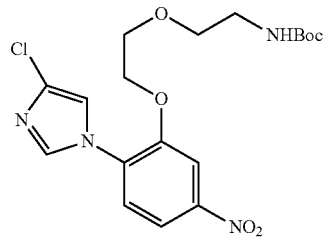 [SMILES: CC(C)(C)OC(=O)NCCOCCOc1cc([N+](=O)[O-])ccc1-n1cnc(Cl)c1]

To a stirred mixture of intermediate E(3) (4.0 g, 11.1 mmol), KOH (0.93 g, 16.6 mmol) in DMSO (30 mL) was added chloroimmidazole (1.69 g, 16.6 mmol) at room temperature. The reaction mixture was stirred at 90° C. for 18 h while monitoring by LC-MS and TLC. The reaction mixture was poured into crushed ice (50 g) and extracted with ethyl acetate (3×200 mL). The organic layer was washed with brine, dried over anhydrous sodium sulphate and concentrated under reduced pressure. The crude compound was purified by column chromatography (60-120 mesh silica) using 60-70% ethyl acetate in pet-ether to give tert-butyl 2-(2-(2-

(4-chloro-1H-imidazol-1-yl)-5-nitrophenoxy)ethoxy)ethyl-carbamate (3.0 g, 63.29%) as a yellow solid. LC-MS (M−100)$^+$=326.2. $^1$H NMR (400 MHz, CDCl$_3$) δ ppm 8.01-7.97 (2H, m), 7.88 (1H, s), 7.46-7.44 (1H, d, J=8.8 Hz), 7.28-7.27 (1H, m), 4.92 (1H, s), 4.34-4.33 (2H, m), 3.86-3.83 (2H, m), 3.59-3.57 (2H, t, J=5.2 Hz), 3.37-3.34 (2H, m), 1.43 (9H, s).

Preparation E 2-(2-(2-(4-chloro-1H-imidazol-1-yl)-5-nitrophe-noxy)ethoxy)ethanamine

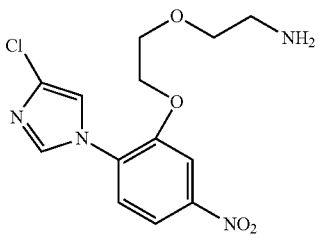 [SMILES: NCCOCCOc1cc([N+](=O)[O-])ccc1-n1cnc(Cl)c1]

To an ice-cold solution of intermediate E(4) (1 g, 2.34 mmol) in THF (20 mL) was added HCl in dioxane (20 mL). The reaction mixture was stirred at room temperature for 3 h while monitoring by TLC and LC-MS. The reaction mixture was concentrated under reduced pressure and taken in up ice cold water (100 mL). The pH was adjusted with saturated sodium bicarbonate solution (100 mL) and extracted with dichloromethane (2×100 mL). The organic layer was dried over anhydrous sodium sulphate and concentrated under reduced pressure to get Preparation E as a light yellow liquid (0.72 g, 94.11%). LC-MS (M+H)$^+$=327.0. $^1$H NMR (400 MHz, DMSO-d6) δ ppm 8.17 (1H, s), 8.09 (1H, s), 7.97 (1H, d, J=8.8 Hz), 7.81-7.78 (2H, m), 4.42-4.40 (2H, m), 3.78-3.76 (2H, m), 3.42 (2H, t, J=6.0 Hz) 2.69-2.66 (2H, m).

Preparation F 3-(2-(4-chloro-1H-imidazol-1-yl)-5-nitrophenoxy)propan-1-amine

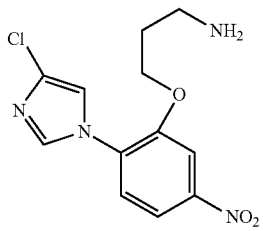 [SMILES: NCCCOc1cc([N+](=O)[O-])ccc1-n1cnc(Cl)c1]

Intermediate F(1)

tert-butyl 3-hydroxypropylcarbamate

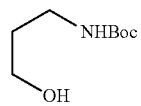

To a solution of 3-aminopropan-1-ol (10 g, 133.3 mmol) in dichloromethane (500 mL) was added triethylamine (26.9 g, 266.6 mmol) followed by Boc-anhydride (31.82 g, 146.6 mmol) dropwise over fifteen minutes at 0° C. The reaction mixture was stirred at room temperature for 18 h while monitoring by TLC. The solvent was removed under reduced pressure and the residue was dissolved in ethyl acetate (400 mL), washed with saturated ammonium chloride solution (2×250 mL). The organic layer was dried over anhydrous sodium sulphate and concentrated in vacuo to give tert-butyl-3-hydroxypropylcarbamate (9.8 g, 42.06%) as a colorless liquid. $^1$H NMR (400 MHz, DMSO-d6) δ ppm 6.72 (1H, s), 4.36 (1H, t, J=5.2 Hz), 3.41-3.37 (2H, q, J=6.4 Hz), 2.99-2.94 (2H, q, J=6.4 Hz), 1.55-1.50 (2H, m), 1.38 (9H, s).

Intermediate F(2)

tert-butyl 3-bromopropylcarbamate

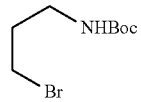

To a solution of tert-butyl 3-hydroxypropylcarbamate (5 g, 28.57 mmol) in dichloromethane (200 mL) was added triphenylphosphine (11.52 g, 42.85 mmol) followed by carbon tetrabromide (14.22 g, 42.85 mmol) at 0° C. The reaction mixture was stirred at rt for 18 h while monitoring by TLC. The solvent was removed under reduced pressure and the residue was purified by column chromatography (60-120 mesh silica gel) using 5-10% ethyl acetate in pet-ether to give tert-butyl 3-bromopropylcarbamate (4.5 g, 66.46%) as a light-brown liquid. $^1$H NMR (400 MHz, CDCl$_3$) δ ppm 4.63

(1H, s), 3.45-3.42 (2H, t, J=6.4 Hz), 3.29-3.24 (2H, q, J=6.4 Hz), 2.08-2.01 (2H, m), 1.44 (9H, s).

Intermediate F(3)

tert-butyl 3-(2-chloro-5-nitrophenoxy)propylcarbamate

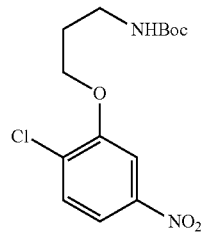 [SMILES: CC(C)(C)OC(=O)NCCCOc1cc([N+](=O)[O-])ccc1Cl]

To a stirred solution of 2-chloro-5-nitrophenol (2 g, 11.62 mmol), cesium carbonate (5.66 g, 17.44 mmol) in DMF (20 mL) was added tert-butyl 3-bromopropylcarbamate (4.13 g, 17.44 mmol) followed by tetrabutylammonium iodide (0.214 g, 0.581 mmol) at room temperature. The reaction mixture was stirred at room temperature for 18 h while monitoring by TLC and LC-MS. The solvent was removed under reduced pressure and the residue was taken up in ethyl acetate (200 mL) and washed with brine (2×200 mL). The organic layer was dried over anhydrous sodium sulphate and concentrated under reduced pressure to give tert-butyl 3-(2-chloro-5-nitrophenoxy)propylcarbamate (2.2 g, 57.4%) as a light-brown solid. LC-MS $(M-100)^+$=230.7 1H NMR (400 MHz, CDCl$_3$) δ ppm 7.82-7.76 (2H, m), 7.52 (1H, d, J=8.4 Hz), 4.99 (1H, s), 4.20 (2H, t, J=5.6 Hz), 3.41-3.37 (2H, q, J=6.0 Hz), 2.12-2.01 (2H, m), 1.43 (9H, s).

Intermediate F(4)

tert-butyl 3-(2-(4-chloro-1H-imidazol-1-yl)-5-nitrophenoxy)propylcarbamate

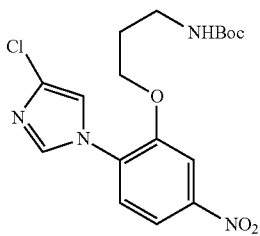 [SMILES: CC(C)(C)OC(=O)NCCCOc1cc([N+](=O)[O-])ccc1-n1cnc(Cl)c1]

To a stirred mixture of tert-butyl 3-(2-chloro-5-nitrophenoxy)propylcarbamate (4.0 g, 12.12 mmol) and KOH (1.018 g, 18.1 mmol) in DMSO (30 mL) was added chloroimidazole (1.84 g, 18.1 mmol) at room temperature. The reaction mixture was stirred at 90° C. 18 h. The reaction mixture was poured to crushed ice (50 g), extracted with ethyl acetate (3×200 mL), and washed with brine (2×100 mL). The organic layer was dried over anhydrous sodium sulphate and concentrated in vacuo. The crude compound was purified by column chromatography (60-120 mesh silica) using 60-70% ethyl acetate in pet-ether to give tert-butyl 3-(2-(4-chloro-1H-imidazol-1-yl)-5-nitrophenoxy)propylcarbamate (3.2 g, 66.6%) as a yellow solid. LC-MS $(M-100)^+$=296.8. $^1$H NMR (400 MHz, CDCl$_3$) δ ppm 7.98-7.93 (2H, m), 7.79 (1H, s), 7.44 (1H, d, J=8.4 Hz), 7.22 (1H, s), 4.61 (1H, s), 4.22 (2H, t, J=6.0 Hz), 3.31-3.26 (2H, m), 2.06-2.00 (2H, m), 1.42 (9H, s).

Intermediate F(5)

tert-butyl 3-(2-(4-chloro-1H-imidazol-1-yl)-5-nitrophenoxy)propylmethyl)carbamate

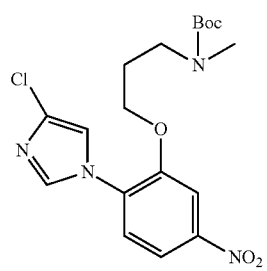 [SMILES: CN(CCCOc1cc([N+](=O)[O-])ccc1-n1cnc(Cl)c1)C(=O)OC(C)(C)C]

To an ice-cold solution of intermediate F(4) (1.2 g, 3.030 mmol) in THF (40 mL) was added sodium hydride (60% in oil, 1.2 g, 30.3 mmol) and the mixture was stirred at room temperature for 10 min. Methyl iodide (4.3 g, 30.30 mmol) was then added at room temperature. The reaction mixture was heated at 70° C. for 2 h. The crude mixture was poured in crushed ice (250 g), extracted with ethyl acetate (2×100 mL) and washed with brine (150 mL). The organic layers were dried over anhydrous sodium sulphate and concentrated under reduced pressure to give tert-butyl 3-(2-(4-chloro-1H-imidazol-1-yl)-5-nitrophenoxy)propyl(methyl)carbamate (1.0 g, 80.64%) as a yellow solid. LC-MS $(M+H)^+$=411.2. $^1$H NMR (400 MHz, CDCl$_3$) δ ppm 7.98-7.93 (2H, m), 7.79 (1H, s), 7.44 (1H, d, J=8.4 Hz), 7.22 (1H, s), 4.19-4.16 (2H, m), 3.38-3.24 (2H, m), 2.81 (3H, s), 2.06-2.00 (2H, m), 1.42 (9H, s).

Preparation F 3-(2-(4-chloro-1H-imidazol-1-yl)-5-nitrophenoxy)propan-1-amine

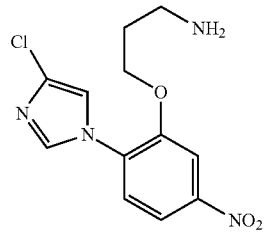 [SMILES: NCCCOc1cc([N+](=O)[O-])ccc1-n1cnc(Cl)c1]

To an ice-cold solution of intermediate F(4) (1 g, 2.5 mmol) in THF (20 mL) was added HCl in dioxane (20 mL). The reaction mixture was stirred at rt for 3 h. It was concentrated under reduced pressure and treated with 50 mL of saturated sodium bicarbonate solution (100 mL). The mixture was extracted with dichloromethane (2×100 mL) and washed with brine (2×50 mL). The organic layers were dried over anhydrous sodium sulphate and concentrated under reduced pressure to get a light yellow liquid (0.62 g, 83.78%). LC-MS $(M+H)^+$=297.0. $^1$H NMR (400 MHz, DMSO-d6) δ ppm 8.08

(1H, s), 8.03 (1H, s), 7.96 (1H, d, J=8.8 Hz), 7.77-7.73 (2H, m), 4.30 (2H, t, J=6.4 Hz), 2.68 (2H, t, J=6.8 Hz), 1.89-1.81 (2H, m).

Preparation G 3-(2-(4-chloro-1H-imidazol-1-yl)-5-nitrophenoxy)-N-methylpropan-1-amine

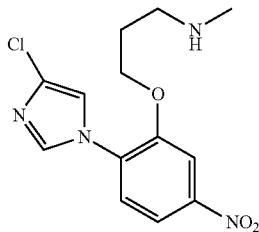 [SMILES: CNCCCOc1cc([N+](=O)[O-])ccc1-n1cnc(Cl)c1]

To an ice-cold solution of intermediate F(5) (1 g, 2.439 mmol) in THF (15 mL) was added HCl in dioxane (15 mL, 4.0 M). The reaction mixture was stirred at room temperature for 3 h while monitoring by LC-MS and TLC. The solvent was removed under reduced pressure. The crude mixture was treated with saturated sodium bicarbonate solution (100 mL) and extracted with dichloromethane (2×100 mL). The organic layers were dried over anhydrous sodium sulphate and concentrated under reduced pressure to get a light yellow liquid (0.6 g, 75%). LC-MS (M+H)$^+$=311.0. $^1$H NMR (400 MHz, DMSO-d6) δ ppm 8.08 (1H, s), 8.03 (1H, s), 7.95 (1H, d, J=8.8 Hz), 7.77-7.73 (2H, m), 4.28 (2H, t, J=6.4 Hz), 2.57-2.50 (2H, m), 2.27 (3H, s), 1.87 (2H, t, J=6.8 Hz).

Preparation H tert-butyl 3-(2-cyano-5-nitrophenoxy)propylcarbamate

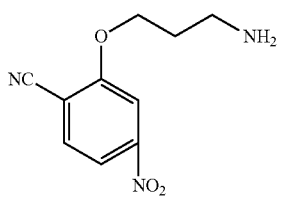 [SMILES: N#Cc1ccc([N+](=O)[O-])cc1OCCCN]

Intermediate H(1)

tert-butyl 3-(2-cyano-5-nitrophenoxy)propylcarbamate

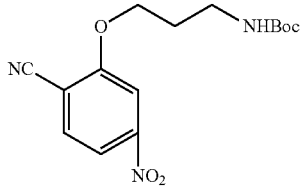 [SMILES: CC(C)(C)OC(=O)NCCCOc1cc([N+](=O)[O-])ccc1C#N]

To a stirred mixture of 2-hydroxy-4-nitrobenzonitrile (4 g, 24.37 mmol) and cesium carbonate (11.91 g, 36.6 mmol) in DMF (40 mL) was added tert-butyl 3-bromopropylcarbamate (8.71 g, 36.6 mmol) at room temperature. The reaction mixture was stirred at room temperature for 18 h. The solvent was removed under reduced pressure and the residue was taken in ethyl acetate (250 mL), washed with brine (2×100 mL). The organic layer was dried over anhydrous sodium sulphate and concentrated in vacuo to give tert-butyl 3-(2-cyano-5-nitrophenoxy)propylcarbamate (5 g, 63.8%) as a yellow solid. LC-MS (M+H)$^+$=321.2. $^1$H NMR (400 MHz, CDCl$_3$) δ ppm 7.89-7.87 (1H, m), 7.81 (1H, s), 7.75 (1H, d, J=8.4 Hz), 4.76 (1H, br s), 4.27-4.24 (2H, t, J=6.4 Hz), 3.40-3.36 (2H, q, J=6.4, 12.8 Hz), 2.15-2.09 (2H, m), 1.43 (9H, s).

Preparation H tert-butyl 3-(2-cyano-5-nitrophenoxy)propylcarbamate

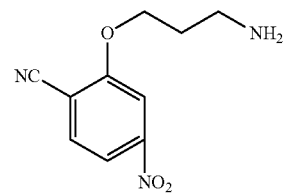

To an ice-cold solution of intermediate H(1) (3 g, 9.34 mmol) in DCM (60 mL) was added TFA (15 mL). The reaction mixture was stirred at room temperature for 2 h. The solvent was removed under reduced pressure and treated with saturated sodium bicarbonate solution (150 mL) and extracted with ethyl acetate (2×150 mL). The organic layer was dried over anhydrous sodium sulphate and concentrated under reduced pressure to get tert-butyl 3-(2-cyano-5-nitrophenoxy)propylcarbamate as a light brown solid (1.3 g, 62.9%). LC-MS (M+H)$^+$=222.0. $^1$H NMR (400 MHz, DMSO-d6) δ ppm 8.10 (1H, d, J=8.4 Hz), 7.97-7.93 (1H, m), 7.70 (1H, s), 4.40 (2H, t, J=6 Hz), 3.00 (2H, t, J=7.2 Hz), 2.12-2.05 (2H, m).

Preparation I 2-(3-(methylamino)propoxy)-4-nitrobenzonitrile

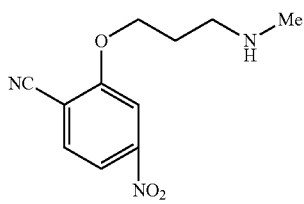

Intermediate I(1)

tert-butyl 3-(2-cyano-5-nitrophenoxy)propyl(methyl)carbamate

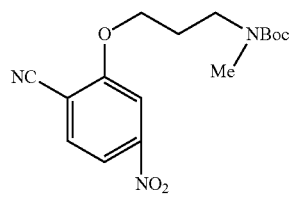 [SMILES: CN(CCCOc1cc([N+](=O)[O-])ccc1C#N)C(=O)OC(C)(C)C]

To an ice-cold solution of preparation H(1) (2 g, 6.22 mmol) in THF (40 mL) was added sodium hydride (2.48 g, 62.2 mmol, 60% suspension in mineral oil) and the mixture was stirred at room temperature for 10 min. Methyl iodide (8.83 g, 62.2 mmol) was added dropwise and stirring was continued at room temperature for 3 h. The crude mixture was poured onto crushed ice (350 g), extracted with ethyl acetate (2×150 mL), and dried over anhydrous sodium sulphate. The crude compound obtained after concentration of the ethyl acetate layer was purified by column chromatography (60-120 mesh silica) using 12% ethyl acetate in pet ether to give tert-butyl 3-(2-cyano-5-nitrophenoxy)propyl(methyl)carbamate (1.0 g, 52.7%) as a solid. LC-MS (M−56)$^+$=279.9. $^1$H NMR (400 MHz, CDCl$_3$) δ ppm 7.88 (1H, d, J=8.4 Hz), 7.80 (1H, s), 7.75 (1H, d, J=8.8 Hz), 4.23 (2H, t, J=4 Hz), 3.48 (2H, t, J=6.8 Hz), 2.91 (3H, s), 2.17-2.11 (2H, m), 1.46 (9H, s).

Preparation I 2-(3-(methylamino)propoxy)-4-nitrobenzonitrile

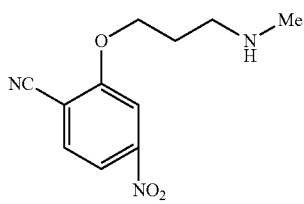 [SMILES: CNCCCOc1cc([N+](=O)[O-])ccc1C#N]

To an ice-cold solution of intermediate I(1) (2.1 g, 2.439 mmol) in DCM (40 mL) was added TFA (10 mL). The reaction mixture was stirred at room temperature for 2 h. The solvent was removed under reduced pressure and treated with saturated sodium bicarbonate solution (150 mL) and extracted with ethyl acetate (2×150 mL). The organic layer was dried over anhydrous sodium sulphate and concentrated under reduced pressure to get a light yellow liquid (1.1 g, 74.4%). LC-MS (M+H)$^+$=236.0. $^1$H NMR (400 MHz, DMSO-d6) δ ppm 8.09 (1H, d, J=8.4 Hz), 7.99 (1H, s), 7.94-7.91 (1H, m), 4.38 (2H, t, J=6 Hz), 2.84 (2H, t, J=7.2 Hz), 2.43 (3H, s), 2.05-1.98 (2H, m).

Preparation J 1-(2-(2-bromoethoxy)-4-nitrophenyl)-3-methyl-1H-1,2,4-triazole

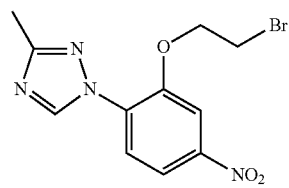

Intermediate J(1)

1-chloro-2-(4-methoxybenzyloxy)-4-nitrobenzene

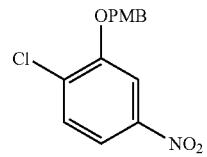

To a solution of 2-chloro-5-nitrophenol (10 g, 57.6 mmol) in acetonitrile (100 mL) was added potassium carbonate (11.7 g, 86 mmol) followed by 4-methoxy benzyl bromide (13.9 g, 69.1 mmol), at room temperature. The reaction mixture was stirred at room temperature for 18 h while monitoring by TLC. It was then filtered and the solid mass was washed with ethyl acetate (100 mL). The solvent was removed under reduced pressure and the residue was purified by column chromatography (60-120 mesh silica gel) using 2% MeOH in CHCl$_3$ to give 1-chloro-2-(4-methoxybenzyloxy)-4-nitrobenzene (15 g, 89%) as a yellow solid. $^1$H NMR (400 MHz, CDCl$_3$) δ ppm 7.85 (1H, s), 7.79 (1H, d, J=8.8 Hz), 7.53-7.51 (1H, d, J=8.4 Hz), 7.41-7.39 (2H, m), 6.95-6.87 (2H, m), 5.17 (2H, s), 3.82 (3H, s).

Intermediates J(2) and J(3)

J(2): 1-(2-(4-methoxybenzyloxy)-4-nitrophenyl)-3-methyl-1H-1,2,4-triazole

J(3): 1-(2-(4-methoxybenzyloxy)-4-nitrophenyl)-5-methyl-1H-1,2,4-triazole

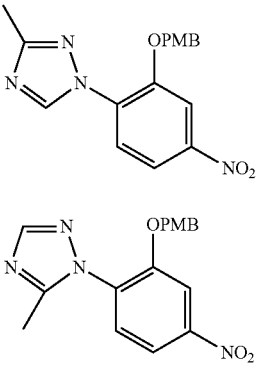

To a solution of 1-chloro-2-(4-methoxybenzyloxy)-4-nitrobenzene (15 g, 51.1 mmol) in DMSO (45 mL) was added potassium hydroxide (4.3 g, 77 mmol) followed by methyl triazole (6.39 g, 77 mmol) at room temperature. The reaction mixture was heated at 95° C. for 18 h. The reaction mixture was poured onto crushed ice (1.5 Kg) and extracted with ethyl acetate (3×250 mL). It was then washed with brine (3×250 mL) and dried over sodium sulphate. The solvent was removed under reduced pressure and the residue was dissolved in dichloromethane (25 mL) and absorbed onto silica (25 g). The resultant slurry of the compound on silica was subjected to flash chromatography using a Teledyne Isco instrument (120 g RediSep silica column, with 50% ethyl acetate in pet-ether) to get Intermediate J(2) (6 g, 34.5%) as a yellow solid and Intermediate J(3) (4.5 g, 24.9%) as a dark brown solid.

Analytical data of J(2): LC-MS (M+H)$^+$=341.2. $^1$H NMR (400 MHz, CDCl$_3$) δ ppm 8.83 (1H, s), 8.13 (1H, d, J=8.8 Hz), 8.06 (1H, s), 8.09 (1H, d, J=8.8 Hz), 7.35 (2H, d, J=8.4 Hz), 6.94 (2H, d, J=6.4 Hz), 5.29 (2H, s), 3.83 (3H, s), 2.47 (3H, s).

Analytical data of J(3): LC-MS (M+H)$^+$=341.2. $^1$H NMR (400 MHz, CDCl$_3$) δ ppm 8.03-7.96 (3H, m), 7.57 (1H, d, J=8.8 Hz), 7.20 (2H, d, J=8.4 Hz), 6.89 (2H, d, J=8.8 Hz), 5.13 (2H, s), 3.80 (3H, s), 2.32 (3H, s).

Preparation J(4)

2-(3-methyl-1H-1,2,4-triazol-1-yl)-5-nitrophenol

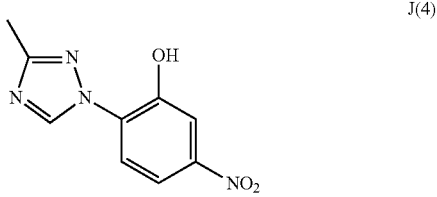 [SMILES: Cc1ncn(-c2ccc([N+](=O)[O-])cc2O)n1]

To a solution of Intermediate J(2) (6 g, 17.63 mmol) in DCM (30 mL) was added TFA (6 mL) at room temperature and the solution was stirred for 1 h. The reaction mixture was concentrated under reduced pressure, diluted with ethyl acetate (100 mL) and washed with saturated sodium bicarbonate (2×50 mL). The organic layer was dried over sodium sulphate and concentrated under reduced pressure to get Intermediate J(4) (3 g, 77%) as a yellow solid. LC-MS (M+H)$^+$=221.0. $^1$H NMR (400 MHz, DMSO-d6) δ ppm 11.61 (1H, s), 9.11 (1H, s), 7.97-7.82 (3H, m), 2.38 (3H, s).

Preparation J 1-(2-(2-bromoethoxy)-4-nitrophenyl)-3-methyl-1H-1,2,4-triazole

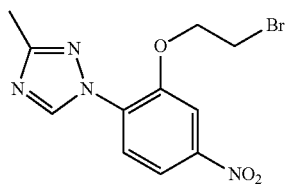 [SMILES: Cc1ncn(-c2ccc([N+](=O)[O-])cc2OCCBr)n1]

To a stirred mixture of 2-(3-methyl-1H-1,2,4-triazol-1-yl)-5-nitrophenol (3 g, 13.63 mmol) and K$_2$CO$_3$ (2.4 g, 17.79 mmol) in MeCN (30 mL) was added 1,2-dibromoethane (3.3 g, 17.71 mmol) at room temperature. The reaction mixture was stirred at room temperature for 18 h. The solvent was removed under reduced pressure and the residue was dissolved in ethyl acetate (100 mL) and washed with brine (2×25 mL). The organic layer was dried over anhydrous sodium sulphate and concentrated in vacuo to give 1-(2-(2-bromoethoxy)-4-nitrophenyl)-3-methyl-1H-1,2,4-triazole (2.2 g, 49.5%) as a light orange solid. LC-MS (M+H)$^+$=327.13. $^1$H NMR (400 MHz, DMSO-d6) δ ppm 9.15 (1H, s), 8.09-8.04 (3H, m), 4.70-4.69 (2H, m), 3.99-3.97 (2H, m), 2.40 (3H, s).

Preparation K 3-(2-(3-methyl-1H-1,2,4-triazol-1-yl)-5-nitrophenoxy)propan-1-amine

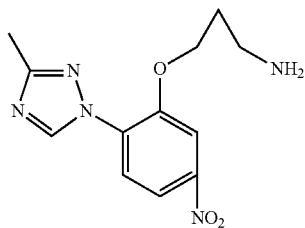 [SMILES: Cc1ncn(-c2ccc([N+](=O)[O-])cc2OCCCN)n1]

Preparation K(1)

tert-butyl 3-(2-(3-methyl-1H-1,2,4-triazol-1-yl)-5-nitrophenoxy)propylcarbamate

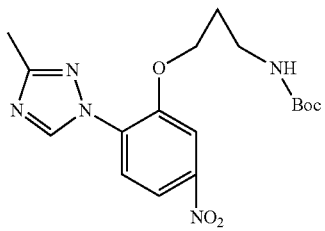 [SMILES: Cc1ncn(-c2ccc([N+](=O)[O-])cc2OCCCNC(=O)OC(C)(C)C)n1]

To a solution of Intermediate J(4) (2 g, 9.08 mmol) in DMF (2.5 mL) was added cesium carbonate (4.44 g, 13.62 mmol) followed by tert-butyl (3-bromopropyl)carbamate (3.24 g, 13.62 mmol) at room temperature. The reaction mixture was stirred at rt for 18 h. The solvent was removed under reduced pressure and the residue was purified by column chromatography (60-120 mesh silica) using 2% MeOH in CHCl₃ to give tert-butyl 3-(2-(3-methyl-1H-1,2,4-triazol-1-yl)-5-nitrophenoxy)propylcarbamate (1.4 g, 40.8%) as a yellow solid. LC-MS (M+H)$^+$=378.2. $^1$H NMR (400 MHz, CDCl₃) δ ppm 8.89 (1H, s), 8.06 (1H, d, J=8.8 Hz), 7.99-7.94 (1H, m), 7.94 (1H, d, J=2.4 Hz), 4.66 (1H, br s), 4.28 (1H, t, J=6.4 Hz), 3.32 (2H, q, J=6 Hz), 2.50 (3H, s), 2.10 (2H, t, J=6.4 Hz), 9.45 (9H, s).

Preparation K 3-(2-(3-methyl-1H-1,2,4-triazol-1-yl)-5-nitrophenoxy)propan-1-amine

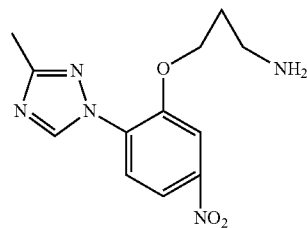 [SMILES: Cc1ncn(-c2ccc([N+](=O)[O-])cc2OCCCN)n1]

To an ice-cold solution of Intermediate K(1) (1 g, 2.65 mmol) in DCM (10 mL) was added TFA (1 mL). The reaction mixture was stirred at room temperature for 1 h. The solvent was removed under reduced pressure, and the crude mixture was treated with saturated sodium bicarbonate solution (50 mL). It was extracted with (2×50 mL) and washed with brine (2×20 mL). The organic layer was dried over anhydrous sodium sulphate and concentrated under reduced pressure to get a light yellow liquid (600 mg, 82%). LC-MS (M+H)$^+$=278.2. $^1$H NMR (400 MHz, DMSO-d6) δ ppm 8.90 (1H, s), 8.08 (1H, d, J=9.6 Hz), 7.98-7.97 (2H, m), 4.35 (2H, t, J=6.4 Hz), 2.95-2.92 (2H, m), 2.50 (3H, s), 2.07-2.03 (2H, m).

Preparation L

N-methyl-3-(2-(3-methyl-1H-1,2,4-triazol-1-yl)-5-nitrophenoxy)propan-1-amine

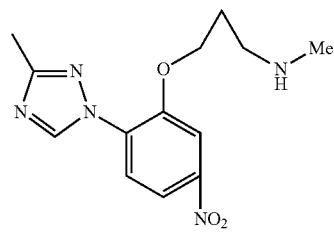 [SMILES: CNCCCOc1cc([N+](=O)[O-])ccc1-n1cnc(C)n1]

Intermediate L(1)

tert-butyl methyl(3-(2-(3-methyl-1H-1,2,4-triazol-1-yl)-5-nitrophenoxy)propyl)carbamate

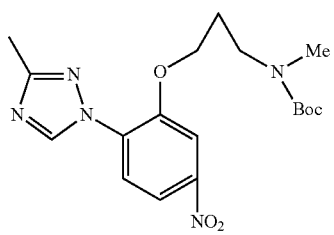 [SMILES: Cc1ncn(-c2ccc([N+](=O)[O-])cc2OCCCN(C)C(=O)OC(C)(C)C)n1]

To an ice-cold solution of Intermediate K(1) (1.4 g, 3.71 mmol) in THF (30 mL) was added sodium hydride (0.742 g, 18.5 mmol, 60% dispersed in mineral oil) and stirred at rt for 10 min, followed by the addition of methyl iodide (5.27 g, 37.1 mmol). The reaction mixture was stirred at room temperature for 1 h. The crude mixture was poured onto crushed ice (250 g), extracted with ethyl acetate (3×100 mL), washed with brine (150 mL) and dried over anhydrous sodium sulphate. The solvent was removed under reduced pressure. The crude compound was subjected to flash chromatography using a Teledyne Isco instrument (40 g RediSep silica column, 15% EtOAc in hexane) to get tert-butyl methyl(3-(2-(3-methyl-1H-1,2,4-triazol-1-yl)-5-nitrophenoxy)propyl)carbamate (1.4 g, 96%) as a yellow solid. LC-MS (M+H)$^+$ =392.2. $^1$H NMR (400 MHz, CDCl$_3$) δ ppm 8.96-8.87 (1H, m), 8.07 (1H, d, J=8.8 Hz), 7.97 (1H, d, J=9.2 Hz), 7.93 (1H, d, J=3.2 Hz), 4.25 (2H, t, J=5.2 Hz), 3.43 (2H, t, J=6.4 Hz), 2.86 (3H, s), 2.50 (3H, s), 2.61-2.09 (1H, m), 1.4 (9H, s).

Preparation L

N-methyl-3-(2-(3-methyl-1H-1,2,4-triazol-1-yl)-5-nitrophenoxy)propan-1-amine

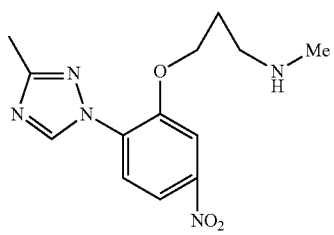 [SMILES: CNCCCOc1cc([N+](=O)[O-])ccc1-n1cnc(C)n1]

To an ice-cold solution of Intermediate L(1) (1.4 g, 3.58 mmol) in DCM (50 mL) was added TFA (20.22 g, 195 mmol). The reaction mixture was stirred at room temperature for 1 h. The solvent was removed under reduced pressure, and the crude mixture was treated with saturated sodium bicarbonate solution (100 mL). It was extracted with (2×100 mL) and washed with brine (2×50 mL). The organic layer was dried over anhydrous sodium sulphate and concentrated under reduced pressure to get a light yellow liquid (1 g, 100%). LC-MS (M+H)$^+$=292.2. $^1$H NMR (400 MHz, DMSO-d6) δ ppm 8.92 (1H, s), 8.07 (1H, d, J=9.6 Hz), 7.98 (1H, s), 7.96 (1H, d, J=2Hz), 4.34 (2H, t, J=6.4 Hz), 2.79 (2H, t, J=6.8 Hz), 2.50 (3H, s), 2.46 (3H, s), 2.09 (2H, t, J=6.4 Hz).

Preparation M

N-methylbut-3-en-1-amine

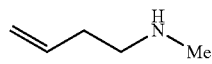

Preparation M(1)

N-Boc-but-3-en-1-amine

To an ice-cold solution of but-3-en-1-amine (5 g, 69.4 mmol) in dichloromethane (50 mL) was added triethylamine (8.41 g, 83.3 mmol) followed by Boc anhydride (15.12 g, 69.4 mmol) dropwise over 15 min. The reaction mixture was stirred at room temperature for 18 h. The solvent was removed under reduced pressure and the residue was dissolved in ethyl acetate (200 mL), washed with saturated ammonium chloride solution (2×150 mL), and brine (100 mL). The organic layer was dried over anhydrous sodium sulphate and concentrated in vacuo to give N-Boc-but-3-en-1-amine (7.2 g, 60.5%) as a colorless liquid. $^1$H NMR (400 MHz, CDCl$_3$) δ ppm 5.78-5.68 (1H, m), 5.09-5.03 (2H, m), 4.57 (1H, s), 3.16 (2H, d, J=6.4 Hz), 2.224-2.189 (2H, m), 1.416 (9H, s).

Preparation M(2)

N-Boc-N-methyl-but-3-en-1-amine

To an ice-cold solution of Intermediate M(1) (5 g, 29.2 mmol) in THF (100 mL) was added sodium hydride (9.35 g, 23.39 mmol, 60% suspension in mineral oil) and stirred at room temperature for one hour followed by dropwise addition of methyl iodide (41.22 g, 290 mmol) at room temperature. The reaction mixture was refluxed for 18 h. The crude mass was treated with ice (500 g) and extracted with ethyl acetate (2×200 mL). The organic layers were washed with brine (150 mL) and dried over anhydrous sodium sulphate. The solvent was removed under reduced pressure to give N-Boc-N-methyl-but-3-en-1-amine (5.4 g, 87.4%) as a yellow liquid. $^1$H NMR (400 MHz, CDCl$_3$) δ ppm 5.82-5.71 (1H, m), 5.09-5.00 (2H, m), 3.26 (2H, s), 2.84 (3H, s), 2.29-2.23 (2H, q, J=21.2 Hz), 1.467 (9H, s).

Preparation M

N-methylbut-3-en-1-amine

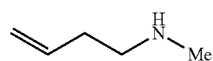

To an ice-cold solution of Intermediate M(2) (4.6 g, 24.8 mmol) in DCM (50 mL) was added HCl in dioxane (20 mL, 4.0 M). The reaction mixture was stirred at room temperature for 4 h. The solvent was removed under reduced pressure to give N-methylbut-3-en-1-amine as a light brown hygroscopic hydrochloride salt (2.69 g, 89.39%). $^1$H NMR (400 MHz, DMSO-d6) δ ppm 9.048 (2H, s), 5.86-5.75 (1H, m), 5.18-5.09 (2H, m), 2.92 (2H, s), 2.51 (3H, s), 2.43-2.38 (2H, q, J=21.2 Hz).

Preparation N 2-(2-bromoethoxy)-4-nitrobenzonitrile

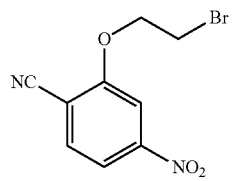

To a mixture of 2-hydroxy-4-nitro-benzonitrile (2 g, 12.19 mmol) and K$_2$CO$_3$ (3.36 g, 24.39 mmol) in MeCN (20 mL) was added 1,2-dibromoethane (3.4 g, 18.29 mmol) at room temperature. The reaction mixture was stirred at room temperature for 18 h while monitoring by TLC. The solvent was removed under reduced pressure and the residue was taken up in ethyl acetate (100 mL) and washed with brine (2×25 mL). The organic layer was dried over anhydrous sodium sulphate and concentrated to give 2-(2-bromoethoxy)-4-nitrobenzonitrile (1.6 g, 49%) as a light red solid. $^1$H NMR (400 MHz, CDCl$_3$) δ ppm 7.94-7.92 (1H, m), 7.82-7.78 (2H, m), 4.52 (2H, t, J=6.4 Hz), 3.73 (2H, t, J=6.4 Hz).

Preparation O 2-(4-aminobutoxy)-4-nitrobenzonitrile

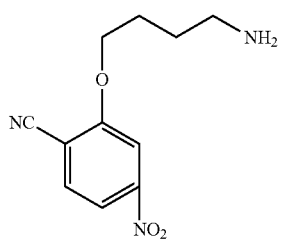 [SMILES: N#Cc1ccc([N+](=O)[O-])cc1OCCCCN]

Intermediate O(1)

tert-butyl 4-bromobutylcarbamate

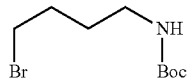

To an ice-cold solution of tert-butyl 4-hydroxybutylcarbamate (5 g, 26.41 mmol) in dichloromethane (200 mL) was added triphenylphosphine (10.38 g, 39.61 mmol) followed by carbon tetrabromide (13.15 g, 39.61 mmol) at 0° C. The reaction mixture was stirred at room temperature for 18 h. The solvent was removed under reduced pressure and the residue was purified by column chromatography (60-120 mesh silica gel) using 10% ethyl acetate in pet-ether to give tert-butyl 4-bromobutylcarbamate (4.2 g, 63.3%) as a light green liquid. $^1$H NMR (400 MHz, CDCl$_3$) δ ppm 4.53 (1H, s), 3.45-3.41 (2H, m), 3.18-3.13 (2H, m), 1.93-1.83 (2H, m), 1.68-1.61 (2H, m), 1.47 (9H, s).

Intermediate O(2)

tert-butyl 4-(2-cyano-5-nitrophenoxy)butylcarbamate

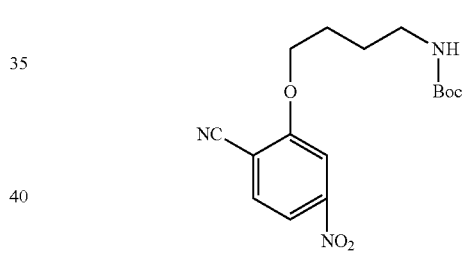

To a stirred mixture of 2-hydroxy-4-nitrobenzonitrile (2 g, 12.19 mmol), cesium carbonate (6 g, 18.29 mmol) and DMF (20 mL) was added tert-butyl 4-bromobutylcarbamate (4.59 g, 18.29 mmol). The reaction mixture was stirred at room temperature for 18 h. The solvent was removed under reduced pressure and the residue was dissolved in ethyl acetate (100 mL), and washed with brine (2×50 mL). The organic layer was dried with anhydrous sodium sulphate and concentrated in vacuo to give tert-butyl 4-(2-cyano-5-nitrophenoxy)butylcarbamate (2.1 g, 52%) as a light yellow solid. LC-MS (M+H)$^+$=335.0. $^1$H NMR (400 MHz, DMSO-d6) δ ppm 8.07 (1H, d, J=8.4 Hz), 7.96 (1H, s), 7.90 (2H, d, J=8.8 Hz), 6.84

(1H, br s), 4.30 (2H, t, J=6.4 Hz), 3.53 (2H, t, J=6.4 Hz), 2.98-2.89 (2H, m), 1.81-1.76 (2H, m), 1.48 (9H, s).

Preparation O 2-(4-aminobutoxy)-4-nitrobenzonitrile

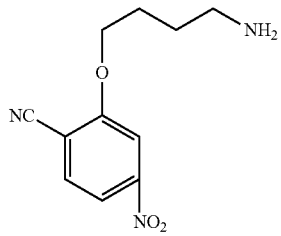 [SMILES: N#Cc1ccc([N+](=O)[O-])cc1OCCCCN]

To an ice-cold solution of Intermediate O(2) (2.1 g, 6.26 mmol) in DCM (10 mL) was added HCl in dioxane (10 mL, 4 M). The reaction mixture was stirred at room temperature for 3 h. The solvent was removed under reduced pressure and the residue was treated with saturated sodium bicarbonate solution (25 mL) and extracted with ethyl acetate (2×50 mL). The organic layer was dried over anhydrous sodium sulphate and concentrated under reduced pressure to get a light yellow liquid (1.2 g, 81.6%). LC-MS (M+H)$^+$=236.0. $^1$H NMR (400 MHz, DMSO-d6) δ ppm 8.07 (1H, d, J=8.4 Hz), 7.96 (1H, s), 7.90 (2H, d, J=8.8 Hz), 4.30 (2H, t, J=6.4 Hz), 2.62 (2H, t, J=6.8 Hz), 1.90-1.80 (2H, m), 1.58-1.48 (2H, m).

Preparation P 5-(2-(3-methyl-1H-1,2,4-triazol-1-yl)-5-nitrophenoxy)pentan-2-amine

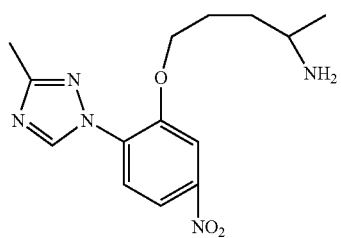 [SMILES: Cc1ncn(-c2ccc([N+](=O)[O-])cc2OCCCC(C)N)n1]

Intermediate P(1)

tert-butyl 5-hydroxypentan-2-ylcarbamate

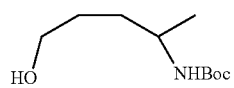

To an ice-cold solution of 4-aminopentan-1-ol (1.0 g, 9.69 mmol) in dichloromethane (100 mL) was added triethylamine (4.05 g, 29.1 mmol) followed by Boc-anhydride (6.75 g, 29.1 mmol) dropwise over ten minutes. The reaction mixture was stirred at rt for 18 h while monitoring by TLC. The reaction mixture was treated with saturated ammonium chloride solution (200 mL), the organic layer was separated, dried over anhydrous sodium sulphate and evaporated in vacuo to give tert-butyl (5-hydroxypentan-2-yl)carbamate (1.2 g, 60.9%). $^1$H NMR: (400 MHz, CDCl$_3$) δ ppm 4.35 (1H, br s), 3.68-3.65 (3H, m), 1.57-1.43 (4H, m), 1.44 (9H, s), 1.13 (3H, d, J=6.4 Hz).

Intermediate P(2)

tert-butyl 5-bromopentan-2-ylcarbamate

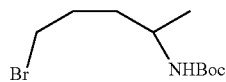

To an ice-cold solution of tert-butyl (5-hydroxypentan-2-yl)carbamate (3.6 g, 17.71 mmol) in dichloromethane (150 mL) was added triphenylphosphine (6.97 g, 26.6 mmol) followed by carbon tetrabromide (8.81 g, 26.6 mmol). The reaction mixture was stirred at room temperature for 18 h while monitoring by TLC. The solvent was removed under reduced pressure and the residue was purified by column chromatography (60-120 mesh silica) using 2-5% ethyl acetate in pet-ether to give tert-butyl (5-bromopentan-2-yl)carbamate (2.5 g, 53%) as a light brown liquid. $^1$H NMR: (400 MHz, CDCl$_3$) δ ppm 4.29 (1H, br s), 3.68 (1H, br s), 3.42 (2H, t, J=6.8 Hz), 1.94-1.86 (2H, m), 1.59-1.46 (2H, m), 1.44 (9H, s), 1.13 (3H, d, J=6.4 Hz).

Intermediate P(3)

tert-butyl (5-(2-(3-methyl-1H-1,2,4-triazol-1-yl)-5-nitrophenoxy)pentan-2-yl)carbamate

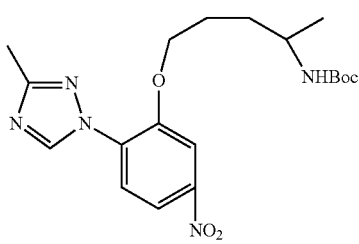 [SMILES: Cc1ncn(-c2ccc([N+](=O)[O-])cc2OCCCC(C)NC(=O)OC(C)(C)C)n1]

To a stirred solution of 2-(3-methyl-1H-1,2,4-triazol-1-yl)-5-nitrophenol (1.1 g, 5.00 mmol), cesium carbonate (2.44 g, 7.49 mmol) in DMF (20 mL) was added tert-butyl (5-bromopentan-2-yl)carbamate (2.45 g, 9.25 mmol) at room temperature. The reaction mixture was stirred at rt for 18 h while monitoring by TLC and LC-MS. The solvent was removed under reduced pressure and the residue was dissolved in ethyl acetate (250 mL) and washed with brine (2×100 mL). The organic layer was concentrated under reduced pressure and was purified by flash chromatography using a Teledyne ISCO instrument (40 g silica column, 2-3% of methanol in chloroform) to give tert-butyl (5-(2-(3-methyl-1H-1,2,4-triazol-1-yl)-5-nitrophenoxy)pentan-2-yl)carbamate (1.5 g, 74.1%) as a light brown solid. LC-MS (M+H)$^+$=406.2. $^1$H NMR: (400 MHz, CDCl$_3$) δ ppm 8.86 (1H, s), 8.09-8.07 (1H, d, J=8.8 Hz), 7.99-7.93 (2H, m), 4.33 (1H, br s), 4.27-4.24 (2H, t, J=6.4 Hz), 3.73 (1H, br s), 2.50 (3H, s), 1.98-1.95 (2H, m), 1.61-1.57 (2H, m), 1.44 (9H, s), 1.17-1.15 (3H, d, J=8 Hz).

Preparation P 5-(2-(3-methyl-1H-1,2,4-triazol-1-yl)-5-nitrophenoxy)pentan-2-amine

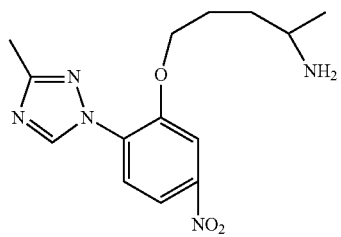 [SMILES: Cc1ncn(-c2ccc([N+](=O)[O-])cc2OCCCC(C)N)n1]

To an ice-cold solution of tert-butyl (5-(2-(3-methyl-1H-1,2,4-triazol-1-yl)-5-nitrophenoxy)pentan-2-yl)carbamate (1.5 g, 3.70 mmol) in DCM (50 mL) was added TFA (5 mL). The reaction mixture was stirred at rt for 1 h. The solvent was removed under reduced pressure and treated with saturated sodium bicarbonate solution (150 mL), and extracted with ethyl acetate (2×150 mL). The organic layer was dried over anhydrous sodium sulphate and evaporated under reduced pressure to get 5-(2-(3-methyl-1H-1,2,4-triazol-1-yl)-5-nitrophenoxy)pentan-2-amine (920 mg, 81%). LC-MS (M+H)$^+$ =306.2. 1H NMR: (400 MHz, CDCl$_3$) δ ppm 8.97 (1H, s), 8.08 (1H, d, J=8.8 Hz), 8.00-7.91 (2H, m), 4.29-4.23 (2H, m), 3.27-3.25 (1H, m), 2.46 (3H, s), 2.16-2.03 (4H, m), 1.32-1.27 (3H, m).

Preparation Q 2-(2-aminoethoxy)-4-nitrobenzonitrile

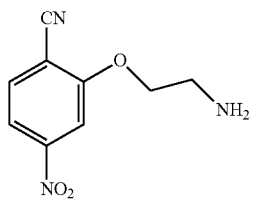

Intermediate Q(1)

tert-butyl (2-(2-cyano-5-nitrophenoxy)ethyl)carbamate

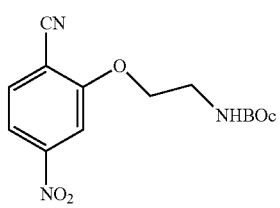

To a stirred solution of 2-hydroxy-4-nitrobenzonitrile (5.0 g, 30.48 mmol) in DMF (25 mL) was added Cs$_2$CO$_3$ (14.89 g, 45.7 mmol). The mixture was cooled to 0° C., and tert-butyl (2-bromoethyl)carbamate (7.17 g, 32 mmol) was added at rt. The reaction mixture was stirred for 12 h at 90° C. under nitrogen. The reaction mixture was cooled to rt and DMF was removed in vacuo. The residue was treated with ethyl acetate (50 mL) and washed with brine (30 mL). The organic layer was dried over anhydrous sodium sulphate and concentrated in vacuo. The residue was taken up in dichloromethane (10 mL) and silica (5 g). The resultant slurry of the compound on silica was subjected to flash chromatography using a Teledyne Isco instrument (40 g RediSep silica column, 50% ethyl acetate in pet-ether) to get tert-butyl (2-(2-cyano-5-nitrophenoxy)ethyl)carbamate (4 g, 42.7%) as a yellow solid. $^1$H NMR (400 MHz, CDCl$_3$) δ ppm 7.90 (1H, d, J=8.4 Hz), 7.82 (1H, s), 7.76 (1H, d, J=8.4 Hz), 5.04 (1H, br s), 4.27-4.24 (2H, m), 3.66-3.60 (2H, m), 1.45 (9H, s).

Preparation Q 2-(2-aminoethoxy)-4-nitrobenzonitrile

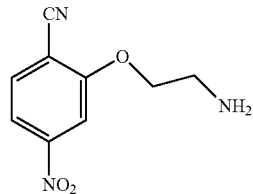 [SMILES: N#Cc1ccc([N+](=O)[O-])cc1OCCN]

To an ice-cold solution of tert-butyl (2-(2-cyano-5-nitrophenoxy)ethyl)carbamate (4 g, 13.02 mmol) in DCM (20 mL) was added TFA (10 mL). The reaction mixture was stirred at rt for 60 min. The solvent was removed under reduced pressure and treated with saturated sodium bicarbonate solution (10 mL) and extracted with ethyl acetate (2×25 mL). The organic layer was dried over anhydrous sodium sulphate and concentrated under reduced pressure to get 2-(2-aminoethoxy)-4-nitrobenzonitrile (2.4 g, 89%) as a yellow solid. LC-MS (M+H)$^+$=208.0. $^1$H NMR (400 MHz, CDCl$_3$) δ ppm 7.89 (1H, d, J=8.4 Hz), 7.83 (1H, s), 7.76 (1H, d, J=8.4 Hz), 4.23 (2H, t, J=5.2 Hz), 3.22 (2H, t, J=5.2 Hz).

Preparation R 2,4-Dichloro-7-phenyl-6,7-dihydro-5H-cyclopenta[d]pyrimidine

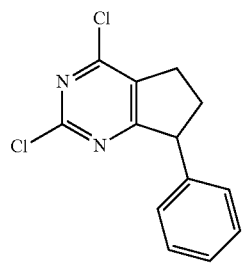 [SMILES: Clc1nc(Cl)c2c(n1)C(c1ccccc1)CC2]

Intermediate R(1)

Cyclopentenylbenzene

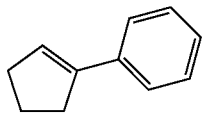 [SMILES: C1=C(c2ccccc2)CCC1]

To a solution of 3.0 M solution of phenylmagnesium bromide in ether (49.7 mL, 149 mmol) was added THF (300 mL). To this solution cooled to 0° C. cyclopentanone (13.23 mL, 149 mmol) was added. The reaction mixture was stirred at room temperature for 30 min, then at reflux for 2 h. Ice (20 g) was added, followed by 6 N HCl, until the precipitate dissolved. The product was extracted with ether. The combined etherial layers were washed with saturated sodium bicarbonate solution, dried over anhydrous magnesium sulfate and filtered. The solvent was removed in vacuo and the residue was purified by column chromatography on silica gel to give cyclopentenylbenzene (21.49 g, 149 mmol, 100% yield) as a colorless oil. LC-MS $(M+H)^+$=145.1. $^1$H NMR (500 MHz, chloroform-d) δ ppm 7.48 (2H, d, J=7.3 Hz), 7.35 (2H, t, J=7.8 Hz), 7.22-7.27 (1H, m), 6.22 (1H, t, J=2.1 Hz), 2.70-2.80 (2H, m), 2.52-2.64 (2H, m), 2.01-2.12 (2H, m).

Intermediate R(2)

2-Phenylcyclopentanone

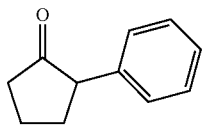 [SMILES: O=C1CCCC1c1ccccc1]

A mixture of 30% hydrogen peroxide (23 mL, 149 mmol) and 85% formic acid (100 mL, 2619 mmol) was heated at 40° C. for 15 min. The mixture was carefully added to cyclopentenylbenzene (21.49 g, 149 mmol) and the resulting two-phase system was vigorously stirred at room temperature for 4 h. An exothermic reaction was observed in the beginning. By the end of the stirring the solution had become homogeneous. The reaction mixture was carefully quenched with a saturated aqueous solution of sodium bicarbonate. The product was extracted with ether. The combined etherial layers were dried over anhydrous magnesium sulfate and filtered. The solvent was removed in vacuo and the product was purified by column chromatography on silica gel to give 2-phenylcyclopentanone (19.995 g, 125 mmol, 84% yield) as a brown oil. LC-MS $(M+H)^+$=161.0. $^1$H NMR (500 MHz, chloroform-d) δ ppm 7.38 (1H, t, J=7.3 Hz), 7.30-7.35 (2H, m), 7.19 (2H, d, J=7.3 Hz), 3.28-3.37 (1H, m), 2.71 (1H, td, J=4.6, 2.7 Hz), 2.58-2.63 (1H, m), 2.43-2.55 (1H, m), 2.29 (1H, ddd, J=19.0, 10.5, 9.0 Hz), 2.07-2.21 (1H, m), 1.88-1.99 (1H, m).

Intermediate R(3)

Ethyl 2-oxo-3-phenylcyclopentanecarboxylate

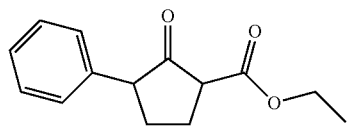 [SMILES: CCOC(=O)C1CCC(c2ccccc2)C1=O]

To a solution of diisopropylamine (6.62 mL, 46.8 mmol) in THF (200 mL) at −78° C. was added a 1.6 M solution of n-butyllithium in hexanes (29.3 mL, 46.8 mmol). The solution was stirred for 30 min at −78° C. and treated with a solution of 2-phenylcyclopentanone (5 g, 31.2 mmol) in 50 mL of dry THF. After stirring for 30 min at −78° C., ethyl carbonocyanidate (3.36 mL, 34.3 mmol) was added to the reaction mixture. The resulting solution was warmed to 25° C. with stirring over 3 h. The reaction mixture was quenched with 10 mL of water, washed with brine, dried over anhydrous sodium sulfate, concentrated in vacuo. The residue was purified by column chromatography on silica gel to afford ethyl 2-oxo-3-phenylcyclopentanecarboxylate (5.3 g, 22.82 mmol, 73% yield) as a colorless oil. LC-MS $(M+K)^+$=273.2. $^1$H NMR (500 MHz, chloroform-d) δ ppm 7.32-7.39 (2H, m), 7.25-7.31 (1H, m), 7.19-7.25 (2H, m), 4.18-4.32 (2H, m), 3.29-3.55 (2H, m), 1.87-2.62 (4H, m), 1.28-1.39 (3H, m).

Intermediate R(4)

2-Amino-7-phenyl-6,7-dihydrocyclopenta[e][1,3]oxazin-4(5H)-one

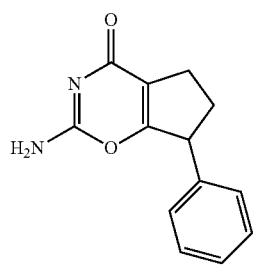 [SMILES: Nc1nc(=O)c2c(o1)C(c1ccccc1)CC2]

2-Methyl-2-thiopseudourea sulfate (1.336 g, 9.61 mmol) was dissolved in water (10 mL) and KOH (1.128 g, 20.10 mmol) was added. While stirring, ethyl 2-oxo-3-phenylcyclopentanecarboxylate (2.03 g, 8.74 mmol) was added and the reaction mixture was stirred at room temperature overnight. The reaction mixture was filtered, washed with water and ether, and dried over anhydrous sodium sulfate to afford 2-amino-7-phenyl-6,7-dihydrocyclopenta[e][1,3]oxazin-4(5H)-one (1.22 g, 5.35 mmol, 61.2% yield) as white solid. LC-MS $(M+H)^+$=229.1. $^1$H NMR (500 MHz, DMSO-d6) δ ppm 7.57-7.85 (2H, m), 7.08-7.47 (5H, m), 4.25-4.38 (1H, m), 1.72-2.73 (3H, m), 1.09-1.31 (1H, m).

Intermediate R(5)

7-Phenyl-6,7-dihydrocyclopenta[e][1,3]oxazine-2,4(3H,5H)-dione

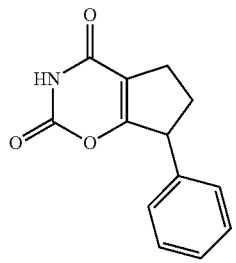 [SMILES: O=c1[nH]c(=O)c2c(o1)C(c1ccccc1)CC2]

2-Amino-7-phenyl-6,7-dihydrocyclopenta[e][1,3]oxazin-4(5H)-one (900 mg, 3.94 mmol) was dissolved in a 3 M aqueous hydrogen chloride solution (32 mL, 96 mmol) while stirring. The mixture was heated at reflux for 1 h. The reaction mixture was cooled and extracted with ethyl acetate. The organic layer was washed with saturated aqueous sodium bicarbonate solution and brine, dried over anhydrous sodium sulfate, and concentrated in vacuo. Purification by column chromatography on silica gel afforded 7-phenyl-6,7-dihydrocyclopenta[e][1,3]oxazine-2,4(3H,5H)-dione (350 mg, 1.527 mmol, 38.7% yield). LC-MS (M+H)$^+$=230.0. $^1$H NMR (500 MHz, CDCl$_3$) δ ppm 8.34 (1H, br s), 7.35 (2H, t, J=7.3 Hz), 7.27-7.32 (1H, m), 7.18 (2H, d, J=7.3 Hz), 4.20 (1H, t, J=7.6 Hz), 2.82-2.91 (1H, m), 2.61-2.79 (2H, m), 2.11-2.21 (1H, m).

Or

A solution of 2-phenylcyclopentanone (19.995 g, 125 mmol) and carbonisocyanatidic chloride (23.70 g, 225 mmol) was stirred at 58° C. for 1 h and at 130° C. for 45 min. The resulting tar was dissolved in ethyl acetate and neutralized with saturated aqueous sodium bicarbonate solution. The organic layer was dried over anhydrous magnesium sulfate and filtered. The product was purified by column chromatography on silica gel to give 7-phenyl-6,7-dihydrocyclopenta[e][1,3]oxazine-2,4(3H,5H)-dione (3.751 g, 16.36 mmol, 13% yield) as a brownish solid. LC-MS (M+H)$^+$=230.0. $^1$H NMR (500 MHz, CDCl$_3$) δ ppm 8.34 (1H, br s), 7.35 (2H, t, J=7.3 Hz), 7.27-7.32 (1H, m), 7.18 (2H, d, J=7.3 Hz), 4.20 (1H, t, J=7.6 Hz), 2.82-2.91 (1H, m), 2.61-2.79 (2H, m), 2.11-2.21 (1H, m).

Intermediate R(6)

7-Phenyl-6,7-dihydro-1H-cyclopenta[d]pyrimidine-2,4(3H,5H)-dione

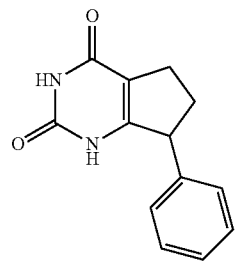 [SMILES: O=c1[nH]c2c(c(=O)[nH]1)CCC2c1ccccc1]

A solution of 7-phenyl-6,7-dihydrocyclopenta[e][1,3]oxazine-2,4(3H,5H)-dione (3.751 g, 16.36 mmol) in concentrated ammonia in water (80 mL, 16.36 mmol) was heated in a 350 mL high-pressure flask for 5 h. The solvent was removed in vacuo to give 7-phenyl-6,7-dihydro-1H-cyclopenta[d]pyrimidine-2,4(3H,5H)-dione (3.73 g, 16.34 mmol, 100% yield) as a brown solid. LC-MS (M+H)$^+$=229.1. $^1$H NMR (500 MHz, DMSO-d6) δ ppm 7.34 (2H, t, J=7.5 Hz), 7.26 (1H, t, J=7.3 Hz), 7.18 (2H, d, J=7.3 Hz), 5.39 (1H, br s), 4.14 (1H, d, J=7.3 Hz), 2.43-2.68 (2H, m), 1.80-1.88 (2H, m).

Preparation R 2,4-Dichloro-7-phenyl-6,7-dihydro-5H-cyclopenta[d]pyrimidine

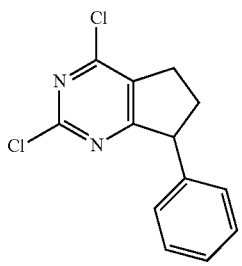 [SMILES: Clc1nc(Cl)c2c(n1)C(c1ccccc1)CC2]

A solution of 7-phenyl-6,7-dihydro-1H-cyclopenta[d]pyrimidine-2,4(3H,5H)-dione (1.241 g, 5.44 mmol) in phosphoryl trichloride (14.93 mL, 163 mmol) was heated in the microwave at 110° C. for 1 h. The resulting material was added to ice. Once the ice melted, the product was extracted with dichloromethane. The combined organic extracts were dried over anhydrous magnesium sulfate and filtered. The solvent was removed in vacuo and the residue was purified by column chromatography on silica gel to give 2,4-dichloro-7-phenyl-6,7-dihydro-5H-cyclopenta[d]pyrimidine (3.132 g, 72%) as a light brown solid. LC-MS (M+H)$^+$=265.0. $^1$H NMR (500 MHz, CDCl$_3$) δ ppm 7.31-7.37 (2H, m), 7.27 (1H, d, J=7.0 Hz), 7.15 (2H, d, J=7.9 Hz), 4.44 (1H, t, J=8.2 Hz), 3.09-3.18 (1H, m), 2.97-3.06 (1H, m), 2.73 (1H, ddd, J=9.0, 4.7, 4.6 Hz), 2.26 (1H, ddd, J=8.5, 7.0, 6.7 Hz).

Preparation Ra

N-allyl-2-chloro-7-phenyl-6,7-dihydro-5H-cyclopenta[d]pyrimidin-4-amine

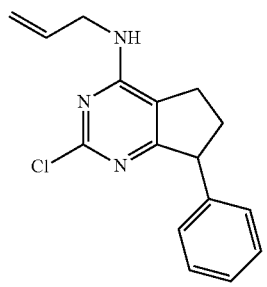 [SMILES: C=CCNc1nc(Cl)nc2c1CCC2c1ccccc1]

To a solution of Preparation R (1 g, 3.80 mmol) in acetonitrile (10 mL) was added diisopropylethylamine (0.973 g, 7.54 mmol) followed by allyl amine (0.29 g, 4.12 mmol) at room temperature. The reaction mixture was stirred at room temperature for 18 h. The solvent was removed under reduced pressure and the residue was purified by column chromatography (60-120 mesh silica) using 30% ethyl acetate in pet-ether to give N-allyl-2-chloro-7-phenyl-6,7-dihydro-5H-cyclopenta[d]pyrimidin-4-amine (0.7 g, 70%) as an off-white solid. LC-MS (M+H)$^+$=286.1. $^1$H NMR (400 MHz, DMSO-d6) δ ppm 7.75-7.72 (1H, m), 7.32-7.28 (3H, m), 7.24-7.13 (2H, m), 5.96-5.91 (1H, m), 5.22-5.11 (2H, m), 4.22-4.20 (1H, t, J=7.20 Hz), 4.02 (2H, t, J=4.00 Hz), 2.82-2.80 (1H, m), 2.79-2.55 (2H, m), 1.99-1.97 (1H, m).

Preparation Rb

N-allyl-2-chloro-N-methyl-7-phenyl-6,7-dihydro-5H-cyclopenta[d]pyrimidin-4-amine

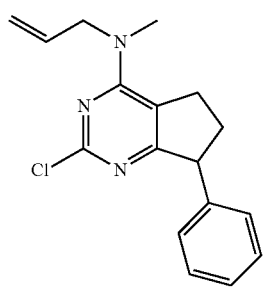 [SMILES: C=CCN(C)c1nc(Cl)nc2c1CCC2c1ccccc1]

To a solution of Preparation R (0.5 g, 1.88 mmol) in acetonitrile (5 mL) was added diisopropylethylamine (0.48 g, 2.28 mmol) followed by methylallylamine (0.22 g, 3.75 mmol) at room temperature. The reaction mixture was stirred at room temperature for 18 h. The solvent was removed under reduced pressure and the residue was purified by column chromatography (60-120 mesh silica) using 30% ethyl acetate in pet-ether to give N-allyl-2-chloro-7-phenyl-6,7-dihydro-5H-cyclopenta[d]pyrimidin-4-amine (0.36 g, 63.6%) as an off-white solid. LC-MS (M+H)$^+$=300.2. $^1$H NMR (400 MHz, DMSO-d6) δ ppm 7.31-7.29 (2H, m), 7.27-7.26 (1H, m), 7.19-7.12 (2H, m), 5.89-5.83 (1H, m), 5.26-5.17 (2H, m), 4.20-4.16 (3H, m), 3.20-3.16 (1H, m), 3.15 (3H, s), 3.09-3.07 (1H, m), 2.56 (1H, m), 2.07-2.03 (1H, m).

Preparation Rc

N-but-(3-enyl)-2-chloro-7-phenyl-6,7-dihydro-5H-cyclopenta[d]pyrimidin-4-amine

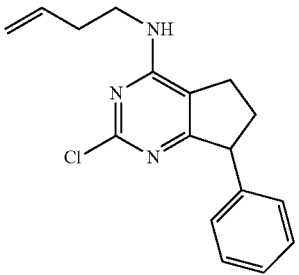 [SMILES: C=CCCNc1nc(Cl)nc2c1CCC2c1ccccc1]

To a solution of Preparation R (1 g, 3.71 mmol) in acetonitrile (10 mL) was added diisopropylethylamine (0.86 g, 7.51 mmol) followed by 3-buten-1-amine (0.29 g, 4.13 mmol) at room temperature. The reaction mixture was stirred at room temperature for 18 h. The solvent was removed under reduced pressure and the residue was purified by column chromatography (60-120 mesh silica) using 30% ethyl acetate in pet-ether to give N-but-(3-enyl)-2-chloro-7-phenyl-6-7-dihydro-5H-cyclopenta[d]pyrimidin-4-amine (0.71 g, 63.3%) as a white solid. LC-MS (M+H)$^+$=300.1. 1H NMR (400 MHz, DMSO-d6) δ ppm 7.61 (1H, s), 7.53-7.52 (2H, m), 7.51-7.32 (1H, m), 7.29-7.13 (2H, m), 5.88-5.82 (1H, m), 5.13-5.039 (2H, m), 4.18 (1H, t, J=8.4 Hz), 3.45-34.40 (2H, m), 2.77 (1H, t, J=4.8 Hz), 2.66-2.58 (1H, m), 2.36-2.31 (2H, m), 2.00-1.98 (1H, m).

Preparation Rd

N-(but-3-enyl)-2-chloro-N-methyl-7-phenyl-6,7-dihydro-5H-cyclopenta[d]pyrimidin-4-amine

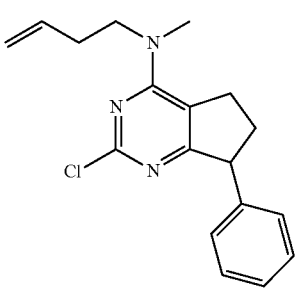 [SMILES: C=CCCN(C)c1nc(Cl)nc2c1CCC2c1ccccc1]

To a solution of Preparation R (2 g, 7.5 mmol) in acetonitrile (50 mL) was added diisopropylethylamine (1.95 g, 15.1 mmol) followed by N-methylbuten-1-amine (Preparation M, 1.064 g, 8.25 mmol) at room temperature. The reaction mixture was stirred at room temperature for 18 h. The solvent was removed under reduced pressure and the residue was purified by column chromatography (60-120 mesh silica) using 20% ethyl acetate in pet-ether to give N-(but-3-enyl)-2-chloro-N-methyl-7-phenyl-6,7-dihydro-5H-cyclopenta[d]pyrimidin- 4-amine as a brown solid (1.1 g, 46.4%). LC-MS (M+H)⁺ =314.2. 1H NMR (400 MHz, CDCl₃) δ ppm 7.30-7.12 (5H, m), 5.81-5.77 (1H, m), 5.15-5.06 (2H, m), 4.2-4.163 (1H, m), 3.68-3.63 (2H, m), 3.2 (3H, s) 3.19-3.15 (1H, m), 3.09-3.06 (1H, m), 2.57-2.52 (1H, m), 2.42-2.40 (2H, m), 2.09-2.06 (1H, m).

Preparation Re 2-chloro-N-(2-(2-(2-(4-chloro-1H-imidazol-1-yl)-5-nitrophenoxy)ethoxy)ethyl)-7-phenyl-6,7-dihydro-5H-cyclopenta[d]pyrimidin-4-amine

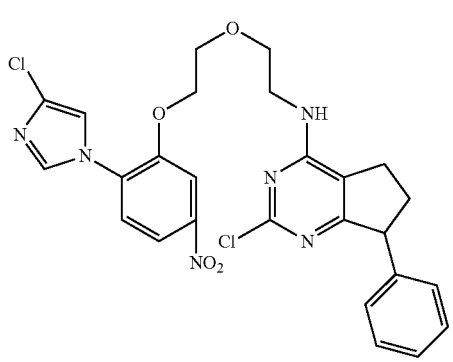 [SMILES: O=[N+]([O-])c1ccc(-n2cnc(Cl)c2)c(OCCOCCNc2nc(Cl)nc3c2CCC3c2ccccc2)c1]

To a solution of Preparation R (0.58 g, 2.208 mmol) in acetonitrile (20 mL) was added diisopropylethylamine (0.56 g, 4.417 mmol) followed by Preparation E (0.72 g, 2.208 mmol) at room temperature. The reaction mixture was stirred at room temperature for 18 h. The solvent was removed under reduced pressure and the residue was purified by column chromatography (60-120 mesh silica) using 30% to 40% of ethyl acetate in pet-ether to give 2-chloro-N-(2-(2-(2-(4-chloro-1H-imidazol-1-yl)-5-nitrophenoxy)ethoxy)ethyl)-7-phenyl-6,7-dihydro-5H-cyclopenta[d]pyrimidin-4-amine (0.5 g, 40.98%). LC-MS (M+H)⁺=555.2. 1H NMR (400 MHz, CDCl₃) δ ppm 8.08 (1H, s), 8.03 (1H, s), 8.00-7.45 (1H, m), 7.44 (1H, d, J=8.4 Hz), 7.30-7.12 (6H, m), 5.50 (1H, s), 4.36-4.26 (2H, m), 4.24-4.22 (1H, m), 3.90-3.88 (2H, m), 3.77-3.75 (4H, m), 2.84-2.62 (3H, m), 2.15-2.04 (1H, m).

Preparation Rf 2-chloro-N-(3-(2-(4-chloro-1H-imidazol-1-yl)-5-nitrophenoxy)propyl)-7-phenyl-6,7-dihydro-5H-cyclopenta[d]pyrimidin-4-amine

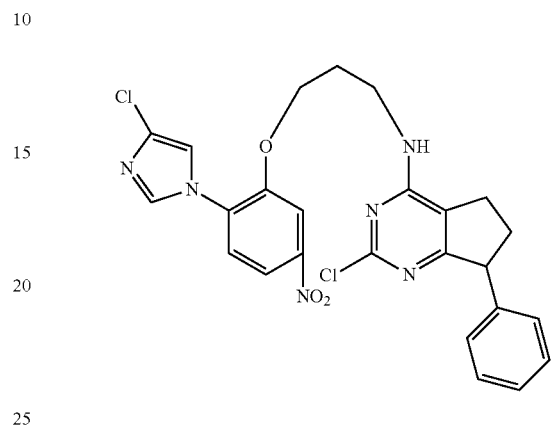

To a solution of Preparation R (0.552 g, 2.11 mmol) in acetonitrile (20 mL) was added diisopropylethylamine (0.54 g, 4.189 mmol) followed by Preparation F (0.62 g, 2.11 mmol) at room temperature. The reaction mixture was stirred at room temperature for 18 h. The solvent was removed under reduced pressure and the residue was purified by column chromatography (60-120 mesh silica) using 30% to 40% of ethyl acetate in pet-ether to give 2-chloro-N-(3-(2-(4-chloro-1H-imidazol-1-yl)-5-nitrophenoxy)propyl)-7-phenyl-6,7-dihydro-5H-cyclopenta[d]pyrimidin-4-amine (0.45 g, 36.2%). LC-MS (M+H)⁺=527.0. 1H NMR (400 MHz, DMSO-d6) δ ppm 8.16 (1H, s), 7.99-7.94 (2H, m), 7.80-7.76 (2H, m), 7.58-7.56 (1H, m), 7.31-7.11 (5H, m), 4.30 (2H, t, J=6 Hz), 4.19-4.15 (1H, m), 3.54-3.48 (2H, m), 2.78-2.52 (3H, m), 2.05-2.02 (2H, m), 1.99-1.94 (1H, m).

Preparation Rg 2-chloro-N-(3-(2-(4-chloro-1H-imidazol-1-yl)-5-nitrophenoxy)propyl)-N-methyl-7-phenyl-6,7-dihydro-5H-cyclopenta[d]pyrimidin-4-amine

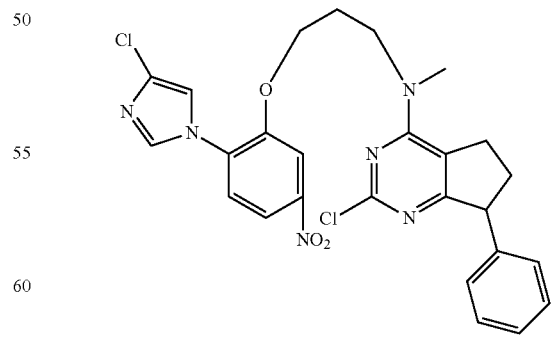

To a solution of Preparation R (0.553 g, 2.09 mmol) in acetonitrile (20 mL) was added diisopropylethylamine (0.54 g, 4.19 mmol) followed by Preparation G (0.62 g, 2.09 mmol) at room temperature. The reaction mixture was stirred at room temperature for 18 h. The solvent was removed under reduced pressure and the residue was purified by column chromatography (60-120 mesh silica) using 50% to 60% ethyl acetate in pet-ether to give 2-chloro-N-(3-(2-(4-chloro-1H-imidazol-1-yl)-5-nitrophenoxy)propyl)-N-methyl-7-phenyl-6,7-dihydro-5H-cyclopenta[d]pyrimidin-4-amine (0.55 g, 49.1%). LC-MS (M+H)$^+$=539.2. 1H NMR (400 MHz, DMSO-d6) δ ppm 8.13 (1H, s), 8.00-7.98 (2H, m), 7.78-7.76 (2H, m), 7.31-7.11 (5H, m), 4.32 (2H, t, J=5.6 Hz), 4.11 (1H, t, J=7.2 Hz), 3.70-3.65 (2H, m), 3.17 (3H, s), 3.13-3.08 (3H, m), 2.52-2.50 (1H, m), 2.12-2.10 (2H, m), 1.99-1.90 (1H, m).

Preparation Rh 4-(but-3-enyl)-2-chloro-7-phenyl-6,7-dihydro-5H-cyclopenta[d]pyrimidine

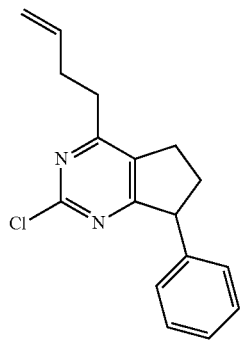 [SMILES: C=CCCc1nc(Cl)nc2c1CCC2c1ccccc1]

A 250 mL three-neck round bottom flask equipped with a refluxed condenser and nitrogen inlet was charged with 2,4-dichloro-7-phenyl-6,7-dihydro-5H-cyclopenta[d]pyrimidine (2 g, 7.54 mmol), Fe(acac)$_2$ (0.400 g, 1.131 mmol), THF (84 mL) and NMP (6.4 mL). The resulting solution was cooled to −78° C. and but-3-enyl magnesium bromide was added (20 mL) dropwise over twenty min. During the addition, the color of the reaction mixture changed from deep red to brown. After stirring for 1 h at −78° C., another 20 mL of but-3-enyl magnesium bromide was added and stirred for further 1 h. The reaction mixture was allowed to warm to 0° C. and quenched with saturated ammonium chloride solution (250 mL). It was then extracted with MTBE (2×200 mL), washed with brine (25 mL), dried over anhydrous sodium sulphate and concentrated in vacuo to get a crude brown oil. It was purified by a Teledyne Isco instrument using a 40 g silica column and 4-7% ethyl acetate in pet ether to get 4-(but-3-enyl)-2-chloro-7-phenyl-6,7-dihydro-5H-cyclopenta[d]pyrimidine (1.1 g, 51.2%). LC-MS (M+H)$^+$=285.2. 1H NMR (400 MHz, CDCl$_3$) δ ppm 7.33-7.24 (3H, m), 7.14-7.12 (2H, m), 5.89-5.83 (1H, m), 5.09-5.00 (2H, m), 4.37 (1H, t, J=7.2 Hz), 3.04-3.01 (1H, m), 2.94-2.92 (1H, m), 2.85-2.81 (2H, m), 2.71-2.66 (1H, m), 2.55-2.51 (2H, m), 2.23-2.19 (1H, m).

Preparation of Ri 2-chloro-N-methyl-N-(3-(2-(3-methyl-1H-1,2,4-triazol-1-yl)-5-nitrophenoxy)propyl)-7-phenyl-6,7-dihydro-5H-cyclopenta[d]pyrimidin-4-amine

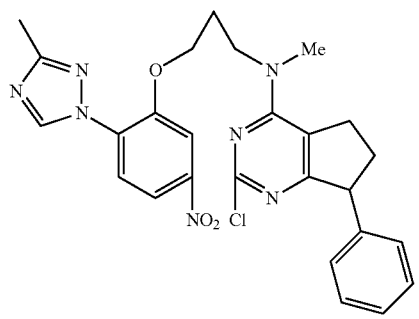

To a solution of N-methyl-3-(2-(3-methyl-1H-1,2,4-triazol-1-yl)-5-nitrophenoxy)propan-1-amine (Preparation L, 1.20 g, 4.15 mmol) in acetonitrile (50 mL) was added diisopropylethylamine (0.731 g, 5.66 mmol) followed by 2,4-dichloro-7-phenyl-6,7-dihydro-5H-cyclopenta[d]pyrimidine (Preparation R, 1 g, 3.77 mmol) at room temperature. The reaction mixture was stirred at room temperature for 18 h. The solvent was removed under reduced pressure and the residue was taken up in dichloromethane (10 mL) and silica (2 g). The resultant slurry of the compound on silica was subjected to flash chromatography using a Teledyne Isco instrument (12 g RediSep silica column, 50% ethyl acetate in pet-ether) to get 2-chloro-N-methyl-N-(3-(2-(3-methyl-1H-1,2,4-triazol-1-yl)-5-nitrophenoxy)propyl)-7-phenyl-6,7-dihydro-5H-cyclopenta[d]pyrimidin-4-amine (1.2 g, 61.2%) as a light yellow solid. LC-MS (M+H)$^+$=518.2. $^1$H NMR (400 MHz, CDCl$_3$) δ ppm 8.95 (1H, s), 8.05-7.93 (3H, m), 7.30-7.11 (5H, m), 4.35-4.31 (2H, m), 4.18-4.14 (1H, m), 3.87-3.70 (2H, s), 3.28 (3H, s), 3.21-3.07 (2H, m), 2.54-2.50 (1H, m), 2.27-2.24 (2H, m), 2.01-1.98 (1H, m).

Preparation Rj 2-(3-((2-chloro-7-phenyl-6,7-dihydro-5H-cyclopenta[d]pyrimidin-4-yl)(methyl)amino)propoxy)-4-nitrobenzonitrile

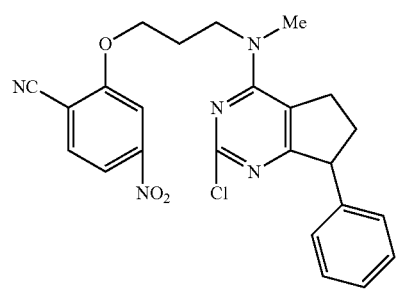 [SMILES: CN(CCCOc1cc([N+](=O)[O-])ccc1C#N)c1nc(Cl)nc2c1CCC2c1ccccc1]

To a solution of Preparation R (1.24 g, 4.68 mmol) in acetonitrile (250 mL) was added diisopropylethylamine (1.20 g, 9.35 mmol) followed by Preparation I (1.10 g, 4.68 mmol) at rt. The reaction mixture was stirred at rt for 18 h. The solvent was removed under reduced pressure and the residue was purified by column chromatography (60-120 mesh silica) using 60-80% of ethyl acetate in pet ether to give 2-(3-((2-chloro-7-phenyl-6,7-dihydro-5H-cyclopenta[d]pyrimidin-4-yl)(methyl)amino)propoxy)-4-nitrobenzonitrile (0.8 g, 36.9%). LC-MS (M+H)$^+$=464.2. 1H NMR (400 MHz, CDCl$_3$) δ ppm 7.82-7.78 (2H, m), 7.55 (1H, d, J=8.4 Hz), 7.54-7.13 (5H, m), 4.37-4.32 (2H, m), 4.15-4.11 (1H, m), 3.93-3.85 (2H, m), 3.34 (3H, s), 3.32-3.30 (1H, m), 3.20-3.17 (1H, m), 2.60-2.50 (1H, m), 2.28-2.23 (2H, m), 2.13-2.04 (1H, m).

Preparation Rk 2-(4-(2-chloro-7-phenyl-6,7-dihydro-5H-cyclopenta[d]pyrimidin-4-ylamino)butoxy)-4-nitrobenzonitrile

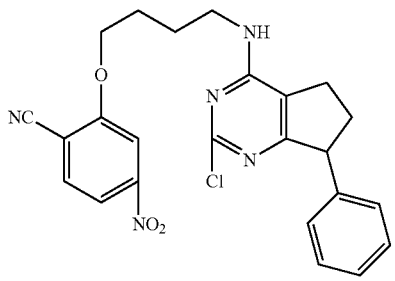 [SMILES: N#Cc1ccc([N+](=O)[O-])cc1OCCCCNc1nc(Cl)nc2c1CCC2c1ccccc1]

To a solution of 2,4-dichloro-7-phenyl-6,7-dihydro-5H-cyclopenta[d]pyrimidine (Preparation of R, 1.1 g, 4.163 mmol) in acetonitrile (40 mL) was added diisopropylethylamine (0.807 g, 6.245 mmol) followed by 2-(4-aminobutoxy)-4-nitrobenzonitrile (Preparation O, 1.174 g, 4.99 mmol) at room temperature. The reaction mixture was stirred at rt for 18 h. The solvent was removed under reduced pressure and the residue was taken up in dichloromethane (10 mL) and silica (2 g). The resultant slurry of the compound on silica was subjected to flash chromatography using a Teledyne Isco instrument (12 g RediSep silica column, with 50% ethyl acetate in pet-ether) to get 2-(4-(2-chloro-7-phenyl-6,7-dihydro-5H-cyclopenta[d]pyrimidin-4-ylamino)butoxy)-4-nitrobenzonitrile (0.9 g, 47%) as a light yellow solid. LC-MS (M+H)$^+$=464.2. 1H NMR (400 MHz, DMSO-d6) δ ppm 8.08 (1H, d, J=8.4 Hz), 7.98 (1H, s), 7.91 (1H, d, J=8.8 Hz), 7.57 (1H, m), 7.32-7.13 (5H, m), 4.39-4.35 (2H, t, J=6.4 Hz), 4.19-4.15 (1H, t, J=8.0 Hz), 3.46-3.33 (2H, m), 2.85-2.75 (1H, m), 2.60-2.50 (2H, m), 1.99-1.00 (1H, m), 1.88-1.75 (4H, m).

Preparation S 2,4-Dichloro-7-(4-fluorophenyl)-6,7-dihydro-5H-cyclopenta[d]pyrimidine

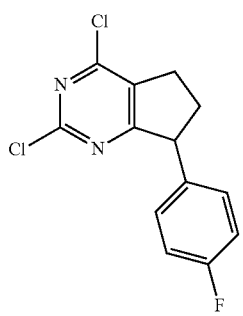 [SMILES: Fc1ccc(C2CCc3c(Cl)nc(Cl)nc32)cc1]

Intermediate S(1)

1-Cyclopentenyl-4-fluorobenzene

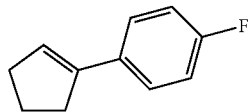 [SMILES: Fc1ccc(C2=CCCC2)cc1]

To a 0.5 M solution of 4-fluorophenylmagnesium bromide (298 mL, 149 mmol) in THF at 0° C. was carefully added cyclopentanone (13.23 mL, 149 mmol). Upon the end of the addition, the reaction mixture was heated at reflux for 2 h. Ice (10 g) and 6 N aqueous hydrochloric acid were added. The reaction mixture was extracted with ether. The combined organic extracts were washed with a saturated aqueous solution of sodium hydrogen sulfite, a saturated aqueous solution of sodium bicarbonate and water. The organic layer was dried over anhydrous magnesium sulfate and filtered. The solvent was removed in vacuo and the residue was purified by column chromatography on silica gel to give 1-cyclopentenyl-4-fluorobenzene (24.155 g, 149 mmol, 100% yield) as a colorless oil. LC-MS (M+H)$^+$=163.0. $^1$H NMR (500 MHz, CDCl$_3$) δ ppm 7.35-7.42 (2H, m), 6.95-7.02 (2H, m), 6.06-6.13 (1H, m), 2.63-2.71 (2H, m), 2.47-2.56 (2H, m), 1.96-2.06 (2H, m).

Intermediate S(2)

2-(4-Fluorophenyl)cyclopentanone

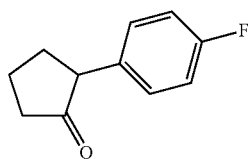 [SMILES: O=C1CCCC1c1ccc(F)cc1]

A mixture of 80% formic acid (100 mL, 2618 mmol) and 30% hydrogen peroxide (23 mL, 149 mmol) was warmed at 40° C. for 10 min. The resulting solution was carefully added to 1-cyclopentenyl-4-fluorobenzene (24.155 g, 149 mmol) while stirring. The two-phase system was initially stirred at room temperature. After a certain period of time, a spontaneous exothermic reaction took place, and the temperature rose to about 50° C. The reaction mixture was stirred at room temperature for 1 h. The reaction mixture was quenched by careful addition of a saturated sodium bicarbonate solution. Ether was added and the contents of the separatory funnel were vigorously shaken. The organic layer was separated and the aqueous layer was extracted with ether. The combined organic extracts were dried over anhydrous magnesium sulfate and filtered. The solvent was removed in vacuo and the residue was purified by column chromatography on silica gel to give 2-(4-fluorophenyl)cyclopentanone (18.557 g, 104 mmol, 69.9% yield) as a colorless oil. LC-MS $(M+H)^+$ =177.2. $^1$H NMR (500 MHz, CDCl$_3$) δ ppm 7.12-7.18 (2H, m), 6.98-7.04 (2H, m), 3.29 (1H, dd, J=11.6, 8.5 Hz), 2.42-2.54 (2H, m), 2.27 (1H, ddd, J=19.1, 10.5, 8.9 Hz), 2.12-2.20 (1H, m), 2.01-2.12 (1H, m), 1.87-1.99 (1H, m).

Intermediate S(3)

7-(4-Fluorophenyl)-6,7-dihydrocyclopenta[e][1,3]oxazine-2,4(3H,5H)-dione

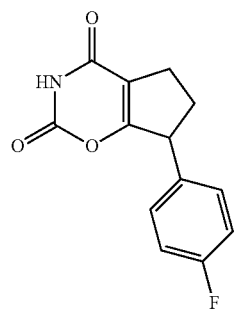 [SMILES: O=c1[nH]c(=O)c2c(o1)C(c1ccc(F)cc1)CC2]

A mixture of 2-(4-fluorophenyl)cyclopentanone (18.557 g, 104 mmol) and carbonisocyanatidic chloride (19.77 g, 187 mmol) was heated at 58° C. for 1 h and at 130° C. for 2 h. Upon cooling to room temperature, the resulting tar was dissolved in ethyl acetate and washed with saturated aqueous solution of sodium bicarbonate. The organic layer was separated and the aqueous layer was extracted with ethyl acetate. The combined organic extracts were dried over anhydrous magnesium sulfate and filtered. The solvent was removed in vacuo and the residue was purified by column chromatography on silica gel to give 7-(4-fluorophenyl)-6,7-dihydrocyclopenta[e][1,3]oxazine-2,4(3H,5H)-dione (13.527 g, 54.7 mmol, 52.5% yield) as a brown solid. LC-MS $(M+H)^+$ =248.1. $^1$H NMR (500 MHz, CDCl$_3$) δ ppm 11.80 (1H, br s), 7.31-7.39 (2H, m), 7.16-7.22 (2H, m), 4.30-4.38 (1H, m), 2.63-2.73 (1H, m), 2.53-2.63 (2H, m), 1.84-1.95 (1H, m).

Intermediate S(4)

7-(4-Fluorophenyl)-6,7-dihydro-1H-cyclopenta[d]pyrimidine-2,4(3H,5H)-dione

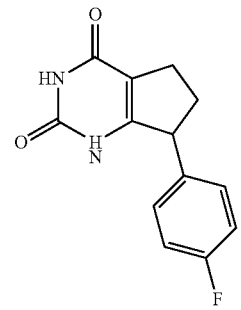 [SMILES: O=c1[nH]c2c(c(=O)[nH]1)CCC2c1ccc(F)cc1]

A solution of 7-(4-fluorophenyl)-6,7-dihydrocyclopenta[e][1,3]oxazine-2,4(3H,5H)-dione (13.527 g, 54.7 mmol) in concentrated ammonium hydroxide (150 mL, 3852 mmol) was heated at 100° C. in a high-pressure (350 mL) vessel overnight. The reaction mixture was cooled to 0° C. and filtered. The precipitate was consecutively washed with water and dried by passing air through the filter and subsequently under vacuum to give 7-(4-fluorophenyl)-6,7-dihydro-1H-cyclopenta[d]pyrimidine-2,4(3H,5H)-dione (4.670 g, 18.97 mmol, 34.7% yield). LC-MS $(M+H)^+$=247.3. $^1$H NMR (500 MHz, CDCl$_3$) δ ppm 11.70-11.81 (2H, br s), 7.31-7.39 (2H, m), 7.16-7.22 (2H, m), 4.30-4.38 (1H, m), 2.63-2.73 (1H, m), 2.53-2.63 (2H, m), 1.84-1.95 (1H, m).

Preparation S 2,4-Dichloro-7-(4-fluorophenyl)-6,7-dihydro-5H-cyclopenta[d]pyrimidine

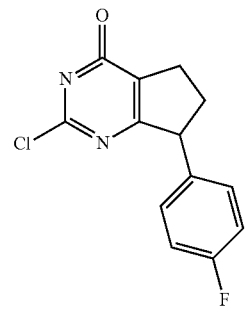

A solution of 7-(4-fluorophenyl)-6,7-dihydro-1H-cyclopenta[d]pyrimidine-2,4(3H,5H)-dione (1 g, 4.06 mmol) in phosphorus oxychloride (11.81 mL, 127 mmol) and N,N-dimethylaniline (3.94 mL, 31.1 mmol) was stirred at 110° C. overnight. The reaction mixture was carefully poured onto ice. Once the ice melted, the aqueous layer was extracted with dichloromethane. The combined organic extracts were dried over anhydrous magnesium sulfate and filtered. The solvent was removed in vacuo and the residue was purified by column chromatography on silica gel to give 2,4-dichloro-7-(4-fluorophenyl)-6,7-dihydro-5H-cyclopenta[d]pyrimidine (700.0 mg, 2.472 mmol, 60.9% yield) as a dark burgundy solid. LC-MS (M+H)+=283.1. ¹H NMR (500 MHz, CDCl₃) δ ppm 7.09-7.15 (2H, m), 7.03 (2H, t, J=8.5 Hz), 4.42 (1H, t, J=8.4 Hz), 3.10 (1H, dd, J=9.2, 4.6 Hz), 3.01 (1H, d, J=8.2 Hz), 2.73 (1H, d, J=8.9 Hz), 2.15-2.27 (1H, m).

Preparation Sa

N-allyl-2-chloro-7-(4-fluorophenyl)-6,7-dihydro-5H-cyclopenta[d]pyrimidin-4-amine

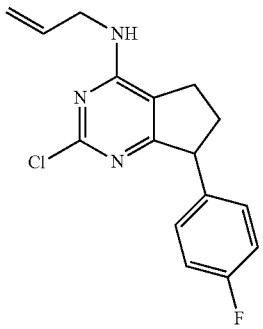 [SMILES: C=CCNc1nc(Cl)nc2c1CCC2c1ccc(F)cc1]

To a solution of Preparation S (1.2 g, 4.25 mmol) in acetonitrile (10 mL) was added diisopropylethylamine (0.824 g, 6.38 mmol) followed by prop-2-en-1-amine (0.393 g, 5.52 mmol) at room temperature. The reaction mixture was stirred at rt for 18 h. The solvent was removed under reduced pressure and the residue was purified by column chromatography (60-120 mesh silica) using 30% ethyl acetate in pet-ether to give N-allyl-2-chloro-7-(4-fluorophenyl)-6,7-dihydro-5H-cyclopenta[d]pyrimidin-4-amine (1 g, 78%) as a light brown solid. LC-MS (M+H)+=304.2. 1H NMR (400 MHz, CDCl₃) δ ppm 7.25-7.07 (2H, m), 7.00-6.95 (2H, m), 5.99-5.93 (1H, m), 5.30-5.20 (2H, m), 4.67 (1H, br s), 4.26-4.17 (3H, m), 2.78-2.64 (3H, m), 2.11-2.05 (1H, m).

Preparation Sb

N-allyl-2-chloro-7-(4-fluorophenyl)-N-methyl-6,7-dihydro-5H-cyclopenta[d]pyrimidin-4-amine

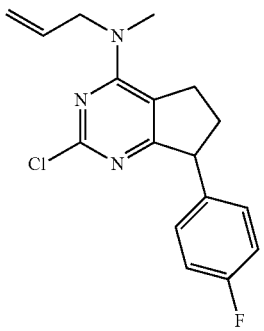 [SMILES: C=CCN(C)c1nc(Cl)nc2c1CCC2c1ccc(F)cc1]

To a solution of Preparation S (5 g, 17.66 mmol) in acetonitrile (100 mL) was added diisopropylethylamine (3.42 g, 26.5 mmol) followed by N-methylprop-2-en-1-amine (1.507 g, 21.19 mmol) at room temperature. The reaction mixture was stirred at room temperature for 18 h. The solvent was removed under reduced pressure and the residue was purified by column chromatography (60-120 mesh silica) using 50% ethyl acetate in pet-ether to give N-allyl-2-chloro-7-(4-fluorophenyl)-N-methyl-6,7-dihydro-5H-cyclopenta[d]pyrimidin-4-amine as a white solid (4.5 g, 80%). LC-MS (M+H)+ =318.0. 1H NMR (400 MHz, CDCl₃) δ ppm 7.11-7.07 (2H, m), 6.99-6.95 (2H, m), 5.89-5.82 (1H, m), 5.29-5.17 (2H, m), 4.2-4.14 (3H, m), 3.19 (3H, s), 3.16-3.05 (2H, m), 2.56-2.51 (1H, m), 1.99-1.97 (1H, m).

Preparation Sc

N1-(2-chloro-7-(4-fluorophenyl)-6,7-dihydro-5H-cyclopenta[d]pyrimidin-4-yl)-N2-(2-(2-(3-methyl-1H-1,2,4-triazol-1-yl)-5-nitrophenoxy)ethyl)ethane-1,2-diamine

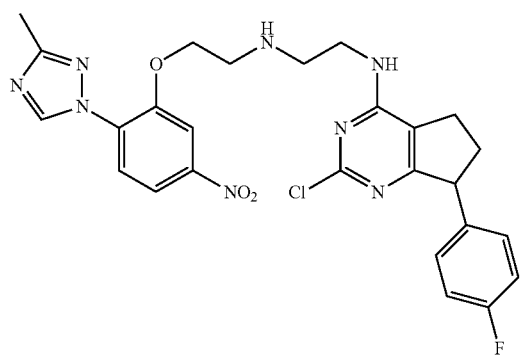

Preparation Sc Step(1)

N1-(2-chloro-7-(4-fluorophenyl)-6,7-dihydro-5H-cyclopenta[d]pyrimidin-4-yl)ethane-1,2-diamine

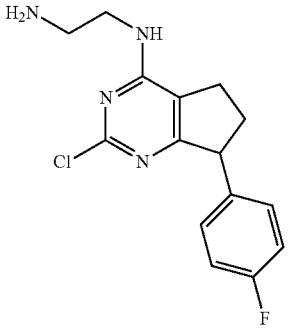 [SMILES: NCCNc1nc(Cl)nc2c1CCC2c1ccc(F)cc1]

To a solution of 2,4-dichloro-7-(4-fluorophenyl)-6,7-dihydro-5H cyclopenta[d]pyrimidine (0.5 g, 1.77 mmol) in acetonitrile (5 mL) was added diisopropylethylamine (0.343 g, 2.659 mmol) followed by ethane-1,2-diamine (0.138 g, 2.30 mmol) at room temperature. The reaction mixture was stirred at room temperature for 18 h. The solvent was removed under reduced pressure and the residue was taken in dichloromethane (5 mL) and silica (1 g). The resultant slurry of the compound on silica was subjected to flash chromatography using a Teledyne Isco instrument (12 g RediSep silica column, 10% methanol in chloroform) to get the title compound N1-(2-chloro-7-(4-fluorophenyl)-6,7-dihydro-5H-cyclopenta[d]pyrimidin-4-yl)ethane-1,2-diamine (0.35 g, 64.5%) as a dark brown solid. LC-MS (M+H)⁺=307.2. ¹H NMR (400 MHz, CDCl₃) δ ppm 7.11-7.08 (2H, m), 6.99-6.95 (2H, m), 5.40 (1H, br s), 4.25-4.22 (1H, m), 3.61-3.57 (2H, m), 2.99-2.98 (2H, m), 2.78-2.62 (3H, m), 2.10-2.09 (1H, m).

Preparation Sc

N1-(2-chloro-7-(4-fluorophenyl)-6,7-dihydro-5H-cyclopenta[d]pyrimidin-4-yl)-N2-(2-(2-(3-methyl-1H-1,2,4-triazol-1-yl)-5-nitrophenoxy)ethyl)ethane-1,2-diamine

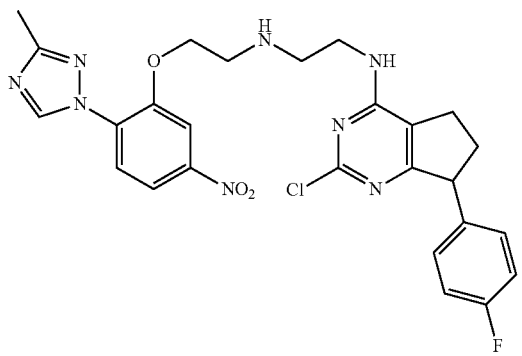

To a solution of N1-(2-chloro-7-(4-fluorophenyl)-6,7-dihydro-5H-cyclopenta[d]pyrimidin-4-yl)ethane-1,2-diamine (0.5 g, 1.63 mmol) in DMF (3 mL) was added TEA (0.247 g, 2.44 mmol) followed by 1-(2-(2-bromoethoxy)-4-nitrophenyl)-3-methyl-1H-1,2,4-triazole (0.798 g, 2.44 mmol) at room temperature. The reaction mixture was stirred at room temperature for 18 h. The solvent was removed under reduced pressure and the residue was dissolved in dichloromethane (5 mL) and silica (1 g). The resultant slurry of the compound in silica was subjected to flash chromatography using a Teledyne Isco instrument (12 g RediSep silica column, 10% methanol in chloroform) to get N1-(2-chloro-7-(4-fluorophenyl)-6,7-dihydro-5H-cyclopenta[d]pyrimidin-4-yl)-N-2-(2-(2-(3-methyl-1H-1,2,4-triazol-1-yl)-5-nitrophenoxy)ethyl)ethane-1,2-diamine (0.25 g, 27.7%) as a brown solid. LC-MS (M+H)⁺=553.2. ¹H NMR (400 MHz, CDCl₃) δ ppm 8.25 (1H, s), 7.14-7.08 (3H, m), 6.99-6.95 (2H, m), 6.41 (1H, s), 6.33-6.31 (1H, d, J=8.4 Hz), 4.39 (1H, br s), 4.16-4.12 (1H, t, J=8.8 Hz), 3.93-3.88 (4H, m), 3.22-3.09 (6H, m), 2.55-2.54 (1H, m), 2.46 (3H, s), 1.99-1.98 (1H, m).

Preparation Sd

N1-(2-chloro-7-(4-fluorophenyl)-6,7-dihydro-5H-cyclopenta[d]pyrimidin-4-yl)-N-2-methyl-N2-(2-(2-(3-methyl-1H-1,2,4-triazol-1-yl)-5-nitrophenoxy)ethyl)ethane-1,2-diamine

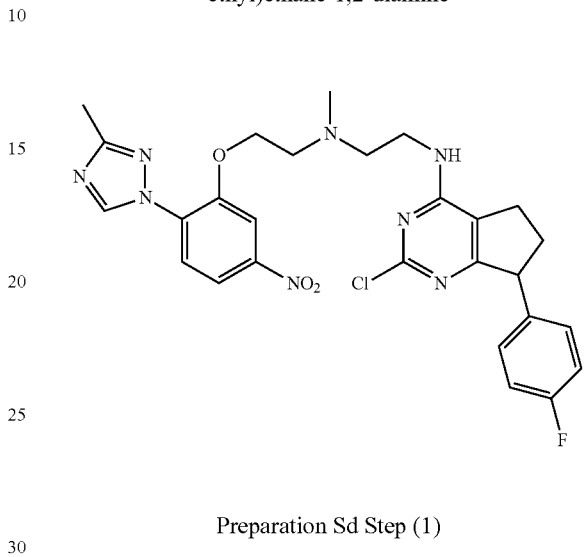

Preparation Sd Step (1)

N1-(2-chloro-7-(4-fluorophenyl)-6,7-dihydro-5H-cyclopenta[d]pyrimidin-4-yl)-N2-methylethane-1,2-diamine

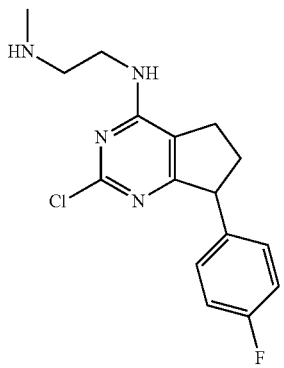 [SMILES: CNCCNc1nc(Cl)nc2c1CCC2c1ccc(F)cc1]

To a solution of 2,4-dichloro-7-(4-fluorophenyl)-6,7-dihydro-5H cyclopenta[d]pyrimidine (2.0 g, 7.06 mmol) in acetonitrile (50 mL) was added diisopropylethylamine (1.369 g, 10.60 mmol) followed by N-1-methylethane-1,2-diamine (0.628 g, 8.48 mmol) at room temperature. The reaction mixture was stirred at rt for 18 h. The solvent was removed under reduced pressure and the residue was taken in dichloromethane (10 mL) and silica (2 g). The resultant slurry of the compound on silica was subjected to flash chromatography using a Teledyne Isco instrument (12 g RediSep silica column, 10% methanol in chloroform) to get N1-(2-chloro-7-(4-fluorophenyl)-6,7-dihydro-5H-cyclopenta[d]pyrimidin-4-yl)-N2-methylethane-1,2-diamine (1.6 g, 70.6%) as a light brown solid. LC-MS (M+H)⁺=321.2. ¹H NMR (400 MHz, DMSO-d₆) δ ppm 8.13 (2H, br s), 7.22-7.11 (4H, m), 4.21-

4.17 (1H, t, J=8.0 Hz), 3.82-3.79 (2H, m), 3.27 (3H, s), 3.19-3.04 (4H, m), 2.55-2.54 (1H, m), 1.99-1.98 (1H, m).

Preparation Sd

N1-(2-chloro-7-(4-fluorophenyl)-6,7-dihydro-5H-cyclopenta[d]pyrimidin-4-yl)-N2-methyl-N2-(2-(2-(3-methyl-1H-1,2,4-triazol-1-yl)-5-nitrophenoxy)ethyl)ethane-1,2-diamine

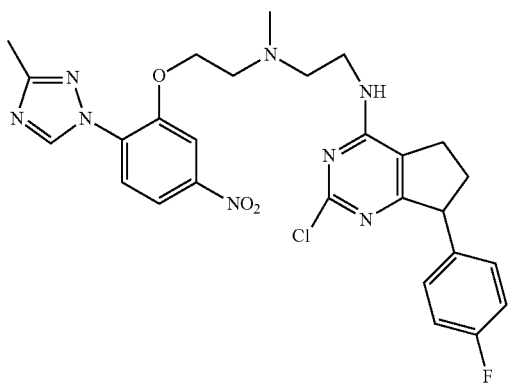 [SMILES: Cc1ncn(-c2ccc([N+](=O)[O-])cc2OCCN(C)CCNc2nc(Cl)nc3c2CCC3c2ccc(F)cc2)n1]

To a solution of N1-(2-chloro-7-(4-fluorophenyl)-6,7-dihydro-5H-cyclopenta[d]pyrimidin-4-yl)-N2-methylethane-1,2-diamine (0.2 g, 0.623 mmol) in DMF (3 mL) was added TEA (0.095 g, 0.935 mmol) followed by 1-(2-(2-bromoethoxy)-4-nitrophenyl)-3-methyl-1H-1,2,4-triazole (Preparation J, 0.245 g, 0.233 mmol) at room temperature. The reaction mixture was stirred at rt for 18 h. The solvent was removed under reduced pressure and the residue was dissolved in dichloromethane (5 mL) and silica (1 g). The resultant slurry of the compound in silica was subjected to flash chromatography using a Teledyne Isco instrument (12 g RediSep silica column, with 10% methanol in chloroform) to get N1-(2-chloro-7-(4-fluorophenyl)-6,7-dihydro-5H-cyclopenta[d]pyrimidin-4-yl)-N2-methyl-N2-(2-(2-(3-methyl-1H-1,2,4-triazol-1-yl)-5-nitrophenoxy)ethyl)ethane-1,2-diamine (0.04 g, 13.12%) as a dark brown solid. LC-MS (M+H)$^+$=567.2. $^1$H NMR (400 MHz, CDCl$_3$) δ ppm 8.25 (1H, s), 7.14-7.08 (3H, m), 6.99-6.95 (2H, m), 6.41 (1H, s), 6.32 (1H, d, J=8.4 Hz), 4.39 (2H, br s), 4.14 (1H, t, J=8.8 Hz), 3.93-3.88 (4H, m), 3.22-3.09 (6H, m), 2.55-2.54 (1H, m), 2.46 (3H, s), 1.99-1.98 (1H, m).

Preparation Se 2-chloro-7-(4-fluorophenyl)-N-methyl-N-(3-(2-(3-methyl-1H-1,2,4-triazol-1-yl)-5-nitrophenoxy)propyl)-6,7-dihydro-5H-cyclopenta[d]pyrimidin-4-amine

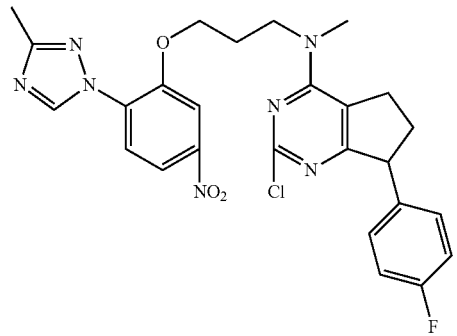 [SMILES: Cc1ncn(-c2ccc([N+](=O)[O-])cc2OCCCN(C)c2nc(Cl)nc3c2CCC3c2ccc(F)cc2)n1]

To a solution of Preparation L (1.1 g, 3.78 mmol) in acetonitrile (50 mL) was added diisopropylethylamine (0.976 g, 7.55 mmol) followed by Preparation S (1.28 g, 4.53 mmol) at room temperature. The reaction mixture was stirred at room temperature for 18 h. The solvent was removed under reduced pressure and the residue was purified by column chromatography (60-120 mesh silica) using 20% to 30% ethyl acetate in pet-ether to afford 2-chloro-7-(4-fluorophenyl)-N-methyl-N-(3-(2-(3-methyl-1H-1,2,4-triazol-1-yl)-5-nitrophenoxy)propyl)-6,7-dihydro-5H-cyclopenta[d]pyrimidin-4-amine (1.2 g, 59.2%). LC-MS (M+H)$^+$=539.2. 1H NMR (400 MHz, DMSO-d6) δ ppm 9.91 (1H, s), 8.04 (1H, d, J=8.8 Hz), 7.99-7.92 (2H, m), 7.09-7.06 (2H, m), 6.97 (1H, t, J=8.8 Hz), 4.33 (2H, t, J=6 Hz), 4.13 (2H, t, J=8 Hz), 3.88-3.76 (2H, m), 3.27 (3H, s), 3.18-3.05 (2H, m), 2.55 (1H, m), 2.53 (3H, s), 2.25 (2H, q, J=6.4 Hz), 2.00-1.96 (1H, m).

Preparation Sf 2-(2-(2-(2-chloro-7-(4-fluorophenyl)-6,7-dihydro-5H-cyclopenta[d]pyrimidin-4-ylamino)ethylamino)ethoxy)-4-nitrobenzonitrile

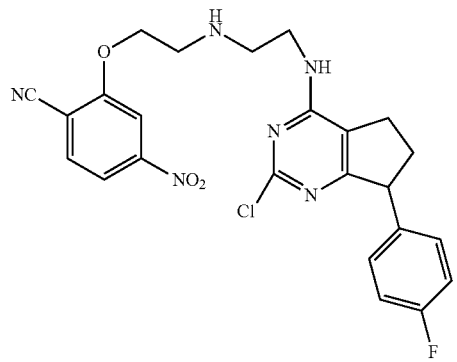 [SMILES: N#Cc1ccc([N+](=O)[O-])cc1OCCNCCNc1nc(Cl)nc2c1CCC2c1ccc(F)cc1]

To a solution of N1-(2-chloro-7-(4-fluorophenyl)-6,7-dihydro-5H-cyclopenta[d]pyrimidin-4-yl)ethane-1,2-diamine {Preparation Sc Step (1), 1.0 g, 3.265 mmol} in DMF (5 mL) was added TEA (0.495 g, 4.89 mmol) followed by 2-(2-bromoethoxy)-4-nitrobenzonitrile (Preparation N, 1.05 g, 3.91 mmol) at room temperature. The reaction mixture was stirred at rt for 18 h. The solvent was removed under reduced pressure and the residue was taken in dichloromethane (5 mL) and silica (1 g). The resultant slurry of the compound in silica was subjected to flash chromatography using a Teledyne Isco instrument (12 g RediSep silica column, 10% methanol in chloroform) to get 2-(2-(2-(2-chloro-7-(4-fluorophenyl)-6,7-dihydro-5H-cyclopenta[d]pyrimidin-4-ylamino)ethylamino)ethoxy)-4-nitrobenzonitrile (0.35 g, 21.7%) as a light yellow solid. LC-MS (M+H)$^+$=497.2. $^1$H NMR (400 MHz, CDCl$_3$) δ ppm 7.93-7.91 (1H, d, J=6.8 Hz), 7.90 (1H, s), 7.86-7.85 (1H, m), 7.12-7.00 (2H, m), 6.98-6.96 (2H, m), 5.30 (1H, br s), 4.34-4.32 (2H, m), 4.26-4.24 (1H, m), 3.70-3.66 (2H, m), 3.21-3.19 (2H, m), 3.04-3.02 (2H, m), 2.78-2.63 (3H, m), 1.99-1.98 (1H, m).

Preparation Sg 2-(2-((2-(2-chloro-7-(4-fluorophenyl)-6,7-dihydro-5H-cyclopenta[d]pyrimidin-4-ylamino)ethyl)(methyl)amino)ethoxy)-4-nitrobenzonitrile

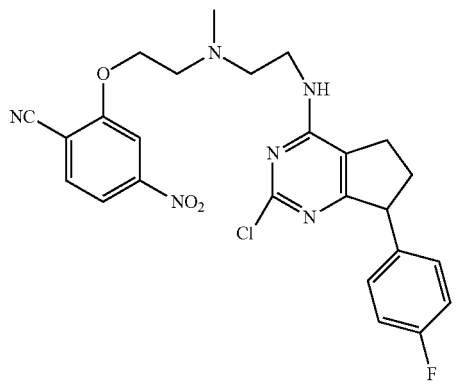 [SMILES: CN(CCNc1nc(Cl)nc2c1CCC2c1ccc(F)cc1)CCOc1cc([N+](=O)[O-])ccc1C#N]

To a solution of N1-(2-chloro-7-(4-fluorophenyl)-6,7-dihydro-5H-cyclopenta[d]pyrimidin-4-yl)-N2-methylethane-1,2-diamine {Preparation Sd Step (1), 0.5 g, 1.56 mmol} in DMF (5 mL) was added TEA (0.234 g, 2.34 mmol) followed by 2-(2-bromoethoxy)-4-nitrobenzonitrile (0.423 g, 1.56 mmol) at room temperature. The reaction mixture was stirred at room temperature for 18 h. The solvent was removed under reduced pressure and the residue was taken in dichloromethane (5 mL) and silica (1 g). The resultant slurry of the compound in silica was subjected to flash chromatography using a Teledyne Isco instrument (12 g RediSep silica column, 10% methanol in chloroform) to get 2-(2-((2-(2-chloro-7-(4-fluorophenyl)-6,7-dihydro-5H-cyclopenta[d]pyrimidin-4-ylamino)ethyl)(methyl)amino)ethoxy)-4-nitrobenzonitrile (0.3 g, 37.68%) as a dark brown solid. LC-MS (M+H)$^+$=511.2. $^1$H NMR (400 MHz, CDCl$_3$) δ ppm 7.91-7.89 (1H, m), 7.85 (1H, s), 7.72-7.70 (1H, m), 7.14-7.10 (2H, m), 6.98-6.96 (2H, m), 4.42-4.39 (2H, m), 4.17-4.15 (1H, m), 3.66-3.56 (2H, m), 3.49 (3H, s), 3.35-3.26 (2H, m), 3.18-3.12 (4H, m), 2.78-2.63 (1H, m), 1.99-1.98 (1H, m).

Preparation Sh tert-butyl 2-(5-amino-2-cyanophenoxy)ethyl(2-(2-chloro-7-(4-fluorophenyl)-6,7-dihydro-5H-cyclopenta[d]pyrimidin-4-yl)ethyl)carbamate

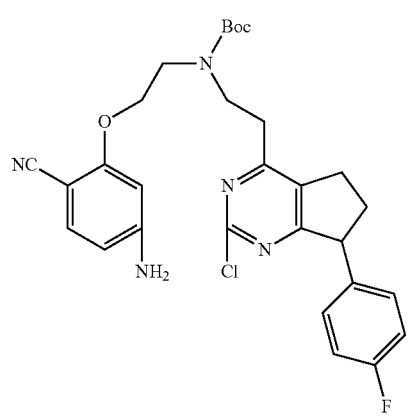 [SMILES: CC(C)(C)OC(=O)N(CCOc1cc(N)ccc1C#N)CCc1nc(Cl)nc2c1CCC2c1ccc(F)cc1]

Preparation Sh Step(1)

2-(2-(2-(2-chloro-7-(4-fluorophenyl)-6,7-dihydro-5H-cyclopenta[d]pyrimidin-4-yl)ethylamino)ethoxy)-4-nitrobenzonitrile

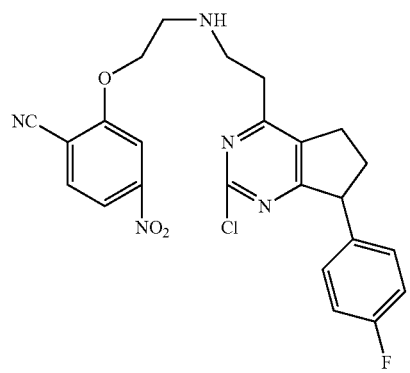 [SMILES: N#Cc1ccc([N+](=O)[O-])cc1OCCNCCc1nc(Cl)nc2c1CCC2c1ccc(F)cc1]

A mixture of 2,4-dichloro-7-(4-fluorophenyl)-6,7-dihydro-5H-cyclopenta[d]pyrimidine (0.1 g, 0.353 mmol), tributylethenylstannane (0.118 g, 0.371 mmol), tetrakis(triphenylphosphine)palladium (0.0081 g, 0.0070 mmol) in toluene (20 mL) was refluxed at 110° C. for 2 h under nitrogen. The solvent was removed under reduced pressure (high vacuum) and the residue was dissolved in 4 mL of THF/MeOH (3:1). 2-(2-Aminoethoxy)-4-nitrobenzonitrile (0.088 g, 0.424 mmol) was added and the mixture was refluxed at 75° C. for 18 h while monitoring by LC-MS. The solvent was removed under reduced pressure and the residue was dissolved in dichloromethane (5 mL) and silica (1 g). The resultant slurry of the compound on silica was subjected to flash chromatography using a Teledyne Isco instrument (4 g RediSep silica column, 10% methanol in chloroform) to get 2-(2-((2-(2-chloro-7-(4-fluorophenyl)-6,7-dihydro-5H-cyclopenta[d]pyrimidin-4-yl)ethyl)amino)ethoxy)-4-nitrobenzonitrile (0.035 g, 20.56%) as a dark brown gummy liquid. LC-MS (M+H)$^+$=482.0. 1H NMR: (400 MHz, CDCl$_3$) δ ppm 7.93 (1H, d, J=8.4 Hz), 7.87 (1H, s), 7.74 (1H, d, J=8.4 Hz), 7.13-7.10 (2H, m), 7.02-6.98 (2H, m), 4.45-4.44 (2H, m), 4.36 (1H, t, J=8.4 Hz), 3.44-3.41 (4H, m), 3.11-3.09 (2H, m), 2.97-2.88 (2H, m), 2.74-2.66 (1H, m), 2.21-2.12 (1H, m).

Preparation Sh Step(2)

tert-butyl 2-(2-chloro-7-(4-fluorophenyl)-6,7-dihydro-5H-cyclopenta[d]pyrimidin-4-yl)ethyl(2-(2-cyano-5-nitrophenoxy)ethyl)carbamate

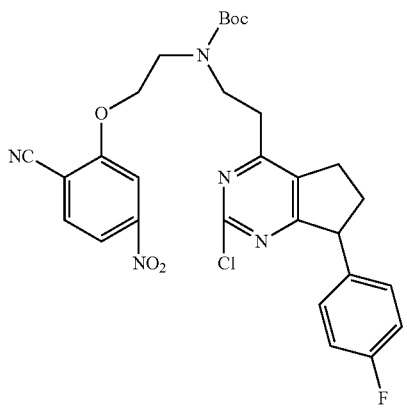 [SMILES: CC(C)(C)OC(=O)N(CCOc1cc([N+](=O)[O-])ccc1C#N)CCc1nc(Cl)nc2c1CCC2c1ccc(F)cc1]

To an ice-cold solution of tert-butyl (2-(2-chloro-7-(4-fluorophenyl)-6,7-dihydro-5H-cyclopenta[d]pyrimidin-4-yl)ethyl)(2-(2-cyano-5-nitrophenoxy)ethyl)carbamate (0.025 g, 0.052 mmol), TEA (0.0052 g, 0.052 mmol) in DCM (3 mL), di-tert-butyl dicarbonate (0.011 g, 0.052 mmol) was added and the mixture stirred at rt for 60 min. The solvent was removed under reduced pressure and the residue was dissolved in dichloromethane (3 mL) and silica (0.5 g). The resultant slurry of the compound on silica was subjected to flash chromatography using a Teledyne Isco instrument (4 g RediSep silica column, 10% methanol in chloroform) to get tert-butyl (2-(2-chloro-7-(4-fluorophenyl)-6,7-dihydro-5H-cyclopenta[d]pyrimidin-4-yl)ethyl)(2-(2-cyano-5-nitrophenoxy)ethyl)carbamate (0.02 g, 66.2%) as a light brown solid. LC-MS (M+H)$^+$=582.2 1H NMR: (400 MHz, CDCl$_3$) δ ppm 7.92 (1H, d, J=8.4 Hz), 7.87 (1H, s), 7.77 (1H, d, J=8.4 Hz), 7.16-7.13 (2H, m), 7.03-7.01 (2H, m), 4.38-4.34 (3H, m), 3.87-3.77 (4H, m), 3.10-2.90 (4H, m), 2.73-2.69 (1H, m), 2.25-2.19 (1H, m), 1.42 (9H, s).

Preparation Sh tert-butyl 2-(5-amino-2-cyanophenoxy)ethyl(2-(2-chloro-7-(4-fluorophenyl)-6,7-dihydro-5H-cyclopenta[d]pyrimidin-4-yl)ethyl)carbamate

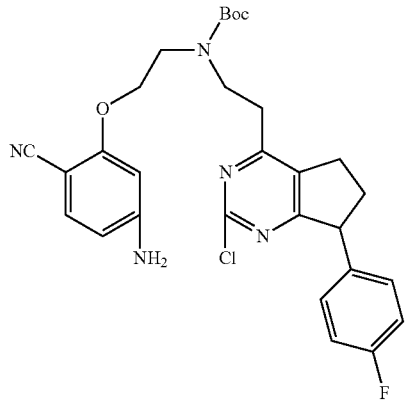 [SMILES: CC(C)(C)OC(=O)N(CCOc1cc(N)ccc1C#N)CCc1nc(Cl)nc2c1CCC2c1ccc(F)cc1]

Iron powder-325 mesh (0.0095 g, 0.172 mmol) was added to a round bottom flask charged with a mixture of tert-butyl (2-(5-amino-2-cyanophenoxy)ethyl)-(2-(2-chloro-7-(4-fluorophenyl)-6,7-dihydro-5H-cyclopenta[d]pyrimidin-4-yl) ethyl)carbamate (0.02 g, 0.034 mmol), 3 mL of methanol:water (2:1), and ammonium chloride (0.0091 g, 0.172 mmol). A water-cooled reflux condenser was attached to the flask and the heterogeneous mixture was heated to 65° C. with vigorous stirring for 150 min. The reaction mixture was filtered and washed with methanol. The solvent was removed in vacuo. EtOAc was added to the residue, and washed with brine. The organic layer was dried over sodium sulfate, filtered, and concentrated. The residue was subjected to flash chromatography using a Teledyne Isco instrument (4 g RediSep silica column, 10% MeOH in CHCl$_3$) to get the title compound (0.01 g, 52.7%) as an off-white solid. LC-MS (M+H)$^+$=552.2 1H NMR: (400 MHz, CDCl$_3$) δ ppm 7.29-7.25 (1H, m), 7.13-6.99 (4H, m), 6.23-6.11 (2H, m), 4.31 (1H, t, J=8.0 Hz), 4.15-4.06 (4H, m), 3.87-3.83 (2H, m), 3.65 (2H, s), 3.15-2.95 (4H, m), 2.72-2.63 (1H, m), 2.17-2.12 (1H, m), 1.56 (9H, s).

Preparation T 2,4-Dichloro-7-(2,4-difluorophenyl)-6,7-dihydro-5H-cyclopenta[d]pyrimidine

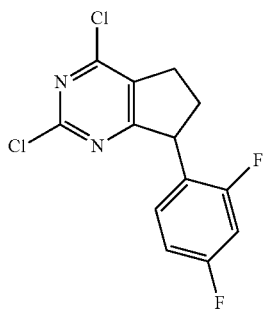 [SMILES: Fc1ccc(C2CCc3c(Cl)nc(Cl)nc32)c(F)c1]

Intermediate T(1)

1-Cyclopentenyl-2,4-difluorobenzene

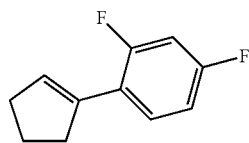 [SMILES: Fc1ccc(C2=CCCC2)c(F)c1]

To a 0.497 M solution of (2,4-difluorophenyl)magnesium bromide (32.4 g, 149 mmol) in THF at 0° C. was carefully added cyclopentanone (13.23 mL, 149 mmol). Upon the end of the addition, the reaction mixture was heated at reflux for 2 h. Ice (10 g) and 6 N aqueous hydrochloric acid were added. The reaction mixture was extracted with ether. The combined organic extracts were washed with a saturated aqueous solution of sodium hydrogen sulfite, a saturated aqueous solution of sodium bicarbonate and water. The organic layer was dried over anhydrous magnesium sulfate and filtered. The solvent was removed in vacuo and the residue was purified by column chromatography on silica gel to give 1-cyclopentenyl-2,4-difluorobenzene (7.064 g, 39.2 mmol, 26.3% yield) as a colorless oil. LC-MS (M+H)$^+$=181.0. $^1$H NMR (500 MHz, CDCl$_3$) δ ppm 7.22-7.31 (1H, m), 6.75-6.85 (2H, m), 6.26-6.31 (1H, m), 2.68-2.74 (2H, m), 2.51-2.58 (2H, m), 1.93-2.02 (2H, m).

Intermediate T(2)

2-(2,4-Difluorophenyl)cyclopentanone

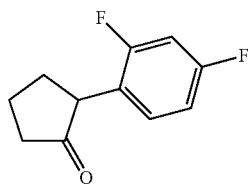 [SMILES: O=C1CCCC1c1ccc(F)cc1F]

A mixture of 90% formic acid (26.4 mL, 689 mmol) and 30% hydrogen peroxide (6.0 mL, 39.2 mmol) was warmed at 40° C. for 10 min. The resulting solution was carefully added to 1-cyclopentenyl-2,4-difluorobenzene (7.064 g, 39.2 mmol) while stirring. The two-phase system was initially stirred at room temperature. After a certain period of time, a spontaneous exothermic reaction took place, and the temperature rose to about 50° C. The reaction mixture was stirred at room temperature for 2 h. The reaction mixture was quenched by careful addition of a saturated sodium bicarbonate solution. Ether was added and the content of the separatory funnel was vigorously shaken. The organic layer was separated and the aqueous layer was extracted with ether. The combined organic extracts were dried over anhydrous magnesium sulfate and filtered. The solvent was removed in vacuo and the residue was purified by column chromatography on silica gel to give 2-(2,4-difluorophenyl)cyclopentanone (3.503 g, 17.85 mmol, 45.5% yield) as a colorless oil. LC-MS (M+H)$^+$=195.2. $^1$H NMR (500 MHz, CDCl$_3$) δ ppm 7.08 (1H, td, J=8.4, 6.4 Hz), 6.76-6.86 (2H, m), 3.42 (1H, dd, J=12.2, 8.9 Hz), 2.42-2.53 (2H, m), 2.28-2.39 (1H, m), 2.13-2.23 (1H, m), 1.86-2.10 (2H, m).

Intermediate T(3)

7-(2,4-Difluorophenyl)-6,7-dihydrocyclopenta[e][1,3]oxazine-2,4(3H,5H)-dione

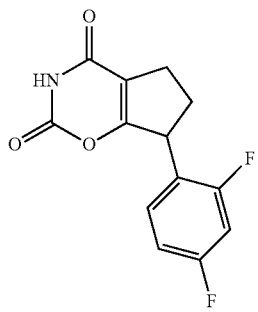 [SMILES: O=c1[nH]c(=O)c2c(o1)C(c1ccc(F)cc1F)CC2]

A mixture of 2-(2,4-difluorophenyl)cyclopentanone (1.014 g, 5.17 mmol) and 50% wt. carbonisocyanatidic chloride solution in toluene (1.963 g, 9.30 mmol) was heated at 58° C. for 1 h and at 120° C. for 3 h. The reaction mixture was dissolved in ethyl acetate and washed with an aqueous solution of sodium bicarbonate. The organic layer was separated and the aqueous layer was extracted with ethyl acetate. The combined organic extracts were dried over anhydrous magnesium sulfate and filtered. The solvent was removed in vacuo and the residue was purified by column chromatography on silica gel to give 7-(2,4-difluorophenyl)-6,7-dihydrocyclopenta[e][1,3]oxazine-2,4(3H,5H)-dione (499.3 mg, 1.883 mmol, 36.4% yield) as a brown solid. LC-MS (M+H)$^+$=266.2. $^1$H NMR (500 MHz, CDCl$_3$) δ ppm 8.19-8.64 (1H, m), 7.10 (1H, td, J=8.5, 6.3 Hz), 6.78-6.92 (2H, m), 4.36-4.49 (1H, m), 2.79-2.92 (1H, m), 2.59-2.78 (2H, m), 2.08 (1H, ddd, J=9.3, 6.9, 6.7 Hz).

Intermediate T(4)

7-(2,4-Difluorophenyl)-6,7-dihydro-1H-cyclopenta[d]pyrimidine-2,4(3H,5H)-dione

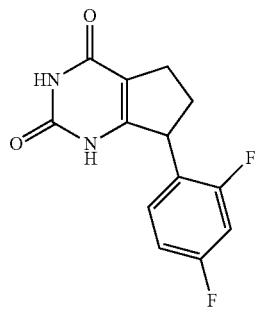 [SMILES: O=c1[nH]c2c(c(=O)[nH]1)CCC2c1ccc(F)cc1F]

In a manner similar to the conditions described for the preparation of Intermediate S(4), Intermediate T(3) was converted to 7-(2,4-Difluorophenyl)-6,7-dihydro-1H-cyclopenta[d]pyrimidine-2,4(3H,5H)-dione. LC-MS (M+H)$^+$=265.1.

Preparation T 2,4-Dichloro-7-(2,4-difluorophenyl)-6,7-dihydro-5H-cyclopenta[d]pyrimidine

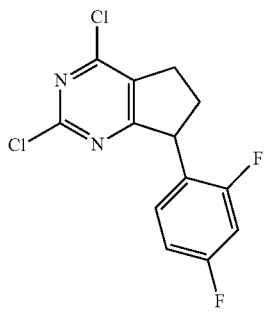 [SMILES: Fc1ccc(C2CCc3c(Cl)nc(Cl)nc32)c(F)c1]

A solution of 7-phenyl-6,7-dihydro-1H-cyclopenta[d]pyrimidine-2,4(3H,5H)-dione (248.5 mg, 0.940 mmol) in phosphoryl trichloride (10 mL) was heated in a microwave at 130° C. for 2 h. The reaction mixture was poured into a beaker of ice. Once the ice melted, the product was extracted with dichloromethane. The combined organic extracts were dried over anhydrous magnesium sulfate and filtered. The solvent was removed in vacuo and the residue was purified by column chromatography on silica gel to give 2,4-dichloro-7-phenyl-6,7-dihydro-5H-cyclopenta[d]pyrimidine (267.9 mg, 95%) as a light brown solid. LC-MS (M−H)$^+$=299.0. 1H NMR (400 MHz, CDCl$_3$) δ ppm 7.08-7.01 (1H, m), 6.88-6.80 (2H, m), 4.60 (1H, t, J=8.8 Hz), 3.17-3.09 (1H, m), 3.05-2.97 (1H, m), 2.78-2.69 (1H, m), 2.22-2.15 (1H, m).

Preparation Ta

N-allyl-2-chloro-7-(2,4-difluorophenyl)-6,7-dihydro-5H-cyclopenta[d]pyrimidin-4-amine

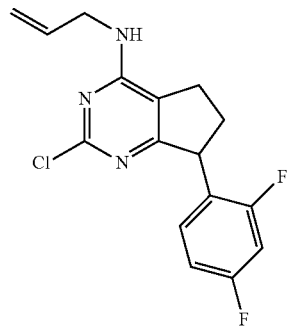 [SMILES: C=CCNc1nc(Cl)nc2c1CCC2c1ccc(F)cc1F]

To a solution of Preparation T (2 g, 7.5 mmol) in acetonitrile (25 mL) was added diisopropylethylamine (2.58 g, 19.9 mmol) followed prop-2-en-1-amine (0.569 g, 9.9 mmol) at room temperature. The reaction mixture was stirred at room temperature for 18 h. The solvent was removed under reduced pressure and the residue was purified by column chromatography (60-120 mesh silica) using 25% ethyl acetate in petether to give N-allyl-2-chloro-7-(2,4-difluorophenyl)-6,7-dihydro-5H-cyclopenta[d]pyrimidin-4-amine as an off-white solid (1.6 g, 75.7%). LC-MS (M+H)$^+$=321.5. 1H NMR (400 MHz, CDCl$_3$) δ ppm 6.97-6.93 (1H, m), 6.81-6.76 (2H, m), 6.00-5.93 (1H, m), 5.31-5.30 (2H, m), 4.67 (1H, m), 4.83 (1H, m), 4.20-4.17 (2H, m), 2.75-2.66 (3H, m), 2.03 (1H, m).

Preparation Tb

N-allyl-2-chloro-7-(2,4-difluorophenyl)-N-methyl-6,7-dihydro-5H-cyclopenta[d]pyrimidin-4-amine

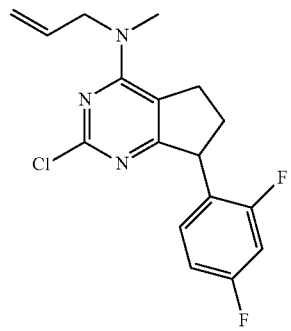 [SMILES: C=CCN(C)c1nc(Cl)nc2c1CCC2c1ccc(F)cc1F]

To a solution of Preparation T (1.4 g, 4.65 mmol) in acetonitrile (25 mL) was added diisopropylethylamine (1.8 g, 13.9 mmol) followed N-methylpro-2-en-1-amine (0.397 g, 5.58 mmol) at room temperature. The reaction mixture was stirred at rt for 18 h. The solvent was removed under reduced pressure and the residue was purified by column chromatography (60-120 mesh silica) using 25% ethyl acetate in pet-ether to give N-allyl-2-chloro-7-(2,4-difluorophenyl)-N-methyl-6,7-dihydro-5H-cyclopenta[d]pyrimidin-4-amine as an off-white solid (0.9 g, 57%). LC-MS (M+H)⁺=336.0. 1H NMR (400 MHz, CDCl₃) δ ppm 6.94-6.91 (1H, m), 6.81-6.76 (2H, m), 5.89-5.83 (1H, m), 5.27-5.17 (2H, m), 4.40 (1H, t, J=8.4 Hz), 3.20 (3H, s), 3.15-3.10 (2H, m), 2.56 (1H, t, J=4.4 Hz).

Preparation Tc 2-(3-(2-chloro-7-(2,4-difluorophenyl)-6,7-dihydro-5H-cyclopenta[d]pyrimidin-4-ylamino)propoxy)-4-nitrobenzonitrile

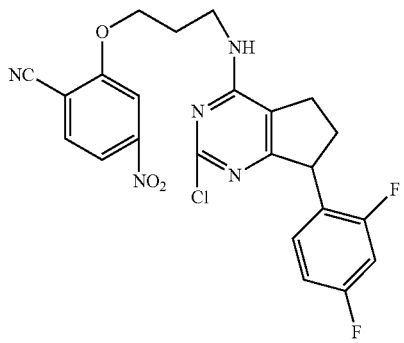 [SMILES: N#Cc1ccc([N+](=O)[O-])cc1OCCCNc1nc(Cl)nc2c1CCC2c1ccc(F)cc1F]

To a solution of Preparation T (1.77 g, 5.88 mmol) in acetonitrile (250 mL) was added diisopropylethylamine (1.51 g, 11.75 mmol) followed by Preparation H (1.30 g, 5.88 mmol) at room temperature. The reaction mixture was stirred at room temperature for 18 h. The solvent was removed under reduced pressure and the residue was purified by column chromatography (60-120 mesh silica) using 10% ethyl acetate in chloroform to give 2-(3-(2-chloro-7-(2,4-difluorophenyl)-6,7-dihydro-5H-cyclopenta[d]pyrimidin-4-ylamino)propoxy)-4-nitrobenzonitrile (1.3 g, 45.5%). LC-MS (M+H)⁺=486.0. 1H NMR (400 MHz, CDCl₃) δ ppm 7.91-7.89 (1H, m), 7.83 (1H, s), 7.76-7.74 (1H, d, J=8.4 Hz), 6.97-6.93 (1H, m), 6.80-6.75 (2H, m), 4.37-4.99 (1H, br s), 4.47-4.45 (1H, m), 3.38-3.35 (2H, m), 3.86-3.82 (2H, m), 2.78-2.67 (3H, m), 2.32-2.29 (2H, m), 2.04-2.03 (1H, m).

Preparation of Td 2-(3-((2-chloro-7-(2,4-difluorophenyl)-6,7-dihydro-5H-cyclopenta[d]pyrimidin-4-yl)(methyl)amino)propoxy)-4-nitrobenzonitrile

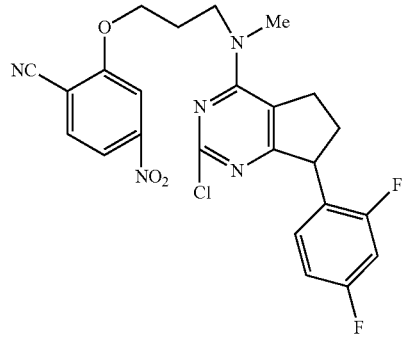 [SMILES: CN(CCCOc1cc([N+](=O)[O-])ccc1C#N)c1nc(Cl)nc2c1CCC2c1ccc(F)cc1F]

To a solution of Preparation T (1.997 g, 6.63 mmol) in acetonitrile (250 mL) was added diisopropylethylamine (1.071 g, 8.29 mmol) followed by Preparation I (1.30 g, 5.53 mmol) at room temperature. The reaction mixture was stirred at room temperature for 18 h. The solvent was removed under reduced pressure and the residue was purified by column chromatography (60-120 mesh silica) using 5% to 10% ethyl acetate in chloroform to give 2-(3-((2-chloro-7-(2,4-difluorophenyl)-6,7-dihydro-5H-cyclopenta[d]pyrimidin-4-yl)(methyl)amino)propoxy)-4-nitrobenzonitrile (1.1 g, 39.8%). LC-MS (M+H)⁺=500.0. 1H NMR (400 MHz, CDCl₃) δ ppm 7.87-7.85 (1H, m), 7.80 (1H, s), 7.71-7.69 (1H, d, J=8.4 Hz), 6.94-6.90 (1H, m), 6.80-6.75 (2H, m), 4.37-4.33 (3H, m), 3.98-3.94 (1H, m), 3.86-3.82 (1H, m), 3.34 (3H, s), 3.26-3.18 (2H, m), 2.59-2.57 (1H, m), 2.29-2.25 (2H, m), 1.95-1.85 (1H, m).

Preparation Te 2-chloro-7-(2,4-difluorophenyl)-N-(3-(2-(3-methyl-1H-1,2,4-triazol-1-yl)-5-nitrophenoxy)propyl)-6,7-dihydro-5H-cyclopenta[d]pyrimidin-4-amine

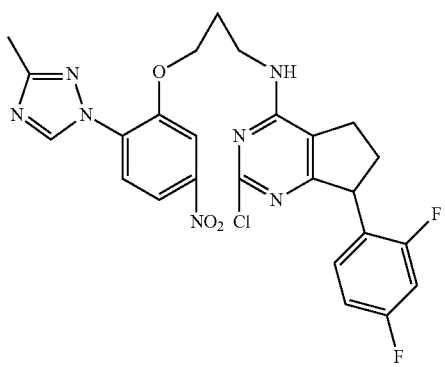 [SMILES: Cc1ncn(-c2ccc([N+](=O)[O-])cc2OCCCNc2nc(Cl)nc3c2CCC3c2ccc(F)cc2F)n1]

To a solution of 2,4-dichloro-7-(2,4-difluorophenyl)-6,7-dihydro-5H-cyclopenta[d]pyrimidine (Preparation T, 0.717 g, 2.38 mmol) in acetonitrile (40 mL) was added diisopropylethylamine (0.420 g, 3.25 mmol) followed by 3-(2-(3-methyl-1H-1,2,4-triazol-1-yl)-5-nitrophenoxy)propan-1-amine (Preparation K, 0.60 g, 2.164 mmol) at room temperature. The reaction mixture was stirred at room temperature for 18 h. The solvent was removed under reduced pressure and the residue was taken in dichloromethane (10 mL) and silica (2 g). The resultant slurry of the compound on silica was subjected to flash chromatography using a Teledyne Isco instrument (12 g RediSep silica column, 50% ethyl acetate in pet-ether) to get 2-chloro-7-(2,4-difluorophenyl)-N-(3-(2-(3-methyl-1H-1,2,4-triazol-1-yl)-5-nitrophenoxy)propyl)-6,7-dihydro-5H-cyclopenta[d]pyrimidin-4-amine (0.65 g, 55.4%) as a light yellow solid. LC-MS (M+H)$^+$=542.0. $^1$H NMR (400 MHz, CDCl$_3$) δ ppm 8.95 (1H, s), 8.05-7.93 (3H, m), 6.95-6.77 (3H, m), 4.86 (1H, br s), 4.86-4.85 (1H, m), 4.37-4.34 (2H, m), 3.75-3.75 (2H, s), 2.69-2.50 (3H, m), 2.50 (3H, s), 2.29-2.26 (2H, m), 2.01-1.98 (1H, m).

Preparation Tf 2-chloro-N-(3-(2-(4-chloro-1H-imidazol-1-yl)-5-nitrophenoxy)propyl)-7-(2,4-difluorophenyl)-N-methyl-6,7-dihydro-5H-cyclopenta[d]pyrimidin-4-amine

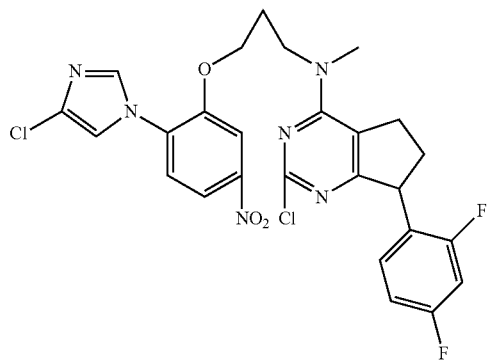 [SMILES: CN(CCCOc1cc([N+](=O)[O-])ccc1-n1cnc(Cl)c1)c1nc(Cl)nc2c1CCC2c1ccc(F)cc1F]

To a solution of Preparation R (1.31 g, 4.38 mmol) in acetonitrile (300 mL) was added diisopropylethylamine (1.13 g, 8.75 mmol) followed by Preparation G (1.36 g, 4.38 mmol) at room temperature. The reaction mixture was stirred at room temperature for 18 h. The solvent was removed under reduced pressure and the residue was purified by column chromatography (60-120 mesh silica) using 15-20% ethyl acetate in pet-ether to give 2-chloro-N-(3-(2-(4-chloro-1H-imidazol-1-yl)-5-nitrophenoxy)propyl)-7-(2,4-difluorophenyl)-N-methyl-6,7-dihydro-5H-cyclopenta[d]pyrimidin-4-amine (1.6 g, 63.5%). LC-MS (M+H)$^+$=576.0. 1H NMR (400 MHz, CDCl$_3$) δ ppm 7.96-7.93 (1H, m), 7.91 (1H, s), 7.78 (1H, s), 7.42 (1H, d, J=8.8 Hz), 7.21 (1H, s), 6.94-6.90 (1H, m), 6.80-6.75 (2H, m), 4.37 (1H, t, J=8.4 Hz), 4.29-4.26 (2H, m), 3.88-3.84 (1H, m), 3.67-3.64 (1H, m), 3.23 (3H, s), 3.15-3.06 (2H, m), 2.58-2.56 (1H, m), 2.19-2.04 (2H, m), 1.95-1.85 (1H, m).

Preparation Tg 2-chloro-7-(2,4-difluorophenyl)-N-(5-(2-(3-methyl-1H-1,2,4-triazol-1-yl)-5-nitrophenoxy)pentan-2-yl)-6,7-dihydro-5H-cyclopenta[d]pyrimidin-4-amine

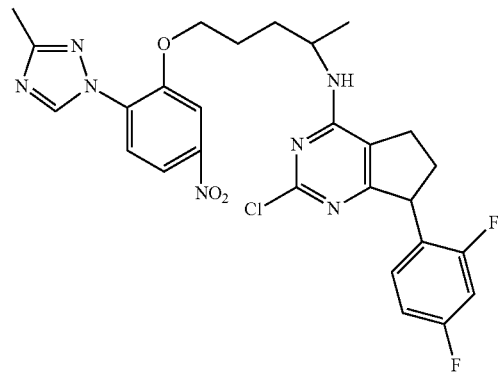 [SMILES: Cc1ncn(-c2ccc([N+](=O)[O-])cc2OCCCC(C)Nc2nc(Cl)nc3c2CCC3c2ccc(F)cc2F)n1]

To a solution of 2,4-dichloro-7-(2,4-difluorophenyl)-6,7-dihydro-5H-cyclopenta[d]pyrimidine (907 mg, 3.01 mmol) in acetonitrile (150 mL) was added diisopropylethylamine (1.05 g, 6.03 mmol) followed by 5-(2-(3-methyl-1H-1,2,4-triazol-1-yl)-5-nitrophenoxy)pentan-2-amine (920 mg, 3.01 mmol) at room temperature. The reaction mixture was stirred at rt for 18 h while monitoring by LC-MS. The solvent was removed under reduced pressure and the residue was purified by column chromatography (60-120 mesh silica) using 2-3% of methanol in chloroform to give 2-chloro-7-(2,4-difluorophenyl)-N-(5-(2-(3-methyl-1H-1,2,4-triazol-1-yl)-5-nitrophenoxy)pentan-2-yl)-6,7-dihydro-5H-cyclopenta[d]pyrimidin-4-amine as a yellow solid (650 mg, 1.140 mmol, 37.8% yield). LC-MS (M+H)$^+$=570.0. 1H NMR: (400 MHz, CDCl$_3$) δ ppm 8.85 (1H, s), 8.07 (1H, d, J=8.4 Hz), 8.00-7.96 (2H, m), 7.00-6.97 (1H, m), 6.81-6.78 (2H, m), 4.47-4.31 (5H, m), 2.72-2.64 (3H, m), 2.50 (3H, s), 2.04-1.98 (3H, m), 1.78-1.74 (2H, m), 1.32-1.25 (3H, m).

Preparation U 2,4-dichloro-7-(4-fluorophenyl)-7-methyl-6,7-dihydro-5H-cyclopenta[d]pyrimidine

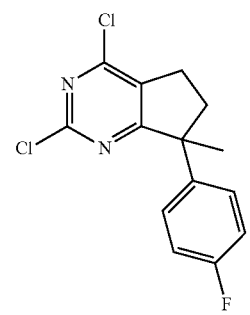 [SMILES: CC1(c2ccc(F)cc2)CCc2c(Cl)nc(Cl)nc21]

To a solution of 2,4-dichloro-7-(4-fluorophenyl)-6,7-dihydro-5H-cyclopenta[d]pyrimidine, (Preparation S, 3.56 g, 12.57 mmol) in DME (Volume: 84 mL) at −78° C. was added KHMDS (0.91 M in THF, 15.20 ml, 13.83 mmol) dropwise. After 10 min, MeI (2.36 mL, 37.7 mmol) was added. The reaction was kept at −78° C. for 10 min, then allowed to come to rt. An aliquot taken while the reaction was still cool was quenched with water and extracted with EtOAc. TLC (10% EtOAc/Hex) and LC/MS showed the clean conversion to a new product. The bulk of the material was then quenched and extracted as above. The combined organic extracts were dried over MgSO4, filtered, and the solvent removed in vacuo. SG chromatography (0 to 40% EtOAc/Hex) gave 2,4-dichloro-7-(4-fluorophenyl)-7-methyl-6,7-dihydro-5H-cyclopenta[d]pyrimidine (3.01 g, 10.13 mmol, 81% yield). LC-MS (*M*+H)$^+$=293.1 (*product reacts with methanol during analysis*). $^1$H NMR (500 MHz, CDCl$_3$) δ ppm 7.21-7.29 (2H, m), 6.96-7.04 (2H, m), 2.88-3.02 (2H, m), 2.62 (1H, ddd, J=13.28, 7.93, 5.04 Hz), 2.26-2.35 (1H, m), 1.68 (3H, s).

Preparation Ua

N-allyl-2-chloro-7-(4-fluorophenyl)-7-methyl-6,7-dihydro-5H-cyclopenta[d]pyrimidin-4-amine

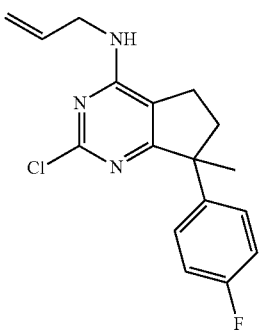 [SMILES: C=CCNc1nc(Cl)nc2c1CCC2(C)c1ccc(F)cc1]

To a solution of 2,4-dichloro-7-(4-fluorophenyl)-7-methyl-6,7-dihydro-5H-cyclopenta[d]pyrimidine (Preparation U, 1.00 g, 3.37 mmol) in DCM (13.46 mL) was added DIPEA (1.176 ml, 6.73 mmol), then allylamine (0.303 ml, 4.04 mmol). The reaction solution was allowed to stir at rt. The reaction was concentrated in vacuo. The residue was applied to silica gel and eluted with a 0 to 50% EtOAc/Hexane gradient to afford N-allyl-2-chloro-7-(4-fluorophenyl)-7-methyl-6,7-dihydro-5H-cyclopenta[d]pyrimidin-4-amine (896.2 mg, 2.82 mmol, 84% yield) as a white solid. LC-MS (M+H)$^+$=316.2. $^1$H NMR (500 MHz, CDCl$_3$) δ ppm 7.18-7.23 (2H, m), 6.91-6.98 (2H, m), 5.90-6.00 (1H, m), 5.26 (1H, dd, J=17.2, 1.4 Hz), 5.20 (1H, dd, J=10.1, 1.2 Hz), 4.62 (1H, br. s), 4.17 (1H, td, J=5.7, 1.7 Hz), 2.56-2.62 (2H, m), 2.43-2.50 (1H, m), 2.19-2.28 (1H, m), 1.63 (3H, s).

Preparation V 2,4-dichloro-8-(4-fluorophenyl)-6-methyl-5,6,7,8-tetrahydropyrido[4,3-d]pyrimidine

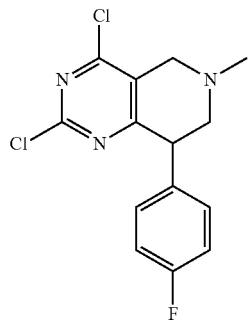 [SMILES: CN1Cc2c(Cl)nc(Cl)nc2C(c2ccc(F)cc2)C1]

Intermediate V(1)

ethyl 2-cyano-2-(4-fluorophenyl)acetate

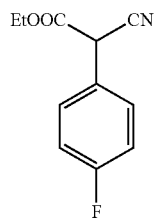

To a solution of sodium hydride (4.2 g, 177.7 mmol) in THF was added 4-fluoro phenyl acetonitrile (10 g, 74.0 mmol) at −10° C. The reaction mixture was stirred for 15 min at the same temperature. Diethyl carbonate (10.5 g, 88.0 mmol) was added to the reaction mixture and the reaction mixture was allowed to come to room temperature and heated to 40° C. (Caution: Reaction will start suddenly and exothermic). The heating path was removed immediately once the reaction was started and the reaction mixture was cooled under ice/acetone. The solution was allowed to come to room temperature and stirred for 1 h. The reaction mass was cooled to 0° C. and quenched with aqueous saturated ammonium chloride and extracted with ethyl acetate (50 mL×3). The combined organic layer was washed with water (50 mL), brine solution (50 mL), dried over anhydrous Na$_2$SO$_4$ and evaporated under reduced pressure to give ethyl 2-cyano-2-(4-fluorophenyl)acetate as crude compound as crude compound (10 g). The crude compound was taken to the next step without further purification. LC-MS (M−H)$^+$=206.2. $^1$H NMR (400 MHz, CDCl₃) δ ppm 7.44 (2H, m), 7.11 (2H, m), 4.69 (1H, s), 4.27-4.22 (2H, q, J=7.2 Hz). 1.26 (3H, m)

Intermediate V(2)

ethyl 3-amino-2-(4-fluorophenyl)propanoate

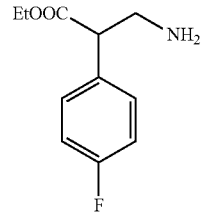 [SMILES: CCOC(=O)C(CN)c1ccc(F)cc1]

To a solution of Intermediate V(1) (10.0 g, 40.0 mmol) in acetic acid was added palladium on carbon (10%, w/w) followed by H₂SO₄ (0.5 vol., 5 mL) at room temperature. The reaction mixture was hydrogenated under 5 kg of hydrogen pressure for 18 h. The reaction mixture was filtered through celite bed and washed with methanol. The filtrate was evaporated under reduced pressure and the residue was neutralized with aqueous saturated bicarbonate solution. The aqueous solution was extracted with ethyl acetate (100 mL×4). The combined organic layer was washed with brine solution (100 mL), dried over anhydrous Na₂SO₄ and evaporated under reduced pressure to get crude compound. The crude compound was purified by column chromatography (Silica gel, 60-120 mesh) using 10% methanol in dichloromethane as mobile phase to give ethyl 3-amino-2-(4-fluorophenyl)propanoate (6.0 g, 59%) as oily liquid. LC-MS (M+H)⁺=212.2. ¹H NMR (400 MHz, CDCl₃): δ ppm 7.26-7.22 (2H, m), 7.04-6.98 (2H, m), 4.15 (2H, m), 3.66 (1H, m), 3.28 (1H, m), 2.99 (1H, m). 1.20 (3H, m).

Intermediate V(3)

ethyl 3-(3-ethoxy-3-oxopropylamino)-2-(4-fluorophenyl)propanoate

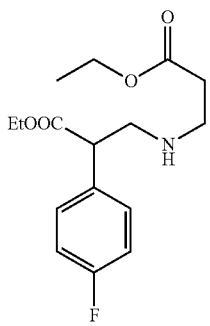 [SMILES: CCOC(=O)CCNCC(C(=O)OCC)c1ccc(F)cc1]

To a solution of Intermediate V(2) (3.0 g, 14.0 mmol) in ethanol was added ethyl acrylate (1.7 g, 17.0 mmol) at room temperature. The reaction mixture was stirred at the same temperature for 18 h. The solvent was evaporated under reduced pressure and the crude compound was purified by column chromatography (Silica gel, 60-120 mesh) using 50% ethyl acetate in pet-ether as mobile phase to give ethyl 3-(3-ethoxy-3-oxopropylamino)-2-(4-fluorophenyl)propanoate (2.5 g, 60%) as yellowish oily liquid. LC-MS (M+H)⁺=313.2. ¹H NMR (400 MHz, CDCl₃): δ ppm 7.27-7.21 (2H, m), 7.03-6.97 (2H, m), 4.13 (4H, m), 3.77 (1H, m), 3.23 (1H, m), 2.89 (3H, m), 2.48 (2H, m). 1.22 (6H, m).

Intermediate V(4)

ethyl 3-((3-ethoxy-3-oxopropyl)(4-methoxybenzyl)amino)-2-(4-fluorophenyl)propanoate

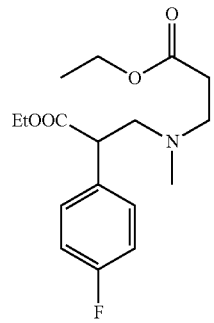 [SMILES: CCOC(=O)CCN(C)CC(C(=O)OCC)c1ccc(F)cc1]

To a solution of Intermediate V(3) (12.0 g, 38.5 mmol) in acetone was added K₂CO₃ (6.38 g, 46.3 mmol) followed by methyl iodide (6.5 g, 46.3 mmol) at 0° C. The reaction mixture was stirred at room temperature for 2 h. The solvent was removed under reduced pressure and the residue was diluted with water. The aqueous layer was extracted with ethyl acetate (50×3). The combined organic layer was washed with brine solution (75 mL), dried over anhydrous Na₂SO₄ and evaporated under reduced pressure to get crude compound. The crude compound was purified by column chromatography (Silica gel, 60-120 mesh) using 20% ethyl acetate in pet-ether as mobile phase to give ethyl 3-((3-ethoxy-3-oxopropyl)(methyl)amino)-2-phenylpropanoate (6.0 g, 50%) as oily liquid. LC-MS (M+H)⁺=326.2. ¹H NMR (400 MHz, CDCl₃): δ ppm 7.01 (2H, m), 6.98, (2H, m), 4.16-4.07 (4H, m), 3.77 (1H, m), 3.13 (1H, t, J=2.4 Hz), 2.75-2.51 (5H, m), 2.17 (3H, s), 1.26-1.19 (6H, m).

Intermediate V(5)

ethyl 5-(4-fluorophenyl)-1-methyl-4-oxopiperidine-3-carboxylate

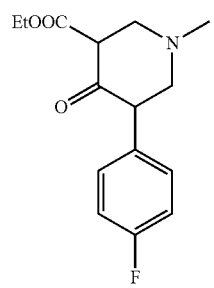 [SMILES: CCOC(=O)C1CN(C)CC(c2ccc(F)cc2)C1=O]

To a cooled solution of Intermediate V(4) (6.0 g, 18.4 mmol) in THF was added t-BuOK (4.1 g, 36.9 mmol). The reaction mixture was stirred at room temperature for 2 h. The reaction mass was quenched with water then evaporated the solvent under reduced pressure. The residue was diluted with water and extracted with ethyl acetate (25 mL×4). The combined organic layer was washed with brine solution (30 mL), dried over anhydrous Na$_2$SO$_4$ and evaporated under reduced pressure to get crude compound. The crude compound was purified by column chromatography (Silica gel, 60-120 mesh) using 20% ethyl acetate in pet-ether as mobile phase to give ethyl 5-(4-fluorophenyl)-1-methyl-4-oxopiperidine-3-carboxylate (3.0 g, 51%) as oily liquid. LC-MS (M+H)$^+$ =278.2. $^1$H NMR (400 MHz, DMSO-d6): δ ppm 7.35 (1H, m), 7.15 (1H, m), 7.12 (1H, m), 6.98 (1H, m), 4.01 (2H, m), 3.88 (1H, m), 2.60 (1H, m), 2.38 (2H, m), 2.19 (3H, s), 1.19-1.08 (3H, m).

Intermediate V(6)

8-(4-fluorophenyl)-6-methyl-5,6,7,8-tetrahydropyrido[4,3-d]pyrimidine-2,4(1H,3H)-dione

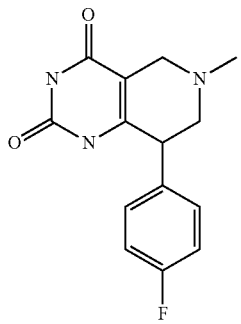 [SMILES: CN1Cc2c([nH]c(=O)[nH]c2=O)C(c2ccc(F)cc2)C1]

To a cooled solution of Intermediate V(5) (3.0 g, 10.75 mmol) in ethanol was added t-BuOK (3.0 g 26.8 mmol) followed by urea (1.6 g, 26.8 mmol). The reaction mixture was heated at reflux for 36 h. The reaction mass was quenched with water and evaporated the solvent under reduced pressure. The residue was diluted with water and extracted with ethyl acetate (25 mL×3). The combined organic layer was washed with brine solution (30 mL), dried over Na$_2$SO$_4$ and evaporated under reduced pressure to get crude compound. The crude compound was purified by column chromatography (Silica gel, 60-120 mesh) using 100% ethyl acetate as mobile phase to give 8-(4-fluorophenyl)-6-methyl-5,6,7,8-tetrahydropyrido[4,3-d]pyrimidine-2,4(1H,3H)-dione (1.5 g, 51%) as pale yellow solid. LC-MS (M+H)$^+$=276.0. $^1$H NMR (400 MHz, DMSO-d6): δ ppm 11.08 (1H, s), 10.59 (1H, s), 7.31 (2H, m), 7.13 (2H, m), 3.74 (1H, m), 3.17 (1H, m), 2.80-2.59 (2H, m), 2.23 (3H, s).

Preparation V 2,4-dichloro-8-(4-fluorophenyl)-6-methyl-5,6,7,8-tetrahydropyrido[4,3-d]pyrimidine

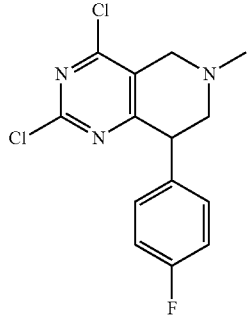 [SMILES: CN1Cc2c(Cl)nc(Cl)nc2C(c2ccc(F)cc2)C1]

A solution of Intermediate V(6) (1.5 g, 5.45 mmol) and catalytic amount of DMF in POCl$_3$ (20 vol.) was heated at reflux for 10 h. The excess of POCl$_3$ was evaporated under reduced pressure. The residue was poured in to crushed ice and stirred for 15 min. The aqueous solution was extracted with ethyl acetate (20 mL×2). The combined organic layer was washed with aqueous saturated NaHCO$_3$ (10 mL×2), brine solution (10 mL), dried over anhydrous Na$_2$SO$_4$ and evaporated under reduced pressure to give 2,4-dichloro-8-(4-fluorophenyl)-6-methyl-5,6,7,8-tetrahydropyrido[4,3-d]pyrimidine (0.7 g, 56%) as brown solid. LC-MS (M+H)$^+$ =312.2.

Preparation Va 2-chloro-8-(4-fluorophenyl)-6-methyl-N-(4-(2-(3-methyl-1H-1,2,4-triazol-1-yl)-5-nitrophenoxy)butyl)-5,6,7,8-tetrahydropyrido[4,3-d]pyrimidin-4-amine, TFA salt

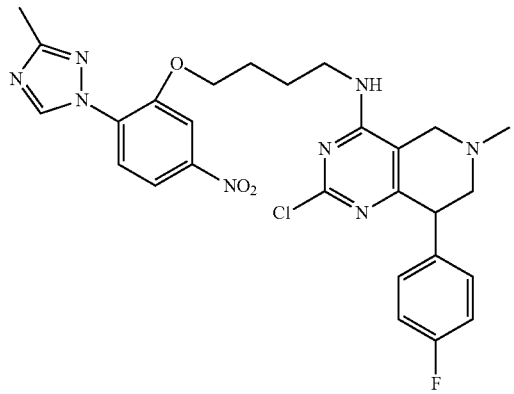 [SMILES: Cc1ncn(-c2ccc([N+](=O)[O-])cc2OCCCCNc2nc(Cl)nc3c2CN(C)CC3c2ccc(F)cc2)n1]

The mixture of 4-(2-(3-methyl-1H-1,2,4-triazol-1-yl)-5-nitrophenoxy)butan-1-amine, 2 TFA (46.6 mg, 0.090 mmol), 2,4-dichloro-8-(4-fluorophenyl)-6-methyl-5,6,7,8-tetrahydropyrido[4,3-d]pyrimidine (20 mg, 0.064 mmol) and DIEA (55.9 μL, 0.320 mmol) in acetonitrile (320 μL) and 2 drops of MeOH was stirred at rt overnight. The crude product was purified by Prep-HPLC to obtain 2-chloro-8-(4-fluorophenyl)-6-methyl-N-(4-(2-(3-methyl-1H-1,2,4-triazol-1-yl)-5-nitrophenoxy)butyl)-5,6,7,8-tetrahydropyrido[4,3-d]pyrimidin-4-amine, 2 TFA (43.6 mg, 82% yield). LC-MS (M+H)$^+$ =567.2. $^1$H NMR (500 MHz, methanol-d$_4$) δ 9.00 (s, 1H), 8.06 (d, J=2.1 Hz, 1H), 8.03-7.95 (m, 2H), 7.21-7.12 (m, 2H), 7.04-6.96 (m, 2H), 4.39 (t, J=6.3 Hz, 2H), 4.00 (s, 1H), 3.60-3.52 (m, 2H), 3.42-3.23 (m, 2H), 2.94 (dd, J=11.7, 5.4 Hz, 1H), 2.68 (dd, J=11.7, 6.0 Hz, 1H), 2.48-2.39 (m, 6H), 1.99 (t, J=6.8 Hz, 2H), 1.84 (td, J=7.2, 3.4 Hz, 2H).

Preparation Vb 4-amino-2-(4-(2-chloro-8-(4-fluorophenyl)-6-methyl-5,6,7,8-tetrahydropyrido[4,3-d]pyrimidin-4-ylamino)butoxy)benzonitrile

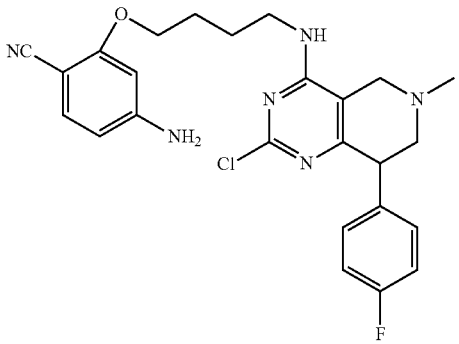 [SMILES: CN1Cc2c(NCCCCOc3cc(N)ccc3C#N)nc(Cl)nc2C(c2ccc(F)cc2)C1]

A mixture of 4-amino-2-(4-aminobutoxy)benzonitrile, 2 TFA salt (Preparation X, 23.32 mg, 0.054 mmol), 2,4-dichloro-8-(4-fluorophenyl)-6-methyl-5,6,7,8-tetrahydropyrido[4,3-d]pyrimidine (Preparation V, 14 mg, 0.045 mmol) and DIEA (39.2 μL, 0.224 mmol) in acetonitrile (224 μL) was stirred at rt for 4 h. The crude product was purified by Prep-HPLC to obtain 4-amino-2-(4-((2-chloro-8-(4-fluorophenyl)-6-methyl-5,6,7,8-tetrahydropyrido[4,3-d]pyrimidin-4-yl)amino)butoxy)benzonitrile, (5.0 mg, 15.72% yield). LC-MS (M+Na)$^+$=481.2. $^1$H NMR (500 MHz, methanol-d$_4$) δ 7.26-7.18 (m, 3H), 7.16-7.08 (m, 2H), 6.33 (d, J=2.0 Hz, 1H), 6.28 (dd, J=8.5, 1.9 Hz, 1H), 4.45 (dd, J=10.5, 6.3 Hz, 1H), 4.30 (d, J=11.6 Hz, 2H), 4.10 (t, J=5.6 Hz, 2H), 3.89 (dd, J=12.4, 6.3 Hz, 1H), 3.70-3.52 (m, 3H), 3.18-3.08 (m, 3H), 2.01-1.80 (m, 4H).

Preparation Vc

N-allyl-2-chloro-8-(4-fluorophenyl)-N,6-dimethyl-5,6,7,8-tetrahydropyrido[4,3-d]pyrimidin-4-amine

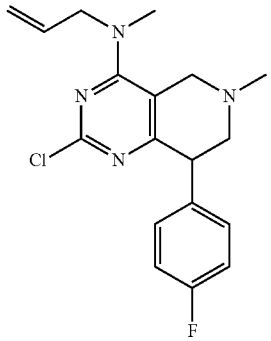 [SMILES: C=CCN(C)c1nc(Cl)nc2c1CN(C)CC2c1ccc(F)cc1]

The mixture of 2,4-dichloro-8-(4-fluorophenyl)-6-methyl-5,6,7,8-tetrahydropyrido[4,3-d]pyrimidine (Preparation V, 408 mg, 1.307 mmol) in NMP (13 mL) was added N-methylprop-2-en-1-amine (465 mg, 6.53 mmol). The resulting reaction mixture was stirred at rt overnight. Water (50 mL) was added to the mixture and stirred for 30 min. The mixture was filtered to get a light tan solid which was dried and purified by flash column chromatography eluting with 30 to 100% EtOAc/Hexane to get N-allyl-2-chloro-8-(4-fluorophenyl)-N,6-dimethyl-5,6,7,8-tetrahydropyrido[4,3-d]pyrimidin-4-amine (453 mg, 100% yield). LC-MS (M+H)$^+$ =347.1.

Preparation W 4-(2-(3-methyl-1H-1,2,4-triazol-1-yl)-5-nitrophenoxy)butan-1-amine, TFA salt

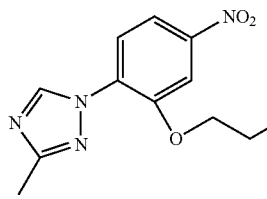

Intermediate W(1)

tert-butyl 4-(2-(3-methyl-1H-1,2,4-triazol-1-yl)-5-nitrophenoxy)butylcarbamate

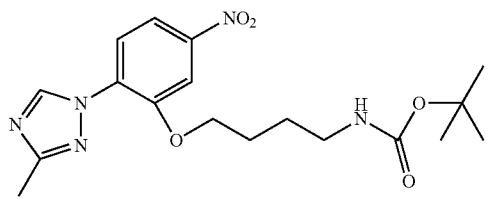 [SMILES: Cc1ncn(-c2ccc([N+](=O)[O-])cc2OCCCCNC(=O)OC(C)(C)C)n1]

Sodium hydride (0.405 g, 10.13 mmol) was suspended in THF (6 mL), and then tert-butyl-(4-hydroxybutyl)carbamate (1.278 g, 6.75 mmol) in THF (6.0 mL) was added. The reaction mixture was stirred at 0° C. for 10 min, followed by the addition of 1-(2-fluoro-4-nitrophenyl)-3-methyl-1H-1,2,4-triazole (1.0 g, 4.50 mmol) in THF (10.0 mL). The mixture was stirred at 0° C. for 1 h and then stirred for an additional 2 h at rt. The reaction was quenched with water and extracted with EtOAc three times. After concentrating the combined EtOAc layers, the residue was purified by flash chromatography (silica gel, 300 g, 0 to 80% EtOAc/Hexane) to get tert-butyl (4-(2-(3-methyl-1H-1,2,4-triazol-1-yl)-5-nitrophenoxy)butyl)carbamate (1.75 g, 99% yield). LC-MS $(M+Na)^+$ =414.5. $^1$H NMR (500 MHz, chloroform-d) δ 8.88 (s, 1H), 8.10 (d, J=8.8 Hz, 1H), 8.00 (dd, J=8.9, 2.3 Hz, 1H), 7.95 (d, J=2.3 Hz, 1H), 4.28 (t, J=6.5 Hz, 2H), 3.22 (d, J=6.4 Hz, 2H), 2.52 (s, 3H), 2.01-1.92 (m, 2H), 1.74-1.68 (m, 2H), 1.46 (s, 9H).

Preparation W 4-(2-(3-methyl-1H-1,2,4-triazol-1-yl)-5-nitrophenoxy)butan-1-amine, TFA salt

The solution of tert-butyl (4-(2-(3-methyl-1H-1,2,4-triazol-1-yl)-5-nitrophenoxy)butyl)carbamate (515 mg, 1.316 mmol) in $CH_2Cl_2$ (4 mL) was treated with TFA (2 mL, 26.0 mmol) at 0° C. The mixture was stirred at rt for 2 h. The reaction mixture was concentrated in vacuo and the residue was triturated with ether to yield a white solid, which was collected by filtration to get 4-(2-(3-methyl-1H-1,2,4-triazol-1-yl)-5-nitrophenoxy)butan-1-amine, TFA (440 mg, 83% yield). LC-MS $(M+H)^+$=292.4. $^1$H NMR (500 MHz, methanol-$d_4$) δ 8.99 (s, 1H), 8.11 (d, J=1.5 Hz, 1H), 8.05 (dd, J=2.1, 1.3 Hz, 2H), 4.38 (t, J=6.2 Hz, 2H), 3.07-2.94 (m, 2H), 2.48 (s, 3H), 2.02 (dd, J=8.8, 6.3 Hz, 2H), 1.84 (d, J=7.5 Hz, 2H).

Preparation X 4-amino-2-(4-aminobutoxy)benzonitrile

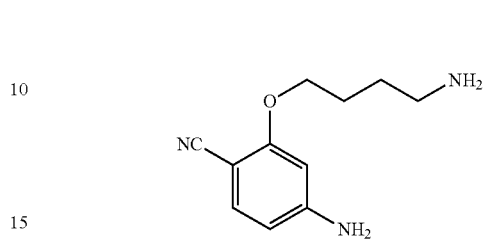

The mixture of 2-(4-aminobutoxy)-4-nitrobenzonitrile, TFA salt (Preparation O, 25 mg, 0.072 mmol) and hydrazine (112 μL, 3.58 mmol) in ethanol (358 μL) was heated at 50° C. for 4.5 h. The crude product was purified by Prep-HPLC to obtain 4-amino-2-(4-aminobutoxy)benzonitrile, 2 TFA salt (23 mg, 74.2% yield). LC-MS $(M+H)^+$=206.1

Preparation Y 4-amino-1-(2-(3-methyl-1H-1,2,4-triazol-1-yl)-5-nitrophenoxy)butan-2-ol

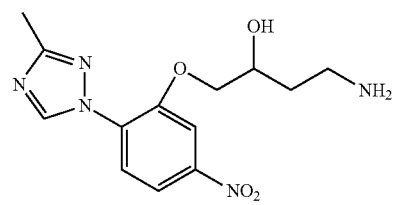

Intermediate Y(1)

2-(3,4-dihydroxybutyl)isoindoline-1,3-dione

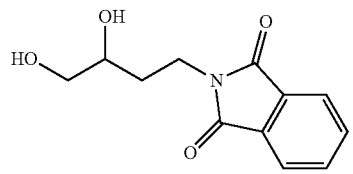 [SMILES: O=C1c2ccccc2C(=O)N1CCC(O)CO]

To a solution of 2-(but-3-enyl)isoindoline-1,3-dione (5.20 g, 25.8 mmol) in THF (86 mL) was added 4-methylmorpholine 4-oxide (4.54 g, 38.8 mmol) followed by osmium(VIII) oxide in water (3.16 mL, 0.517 mmol) dropwise. The reaction mixture was stirred at rt for 6 h. A saturated $Na_2S_2SO_3$ solution was added to the reaction mixture and stirred for another 10 min. The aqueous layer was separated and extracted with EtOAc three times, and the combined organic layers were washed with water, brine and dried over $Na_2SO_4$. The solids were filtered off, and the filtrate was concentrated in vacuo to get 2-(3,4-dihydroxybutyl)isoindoline-1,3-dione which was used as-is in the next step. LC-MS $(M+Na)^+$=258.1. $^1$H NMR (500 MHz, methanol-$d_4$) δ 7.92-7.85 (m, 2H), 7.85-7.75 (m, 2H), 3.91-3.75 (m, 2H), 3.65 (dtd, J=9.1, 5.5, 3.7 Hz, 1H), 3.55-3.43 (m, 2H), 1.95-1.85 (m, 1H), 1.80-1.65 (m, 1H).

Intermediate Y(2)

2-(3-hydroxy-4-(2-(3-methyl-1H-1,2,4-triazol-1-yl)-5-nitrophenoxy)butylcarbamoyl)benzoic acid

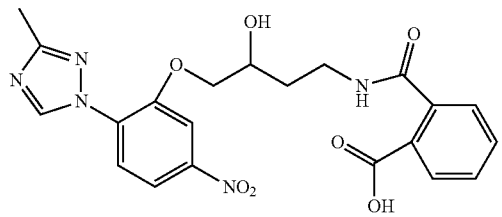 [SMILES: Cc1ncn(-c2ccc([N+](=O)[O-])cc2OCC(O)CCNC(=O)c2ccccc2C(=O)O)n1]

Sodium hydride (0.827 g, 20.67 mmol) was suspended in THF (10 mL), and then 2-(3,4-dihydroxybutyl)isoindoline-1,3-dione (3.24 g, 13.78 mmol) in THF (20.0 mL) was added. This reaction mixture was stirred at 0° C. for 10 min, followed by the addition of 1-(2-fluoro-4-nitrophenyl)-3-methyl-1H-1,2,4-triazole (2.041 g, 9.19 mmol) in THF (16.0 mL). The mixture was stirred at 0° C. for 1 h and then stirred for an additional 2 h at rt. The reaction was quenched with water and washed with EtOAc. The aqueous layer was acidified to pH 2~4 and then extracted with EtOAc. The combined EtOAc layers were concentrated in vacuo to get 2-(3-hydroxy-4-(2-(3-methyl-1H-1,2,4-triazol-1-yl)-5-nitrophenoxy)butylcarbamoyl)benzoic acid, which is used as-is in the next step. LC-MS (M+H)$^+$=456.1. $^1$H NMR (500 MHz, methanol-d$_4$) δ 9.31 (s, 1H), 8.15-8.01 (m, 3H), 7.86-7.76 (m, 2H), 7.51-7.46 (m, 2H), 4.43-4.42 (m, 1H), 4.29-4.27 (m, 1H), 3.91-3.87 (m, 1H), 3.63-3.47 (m, 2H), 2.47 (s, 3H), 2.05-1.98 (m, 1H), 1.87-1.84 (m, 1H).

Intermediate Y(3)

2-(3-hydroxy-4-(2-(3-methyl-1H-1,2,4-triazol-1-yl)-5-nitrophenoxy)butyl)isoindoline-1,3-dione

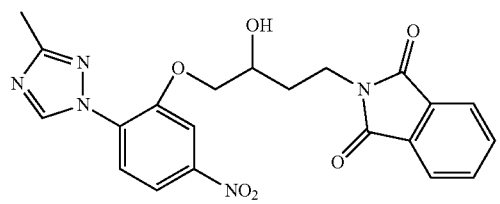 [SMILES: Cc1ncn(-c2ccc([N+](=O)[O-])cc2OCC(O)CCN2C(=O)c3ccccc3C2=O)n1]

A mixture of 2-(3-hydroxy-4-(2-(3-methyl-1H-1,2,4-triazol-1-yl)-5-nitrophenoxy)butylcarbamoyl)benzoic acid (2.56 g, 5.62 mmol) and hydrogen chloride in dioxane (42.2 mL, 169 mmol) was heated at 100° C. for 45 min. The reaction was cooled to rt, and then extracted with EtOAc. The combined organic layers were concentrated to get 2-(3-hydroxy-4-(2-(3-methyl-1H-1,2,4-triazol-1-yl)-5-nitrophenoxy)butyl)isoindoline-1,3-dione which was used as-is in the next step. LC-MS (M+H)$^+$=438.2. $^1$H NMR (500 MHz, methanol-d$_4$) δ 9.26 (s, 1H), 8.13-7.97 (m, 3H), 7.87-7.83 (m, 2H), 7.83-7.77 (m, 2H), 4.36 (dd, J=9.9, 3.5 Hz, 1H), 4.27 (dd, J=9.8, 6.1 Hz, 1H), 4.12 (dt, J=6.0, 2.9 Hz, 1H), 3.95-3.81 (m, 2H), 2.48 (s, 3H), 2.08-1.87 (m, 2H).

Preparation Y 4-amino-1-(2-(3-methyl-1H-1,2,4-triazol-1-yl)-5-nitrophenoxy)butan-2-ol

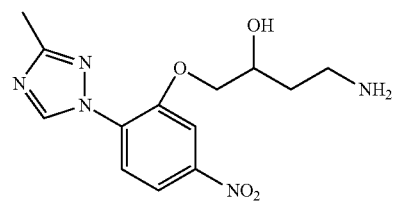 [SMILES: Cc1ncn(-c2ccc([N+](=O)[O-])cc2OCC(O)CCN)n1]

To a mixture of 2-(3-hydroxy-4-(2-(3-methyl-1H-1,2,4-triazol-1-yl)-5-nitrophenoxy)butyl)isoindoline-1,3-dione (2.458 g, 5.62 mmol) in EtOH (28.1 mL) was added hydrazine (8.82 mL, 281 mmol). The mixture was heated at 50° C. for 1.5 h. The reaction mixture was cooled to rt and filtered. The filtrate was concentrated and taken up in CH$_2$Cl$_2$. Again, the solid was filtered off, and the filtrate was concentrated and purified by Prep-HPLC to obtain 4-amino-1-(2-(3-methyl-1H-1,2,4-triazol-1-yl)-5-nitrophenoxy)butan-2-ol (1.4 g, 81% yield). LC-MS (M+H)$^+$=308.2 $^1$H NMR (500 MHz, methanol-d$_4$) δ 9.25 (s, 1H), 8.12 (d, J=2.1 Hz, 1H), 8.10-7.98 (m, 2H), 4.39-4.26 (m, 2H), 4.26-4.15 (m, 1H), 3.25-3.08 (m, 2H), 2.48 (s, 3H), 2.05-1.86 (m, 2H).

Preparation Ya 4-(2-chloro-7-(4-fluorophenyl)-6,7-dihydro-5H-cyclopenta[d]pyrimidin-4-ylamino)-1-(2-(3-methyl-1H-1,2,4-triazol-1-yl)-5-nitrophenoxy)butan-2-ol

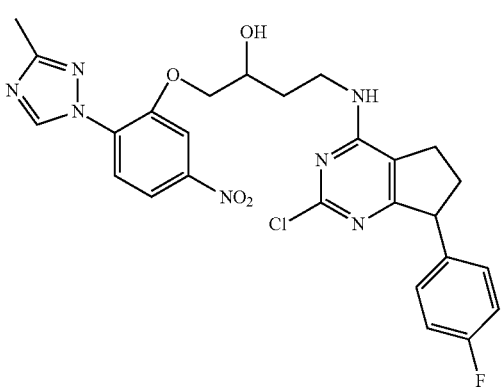 [SMILES: Cc1ncn(-c2ccc([N+](=O)[O-])cc2OCC(O)CCNc2nc(Cl)nc3c2CCC3c2ccc(F)cc2)n1]

The mixture of 4-amino-1-(2-(3-methyl-1H-1,2,4-triazol-1-yl)-5-nitrophenoxy)butan-2-ol, TFA salt (1.4 g, 3.32 mmol), 2,4-dichloro-7-(4-fluorophenyl)-6,7-dihydro-5H-cyclopenta[d]pyrimidine (1.223 g, 4.32 mmol) and N-ethyl-N-isopropylpropan-2-amine (2.321 mL, 13.29 mmol) in acetonitrile (16.61 mL) was stirred at rt overnight. The reaction mixture was concentrated and purified by flash column chromatography eluting with 5 to 25% MeOH/CH$_2$Cl$_2$ to get 4-(2-chloro-7-(4-fluorophenyl)-6,7-dihydro-5H-cyclopenta[d]pyrimidin-4-ylamino)-1-(2-(3-methyl-1H-1,2,4-triazol- 1-yl)-5-nitrophenoxy)butan-2-ol (791 mg, 43.0% yield). LC-MS (M+H)⁺=554.3. ¹H NMR (500 MHz, chloroform-d) δ 9.08-9.02 (m, 1H), 8.10-7.93 (m, 3H), 7.18-6.97 (m, 5H), 5.23 (t, J=6.4 Hz, 1H), 4.36-4.23 (m, 3H), 4.19-4.06 (m, 2H), 3.52 (dt, J=14.5, 5.1 Hz, 1H), 2.83-2.65 (m, 3H), 2.54-2.48 (m, 3H), 2.16-2.09 (m, 1H), 1.91-1.84 (m, 1H).

Preparation Z 4-amino-2-(4-amino-2-hydroxybutoxy)benzonitrile

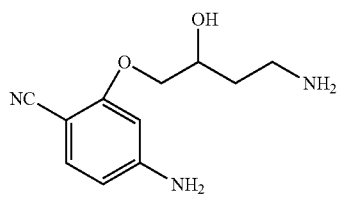 [SMILES: N#Cc1ccc(N)cc1OCC(O)CCN]

Intermediate Z(1)

2-(4-(2-cyano-5-nitrophenoxy)-3-hydroxybutylcarbamoyl)benzoic acid

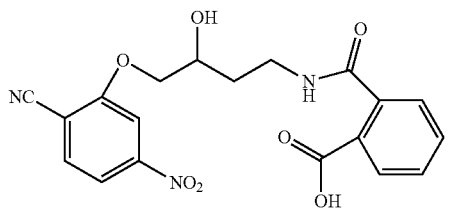 [SMILES: N#Cc1ccc([N+](=O)[O-])cc1OCC(O)CCNC(=O)c1ccccc1C(=O)O]

2-(3,4-dihydroxybutyl)isoindoline-1,3-dione was reacted as described in Intermediate Y(2) with sodium hydride and 2-fluoro-4-nitrobenzonitrile in THF to get 2-(4-(2-cyano-5-nitrophenoxy)-3-hydroxybutylcarbamoyl)benzoic acid which is used as-is in the next step. LC-MS (M+H)⁺=400.1.

Intermediate Z(2)

2-(4-(1,3-dioxoisoindolin-2-yl)-2-hydroxybutoxy)-4-nitrobenzonitrile

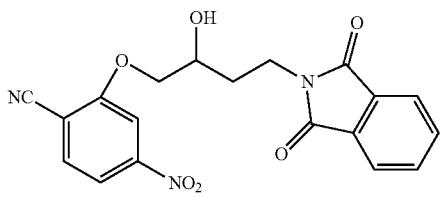 [SMILES: N#Cc1ccc([N+](=O)[O-])cc1OCC(O)CCN1C(=O)c2ccccc2C1=O]

2-(4-(2-cyano-5-nitrophenoxy)-3-hydroxybutylcarbamoyl)benzoic acid was reacted as described in Intermediate Y(3) with hydrogen chloride in dioxane to get 2-(4-(1,3-dioxoisoindolin-2-yl)-2-hydroxybutoxy)-4-nitrobenzonitrile which is used as-is in the next step. LC-MS (M+Na)⁺=404.1.

Preparation Z 4-amino-2-(4-amino-2-hydroxybutoxy)benzonitrile

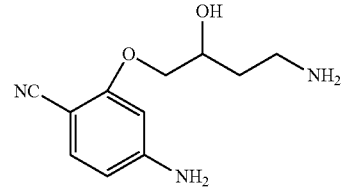

To a mixture of 2-(4-(1,3-dioxoisoindolin-2-yl)-2-hydroxybutoxy)-4-nitrobenzonitrile (2.96 g, 7.76 mmol) in EtOH (28.1 mL) was added hydrazine (12.18 mL, 388 mmol). The reaction mixture was heated at 50° C. for 1.5 h. The reaction mixture was cooled to rt and filtered. The filtrate was concentrated and taken up in CH2Cl2. The solid was filtered off again, and the filtrate was concentrated and purified by Prep-HPLC to obtain 4-amino-2-(4-amino-2-hydroxybutoxy)benzonitrile (1.015 g, 59.1% yield). LC-MS (M+H)⁺=222.1. ¹H NMR (500 MHz, methanol-d₄) δ 7.24 (d, J=8.5 Hz, 1H), 6.35-6.26 (m, 2H), 4.17-4.09 (m, 1H), 4.05 (dd, J=9.5, 4.9 Hz, 1H), 3.97 (dd, J=9.5, 5.5 Hz, 1H), 3.20 (t, J=7.0 Hz, 2H), 2.08 (td, J=7.1, 3.5 Hz, 1H), 2.01-1.86 (m, 1H).

Preparation Za 4-amino-2-(4-(2-chloro-7-(4-fluorophenyl)-6,7-dihydro-5H-cyclopenta[d]pyrimidin-4-ylamino)-2-hydroxybutoxy)benzonitrile

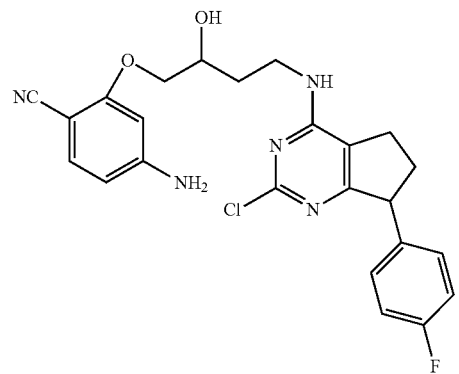 [SMILES: N#Cc1ccc(N)cc1OCC(O)CCNc1nc(Cl)nc2c1CCC2c1ccc(F)cc1]

The mixture of 4-amino-2-(4-amino-2-hydroxybutoxy)benzonitrile, 2 TFA salt (Preparation Z, 50 mg, 0.111 mmol), 2,4-dichloro-7-(4-fluorophenyl)-6,7-dihydro-5H-cyclopenta[d]pyrimidine (Preparation R, 31.5 mg, 0.111 mmol) and N-ethyl-N-isopropylpropan-2-amine (97 μL, 0.556 mmol) in acetonitrile (556 μL) was stirred at rt for 24 h. The reaction mixture was concentrated and purified by Prep-HPLC to obtain 4-amino-2-(4-(2-chloro-7-(4-fluorophenyl)-6,7-dihydro-5H-cyclopenta[d]pyrimidin-4-ylamino)-2-hydroxybutoxy)benzonitrile, TFA (14.73 mg, 22.75% yield). LC-MS (M+H)⁺=468.2. ¹H NMR (500 MHz, methanol-d₄) δ 7.27-7.15 (m, 3H), 7.14-7.01 (m, 2H), 6.40-6.24 (m, 2H), 4.44-

4.33 (m, 1H), 4.17-4.04 (m, 2H), 4.03-3.95 (m, 1H), 3.89-3.66 (m, 2H), 2.94-2.81 (m, 1H), 2.81-2.67 (m, 2H), 2.14 (td, J=7.5, 4.0 Hz, 1H), 2.10-2.00 (m, 1H), 1.95 (dd, J=14.0, 6.4 Hz, 1H).

Synthon RaA

N4-allyl-N2-(3-(allyloxy)-4-(4-chloro-1H-imidazol-1-yl)phenyl)-7-phenyl-6,7-dihydro-5H-cyclopenta[d]pyrimidine-2,4-diamine

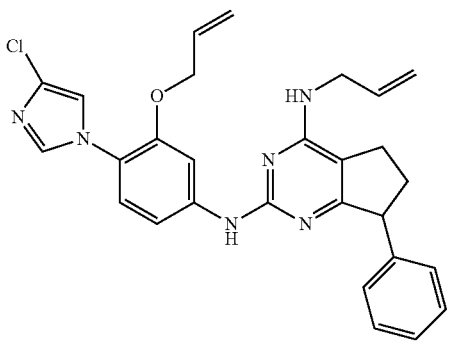 [SMILES: C=CCNc1nc(Nc2ccc(-n3cnc(Cl)c3)c(OCC=C)c2)nc2c1CCC2c1ccccc1]

Preparation Ra (0.5 g, 1.754 mmol) and Preparation A (0.483 g, 1.754 mmol) were heated at 150° C. for 20 min while monitoring by LC-MS. After the completion of the reaction, it was cooled to rt and the reaction mass was taken up in dichloromethane (5 mL) and silica (1 g). The resultant slurry of the compound on silica was subjected to column chromatography (60-120 mesh silica) using 5% methanol in chloroform as the mobile phase to give N4-allyl-N2-(3-(allyloxy)-4-(4-chloro-1H-imidazol-1-yl)phenyl)-7-phenyl-6,7-dihydro-5H-cyclopenta[d]pyrimidine-2,4-diamine (0.480 g, 26.3%) as an off-brown solid. LC-MS (M+H)$^+$=499.1. $^1$H NMR (400 MHz, DMSO-d6): δ ppm 9.17 (1H, s), 8.00 (1H, s), 7.75 (1H, s), 7.31 (1H, s), 7.29-7.19 (2H, m), 7.17-7.13 (6H, m), 6.04-5.89 (2H, m), 5.25-5.10 (4H, m), 4.31 (2H, m), 4.15-4.12 (3H, m), 2.80-2.79 (1H, m), 2.78-2.49 (2H, m), 1.95-1.92 (1H, m).

Synthon RbA

N4-allyl-N2-(3-(allyloxy)-4-(4-chloro-1H-imidazol-1-yl)phenyl)-N4-methyl-7-phenyl-6,7-dihydro-5H-cyclopenta[d]pyrimidine-2,4-diamine

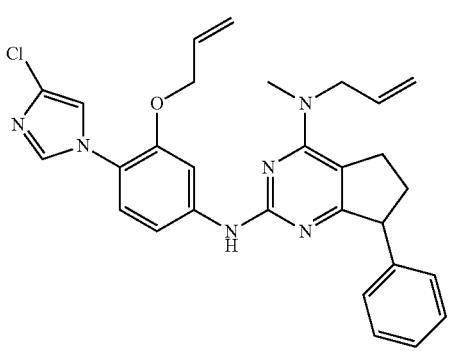 [SMILES: C=CCOc1cc(Nc2nc3c(c(N(C)CC=C)n2)CCC3c2ccccc2)ccc1-n1cnc(Cl)c1]

Preparation Rb (0.500 g, 1.610 mmol) Preparation A (0.41 g, 1.610 mmol) were heated at 150° C. for 20 min while monitoring by LC-MS. After the completion of the reaction, it was cooled to rt and the reaction mass was taken up in dichloromethane (5 mL) and silica (1 g). The resultant slurry of the compound on silica was subjected to column chromatography (60-120 mesh, silica) using 5% methanol in chloroform as the mobile phase to give N4-allyl-N2-(3-(allyloxy)-4-(4-chloro-1H-imidazol-1-yl)phenyl)-N4-methyl-7-phenyl-6,7-dihydro-5H-cyclopenta[d]pyrimidine-2,4-diamine (0.420 g, 50.6%) as an off-white solid. LC-MS (M+H)$^+$=513.2. $^1$H NMR (400 MHz, DMSO-d6): δ ppm 9.17 (1H, s), 8.00 (1H, s), 7.75 (1H, s), 7.31 (1H, s), 7.29-7.19 (2H, m), 7.17-7.13 (6H, m), 6.04-5.89 (2H, m), 5.25-5.10 (4H, m), 4.31 (2H, m), 4.15-4.12 (3H, m), 3.12 (3H, s) 2.80-2.79 (1H, m), 2.78-2.49 (2H, m), 1.95-1.92 (1H, m).

Synthon RcA

N2-(3-(allyloxy)-4-(4-chloro-1H-imidazol-1-yl)phenyl)-N4-(but-3-enyl)-7-phenyl-6,7-dihydro-5H-cyclopenta[d]pyrimidine-2,4-diamine

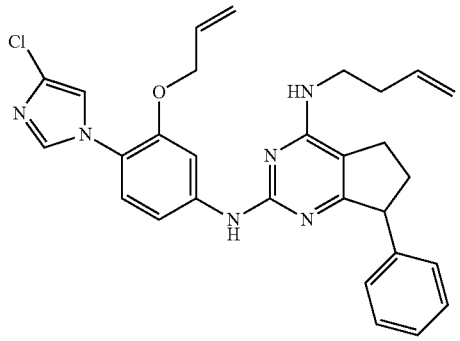 [SMILES: C=CCCNc1nc(Nc2ccc(-n3cnc(Cl)c3)c(OCC=C)c2)nc2c1CCC2c1ccccc1]

Preparation Rc (0.700 g, 2.31 mmol) and Preparation A (0.581 g, 2.31 mmol) were heated at 150° C. for 20 min while monitoring by LC-MS. After the completion of the reaction, it was cooled to rt and the reaction mass was taken up in dichloromethane (5 mL) and silica (1 g). The resultant slurry of the compound on silica was subjected to column chromatography (60-120 mesh silica) using 5% methanol in chloroform as the mobile phase to give N2-(3-(allyloxy)-4-(4-chloro-1H-imidazol-1-yl)phenyl)-N4-(but-3-enyl)-7- phenyl-6,7-dihydro-5H-cyclopenta[d]pyrimidine-2,4-diamine (0.590 g, 54.5%) as a white solid. LC-MS (M+H)⁺=513.2.

Synthon RdA

N2-(3-(allyloxy)-4-(4-chloro-1H-imidazol-1-yl)phenyl)-N4-(but-3-enyl)-N4-methyl-7-phenyl-6,7-dihydro-5H-cyclopenta[d]pyrimidine-2,4-diamine

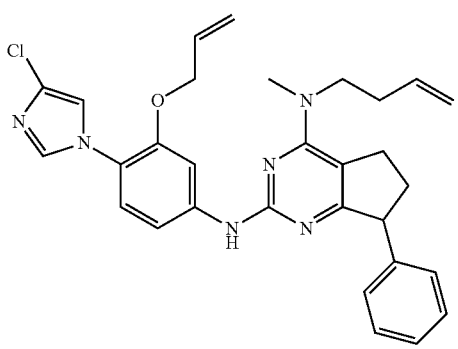 [SMILES: C=CCCN(C)c1nc(Nc2ccc(-n3cnc(Cl)c3)c(OCC=C)c2)nc2c1CCC2c1ccccc1]

Preparation Rd (1.1 g, 3.5 mmol) and Preparation A (0.785 g, 3.15 mmol) were heated at 150° C. for 20 min while monitoring by LC-MS. After the completion of the reaction, it was cooled to rt and the reaction mass was taken up in dichloromethane (5 mL) and silica (1 g). The resultant slurry of the compound on silica was subjected to column chromatography (60-120 mesh silica) using 5% methanol in chloroform to obtain the title compound (1.0 g, 54.34%) as brown solid. LC-MS (M+H)⁺=527.2. 1H NMR (400 MHz, DMSO-d6) δ ppm 10.10 (1H, s), 7.85 (1H, s), 7.52 (1H, s), 7.40-7.37 (4H, m), 7.32-7.23 (4H, m), 6.02-6.00 (1H, m), 5.98-5.82 (1H, m), 5.31-5.27 (2H, m), 5.26-5.24 (2H, m), 4.55 (2H, m), 4.39 (1H, m), 3.80-3.72 (2H, m), 3.36 (3H, s), 3.36-3.33 (2H, m), 2.61-2.59 (1H, m), 2.52-2.50 (2H, m), 1.99 (1H, m).

Synthon ReA

N-(2-(2-(5-amino-2-(4-chloro-1H-imidazol-1-yl)phenoxy)ethoxy)ethyl)-2-chloro-7-phenyl-6,7-dihydro-5H-cyclopenta[d]pyrimidin-4-amine

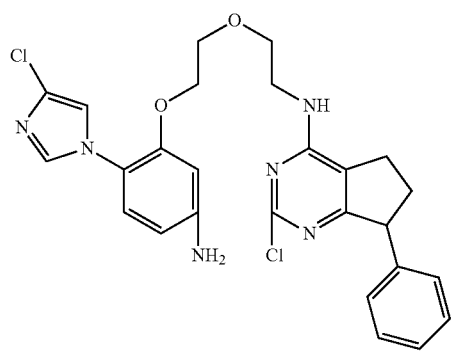 [SMILES: Nc1ccc(-n2cnc(Cl)c2)c(OCCOCCNc2nc(Cl)nc3c2CCC3c2ccccc2)c1]

Iron powder-325 mesh (0.252 g, 4.5 mmol) was added to a round bottom flask charged with a mixture of Preparation Re (0.5 g, 0.903 mmol), absolute methanol (20 mL), and ammonium chloride (0.24 g, 4.5 mmol). A water-cooled reflux condenser was attached to the flask and the heterogeneous mixture was heated to 65° C. with vigorous stirring for 5 h. The reaction mixture was filtered, and washed with methanol. The solvent was removed in vacuo. EtOAc was added to the residue, and washed with water and brine. The organic layer was dried over sodium sulfate, filtered, and concentrated to afford the title compound (0.35 g, 74.15%) as a yellow solid. LC-MS (M+H)⁺=527.2. 1H NMR (400 MHz, DMSO-d6) δ ppm 7.72 (1H, s), 8.70 (1H, s), 7.52 (1H, s), 7.38-7.28 (7H, m), 7.14-7.12 (1H, m), 6.37 (1H, s), 6.22-6.20 (1H, m), 5.41 (1H, s), 4.19-4.02 (3H, m), 3.73-3.71 (2H, m), 3.59-3.51 (4H, m), 2.80-2.55 (3H, m), 1.99-1.93 (1H, m).

Synthon RfA

N-(3-(5-amino-2-(4-chloro-1H-imidazol-1-yl)phenoxy)propyl)-2-chloro-7-phenyl-6,7-dihydro-5H-cyclopenta[d]pyrimidin-4-amine

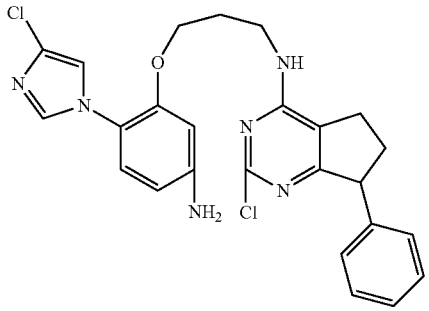 [SMILES: Nc1ccc(-n2cnc(Cl)c2)c(OCCCNc2nc(Cl)nc3c2CCC3c2ccccc2)c1]

Iron powder-325 mesh (0.239 g, 4.29 mmol) was added to a round bottom flask charged with a mixture of Preparation Rf (0.45 g, 0.858 mmol), absolute methanol (20 mL), and ammonium chloride (0.229 g, 4.29 mmol). A water-cooled reflux condenser was attached to the flask and the heterogeneous mixture was heated to 65° C. with vigorous stirring for 5 h. The reaction mixture was filtered and washed with methanol. The solvent was removed in vacuo. EtOAc was added to the residue, and washed with water and brine. The organic layer was dried over sodium sulfate, filtered, and concentrated to afford the title compound (0.23 g, 54.24%) as a yellow solid. LC-MS (M+H)⁺=495.2. 1H NMR (400 MHz, DMSO-d6) δ ppm 7.73 (1H, s), 7.54 (1H, s), 7.39 (1H, s), 7.30-7.09 (6H, m), 7.01-6.99 (2H, d, J=8.4 Hz), 6.37-6.36 (1H, m), 6.21-6.18 (1H, m), 4.18-3.96 (3H, m), 3.47-3.31 (2H, m), 2.78-2.50 (3H, m), 1.99-1.92 (3H, m).

Synthon RgA

N-(3-(5-amino-2-(4-chloro-1H-imidazol-1-yl)phenoxy)propyl)-2-chloro-N-methyl-7-phenyl-6,7-dihydro-5H-cyclopenta[d]pyrimidin-4-amine

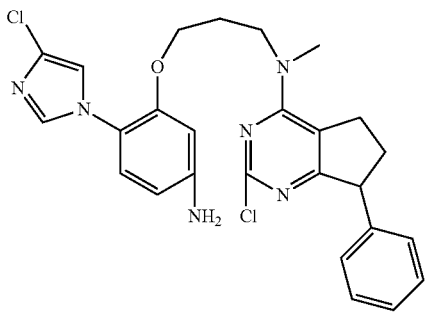 [SMILES: CN(CCCOc1cc(N)ccc1-n1cnc(Cl)c1)c1nc(Cl)nc2c1CCC2c1ccccc1]

Iron powder-325 mesh (0.519 g, 9.29 mmol) was added to a round bottom flask charged with a mixture of Preparation Rg (0.5 g, 0.929 mmol), absolute methanol (10 mL), water (10 mL) and ammonium chloride (0.496 g, 9.29 mmol). A water-cooled reflux condenser was attached to the flask and the heterogeneous mixture was heated to 65° C. with vigorous stirring for 5 h. The reaction mixture was filtered and washed with methanol. The solvent was removed in vacuo. EtOAc was added to the residue, and washed with water and brine. The organic layer was dried over sodium sulfate, filtered, and concentrated to afford the title compound (0.20 g, 42.37%) as a yellow solid. LC-MS (M+H)$^+$=539.2. 1H NMR (400 MHz, DMSO-d6) δ ppm 7.78 (1H, s), 7.37 (1H, s), 7.32-7.01 (8H, m), 6.36 (1H, s), 6.22-6.20 (1H, m), 4.11-4.03 (3H, m), 3.17 (3H, s), 3.12-3.0 (3H, m), 2.51-2.47 (2H, m), 1.99-1.92 (3H, m).

Synthon TaA

N4-allyl-N2-(3-(allyloxy)-4-(4-chloro-1H-imidazol-1-yl)phenyl)-7-(2,4-difluorophenyl)-6,7-dihydro-5H-cyclopenta[d]pyrimidine-2,4-diamine

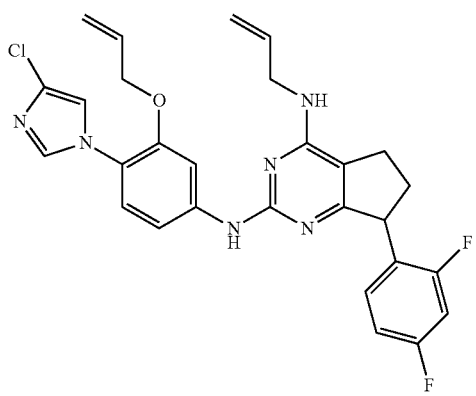 [SMILES: C=CCNc1nc(Nc2ccc(-n3cnc(Cl)c3)c(OCC=C)c2)nc2c1CCC2c1ccc(F)cc1F]

Preparation A (0.300 g, 1.245 mmol) and Preparation Ta (400 g, 1.245 mmol) were heated at 150° C. for 45 min while monitoring by LC-MS. After the completion of the reaction, it was cooled to rt and the reaction mass was taken up in dichloromethane (15 mL) and silica (1 g). The resultant slurry of the compound on silica was subjected to flash chromatography using a Teledyne Isco instrument (40 g RediSep silica column, 10% MeOH in CHCl$_3$) to get the title compound (200 mg, 30%) as a light yellow solid. LC-MS (M+H)$^+$=535.2. $^1$H NMR (400 MHz, CDCl$_3$): δ ppm 7.86 (1H, s), 7.54 (1H, s), 7.26-7.03 (4H, m), 6.84-6.78 (3H, m), 6.01-5.98 (1H, m), 5.86-5.84 (1H, m), 5.32-5.20 (4H, m), 4.55-4.46 (2H, m), 4.32-4.29 (2H, m), 4.23-4.19 (1H, m), 2.71-2.61 (3H, m), 2.12-1.98 (2H, m).

Synthon RhA

N-(3-(allyloxy)-4-(4-chloro-1H-imidazol-1-yl)phenyl)-4-(but-3-enyl)-7-phenyl-6,7-dihydro-5H-cyclopenta[d]pyrimidin-2-amine

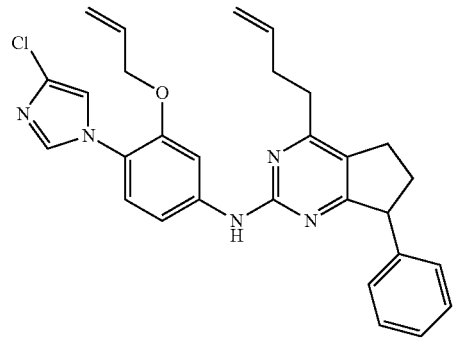 [SMILES: C=CCCc1nc(Nc2ccc(-n3cnc(Cl)c3)c(OCC=C)c2)nc2c1CCC2c1ccccc1]

Preparation A (0.6 g, 2.4 mmol) and Preparation Rh (0.6 g, 2.11 mmol) were heated at 150° C. for 45 min while monitoring by LC-MS. After the completion of the reaction, it was cooled to rt and the reaction mass was taken up in dichloromethane (50 mL) and silica (2 g). The resultant slurry of the compound on silica was subjected to flash chromatography using a Teledyne Isco instrument (12 g RediSep silica column, 10% MeOH in CHCl$_3$) to get the title compound (0.5 g, 47.6%) as a light brown solid. LC-MS (M+H)$^+$=498.2. 1H NMR (400 MHz, CDCl$_3$) δ ppm 7.96 (1H, s), 7.53 (1H, s), 7.34-7.18 (7H, m), 7.08-7.02 (2H, m), 6.77-6.75 (1H, d, J=8.8

Hz), 5.93-5.82 (2H, m), 5.26-5.02 (4H, m), 4.29-4.19 (3H, m), 2.89-2.55 (7H, m), 2.15-2.05 (1H, m).

Synthon TbA

N4-allyl-N2-(3-(allyloxy)-4-(4-chloro-1H-imidazol-1-yl)phenyl)-7-(2,4-difluorophenyl)-N4-methyl-6,7-dihydro-5H-cyclopenta[d]pyrimidine-2,4-diamine

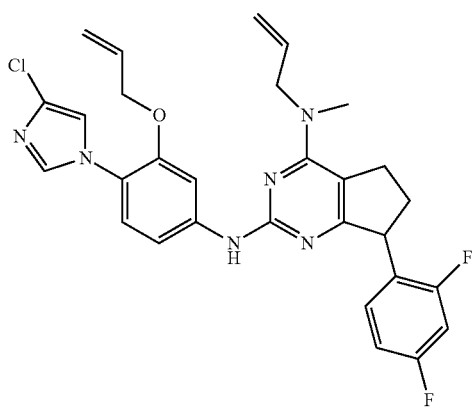 [SMILES: C=CCOc1cc(Nc2nc3c(c(N(C)CC=C)n2)CCC3c2ccc(F)cc2F)ccc1-n1cnc(Cl)c1]

Preparation A (1.48, mmol) and Preparation Tb (2 g, 5.961 mmol) were heated at 150° C. for 45 min while monitoring by LC-MS. After the completion of the reaction, it was cooled to rt and the reaction mass was taken up in dichloromethane (15 mL) and silica (3 g). The resultant slurry of the compound on silica was subjected to flash chromatography using a Teledyne Isco instrument (40 g RediSep silica column, 10% MeOH in CHCl$_3$) to get the title compound (1.2 g, 37%) as a light brown solid. LC-MS (M+H)$^+$=549.2. $^1$H NMR (400 MHz, CDCl$_3$): δ ppm 9.41 (1H, s), 7.57 (1H, s), 7.41 (1H, s), 7.27-7.06 (4H, m), 6.89-6.82 (2H, m), 5.94-5.85 (2H, m), 5.34-5.22 (4H, m), 4.43-4.29 (5H, m), 3.30 (3H, s), 3.24-3.15 (2H, m), 2.61 (1H, m), 2.09 (1H, m).

Synthon TfA

N-(3-(5-amino-2-(4-chloro-1H-imidazol-1-yl)phenoxy)propyl)-2-chloro-7-(2,4-difluorophenyl)-N-methyl-6,7-dihydro-5H-cyclopenta[d]pyrimidin-4-amine

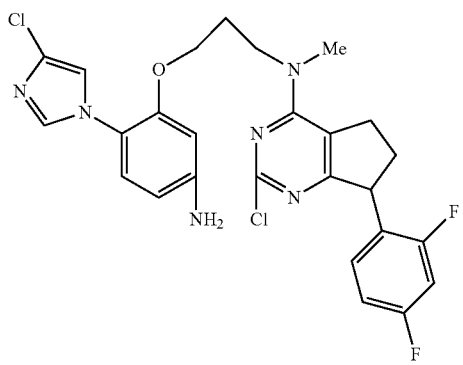 [SMILES: CN(CCCOc1cc(N)ccc1-n1cnc(Cl)c1)c1nc(Cl)nc2c1CCC2c1ccc(F)cc1F]

Iron powder-325 mesh (1.553 g, 27.8 mmol) was added to a round bottom flask charged with a mixture of Preparation Tf (1.6 g, 2.78 mmol), absolute methanol (20 mL), water (20 mL), THF (15 mL) and ammonium chloride (1.48 g, 27.8 mmol). A water-cooled reflux condenser was attached to the flask and the heterogeneous mixture was heated to 65° C. with vigorous stirring for 3 h. The reaction mixture was filtered and washed with methanol. The solvent was removed in vacuo. EtOAc was added to the residue, and washed with water and brine. The organic layer was dried over sodium sulfate, filtered, and concentrated to afford the title compound (1.3 g, 86% yield) as a yellow solid. LC-MS (M+H)$^+$=545.0. 1H NMR (400 MHz, CDCl$_3$) δ ppm 7.45 (1H, s), 6.99-6.89 (3H, m), 6.79-6.74 (2H, m), 6.30-6.27 (2H, m), 4.38-4.34 (1H, t, J=8 Hz), 4.08-3.99 (2H, m), 3.99 (2H, br s), 3.68-3.60 (2H, m), 3.16 (3H, s), 3.08-2.99 (2H, m), 2.56-2.53 (1H, m), 2.06-2.03 (2H, m), 1.95-1.91 (1H, m).

Synthon RaD 4-(4-(allylamino)-7-phenyl-6,7-dihydro-5H-cyclopenta[d]pyrimidin-2-ylamino)-2-(allyloxy)benzonitrile

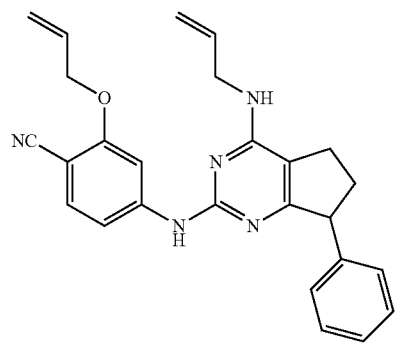 [SMILES: C=CCNc1nc(Nc2ccc(C#N)c(OCC=C)c2)nc2c1CCC2c1ccccc1]

Preparation D (1.22 g, 0.70 mmol) and Preparation Ra (2.0 g, 0.70 mmol) were heated at 150° C. for 45 min while monitoring by LC-MS. After the completion of the reaction, it was cooled to rt and the reaction mass was taken up in dichloromethane (15 mL) and silica (6 g). The resultant slurry of the compound on silica was subjected to flash chromatography using a Teledyne Isco instrument (40 g RediSep silica 5% MeOH in CHCl$_3$) to get the title compound (2.0 g, 67.5%) as a brown solid. LC-MS (M+H)$^+$=424.2. 1H NMR (400 MHz, CDCl$_3$) δ ppm 9.48 (1H, s), 8.01 (1H, s), 7.43-7.13 (7H, m), 6.01-5.95 (2H, m), 5.42-5.37 (4H, m), 5.30-5.11 (4H, m), 4.39-4.15 (2H, m), 2.67-2.49 (3H, m), 1.98-1.85 (1H, m).

Synthon RkN 4-amino-2-(4-(2-chloro-7-phenyl-6,7-dihydro-5H-cyclopenta[d]pyrimidin-4-ylamino)butoxy)benzonitrile

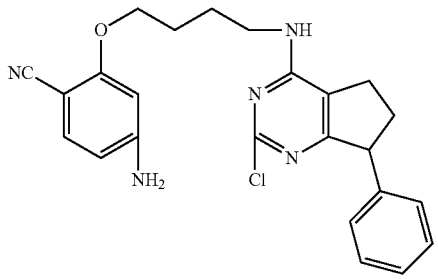 [SMILES: N#Cc1ccc(N)cc1OCCCCNc1nc(Cl)nc2c1CCC2c1ccccc1]

Iron powder-325 mesh (0.600 g, 10.79 mmol) was added to a round bottom flask charged with a mixture of Preparation Rk (1.0 g, 2.158 mmol), 3:1 methanol:water (60 mL), and ammonium chloride (0.580 g, 10.79 mmol). A water-cooled reflux condenser was attached to the flask and the heterogeneous mixture was heated to 65° C. with vigorous stirring for 120 min. The reaction mixture was filtered and washed with methanol. The solvent was removed in vacuo. EtOAc was added to the residue, and washed with water and brine. The organic layer was dried over sodium sulfate, filtered, and concentrated to afford the title compound (700 mg, 75% yield) as a yellow solid. LC-MS (M+H)$^+$=434.2. 1H NMR (400 MHz, DMSO-d6) δ ppm 7.56-7.53 (1H, m), 7.32-7.14 (6H, m), 6.25 (1H, s), 6.24-6.18 (1H, d, J=8.8 Hz), 6.13 (2H, s), 4.20-4.16 (1H, t, J=8 Hz), 4.04-4.01 (2H, m), 3.45-3.32 (2H, m), 2.85-2.67 (3H, m), 2.01-1.97 (1H, m), 1.82-1.71 (4H, m).

Synthon TaD 4-(4-(allylamino)-7-(2,4-difluorophenyl)-6,7-dihydro-5H-cyclopenta[d]pyrimidin-2-ylamino)-2-(allyloxy)benzonitrile

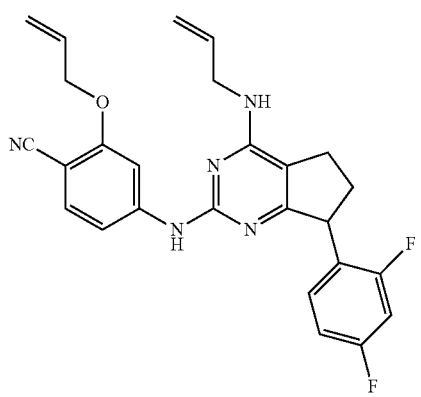 [SMILES: C=CCNc1nc(Nc2ccc(C#N)c(OCC=C)c2)nc2c1CCC2c1ccc(F)cc1F]

Preparation D (0.271 g, 1.557 mmol) and Preparation Ta (0.500 g, 1.557 mmol) were heated at 150° C. for 45 min while monitoring by LC-MS. After the completion of the reaction, it was cooled to rt and the reaction mass was taken up in dichloromethane (150 mL) and silica (1.5 g). The resultant slurry of the compound on silica was subjected to flash chromatography using a Teledyne Isco instrument (40 g RediSep silica column, 10% MeOH in CHCl$_3$) to get the title compound (380 mg, 53.3%) as a brown solid. LC-MS (M+H)$^+$=460.2. $^1$H NMR (400 MHz, DMSO-d$_6$): δ ppm 7.84 (1H, s), 7.36 (1H, d, J=8.4 Hz), 7.07-7.06 (1H, m), 6.86-6.79 (2H, m), 5.97-5.86 (2H, m), 5.45-5.20 (4H, m), 4.42-4.21 (6H, m), 3.22-3.19 (2H, m), 2.65 (1H, m), 1.93 (1H, m).

Synthon SfN 4-amino-2-(2-(2-(2-chloro-7-(4-fluorophenyl)-6,7-dihydro-5H-cyclopenta[d]pyrimidin-4-ylamino)ethylamino)ethoxy)benzonitrile

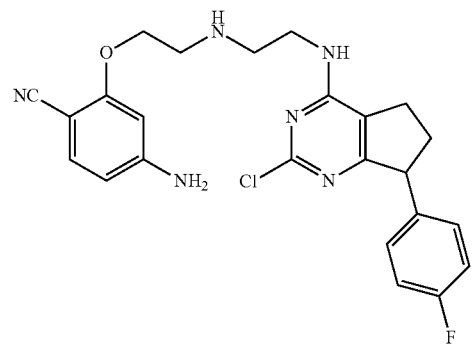 [SMILES: N#Cc1ccc(N)cc1OCCNCCNc1nc(Cl)nc2c1CCC2c1ccc(F)cc1]

Iron powder-325 mesh (0.205 mg, 3.52 mmol) was added to a round bottom flask charged with a mixture of Preparation Sf (0.35 g, 0.704 mmol), 3:1 methanol:water (20 mL), and ammonium chloride (0.187 g, 3.52 mmol). A water-cooled reflux condenser was attached to the flask and the heterogeneous mixture was heated to 65° C. with vigorous stirring for 120 min. The reaction mixture was filtered and washed with methanol. The solvent was removed in vacuo. EtOAc was added to the residue, and washed with water and brine. The organic layer was dried over sodium sulfate, filtered, and concentrated to afford the title compound (250 mg, 76% yield) as a yellow solid. LC-MS (M+H)$^+$=467.2. 1H NMR (400 MHz, DMSO-d6) δ ppm 7.67 (1H, br s), 7.29-7.13 (6H, m), 6.26-6.23 (3H, m), 4.27-4.04 (3H, m), 3.81-3.80 (2H, m), 3.69-3.60 (2H, m), 3.32-3.27 (2H, m), 2.85-2.67 (3H, m), 2.01-1.97 (1H, m).

Synthon SgN 4-amino-2-(2-((2-(2-chloro-7-(4-fluorophenyl)-6,7-dihydro-5H-cyclopenta[d]pyrimidin-4-ylamino)ethyl)(methyl)amino)ethoxy)benzonitrile

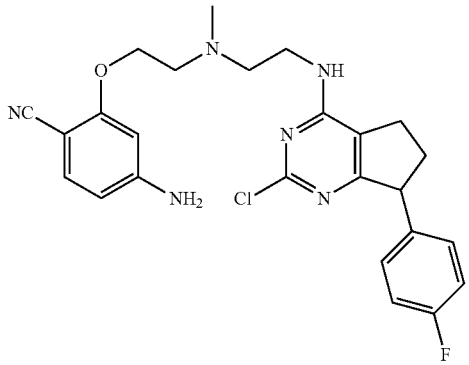 [SMILES: CN(CCNc1nc(Cl)nc2c1CCC2c1ccc(F)cc1)CCOc1cc(N)ccc1C#N]

Iron powder-325 mesh (530 mg, 9.80 mmol) was added to a round bottom flask charged with a mixture of Preparation Sg (0.5 g, 0.980 mmol), 1:1 methanol:water (30 mL), and ammonium chloride (0.508 g, 9.80 mmol). A water-cooled reflux condenser was attached to the flask and the heterogeneous mixture was heated to 65° C. with vigorous stirring for 150 min. The reaction mixture was filtered and washed with methanol. The solvent was removed in vacuo. EtOAc was added to the residue, and washed with water and brine. The organic layer was dried over sodium sulfate, filtered, and concentrated to afford the title compound (350 mg, 74.4% yield) as a dark brown solid. LC-MS (M+H)$^+$=481.2. 1H NMR (400 MHz, DMSO-d6) δ ppm 7.25-7.10 (5H, m), 6.25-6.15 (4H, m), 4.15-4.03 (5H, m), 3.70-3.60 (2H, m), 3.3-3.27 (1H, m), 3.20 (3H, s), 3.17-3.15 (1H, m), 2.51-2.45 (1H, m), 2.09-2.06 (2H, m), 1.99-1.91 (1H, m).

Synthon TbD 4-(4-(allyl(methyl)amino)-7-(2,4-difluorophenyl)-6,7-dihydro-5H-cyclopenta[d]pyrimidin-2-ylamino)-2-(allyloxy)benzonitrile

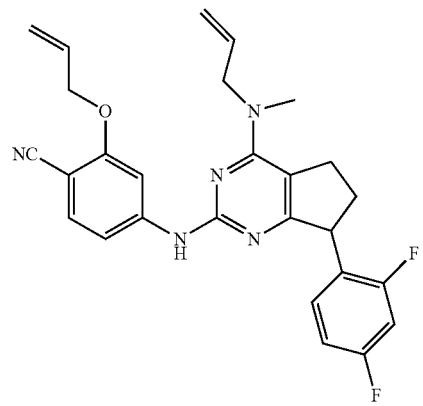 [SMILES: C=CCOc1cc(Nc2nc3c(c(N(C)CC=C)n2)CCC3c2ccc(F)cc2F)ccc1C#N]

Preparation D (1.089 g, 6.25 mmol) and Preparation Tb (2.1 g, 6.25 mmol) were heated at 150° C. for 60 min while monitoring by LC-MS. After the completion of the reaction, it was cooled to rt and the reaction mass was taken up in dichloromethane (25 mL) and silica (5 g). The resultant slurry of the compound on silica was subjected to flash chromatography using a Teledyne Isco instrument (40 g RediSep silica column, 10% MeOH in CHCl$_3$) to get the title compound (1.8 g, 60%) as a dark brown solid. LC-MS (M+H)$^+$=474.2. $^1$H NMR (400 MHz, DMSO-d$_6$): δ ppm 7.74 (1H, s), 7.36 (1H, d, J=8.4 Hz), 7.07-7.06 (1H, m), 6.86-6.79 (2H, m), 5.97-5.86 (2H, m), 5.45-5.20 (4H, m), 4.42-4.21 (6H, m), 3.22 (3H, s), 3.22-3.19 (2H, m), 2.56 (1H, m), 1.93 (1H, m).

Synthon RbD 4-(4-(allyl(methyl)amino)-7-phenyl-6,7-dihydro-5H-cyclopenta[d]pyrimidin-2-ylamino)-2-(allyloxy)benzonitrile

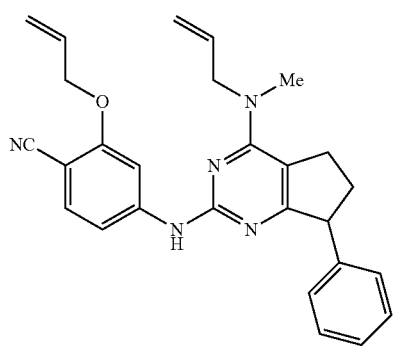 [SMILES: C=CCOc1cc(Nc2nc3c(c(N(C)CC=C)n2)CCC3c2ccccc2)ccc1C#N]

Preparation D (0.872 g, 5.0 mmol) and Preparation Rb (1.5 g, 5.0 mmol) were heated at 150° C. for 90 min while monitoring by LC-MS. After the completion of the reaction, it was cooled to rt and the reaction mass was taken up in dichloromethane (50 mL) and silica (5 g). The resultant slurry of the compound on silica was subjected to flash chromatography using a Teledyne Isco instrument (40 g RediSep silica column, 60% of ethyl acetate in hexane) to get the title compound (1.1 g, 50.2%) as a brown solid. LC-MS (M+H)⁺=438.2. 1H NMR (400 MHz, CDCl₃) δ ppm 7.45-7.2 (8H, m), 6.02-5.86 (2H, m), 5.49-5.23 (4H, m), 4.55-4.54 (2H, m), 4.36-4.31 (3H, m), 3.34 (3H, s), 3.31-3.14 (3H, m), 2.66-2.63 (1H, m), 2.29-2.24 (1H, m).

Synthon RjI 4-amino-2-(3-((2-chloro-7-phenyl-6,7-dihydro-5H-cyclopenta[d]pyrimidin-4-yl)(methyl)amino)propoxy)benzonitrile

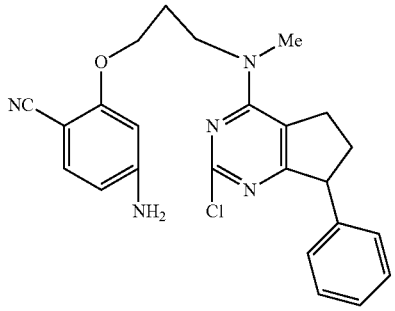 [SMILES: CN(CCCOc1cc(N)ccc1C#N)c1nc(Cl)nc2c1CCC2c1ccccc1]

Iron powder-325 mesh (963 mg, 17.24 mmol) was added to a round-bottom flask charged with a mixture of Preparation Rj (0.8 g, 1.724 mmol), 1:1 methanol:water (40 mL), and ammonium chloride (0.92 g, 17.24 mmol). A water-cooled reflux condenser was attached to the flask and the heterogeneous mixture was heated to 65° C. with vigorous stirring for 45 min. The reaction mixture was filtered and washed with methanol. The solvent was removed in vacuo. EtOAc was added to the residue, and washed with water and brine. The organic layer was dried over sodium sulfate, filtered, and concentrated to afford the title compound (550 mg, 73.5% yield) as a puffy light-yellow colored solid. LC-MS (M+H)⁺=434.2. 1H NMR (400 MHz, DMSO-d6) δ ppm 7.29-7.1 (6H, m), 6.21-6.17 (4H, m), 4.12-4.02 (3H, m), 3.79-3.75 (2H, m), 3.3-3.27 (1H, m), 3.20 (3H, s), 3.17-3.15 (1H, m), 2.51-2.45 (1H, m), 2.09-2.06 (2H, m), 1.99-1.91 (1H, m).

Synthon TcH 4-amino-2-(3-(2-chloro-7-(2,4-difluorophenyl)-6,7-dihydro-5H-cyclopenta[d]pyrimidin-4-ylamino)propoxy)benzonitrile

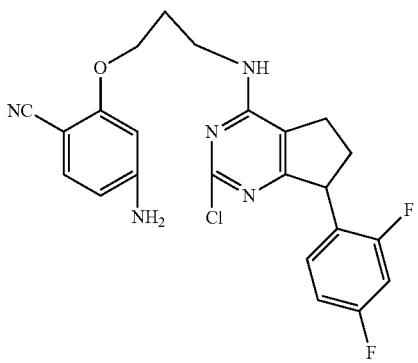 [SMILES: N#Cc1ccc(N)cc1OCCCNc1nc(Cl)nc2c1CCC2c1ccc(F)cc1F]

Iron powder-325 mesh (1.49 g, 26.8 mmol) was added to a round bottom flask charged with a mixture of Preparation Tc (1.3 g, 2.68 mmol), 1:1 methanol:water (35 mL), and ammonium chloride (1.43 g, 26.8 mmol). A water-cooled reflux condenser was attached to the flask and the heterogeneous mixture was heated to 65° C. with vigorous stirring for 3 h. The reaction mixture was filtered and washed with methanol. The solvent was removed in vacuo. EtOAc was added to the residue, and washed with water and brine. The organic layer was dried over sodium sulfate, filtered, and concentrated to afford the title compound (800 mg, 65.6% yield) as a light yellow solid. LC-MS (M+H)⁺=456.0. 1H NMR (400 MHz, CDCl₃) δ ppm 7.28-7.25 (1H, d, J=10 Hz), 6.94-6.74 (3H, m), 6.26-6.16 (2H, m), 5.29-5.24 (1H, m), 4.47-4.45 (1H, m), 4.16-4.11 (2H, m), 3.81-3.78 (2H, m), 2.72-2.67 (4H, m), 2.24-2.19 (2H, m), 2.04-1.98 (1H, m).

Synthon TdI 4-amino-2-(3-((2-chloro-7-(2,4-difluorophenyl)-6,7-dihydro-5H-cyclopenta[d]pyrimidin-4-yl)(methyl)amino)propoxy)benzonitrile

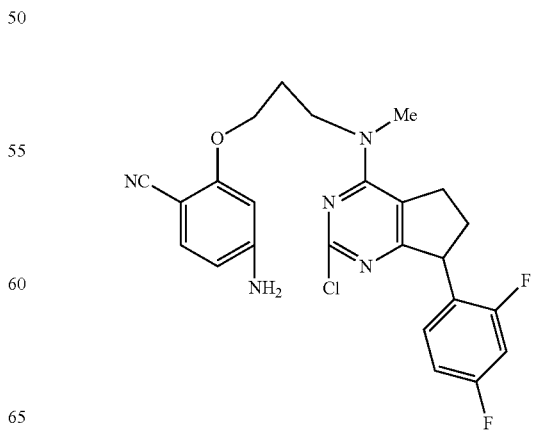

Iron powder-325 mesh (1.22 g, 22.0 mmol) was added to a round bottom flask charged with a mixture of Preparation Td (1.1 g, 2.20 mmol), 1:1 methanol:water (60 mL) and ammonium chloride (1.17 g, 22.0 mmol). A water-cooled reflux condenser was attached to the flask and the heterogeneous mixture was heated to 65° C. with vigorous stirring for 3 h. The reaction mixture was filtered and washed with methanol. The solvent was removed in vacuo. EtOAc was added to the residue, and washed with water and brine. The organic layer was dried over sodium sulfate, filtered, and concentrated to afford title compound (860 mg, 83% yield) as a light yellow solid. LC-MS (M+H)$^+$=470.0. 1H NMR (400 MHz, DMSO-d6) δ ppm 7.25 (1H, s), 7.25-6.74 (3H, m), 6.22-6.19 (1H, d, J=8.4 Hz), 6.10 (1H, s), 4.33 (1H, t, J=8 Hz), 4.31-4.07 (2H, m), 3.89-3.85 (2H, m), 3.30 (3H, s), 3.25-3.16 (5H, m), 2.57-2.55 (1H, m), 2.19-2.04 (2H, m), 1.96-1.85 (1H, m).

Synthon RhD 2-(allyloxy)-4-(4-(but-3-enyl)-7-phenyl-6,7-dihydro-5H-cyclopenta[d]pyrimidin-2-ylamino)benzonitrile

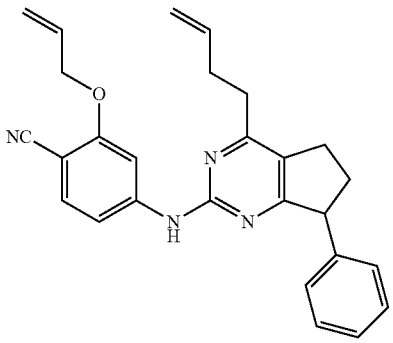 [SMILES: C=CCCc1nc(Nc2ccc(C#N)c(OCC=C)c2)nc2c1CCC2c1ccccc1]

Preparation D (0.673 g, 3.86 mmol) and Preparation Rh (1.1 g, 3.86 mmol) were heated at 150° C. for 90 min while monitoring by LC-MS. After the completion of the reaction, it was cooled to rt and the reaction mass was taken up in dichloromethane (15 mL) and silica (5 g). The resultant slurry of the compound on silica was subjected to flash chromatography using a Teledyne Isco instrument (40 g RediSep silica column, 4% MeOH in CHCl$_3$) to get the title compound (0.5 g, 30.6%) as a light brown solid. LC-MS (M+H)$^+$=423.2. 1H NMR (400 MHz, CDCl$_3$) δ ppm 7.95 (1H, s), 7.36-7.17 (6H, m), 6.68-6.66 (1H, d, J=8.4 Hz), 5.94-5.90 (2H, m), 5.43-5.25 (2H, m), 5.12-5.02 (2H, m), 4.30-4.26 (3H, m), 2.98-2.55 (7H, m), 2.14-2.10 (1H, m).

Synthon RaB

N2-(3-(allyloxy)-4-(3-methyl-1H-1,2,4-triazol-1-yl)phenyl)-7-phenyl-N4-propyl-6,7-dihydro-5H-cyclopenta[d]pyrimidine-2,4-diamine

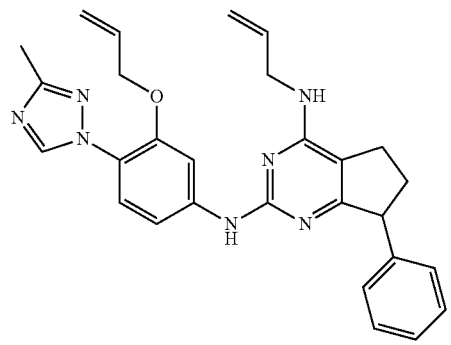 [SMILES: C=CCNc1nc(Nc2ccc(-n3cnc(C)n3)c(OCC=C)c2)nc2c1CCC2c1ccccc1]

Preparation B (0.0807 g, 0.350 mmol) and Preparation Ra (0.1 g, 0.350 mmol) were heated at 150° C. for 30 min while monitoring by LC-MS. After the completion of the reaction, it was cooled to rt and the reaction mass was taken up in dichloromethane (5 mL) and silica (1 g). The resultant slurry of the compound on silica was subjected to flash chromatography using a Teledyne Isco instrument (4 g RediSep silica column, 10% methanol in chloroform) to get the title compound (0.07 g, 42%) as a light green solid. LC-MS (M+H)$^+$=480.2. 1H NMR (400 MHz, DMSO-d6) δ ppm 10.25 (1H, s), 8.76 (1H, s), 7.64-7.56 (2H, m), 7.53-7.17 (7H, m), 6.06-5.95 (2H, m), 5.33-5.17 (4H, m), 4.58 (2H, br s), 4.44 (1H, br s), 4.17 (2H, br s), 2.91-2.74 (3H, m), 2.33 (3H, s), 2.05-2.03 (1H, m).

Synthon RbC

N4-allyl-N2-(3-(allyloxy)-4-(5-methyl-1H-1,2,4-triazol-1-yl)phenyl)-N4-methyl-7-phenyl-6,7-dihydro-5H-cyclopenta[d]pyrimidine-2,4-diamine

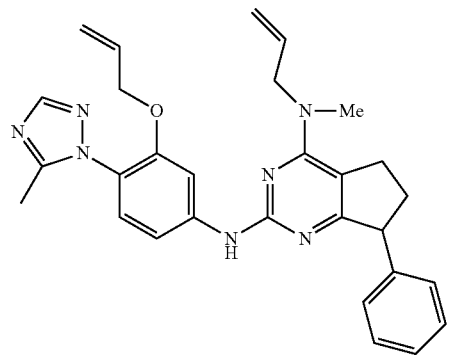 [SMILES: C=CCOc1cc(Nc2nc3c(c(N(C)CC=C)n2)CCC3c2ccccc2)ccc1-n1ncnc1C]

Preparation C (1.53 g, 6.521 mmol) and Preparation Rb(2 g, 6.688 mmol) were heated at 150° C. for 45 min while monitoring by LC-MS. After the completion of the reaction, it was cooled to rt and the reaction mass was taken up in dichloromethane (20 mL) and silica (4 g). The resultant slurry of the compound on silica was subjected to flash chromatography using a Teledyne Isco instrument (40 g RediSep silica column, 5% MeOH in CHCl$_3$) to get the title compound (1.6 g, 50%) as a brown solid. LC-MS (M+H)$^+$=494.2. $^1$H NMR (400 MHz, DMSO-d$_6$): δ ppm 9.8 (1H, br s), 7.91 (1H, s), 7.77 (1H, s), 7.35-7.31 (2H, m), 7.24-7.22 (5H, m), 5.96-5.84 (2H, m), 5.25-5.11 (4H, m), 4.63-4.22 (5H, m), 3.28 (3H, s), 3.25-3.10 (2H, m), 2.21 (3H, s), 2.51 (1H, m), 1.93-1.91 (1H, t, J=4.4 Hz).

Synthon RaC

N4-allyl-N2-(3-(allyloxy)-4-(5-methyl-1H-1,2,4-triazol-1-yl)phenyl)-7-phenyl-6,7-dihydro-5H-cyclopenta[d]pyrimidine-2,4-diamine

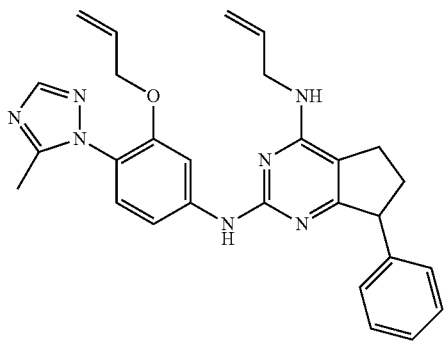 [SMILES: C=CCNc1nc(Nc2ccc(-n3ncnc3C)c(OCC=C)c2)nc2c1CCC2c1ccccc1]

Preparation C (1.61 g, 7.01 mmol) and Preparation Ra (2 g, 7.01 mmol) were heated at 150° C. for 45 min while monitoring by LC-MS. After the completion of the reaction, it was cooled to rt and the reaction mass was taken up in dichloromethane (20 mL) and silica (2 g). The resultant slurry of the compound on silica was subjected to flash chromatography using a Teledyne Isco instrument (12 g RediSep silica column, 10% MeOH in CHCl$_3$) to get the title compound (1.4 g, 41%) as a light brown solid. LC-MS (M+H)$^+$=480.2. 1H NMR (400 MHz, DMSO-d6) δ ppm 10.01 (1H, s), 8.01 (1H, s), 7.60-7.50 (2H, m), 7.49-7.1 (7H, m), 6.02-5.90 (2H, m), 5.30-5.11 (4H, m), 4.52 (2H, br s), 4.40 (1H, br s), 4.12 (2H, br s), 2.90-2.69 (3H, m), 2.21 (3H, s), 1.99-1.94 (1H, m).

Synthon RbB

N4-allyl-N2-(3-(allyloxy)-4-(3-methyl-1H-1,2,4-triazol-1-yl)phenyl)-N4-methyl-7-phenyl-6,7-dihydro-5H-cyclopenta[d]pyrimidine-2,4-diamine

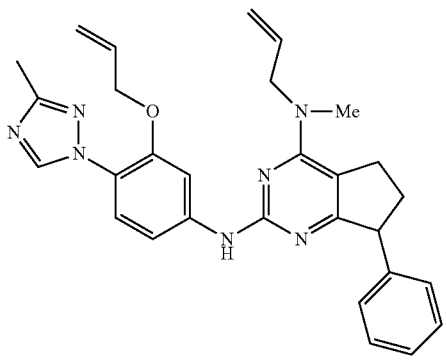 [SMILES: C=CCOc1cc(Nc2nc3c(c(N(C)CC=C)n2)CCC3c2ccccc2)ccc1-n1cnc(C)n1]

Preparation B (1.53 g, 6.521 mmol) and Preparation Rb (2 g, 6.688 mmol) were heated at 150° C. for 45 min while monitoring by LC-MS. After the completion of the reaction, it was cooled to rt and the reaction mass was taken up in dichloromethane (15 mL) and silica (4 g). The resultant slurry of the compound on silica was subjected to flash chromatography using a Teledyne Isco instrument (40 g RediSep silica column, 5% MeOH in CHCl$_3$) to get the title compound (1.6 g, 50%) as a brown solid. LC-MS (M+H)$^+$=494.2. $^1$H NMR (400 MHz, DMSO-d$_6$): δ ppm 10.01 (1H, br s), 8.71 (1H, s), 7.54 (1H, d, J=8.4 Hz), 7.40-7.38 (1H, m), 7.36-7.19 (6H, m), 6.06-5.93 (2H, m), 5.33-5.23 (4H, m), 4.56-4.37 (5H, m), 3.35 (3H, s), 3.27-3.15 (2H, m), 2.60-2.51 (1H, m), 2.34 (3H, s), 1.97 (1H, t, J=7.6 Hz).

Synthon SaB

N4-allyl-N2-(3-(allyloxy)-4-(3-methyl-1H-1,2,4-triazol-1-yl)phenyl)-7-(4-fluorophenyl)-6,7-dihydro-5H-cyclopenta[d]pyrimidine-2,4-diamine

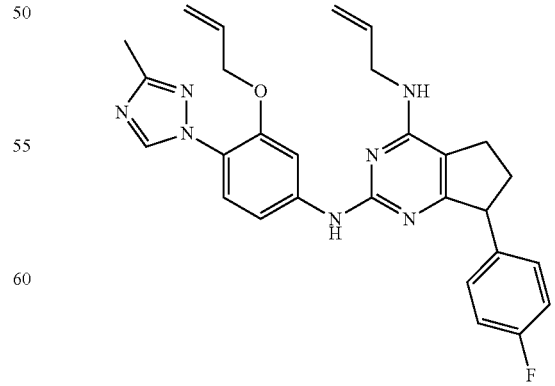

Preparation B (1.06 g, 4.618 mmol) and Preparation Sa (1.4 g, 4.618 mmol) were heated at 150° C. for 45 min while monitoring by LC-MS. After the completion of the reaction, it was cooled to rt and the reaction mass was taken up in dichloromethane (20 mL) and silica (2 g). The resultant slurry of the compound on silica was subjected to flash chromatography using a Teledyne Isco instrument (12 g RediSep silica column, 10% MeOH in CHCl$_3$) to get the title compound (1.4 g, 61%) as a light brown solid. LC-MS (M+H)$^+$=498.2. 1H NMR (400 MHz, DMSO-d6) δ ppm 10.15 (1H, s), 8.72 (1H, m), 7.64-7.54 (2H, m), 7.35-7.18 (5H, m), 6.04-5.96 (2H, m), 5.34-5.18 (4H, m), 4.58 (2H, br s), 4.47 (1H, br s), 4.17 (2H, br s), 2.88-2.67 (3H, m), 2.34 (3H, s), 1.99-1.94 (1H, m).

Synthon TaB

N4-allyl-N2-(3-(allyloxy)-4-(3-methyl-1H-1,2,4-triazol-1-yl)phenyl)-7-(2,4-difluorophenyl)-6,7-dihydro-5H-cyclopenta[d]pyrimidine-2,4-diamine

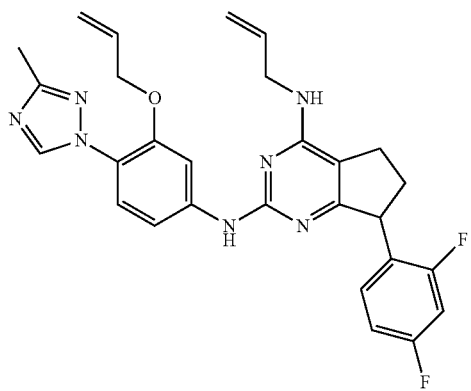 [SMILES: C=CCNc1nc(Nc2ccc(-n3cnc(C)n3)c(OCC=C)c2)nc2c1CCC2c1ccc(F)cc1F]

Preparation B (0.788 g, 3.426 mmol) and Preparation Ta (1.2 g, 3.738 mmol) were heated at 150° C. for 45 min while monitoring by LC-MS. After the completion of the reaction, it was cooled to rt and the reaction mass was taken up in dichloromethane (20 mL) and silica (3 g). The resultant slurry of the compound on silica was subjected to flash chromatography using a Teledyne Isco instrument (40 g RediSep silica column, 5% MeOH in CHCl$_3$) to get the title compound (1.2 g, 63%) as a light brown solid. LC-MS (M+H)$^+$=516.2. $^1$H NMR (400 MHz, CDCl$_3$): δ ppm 8.60 (1H, s), 7.65 (1H, d, J=8.8 Hz), 7.47 (1H, s), 7.32-7.27 (1H, m), 7.22-7.16 (1H, m), 6.92-6.82 (2H, m), 6.02-5.94 (2H, m), 5.37-5.28 (5H, m), 4.55 (3H, t, J=8 Hz), 4.25 (2H, t, J=5.2 Hz), 2.85-2.7 (3H, m), 2.48 (3H, s), 2.21-2.17 (1H, m).

Synthon TaC

N4-allyl-N2-(3-(allyloxy)-4-(5-methyl-1H-1,2,4-triazol-1-yl)phenyl)-7-(2,4-difluorophenyl)-6,7-dihydro-5H-cyclopenta[d]pyrimidine-2,4-diamine

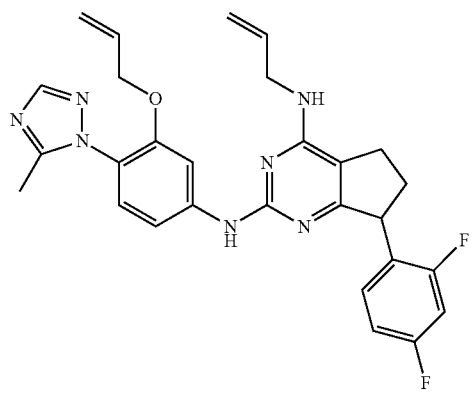 [SMILES: C=CCNc1nc(Nc2ccc(-n3ncnc3C)c(OCC=C)c2)nc2c1CCC2c1ccc(F)cc1F]

Preparation C (0.322 g, 1.401 mmol) and Preparation Ta (0.450 g, 1.401 mmol) were heated at 150° C. for 45 min while monitoring by LC-MS. After the completion of the reaction, it was cooled to rt and the reaction mass was taken up in dichloromethane (15 mL) and silica (1.5 g). The resultant slurry of the compound on silica was subjected to flash chromatography using a Teledyne Isco instrument (40 g RediSep silica column, 5% MeOH in CHCl$_3$) to get the title compound (290 mg, 40%) as a dark brown solid. LC-MS (M+H)$^+$=516.2. $^1$H NMR (400 MHz, CDCl$_3$): δ ppm 7.89 (1H, s), 7.88 (1H, s), 7.18-7.15 (1H, d, J=8.4 Hz), 7.09-7.07 (2H, m), 6.86-6.78 (3H, m), 6.01-5.98 (1H, m), 5.77 (1H, m), 5.32-5.12 (4H, m), 4.56-4.47 (2H, m), 4.28-4.27 (4H, m), 2.71-2.69 (1H, m), 2.30 (3H, s), 2.04-1.92 (1H, m).

Synthon ScJ

N1-(2-(5-amino-2-(3-methyl-1H-1,2,4-triazol-1-yl)phenoxy)ethyl)-N2-(2-chloro-7-(4-fluorophenyl)-6,7-dihydro-5H-cyclopenta[d]pyrimidin-4-yl)ethane-1,2-diamine

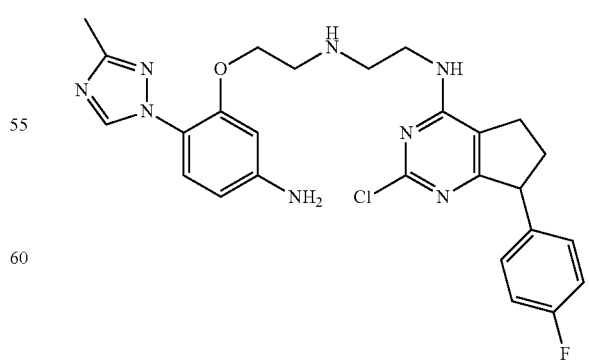

Iron powder-325 mesh (0.129 mg, 2.21 mmol) was added to a round bottom flask charged with a mixture of Preparation Sc (0.2 g, 0.442 mmol), 2:1 methanol:water (7.5 mL), and ammonium chloride (0.119 g, 2.21 mmol). A water-cooled reflux condenser was attached to the flask and the heterogeneous mixture was heated to 65° C. with vigorous stirring for 120 min. The reaction mixture was filtered and washed with methanol. The solvent was removed in vacuo. EtOAc was added to the residue, and washed with water and brine. The organic layer was dried over sodium sulfate, filtered, and concentrated. The residue was subjected to flash chromatography using a Teledyne Isco instrument (4 g RediSep silica column, 10% MeOH in CHCl$_3$) to get the title compound (150 mg, 80% yield) as a pale yellow solid. LC-MS (M+H)$^+$ =523.2, 1H NMR (400 MHz, CDCl$_3$) δ ppm 8.31 (1H, s), 7.25-6.94 (5H, m), 6.36-6.34 (3H, m), 4.32-4.25 (2H, m), 4.22-4.20 (2H, m), 4.93-4.90 (2H, m), 3.81-3.78 (2H, m), 3.20 (2H, br s), 3.10 (2H, br s), 2.85-2.67 (3H, m), 2.44 (3H, s), 2.01-1.97 (1H, m).

Synthon SdJ

N1-(2-(5-amino-2-(3-methyl-1H-1,2,4-triazol-1-yl) phenoxy)ethyl)-N2-(2-chloro-7-(4-fluorophenyl)-6, 7-dihydro-5H-cyclopenta[d]pyrimidin-4-yl)-N1-methylethane-1,2-diamine

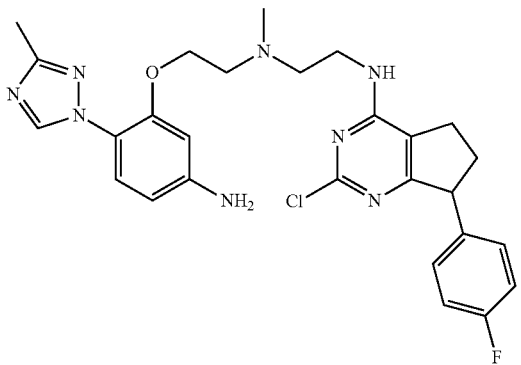 [SMILES: Cc1ncn(-c2ccc(N)cc2OCCN(C)CCNc2nc(Cl)nc3c2CCC3c2ccc(F)cc2)n1]

Iron powder-325 mesh (0.345 mg, 6.17 mmol) was added to a round bottom flask charged with a mixture of Preparation Sd (0.7 g, 1.235 mmol), 2:1 methanol:water (45 mL), and ammonium chloride (0.330 g, 6.17 mmol). A water-cooled reflux condenser was attached to the flask and the heterogeneous mixture was heated to 65° C. with vigorous stirring for 120 min. The reaction mixture was filtered and washed with methanol. The solvent was removed in vacuo. EtOAc was added to the residue, and washed with water and brine. The organic layer was dried over sodium sulfate, filtered, and concentrated. The residue was subjected to flash chromatography using a Teledyne Isco instrument (12 g RediSep silica column, 10% MeOH in CHCl$_3$) to get the title compound (305 mg, 46% yield) as a pale yellow solid. LC-MS (M+H)$^+$ =537.2, 1H NMR (400 MHz, CDCl$_3$) δ ppm 8.35 (1H, s), 7.14-7.08 (6H, m), 6.41 (1H, s), 6.33-6.31 (1H, d, J=8.4 Hz), 4.39-4.35 (2H, m), 4.16-4.13 (1H, t, J=7.2 Hz), 3.93-3.88 (4H, m), 3.34 (3H, s), 3.22-3.11 (6H, m), 3.55-3.46 (1H, m), 2.46 (3H, s), 2.01-1.98 (1H, m).

Synthon TbB

N4-allyl-N2-(3-(allyloxy)-4-(3-methyl-1H-1,2,4-triazol-1-yl)phenyl)-7-(2,4-difluorophenyl)-N4-methyl-6,7-dihydro-5H-cyclopenta[d]pyrimidine-2,4-diamine

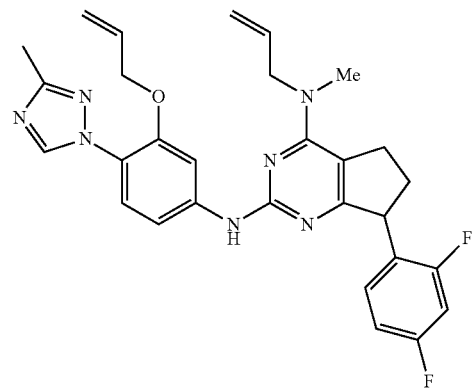 [SMILES: C=CCOc1cc(Nc2nc3c(c(N(C)CC=C)n2)CCC3c2ccc(F)cc2F)ccc1-n1cnc(C)n1]

Preparation B (0.686 g, 2.98 mmol) and Preparation Tb (1 g, 2.98 mmol) were heated at 150° C. for 60 min while monitoring by LC-MS. After the completion of the reaction, it was cooled to rt and the reaction mass was taken up in dichloromethane (15 mL) and silica (2 g). The resultant slurry of the compound on silica was subjected to flash chromatography using a Teledyne Isco instrument (40 g RediSep silica column, 5% MeOH in CHCl$_3$) to get the title compound (700 mg, 44.4%) as a brown solid. LC-MS (M+H)$^+$=530.2. $^1$H NMR (400 MHz, CDCl$_3$): δ ppm 8.51 (1H, s), 7.70 (1H, s), 7.53 (1H, d, J=8.8 Hz), 7.10-7.08 (2H, m), 6.83-6.79 (2H, m), 5.93-5.86 (2H, m), 5.32-5.19 (4H, m), 4.42-4.21 (5H, m), 3.21 (3H, s), 3.09 (2H, m), 2.56-2.48 (1H, m), 2.46 (3H, s), 1.92 (1H, m).

Synthon RhB

N-(3-(allyloxy)-4-(3-methyl-1H-1,2,4-triazol-1-yl) phenyl)-4-(but-3-enyl)-7-phenyl-6,7-dihydro-5H-cyclopenta[d]pyrimidin-2-amine

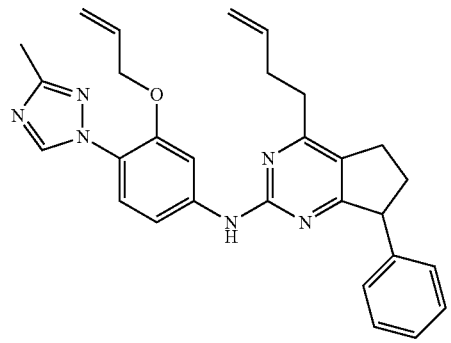 [SMILES: C=CCCc1nc(Nc2ccc(-n3cnc(C)n3)c(OCC=C)c2)nc2c1CCC2c1ccccc1]

Preparation B (0.873 g, 3.79 mmol) and Preparation Rh (0.900 g, 3.16 mmol) were heated at 150° C. for 45 min while monitoring by LC-MS. After the completion of the reaction, it was cooled to rt and the reaction mass was taken up in dichloromethane (10 mL) and silica (4.5 g). The resultant slurry of the compound on silica was subjected to flash chromatography using a Teledyne Isco instrument (12 g RediSep silica column, 4% MeOH in CHCl$_3$) to get the title compound (0.625 g, 41.3%) as a light brown solid. LC-MS (M+H)$^+$ =479.2 1H NMR (400 MHz, DMSO-d6) δ ppm 9.75 (1H, s), 8.60 (1H, s), 8.10 (1H, s), 7.38-7.16 (7H, m), 5.98-5.94 (2H, m), 5.30-5.23 (2H, m), 5.13-5.01 (2H, m), 4.35-4.31 (3H, m), 2.81-2.77 (1H, m), 2.56-2.51 (6H, m), 2.32 (3H, s), 2.05-1.95 (1H, m).

Synthon RiL

N-(3-(5-amino-2-(3-methyl-1H-1,2,4-triazol-1-yl)phenoxy)propyl)-2-chloro-N-methyl-7-phenyl-6,7-dihydro-5H-cyclopenta[d]pyrimidin-4-amine

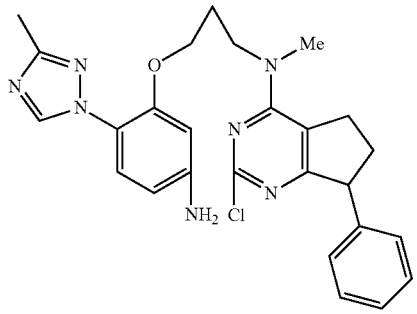

Iron powder-325 mesh (0.644 mg, 11.54 mmol) was added to a round bottom flask charged with a mixture of Preparation Ri (1.2 g, 2.308 mmol), 3:1 methanol:water (45 mL), and ammonium chloride (0.617 g, 11.54 mmol). A water-cooled reflux condenser was attached to the flask and the heterogeneous mixture was heated to 65° C. with vigorous stirring for 120 min. The reaction mixture was filtered and washed with methanol. The solvent was removed in vacuo. EtOAc was added to the residue, and washed with water and brine. The organic layer was dried over sodium sulfate, filtered, and concentrated. The residue was subjected to flash chromatography using a Teledyne Isco instrument (12 g RediSep silica column, 10% MeOH in CHCl$_3$) to get the title compound (900 mg, 80% yield) as a yellow solid. LC-MS (M+H)$^+$ =490.2, 1H NMR (400 MHz, CDCl$_3$) δ ppm 8.35 (1H, s), 7.36-7.11 (6H, m), 6.35-6.33 (2H, m), 4.17-4.04 (2H, m), 3.84 (2H, br s), 3.70-3.66 (2H, m), 3.18 (3H, s), 3.15-3.00 (2H, m), 3.55-3.48 (2H, m), 3.45 (3H, s), 2.12-2.04 (3H, m).

Synthon TeK

N-(3-(5-amino-2-(3-methyl-1H-1,2,4-triazol-1-yl)phenoxy)propyl)-2-chloro-7-(2,4-difluorophenyl)-6,7-dihydro-5H-cyclopenta[d]pyrimidin-4-amine

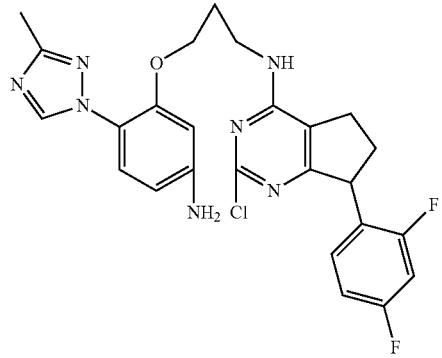 [SMILES: Cc1ncn(-c2ccc(N)cc2OCCCNc2nc(Cl)nc3c2CCC3c2ccc(F)cc2F)n1]

Iron powder-325 mesh (0.309 mg, 5.54 mmol) was added to a round bottom flask charged with a mixture of Preparation Te (0.6 g, 1.107 mmol), 3:1 methanol:water (16 mL), and ammonium chloride (0.296 g, 5.54 mmol). A water-cooled reflux condenser was attached to the flask and the heterogeneous mixture was heated to 65° C. with vigorous stirring for 120 min. The reaction mixture was filtered and washed with methanol. The solvent was removed in vacuo. EtOAc was added to the residue, and washed with water and brine. The organic layer was dried over sodium sulfate, filtered, and concentrated. The residue was subjected to flash chromatography using a Teledyne Isco instrument (12 g RediSep silica column, 10% methanol in chloroform) to get the title compound (500 mg, 88% yield) as a pale yellow solid. LC-MS (M+H)$^+$=512.2. 1H NMR (400 MHz, CDCl$_3$) δ ppm 8.35 (1H, s), 7.29-7.27 (1H, m), 6.94-6.76 (3H, m), 6.35-6.33 (2H, m), 5.34 (1H, br s), 4.44-4.13 (1H, t, J=8.8 Hz), 4.13-4.06

(2H, m), 3.86 (2H, s), 3.62-3.59 (2H, m), 3.59-3.52 (3H, m), 3.45 (3H, s), 2.13-2.10 (2H, m), 1.99-1.94 (1H, m).

Synthon SeL

N-(3-(5-amino-2-(3-methyl-1H-1,2,4-triazol-1-yl)phenoxy)propyl)-2-chloro-7-(4-fluorophenyl)-N-methyl-6,7-dihydro-5H-cyclopenta[d]pyrimidin-4-amine

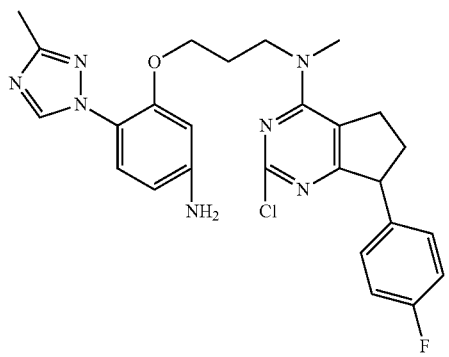 [SMILES: Cc1ncn(-c2ccc(N)cc2OCCCN(C)c2nc(Cl)nc3c2CCC3c2ccc(F)cc2)n1]

Iron powder-325 mesh (1.142 g, 20.45 mmol) was added to a round bottom flask charged with a mixture of Preparation Se (1.10 g, 2.045 mmol), 1:1:3 methanol:water:THF (100 mL), and ammonium chloride (1.094 g, 20.45 mmol). A water-cooled reflux condenser was attached to the flask and the heterogeneous mixture was heated to 65° C. with vigorous stirring for 2 h. The reaction mixture was filtered and washed with methanol. The solvent was removed in vacuo. EtOAc was added to the residue, and washed with water and brine. The organic layer was dried over sodium sulfate, filtered, and concentrated to afford the title compound (850 mg, 82% yield) as a yellow solid. LC-MS (M+H)$^+$=508.2. $^1$H NMR (400 MHz, CDCl$_3$): δ ppm 9.30 (1H, s), 7.34 (1H, d, J=8.4 Hz), 7.09-7.07 (2H, m), 6.98-6.94 (2H, m), 6.35-6.28 (1H, m), 4.14-4.09 (3H, m), 4.10 (2H, m), 3.83 (2H, m), 3.16 (1H, s), 3.01 (2H, m), 2.49-2.4 (1H, m), 2.45 (3H, s), 2.09-2.90 (4H, m).

Synthon TgP

N-(5-(5-amino-2-(3-methyl-1H-1,2,4-triazol-1-yl)phenoxy)pentan-2-yl)-2-chloro-7-(2,4-difluorophenyl)-6,7-dihydro-5H-cyclopenta[d]pyrimidin-4-amine

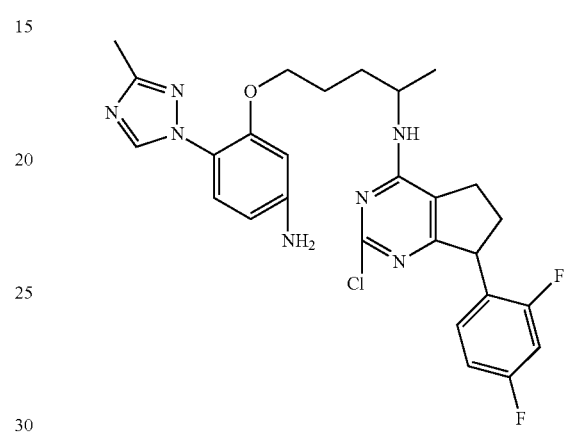

Iron powder-325 mesh (0.63 g, 11.4 mmol) was added to a round bottom flask charged with a mixture of 2-chloro-7-(2,4-difluorophenyl)-N-(5-(2-(3-methyl-1H-1,2,4-triazol-1-yl)-5-nitrophenoxy)pentan-2-yl)-6,7-dihydro-5H-cyclopenta[d]pyrimidin-4-amine (0.65 g, 1.14 mmol), methanol (15 mL), THF (30 mL), water (15 mL) and ammonium chloride (0.61 g, 11.4 mmol). A water-cooled reflux condenser was attached to the flask and the heterogeneous mixture was heated at 70° C. with vigorous stirring for 2 h. The reaction mixture was filtered and washed with methanol. The filtrate was concentrated in vacuo. EtOAc (250 mL) was added to the residue and was washed with brine. The organic layer was dried over anhydrous sodium sulfate, filtered, and concentrated to afford the light yellow solid N-(5-(5-amino-2-(3-methyl-1H-1,2,4-triazol-1-yl)phenoxy)pentan-2-yl)-2-chloro-7-(2,4-difluorophenyl)-6,7-dihydro-5H-cyclopenta[d]pyrimidin-4-amine (500 mg, 81%). LC-MS (M+H)$^+$=540.2. 1H NMR (400 MHz, CDCl$_3$) δ ppm 8.32 (1H, s), 7.32-7.30 (1H, m), 6.96-6.94 (1H, m), 6.81-6.75 (2H, m), 6.34-6.29 (2H, m), 4.83 (1H, br m), 4.44-4.43 (2H, m), 4.09-

4.00 (2H, m), 3.77 (2H, br s), 3.13-3.12 (1H, m), 2.64-2.56 (2H, m), 2.47 (3H, s), 1.94-1.80 (3H, m), 1.63-1.61 (2H, m), 1.27-1.22 (3H, m).

Synthon ShQ tert-butyl 7-cyano-18-(4-fluorophenyl)-10,11,14,16,17,18-hexahydro-3H-15,2-(azeno)-4,8-(metheno)cyclopenta[h][1,4,10,12]oxatriazacycloheptadecine-12(13H)-carboxylate

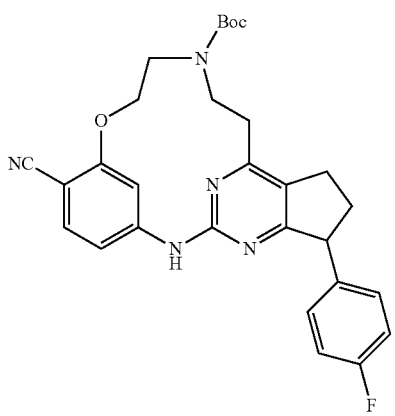 [SMILES: CC(C)(C)OC(=O)N1CCOc2cc(ccc2C#N)Nc2nc(c3c(n2)C(c2ccc(F)cc2)CC3)CC1]

A mixture of tert-butyl (2-(5-amino-2-cyanophenoxy)ethyl)(2-(2-chloro-7-(4-fluorophenyl)-6,7-dihydro-5H-cyclopenta[d]pyrimidin-4-yl)ethyl)carbamate (0.01 g, 0.18 mmol), xanthphos (1.57 mg, 0.0027 mmol), and cesium carbonate (0.012 g, 0.036 mmol) in 1,4-dioxane (3 mL) was degassed with nitrogen for 1 h and then Pd(OAc)2 (0.407 mg, 0.00181 mmol) was added. The reaction mixture was heated at 110° C. for 60 min. The solvent was removed under reduced pressure and the residue was dissolved in ethyl acetate (3 mL) and filtered through celite. The filtrate was concentrated and the crude compound was purified by column chromatography (60-120 mesh silica) using 10% methanol in chloroform to give the title compound (0.002 g, 21.41%) as a light yellow solid. LC-MS (M+H)$^+$=516.2. 1H NMR (400 MHz, CDCl$_3$) δ ppm 9.01 (1H, s), 7.39 (1H, d, J=8.4 Hz), 7.14-7.11 (3H, m), 7.04-6.99 (2H, m), 6.38 (1H, d, J=8.0 Hz), 4.55-4.49 (2H, m), 4.24 (1H, t, J=8.8 Hz), 3.80-3.75 (4H, m), 3.05-2.95 (4H, m), 2.72-2.63 (1H, m), 2.17-2.12 (1H, m), 1.55 (9H, s).

Synthon UaD 4-(4-(allylamino)-7-(4-fluorophenyl)-6,7-dihydro-5H-cyclopenta[d]pyrimidin-2-ylamino)-2-(allyloxy)benzonitrile

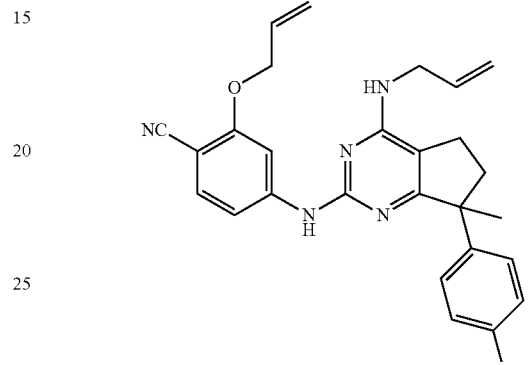

To a solution of 2-(allyloxy)-4-aminobenzonitrile (Preparation D, 168 mg, 0.963 mmol), and N-allyl-2-chloro-7-(4-fluorophenyl)-7-methyl-6,7-dihydro-5H-cyclopenta[d]pyrimidin-4-amine (Preparation Ua, 204 mg, 0.642 mmol) in N-Methyl-2-pyrrolidinone (5135 μL) was added H$_2$SO$_4$ (54.7 μL, 1.027 mmol). The mixture was stirred at 100° C. overnight. The crude reaction mixture was purified by PREP HPLC: (50×250 mm HPLC XTerra C18.15 to 100% A:B over 40 min, 3 min at 100% B (A is 90:10:0.1 water:MeOH:TFA; B is 90:10:0.1 MeOH:water:TFA)). The appropriate fractions were concentrated in vacuo to afford 4-(4-(allylamino)-7-(4- fluorophenyl)-6,7-dihydro-5H-cyclopenta[d]pyrimidin-2-ylamino)-2-(allyloxy)benzonitrile (74 mg, 25% yield). LC-MS (M+H)⁺=456.1.

Synthon VaB

N-(4-(5-amino-2-(3-methyl-1H-1,2,4-triazol-1-yl)phenoxy)butyl)-2-chloro-8-(4-fluorophenyl)-6-methyl-5,6,7,8-tetrahydropyrido[4,3-d]pyrimidin-4-amine

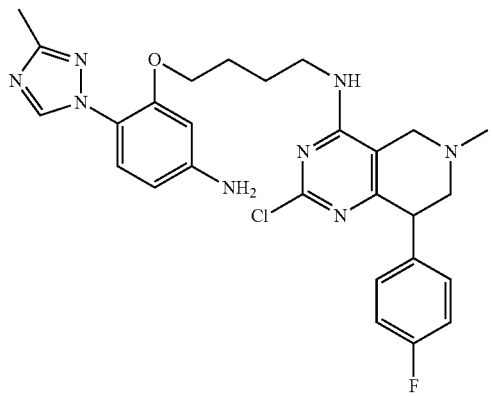 [SMILES: Cc1ncn(-c2ccc(N)cc2OCCCCNc2nc(Cl)nc3c2CN(C)CC3c2ccc(F)cc2)n1]

The mixture of 2-chloro-8-(4-fluorophenyl)-6-methyl-N-(4-(2-(3-methyl-1H-1,2,4-triazol-1-yl)-5-nitrophenoxy)butyl)-5,6,7,8-tetrahydropyrido[4,3-d]pyrimidin-4-amine, TFA salt (420 mg, 0.617 mmol), iron (207 mg, 3.70 mmol) and ammonium chloride (330 mg, 6.17 mmol) in MeOH (4.1 mL)/water (2.1 mL) was heated at 80° C. for 1 h. The reaction mixture was cooled to rt and the solid was filtered off. The filtrate was concentrated in vacuo and the residue was purified by Prep-HPLC to get N-(4-(5-amino-2-(3-methyl-1H-1,2,4-triazol-1-yl)phenoxy)butyl)-2-chloro-8-(4-fluorophenyl)-6-methyl-5,6,7,8-tetrahydropyrido[4,3-d]pyrimidin-4-amine, (215 mg, 65% yield). LC-MS (M+H)⁺=537.2. ¹H NMR (500 MHz, methanol-d₄) δ 8.93 (br. s., 1H), 7.64-7.59 (m, 1H), 7.43 (dd, J=8.8, 5.0 Hz, 1H), 7.24-7.18 (m, 2H), 7.15-7.08 (m, 2H), 6.95 (br. s., 1H), 6.86-6.78 (m, 1H), 4.46 (dd, J=10.4, 6.4 Hz, 1H), 4.28 (d, J=18.3 Hz, 2H), 4.21 (t, J=6.1 Hz, 2H), 3.89 (dd, J=12.5, 6.3 Hz, 1H), 3.61-3.52 (m, 3H), 3.15-3.08 (m, 3H), 2.46 (s, 3H), 1.96-1.87 (m, 2H), 1.84-1.72 (m, 2H).

Synthon YaB 1-(5-amino-2-(3-methyl-1H-1,2,4-triazol-1-yl)phenoxy)-4-(2-chloro-7-(4-fluorophenyl)-6,7-dihydro-5H-cyclopenta[d]pyrimidin-4-ylamino)butan-2-ol

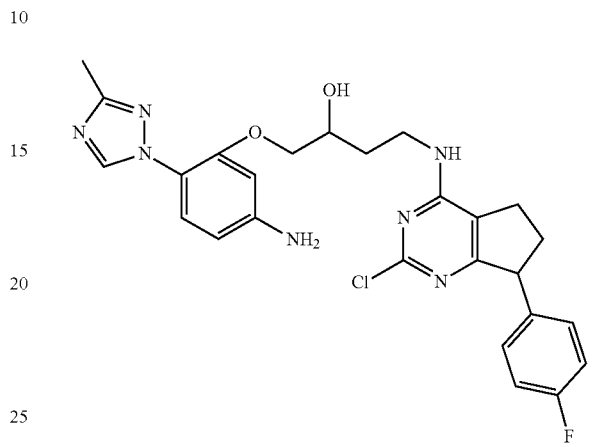

The mixture of 4-(2-chloro-7-(4-fluorophenyl)-6,7-dihydro-5H-cyclopenta[d]pyrimidin-4-ylamino)-1-(2-(3-methyl-1H-1,2,4-triazol-1-yl)-5-nitrophenoxy)butan-2-ol (70 mg, 0.126 mmol), iron (42.3 mg, 0.758 mmol) and ammonium chloride (67.6 mg, 1.264 mmol) in MeOH (842 µL) and water (421 µL) was heated at 80° C. for 1 h. The crude product was purified by Prep-HPLC to obtain 1-(5-amino-2-(3-methyl-1H-1,2,4-triazol-1-yl)phenoxy)-4-(2-chloro-7-(4-fluorophenyl)-6,7-dihydro-5H-cyclopenta[d]pyrimidin-4-ylamino)butan-2-ol (53 mg, 80% yield). LC-MS (M+H)⁺=524.3. ¹H NMR (500 MHz, methanol-d₄) δ 9.30 (s, 1H), 7.70 (d, J=8.5 Hz, 1H), 7.23-7.15 (m, 2H), 7.10-7.04 (m, 2H), 6.98 (s, 1H), 6.84 (dd, J=8.9, 1.8 Hz, 1H), 4.38-4.32 (m, 1H), 4.24-4.20 (m, 1H), 4.19-4.07 (m, 2H), 3.77-3.67 (m, 2H), 2.88-2.80 (m, 1H), 2.76-2.70 (m, 2H), 2.50 (d, J=1.5 Hz, 3H), 2.09-2.03 (m, 1H), 2.01-1.94 (m, 1H), 1.87 (d, J=5.5 Hz, 1H).

Synthon VcD 4-(4-(allyl(methyl)amino)-8-(4-fluorophenyl)-6-methyl-5,6,7,8-tetrahydropyrido[4,3-d]pyrimidin-2-ylamino)-2-(allyloxy)benzonitrile

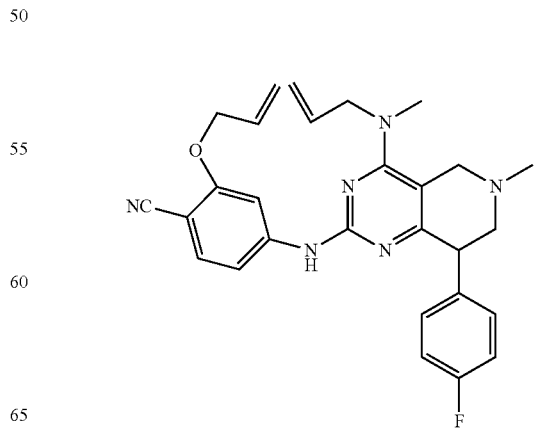

The mixture of N-allyl-2-chloro-8-(4-fluorophenyl)-N,6-dimethyl-5,6,7,8-tetrahydropyrido[4,3-d]pyrimidin-4-amine (Preparation Vc, 655 mg, 1.889 mmol), 2-(allyloxy)-4-aminobenzonitrile (Preparation D, 329 mg, 1.889 mmol) and $H_2SO_4$ (232 µL, 4.34 mmol) in NMP (3.8 mL) was heated at 90° C. overnight. The crude product was purified by Prep-HPLC to obtain 4-((4-(allyl(methyl)amino)-8-(4-fluorophenyl)-6-methyl-5,6,7,8-tetrahydropyrido[4,3-d]pyrimidin-2-yl)amino)-2-(allyloxy)benzonitrile, TFA salt (158 mg, 13.98% yield). LC-MS (M+H)$^+$=485.6. $^1$H NMR (400 MHz, methanol-$d_4$) δ 7.68 (d, J=1.8 Hz, 1H), 7.41-7.32 (m, 3H), 7.22-7.13 (m, 2H), 7.05 (dd, J=8.5, 1.8 Hz, 1H), 6.12-5.92 (m, 2H), 5.53-5.25 (m, 4H), 4.71-4.60 (m, 1H), 4.57-4.39 (m, 2H), 4.39-4.30 (m, 1H), 4.30-4.17 (m, 1H), 4.12-3.85 (m, 2H), 3.59-3.42 (m, 1H), 3.17-2.96 (m, 7H).

EXAMPLES 1 and 2

(11Z)-7-(4-chloro-1H-imidazol-1-yl)-18-phenyl-10,13,14,16,17,18-hexahydro-15,2-(azeno)-8,4-(metheno)cyclopenta[h][1,6,10,12]oxatriazacycloheptadecine and (11E)-7-(4-chloro-1H-imidazol-1-yl)-18-phenyl-10,13,14,16,17,18-hexahydro-15,2-(azeno)-8,4-(metheno)cyclopenta[h][1,6,10,12]oxatriazacycloheptadecine Example 1

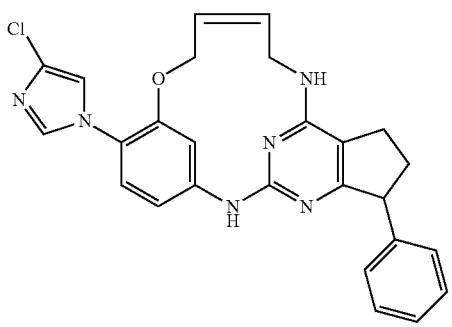

Example 2

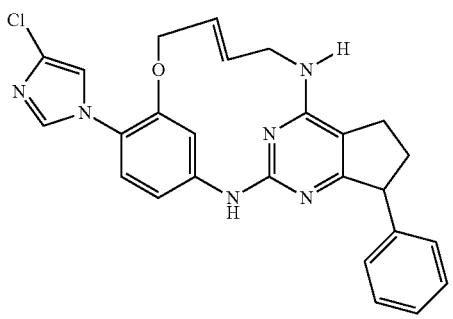

A solution of Synthon RaA (2.0 g, 4.016 mmol) in 1,2-dicholoethane (2 L) was taken in a 5 L three-necked round bottom flask equipped with a reflux condenser and nitrogen inlet. The solution was degassed with nitrogen for 1 h and Hoveyda-Grubbs II generation catalyst (0.63 g, 1.0 mmol) was added. The mixture was heated at 85° C. for 16 h under nitrogen while monitoring by LC-MS. The solvent was evaporated under reduced pressure and the residue was subjected to flash chromatography using a Teledyne Isco instrument (120 g RediSep silica column, 10% MeOH in $CHCl_3$) to remove metallic and other impurities. The fractions having the desired compound were concentrated and the component isomers were further separated by chiral SFC (chiral cel-OJ-H, 30×250 mm, 5 µm column, 120 mL/min of 50% MeOH (0.5% DEA) in $CO_2$ at 100 bar and 35° C.

EXAMPLE 1

Analytical data of cis-(+)-enantiomer (1A): (210 mg, 11.2%) of off-white solid. Retention time 2.71 min. LC-MS (M+H)$^+$=471.2. $^1$H NMR (400 MHz, DMSO-d6): δ ppm 9.74 (1H, s), 9.35 (1H, s), 7.79 (1H, s), 7.79-7.47 (1H, m), 7.46 (1H, s), 7.30-7.26 (2H, m), 7.21-7.10 (4H, m), 6.63-6.11 (1H, m), 5.62-5.58 (2H, m), 5.1 (1H, m), 4.62-4.58 (1H, d, J=14.8 Hz), 4.12-4.10 (1H, m), 3.57 (1H, m), 2.79-2.77 (1H, m), 2.66-2.62 (1H, m), 1.93-1.92 (1H, m).

Analytical data of cis-(−)-enantiomer (1B): (231 mg, 12.3%) of off-white solid. Retention time 3.95 min. LC-MS (M+H)$^+$=471.2. $^1$H NMR (400 MHz, DMSO-d6): identical to its antipode 1A.

EXAMPLE 2

Analytical data of trans-(+)-enantiomer (2A): (222 mg, 11.7%) of off-white solid. Retention time 9.30 min. LC-MS (M+H)$^+$=471.1. $^1$H NMR (400 MHz, DMSO-d6): δ ppm 9.25 (1H, s), 8.31 (1H, s), 7.77 (1H, s), 7.45 (1H, s), 7.32-7.10 (8H, m), 6.59-6.57 (1H, m), 6.01-5.67 (1H, d, J=15.6 Hz), 5.68-5.64 (1H, d, J=16 Hz), 4.80 (2H, m), 4.12-4.08 (1H, t, J=16 Hz), 3.89 (2H, m), 2.81-2.76 (1H, m), 2.68-2.51 (2H, m), 1.97-1.94 (1H, m).

Analytical data of trans-(−)-enantiomer (2B): (222 mg, 11.7%) of off-white solid. Retention time 12.37 min. LC-MS (M+H)$^+$=471.1. $^1$H NMR (400 MHz, DMSO-d6): identical to its antipode 2A.

EXAMPLES 3 and 4

(11Z)-7-(4-chloro-1H-imidazol-1-yl)-14-methyl-18-phenyl-10,13,14,16,17,18-hexahydro-15,2-(azeno)-8,4-(metheno)cyclopenta[h][1,6,10,12]oxatriazacycloheptadecine and (11E)-7-(4-chloro-1H-imidazol-1-yl)-14-methyl-18-phenyl-10,13,14,16,17,18-hexahydro-15,2-(azeno)-8,4-(metheno)cyclopenta[h][1,6,10,12]oxatriazacycloheptadecine Example 3

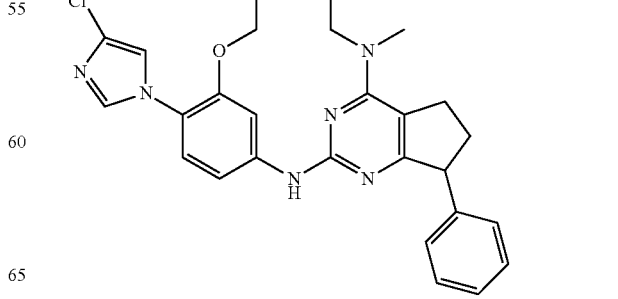

-continued

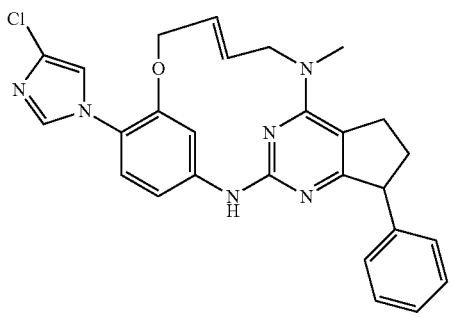

Example 4

A solution of Synthon RbA (1 g, 1.92 mmol) in 1,2-dichoroethane (2 L) was taken in a 5 L three-necked round bottom flask equipped with a reflux condenser and nitrogen inlet. The solution was degassed with nitrogen for 1 h and Hoveyda-Grubbs II generation catalyst (0.1 g, 0.15 mmol) was added. The mixture was heated at 100° C. for 18 h under nitrogen while monitoring by LC-MS. The solvent was evaporated under reduced pressure and the residue was subjected to flash chromatography using Teledyne Isco instrument (24 g RediSep silica column, 10% MeOH in $CHCl_3$) to remove metallic and other impurities. The fractions having desired compound were concentrated and the component isomers were further separated by chiral SFC (Chiralcel OD-H 30×250 mm, 5 μm column, 70 mL/min of 35% MeOH (0.1% DEA) in $CO_2$ at 150 bar and 35° C.).

EXAMPLE 3

Analytical data of cis-enantiomer I (3A): (38.8 mg, 3.9%) of a brown solid. Retention time 26.45 min. LC-MS $(M+H)^+$ =485.6. $^1H$ NMR (400 MHz, DMSO-d6): δ ppm 9.44 (1H, s), 9.34 (1H, s), 7.79 (1H, m), 7.46 (1H, s), 7.46-7.11 (6H, m), 6.67 (1H, d, J=8.8 Hz), 5.80 (1H, d, J=10 Hz), 5.62 (1H, m), 5.16-5.01 (2H, m), 4.60 (1H, m), 4.10-4.05 (1H, m), 3.52-3.48 (1H, m), 3.39 (3H, s), 3.32-3.15 (2H, m), 2.51-2.01 (1H, m), 1.92-1.90 (1H, m).

Analytical data of cis-enantiomer II (3B): (35.5 mg, 3.6%) of a brown solid. Retention time 32.85 min. LC-MS $(M+H)^+$ =485.6. $^1H$ NMR (400 MHz, DMSO-d6): identical to its antipode 3A.

EXAMPLE 4

Analytical data of trans-enantiomer I (4A): (20.1 mg, 2.1%) of a light brown solid. Retention time 19.80 min. LC-MS $(M+H)^+$=485.6. $^1H$ NMR (400 MHz, DMSO-d6): δ ppm 9.24 (1H, s), 7.94 (1H, s), 7.94 (1H, m), 7.77 (1H, s), 7.76-7.45 (2H, m), 7.32-7.28 (3H, m), 7.19-7.09 (1H, m), 6.58-6.56 (1H, m), 6.05 (1H, t, J=16.4 Hz), 5.50 (1H, m), 4.81 (2H, d, J=5.2 Hz), 4.09-4.00 (3H, m), 3.32 (3H, s), 3.21-3.12 (2H, m), 2.50-2.44 (2H, s).

Analytical data of trans-enantiomer II (4B): (19.3 mg, 2.1%) of a light brown solid. Retention time 23.46 min. LC-MS $(M+H)^+$=485.6. $^1H$ NMR (400 MHz, DMSO-d6): identical to its antipode 4A.

EXAMPLE 5

(11E)-7-(4-chloro-1H-imidazol-1-yl)-19-phenyl-3,10,13,14,15,17,18,19-octahydro-2,16-(azeno)-8,4-(metheno)cyclopenta[j][1,7,9,13]oxatriazacyclooctadecine

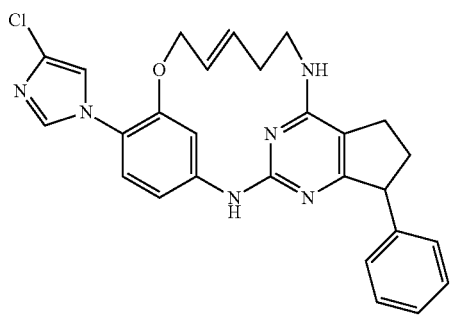

Example 5

A solution of synthon RcA (1 g, 1.95 mmol) in 1,2-dichoroethane (2 L) was taken in a 5 L three-necked round bottom flask equipped with a reflux condenser and nitrogen inlet. The solution was degassed by nitrogen for 1 h and Hoveyda-Grubbs II generation catalyst (0.1 g, 0.15 mmol) was added. The mixture was heated at 100° C. for 18 h under nitrogen while monitoring by LC-MS. The solvent was evaporated under reduced pressure and the residue was subjected to flash chromatography using Teledyne Isco instrument (24 g RediSep silica column, 10% MeOH in $CHCl_3$) to remove metallic and other impurities. The fractions having desired compound were concentrated and its component isomers were further separated by chiral HPLC [CHRIAL PAK IC (250×4.6) mm, mobile phase A: n-Hexane (60%), B: EtOH 40%]

EXAMPLE 5A

Trans-(+) isomer (0.250 g, 27.7%). Retention time 7.09 min. LC-MS $(M+H)^+$=485.4. $^1H$ NMR (400 MHz, $CDCl_3$): δ ppm 7.87 (1H, s), 7.54 (1H, s), 7.34-7.20 (5H, m), 7.18-7.02 (2H, m), 6.93 (1H, s), 6.36 (1H, q, J=2.4 Hz), 6.10 (1H, t, J=8.00 Hz), 5.63 (1H, t, J=7.60 Hz), 4.69-4.59 (2H, m), 4.18 (1H, t, J=6.8 Hz), 3.72 (2H, m), 2.77-2.62 (2H, m), 2.34-2.11 (2H, m), 2.10-2.04 (1H, m).

EXAMPLE 5B

Trans-(−) isomer (0.250 g, 27.7%). Retention time 8.71 min. LC-MS (M+H)⁺=485.4. $^1$H NMR (400 MHz, CDCl$_3$): identical to its antipode 5A.

EXAMPLES 6 and 7

(11Z)-7-(4-chloro-1H-imidazol-1-yl)-14-methyl-19-phenyl-3,10,13,14,15,17,18,19-octahydro-2,16-(azeno)-8,4-(metheno)cyclopenta[j][1,7,9,13]oxatriazacyclooctadecine and (11E)-7-(4-chloro-1H-imidazol-1-yl)-14-methyl-19-phenyl-3,10,13,14,15,17,18,19-octahydro-2,16-(azeno)-8,4-(metheno)cyclopenta[j][1,7,9,13]oxatriazacyclooctadecine

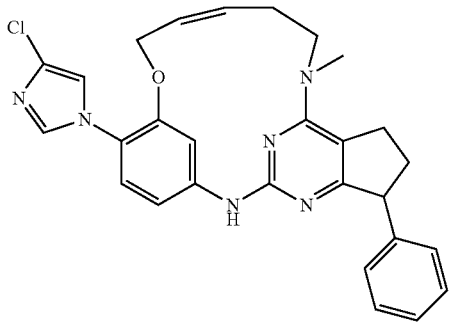

Example 6

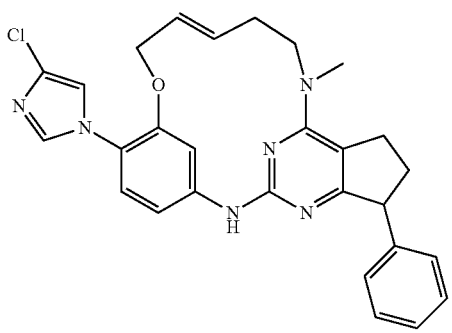

Example 7

A solution of Synthon RdA (0.975 g, 1.85 mmol) in 1,2-dicholoethane (2.5 L) was taken in a 5 L three-necked round bottom flask equipped with a reflux condenser and nitrogen inlet. The solution was degassed by nitrogen for 1 h and Hoveyda-Grubbs II generation catalyst (0.1 g, 0.15 mmol) was added. The mixture was heated at 100° C. for 18 h under nitrogen while monitoring by LC-MS. The solvent was evaporated under reduced pressure and the residue was subjected to column chromatography using 60% ethyl acetate in dichloromethane to remove metallic and other impurities. The fractions having the desired compounds were concentrated and the component isomers were further separated in two stages: the cis/trans mixture was purified by reverse phase HPLC {symmetry shield RP18 (250×4.6 mm), Mobile phase A: 20 mM ammonium acetate in water Mobile phase B: acetonitrile} to get cis (100 mg) and trans (250 mg) isomers. Chiral separation of the cis-enantiomers and trans-enantiomers were performed by chiral preparative HPLC [WHELK (250×4.6) mm, mobile phase A: n-heptanes (70%), B: MeOH+EtOH (1:1) 30%]

EXAMPLE 6A

Cis-(+) isomer. (23 mg, 2.4%). Retention time 18.12 min. LC-MS (M+H)⁺=499.0. $^1$H NMR (400 MHz, DMSO-d6) δ ppm 9.08 (1H, s), 8.15 (1H, s), 7.75 (1H, s), 7.42 (1H, s), 7.32-7.13 (6H, m), 6.67-6.64 (1H, m), 5.63-5.61 (2H, m), 4.79-4.76 (2H, m), 4.077-4.03 (1H, t), 3.54 (2H, m), 3.37 (3H, s), 3.33-3.29 (1H, m), 3.15-3.13 (1H, m), 2.52-2.48 (3H, m), 1.90-1.89 (1H, m).

EXAMPLE 6B

Cis-(−) isomer (21 mg, 2.27%). Retention time 22.25 min. LC-MS (M+H)⁺=499.0. $^1$H NMR (400 MHz, DMSO-d6) identical to its antipode 6A.

EXAMPLE 7A

Trans-(+) isomer (45 mg, 4.8%). Retention time 16.65 min. LC-MS (M+H)⁺=499.0. $^1$H NMR (400 MHz, DMSO-d6): δ ppm 9.08 (1H, s), 7.77 (1H, s), 7.60 (1H, s), 7.45 (1H, s), 7.44-7.13 (6H, m), 6.56-6.55 (1H, m), 6.03-5.97 (1H, m), 5.60-5.55 (1H, m), 4.64 (2H, s), 4.08 (1H, s), 3.40-3.32 (4H, m), 3.24 (3H, s), 2.52-2.48 (3H, m), 1.94-1.91 (1H, m).

EXAMPLE 7B

Trans-(−)-isomer (48 mg, 5.1%). Retention time 20.54 min. LC-MS (M+H)⁺=499.0. $^1$H NMR (400 MHz, DMSO-d6): identical to its antipode 7A.

EXAMPLE 8

7-(4-chloro-1H-imidazol-1-yl)-19-phenyl-10,11,13,14,15,17,18,19-octahydro-16,2-(azeno)-8,4-(metheno)cyclopenta[i][1,4,7,11,13]dioxatriazacyclooctadecine

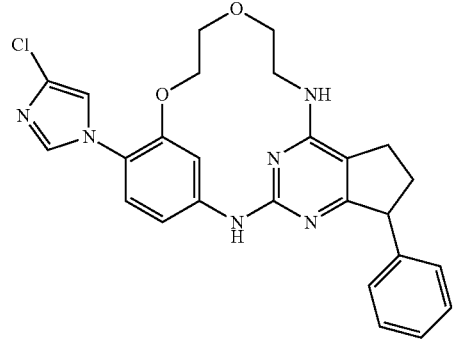

Example 8

A mixture of Synthon ReA (0.35 g, 0.66 mmol), xanthphos (0.57 g, 0.1 mmol), and cesium carbonate (0.325 g, 1.0 mmol) in 1,4-dioxane (20 mL) was degassed with nitrogen for 1 h. Then, Pd(dba)$_3$ (0.06 g, 0.066 mmol) was added, and the reaction mixture was stirred at 110° C. for 14 h. The solvent was removed under reduced pressure and the residue was dissolved in ethyl acetate (200 mL) and filtered through celite. The filtrate was concentrated under reduced pressure and the crude residue was purified by column chromatography (60-120 mesh silica) using 50-70% ethyl acetate in chloroform as mobile phase to give the racemic title compound. The enantiomers were separated by chiral chromatography [Chiral pak IC (250×4.6 mm), mobile phase: A: O$_2$% of DEA in n-hexane (50) B: ethanol (50)] to yield two enantiomers.

EXAMPLE 8

Analytical data of (+)-enantiomer (8A): (0.04 g, 13.79%) of off-white solid. Retention time 12.67 min. LC-MS (M+H)$^+$ =489.2. $^1$H NMR (400 MHz, DMSO-d6): δ ppm 8.64 (1H, s), 7.76 (1H, s), 7.44 (1H, s), 7.31 (1H, s), 7.27-7.12 (7H, m), 6.66-6.64 (1H, m), 4.27-4.26 (2H, m), 4.12-4.08 (1H, Tj=8), 3.77-3.70 (2H, m), 3.68-3.54 (4H, m), 2.77-2.50 (3H, m), 1.94-1.91 (1H, m).

Analytical data of (−)-enantiomer (8B): (0.03 g, 10.34%) of off white solid. Retention time 8.84 min. LC-MS (M+H)$^+$ =489.2. $^1$H NMR (400 MHz, DMSO-d6): identical to its antipode 8A.

EXAMPLE 9

7-(4-chloro-1H-imidazol-1-yl)-17-phenyl-11,12,13, 15,16,17-hexahydro-10H-14,2-(azeno)-8,4-(metheno)cyclopenta[g][1,5,9,11]oxatriazacyclohexadecine

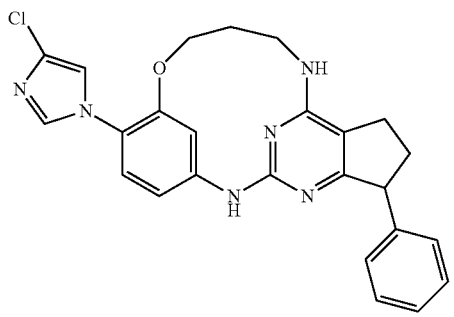

Example 9

A mixture of Synthon RfA (0.23 g, 0.46 mmol), xanthphos (0.040 g, 0.06 mmol), and cesium carbonate (0.226 g, 0.696 mmol) in 1,4-dioxane (15 mL) was degassed with nitrogen for 1 h and then Pd(dba)$_3$ (0.042 g, 0.046 mmol) was added. The reaction mixture was heated at 110° C. for 14 h. The solvent was removed under reduced pressure and the residue was dissolved in ethyl acetate (200 ml) and filtered through celite. The filtrate was concentrated and the crude compound was purified by column chromatography (60-120 mesh silica) using 50-60% ethyl acetate in chloroform as mobile phase to give the racemic title compound. The enantiomers were separated by chiral chromatography [Chiralpak IC (250×4.6 mm), mobile phase: A: O$_2$% of DEA in n-hexane (50%) B: ethanol (50%)} to give the following enantiomers.

Analytical data of (+)-enantiomer (9A): (6 mg 2.83%) of off-white solid: Retention time 5.87 min LC-MS (M+H)$^+$ =459.0. $^1$H NMR (400 MHz, CDCl$_3$): δ ppm 9.01 (1H, s), 7.58 (1H, s), 7.32-7.02 (7H, m), 6.53 (1H, d, J=8 Hz), 4.92 (1H, m), 4.38-4.35 (2H, m), 4.18-4.16 (1H, m), 3.62-3.54 (2H, m), 2.75-2.59 (3H, m), 2.39-2.34 (3H, m), 2.09-2.03 (1H, m).

Analytical data of (−)-enantiomer (9B): (4 mg, 1.88%) of off-white solid: LC-MS (M+H)$^+$=459.0 Chiral HPLC retention time 7.4 min. $^1$H NMR (400 MHz, CDCl$_3$): identical to its antipode 9A.

EXAMPLE 10

7-(4-chloro-1H-imidazol-1-yl)-13-methyl-17-phenyl-11,12,13,15,16,17-hexahydro-10H-14,2-(azeno)-8,4-(metheno)cyclopenta[g][1,5,9,11]oxatriazacyclohexadecine

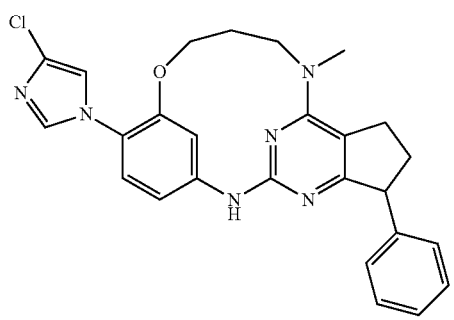

Example 10

A mixture of Synthon RgA (0.17 g, 0.35 mmol), xanthphos (0.040 g, 0.05 mmol), and cesium carbonate (0.163 g, 0.502 mmol) in 1,4-dioxane (15 mL) was degassed with nitrogen for one hour and then Pd (dba)$_3$ (0.042 g, 0.046 mmol) was added. The reaction mixture was heated at 110° C. for 14 h. The solvent was removed under reduced pressure and the residue was dissolved in ethyl acetate (150 mL) and filtered through celite. The filtrate was concentrated, and the crude compound was purified by column chromatography (60-120 mesh silica) using 50-60% ethyl acetate in pet ether as mobile phase to give the racemate (25 mg). The enantiomers were separated by chiral chromatography [Chiral pak IA (250×4.6 mm), mobile phase: A: O$_2$% of DEA in n-hexane (70%) B: ethanol (30%)] to give the enantiomers.

EXAMPLE 10

Analytical data of (+)-enantiomer (10A): (0.004 g, 2.53%), off-white solid. Retention time 10.65 min. LC-MS (M+H)$^+$ =473.2. $^1$H NMR (400 MHz, CDCl$_3$): δ ppm 8.7 (1H, s), 7.60 (1H, s), 7.34-6.99 (8H, m), 6.75 (1H, s), 4.27-4.22 (3H, m) 3.31 (3H, s), 3.22-3.08 (2H, m), 2.61-2.58 (3H, m), 2.3-2.05 (3H, m).

Analytical data of (−)-enantiomer (10B): (0.004 g, 2.53%) of off-white solid. Retention time 14.42 min. LC-MS (M+H)⁺ =473.2. ¹H NMR (400 MHz, CDCl₃): identical to its antipode 10A.

EXAMPLE 11

7-(4-chloro-1H-imidazol-1-yl)-19-phenyl-3,10,11,12,13,14,15,17,18,19-decahydro-2,16-(azeno)-8,4-(metheno)cyclopenta[f][1,7,9,13]oxatriazacyclooctadecine

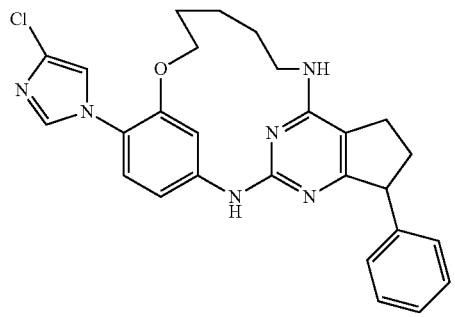

Example-11

Example 5A (0.110 g, 0.227 mmol) in 10 mL of 1:1 (MeOH:THF) was hydrogenated (balloon of H₂) at room temperature in presence of platinum(IV)oxide (0.011 g, 0.048 mmol) for 40 min. The reaction mixture was degassed with nitrogen and filtered through celite. Solvents were removed under reduced pressure and the residue was purified by chiral preparative HPLC [Chiralpak IA (250×4.6 mm), 5 micron, mobile Phase: n-hexane:ethanol (50:50)] to give Example 11A along with the ring opened phenolic compound. Example 5B was also similarly hydrogenated on the same scale to get Example 11B and the corresponding ring opened phenolic compound.

EXAMPLE 11

Analytical data of (+)-Enantiomer (11A): (36 mg, 32%) of off-white solid. Retention time 5.24 min. LC-MS (M+H)⁺ =487.2 ¹H NMR (400 MHz, DMSO-d6) δ ppm 9.22 (1H, s), 8.42 (1H, s), 8.41 (1H, s), 7.42 (1H, s), 7.31-7.27 (2H, m), 7.25-7.14 (5H, m), 6.69-6.66 (1H, dd J=2.0, 8.8 Hz), 4.19-4.15 (2H, m), 4.10 (1H, t J=8.4 Hz), 3.40-3.06 (2H, m), 2.82-2.75 (1H, m), 2.68-2.54 (2H, m), 1.95-1.86 (3H, m), 1.72 (2H, m), 1.27-1.24 (2H, m).

Analytical data of (−)-Enantiomer (11B): (29 mg, 26%) of off-white solid. Retention time 7.17 min. LC-MS (M+H)⁺ =487.2. ¹H NMR (400 MHz, DMSO-d6) identical to its antipode 11A.

EXAMPLE 12

7-(4-chloro-1H-imidazol-1-yl)-18-phenyl-10,11,12,13,14,16,17,18-octahydro-15,2-(azeno)-8,4-(metheno)cyclopenta[h][1,6,10,12]oxatriazacycloheptadecine

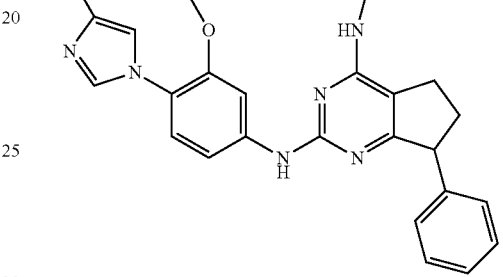

Example 12

A mixture of Examples 1 and 2 (0.250 g, 0.53 mmol) in 10 mL of 1:1 (MeOH:THF) was hydrogenated at room temperature in the presence of platinum(IV)oxide (0.011 g, 0.048 mmol) for 40 min. Reaction mixture was degassed with nitrogen and filtered through celite. Solvents were removed under reduced pressure and the residue was purified by chiral preparative HPLC [Chiralpak IA (250×4.6 mm), 5 micron, mobile phase: n-hexane:ethanol (80:20)] to give Example 12 along with ring opened phenolic compounds.

EXAMPLE 12

Analytical data of (+)-Enantiomer (12A): (30 mg, 12%) of off-white solid. Retention time 10.61. LC-MS (M+H)⁺ =473.2. ¹H NMR (400 MHz, CDCl₃) δ ppm 9.26 (1H, s), 7.56 (1H, s), 7.33-7.15 (5H, m), 7.06-7.02 (3H, m), 6.38-6.36 (1H, dd, J=5.6, 8.4 Hz), 4.86 (1H, m), 4.38-4.36 (2H, t, J=6 Hz), 4.20-4.17 (1H, m), 3.58-3.55 (2H, m), 2.75-2.61 (3H, m), 2.10-2.00 (3H, m), 1.94-1.96 (2H, m).

Analytical data of (−)-Enantiomer (12B): (30 mg, 12%) of off-white solid. Retention time 13.3 min. LC-MS (M+H)$^+$ =473.2. $^1$H NMR (400 MHz, CDCl$_3$) identical to its (+)-antipode.

EXAMPLE 13

7-(4-chloro-1H-imidazol-1-yl)-14-methyl-18-phenyl-10,11,12,13,14,16,17,18-octahydro-15,2-(azeno)-8,4-(metheno)cyclopenta[h][1,6,10,12]oxatriazacycloheptadecine

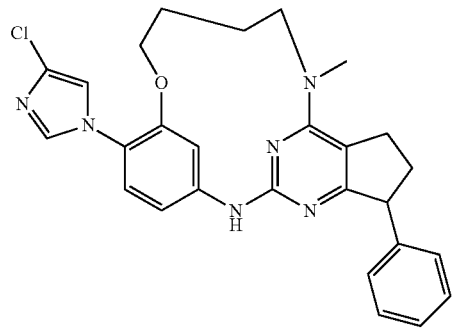

Example 13

A suspension of Example 3 (cis-racemic, 0.320 g, 0.659 mmol) in 20 mL of 1:1 (MeOH:THF) was hydrogenated (balloon of H$_2$) at room temperature in presence of platinum (IV)oxide (0.032 g, 0.155 mmol) for 40 min. The reaction mixture was degassed with nitrogen and filtered through celite. Solvents were removed under reduced pressure and the residue was purified by chiral preparative HPLC [Chiralpak IA (250×4.6 mm), 5 micron, mobile Phase: n-hexane:ethanol (50:50)] to give Example 13 along with ring opened phenolic compounds.

EXAMPLE 13

Analytical data of (+)-Enantiomer (13A): (0.024 g, 2.4%) off-white solid. Retention time 7.41 min. LC-MS (M+H)$^+$ =487.2. $^1$H NMR (400 MHz, DMSO-d6): δ ppm 9.30 (1H, s), 9.25 (1H, s), 7.78 (1H, s), 7.46 (1H, s), 7.32-7.28 (2H, m), 7.22-7.12 (4H, m), 6.71-6.68 (1H, d, J=8.4 Hz), 4.35 (2H, brs), 4.10-4.06 (1H, t, J=8.4 Hz), 3.31 (3H, s), 3.29-3.13 (2H, m), 2.52-2.50 (3H, m), 1.97-1.85 (5H, m).

Analytical data of (−)-Enantiomer (13B): (0.044 g, 4.41%) off-white solid. Retention time 9.94 min. LC-MS (M+H)$^+$ =487.2 $^1$H NMR (400 MHz, DMSO-d6): identical to its antipode 13A.

EXAMPLE 14 and 15

(11Z)-7-(4-chloro-1H-imidazol-1-yl)-18-(2,4-difluorophenyl)-10,13,14,16,17,18-hexahydro-15,2-(azeno)-8,4-(metheno)cyclopenta[h][1,6,10,12]oxatriazacycloheptadecine and (11E)-7-(4-chloro-1H-imidazol-1-yl)-18-(2,4-difluorophenyl)-10,13,14,16,17,18-hexahydro-15,2-(azeno)-8,4-(metheno)cyclopenta[h][1,6,10,12]oxatriazacycloheptadecine

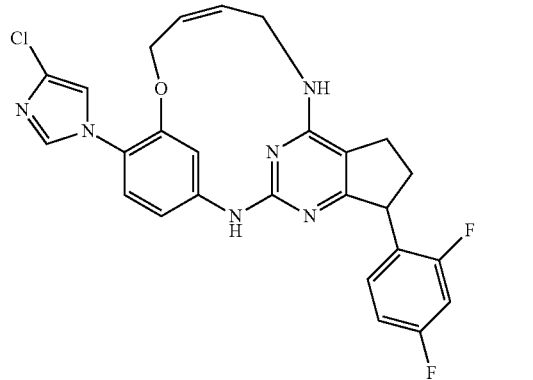

Example 14

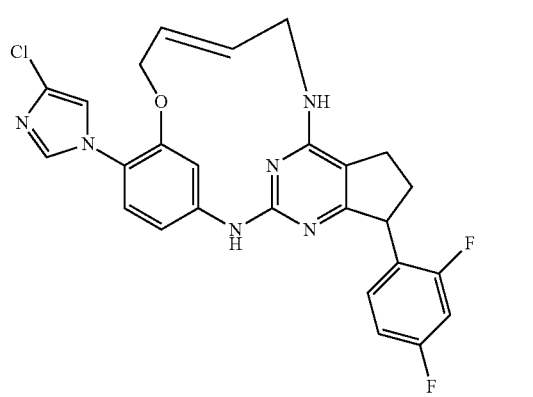

Example 15

In a 5 L round bottom flask, 1,2-dicholoethane (2 L) was degassed for 1 h with nitrogen. Synthon TaA (0.600 g, 1.122 mmol) was added followed by Hoveyda-Grubbs II generation catalyst (0.100 g, 0.162 mmol). The mixture was heated at 85° C. for 16 h. The solvent was removed under reduced pressure. After removal of metallic impurities via silica gel column chromatography, the components were separated via chiral SFC [Chiralcel OJ-H 250×4.6 mm, 5 micron, 0.2% DEA in Hexane (60%)/Ethanol (40%)] to give Example 14 and Example 15.

EXAMPLE 14

Analytical data of cis-(+)-enantiomer (14A): (30.01 mg, 5.28%) of a dark ash solid. Retention time 11.01 min. LC-MS (M+H)$^+$=507.0 $^1$H NMR (400 MHz, CDCl$_3$) δ ppm 9.73 (1H, s), 7.58 (1H, s), 7.08-7.00 (4H, m), 6.98-6.80 (2H, m), 6.33-

6.30 (1H, m), 5.73-5.65 (2H, m), 5.14-5.05 (2H, m), 4.66-4.62 (2H, m), 4.44-4.40 (1H, t, J=8 Hz), 2.75-2.70 (3H, m), 2.00-1.97 (1H, m).

Analytical data of cis-(−)-enantiomer (14B): (32.7 mg, 5.75%) of a dark ash solid. Retention time 4.00 min. LC-MS (M+H)$^+$=507.0 $^1$H NMR (400 MHz, CDCl$_3$): identical to its antipode 14A.

EXAMPLE 15

Analytical data of trans-(+)-Enantiomer (15A): (14.48 mg, 2.25%) of dark ash solid. Retention time 3.91 min. LC-MS (M+H)$^+$=507.0 $^1$H NMR (400 MHz, CDCl$_3$) δ ppm 8.36 (1H, s), 7.56 (1H, s), 7.06-7.00 (4H, m), 6.84-6.81 (2H, m), 6.40-6.37 (1H, d, J=2 Hz), 6.00-5.95 (1H, d, J=6 Hz), 5.75-5.71 (2H, d, J=6.4 Hz), 4.84-4.82 (2H, m), 4.44-4.40 (1H, t, J=7.2 Hz), 4.06-4.00 (2H, m), 2.74-2.64 (3H, m), 2.02-1.96 (1H, m).

Analytical data of trans-(−)-enantiomer (15B): (17.07 mg, 3.30%) of a dark ash solid. Retention time 9.16 min. LC-MS (M+H)$^+$=507.0. $^1$H NMR (400 MHz, CDCl$_3$) identical to its antipode 15A.

EXAMPLE 16 and 17

(11Z)-7-(4-chloro-1H-imidazol-1-yl)-18-phenyl-10,13,14,16,17,18-hexahydro-15,2-(azeno)-8,4-(metheno)cyclopenta[h][1,10,12]oxadiazacycloheptadecine and (11E)-7-(4-chloro-1H-imidazol-1-yl)-18-phenyl-10,13,14,16,17,18-hexahydro-15,2-(azeno)-8,4-(metheno)cyclopenta[h][1,10,12]oxadiazacycloheptadecine Example 16

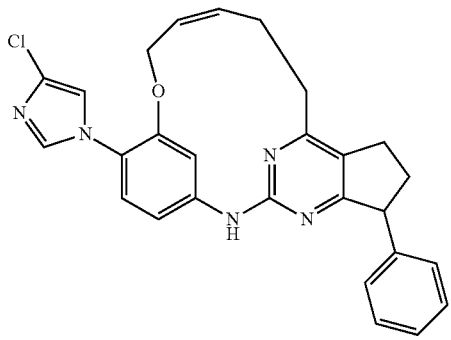

Example 17

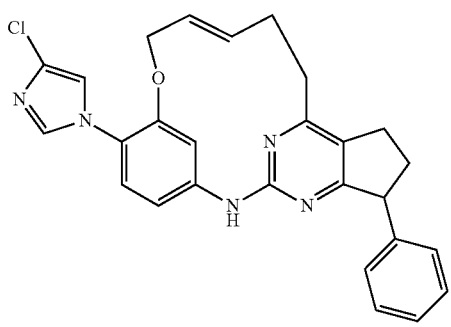

A solution of Synthon RhA (0.4 g, 0.8032 mmol) in 1.5 L of 1,2-dichloroethane was degassed for 2 h with nitrogen. Hoveyda-Grubbs II (0.04 g, 0.063 mmol) was added and the mixture was heated at reflux for 18 h. The solvent was removed under reduced pressure and the residue was purified by column chromatography using 60% ethyl acetate in chloroform to get 0.3 g of Example 16 and Example 17. The mixture of four compounds was separated into the components by chiral reverse-phase supercritical fluid chromatography (Chiralcel OD-H 30×250 mm, 5 μm column, 70 mL/min of 35% MeOH (0.1% DEA) in CO$_2$ at 150 bar and 35° C.

EXAMPLE 16

Analytical data of cis-(+)-enantiomer (16A): (18.6 mg) of an off-white wax: Retention time 21.5 min. LC-MS (M+H)$^+$=470.1. $^1$H NMR (500 MHz, CDCl$_3$): δ ppm 9.62 (1H, d, J=1.8 Hz), 7.57 (1H, s), 7.32 (2H, t, J=7.3 Hz), 7.22-7.27 (1H, m), 7.11-7.19 (3H, m), 7.07 (1H, s), 7.02 (1H, d, J=8.2 Hz), 6.32 (1H, d, J=7.9 Hz), 5.62-5.73 (1H, m), 5.48-5.57 (1H, m), 5.10 (1H, t, J=11.9 Hz), 4.67 (1H, t, J=13.4 Hz), 4.24 (1H, d, J=1.2 Hz), 3.23-3.26 (1H, m), 3.08-3.22 (1H, m), 2.89-3.01 (2H, m), 2.78-2.87 (1H, m), 2.60-2.71 (1H, m), 2.29-2.40 (1H, m), 2.06-2.17 (1H, m).

Analytical data of cis-(−)-enantiomer (16B): (23.2 mg) of an off-white wax: Retention time 43.1 min. LC-MS (M+H)$^+$=470.2. $^1$H NMR (500 MHz, CDCl$_3$): identical to the antipode 16A.

EXAMPLE 17

Analytical data of trans-(+)-enantiomer (17A): (12.6 mg) of an off-white wax: Retention time 17.7 min. LC-MS (M+H)$^+$=470.1. $^1$H NMR (500 MHz, CDCl$_3$): δ ppm 8.71 (1H, d, J=2.1 Hz), 7.55 (1H, d, J=1.2 Hz), 7.33 (2H, t, J=7.6 Hz), 7.22-7.29 (1H, m), 7.16 (2H, d, J=7.0 Hz), 7.10 (1H, s), 7.00-7.07 (2H, m), 6.37 (1H, dd, J=8.4, 2.3 Hz), 5.95 (1H, dt, J=15.6, 5.9 Hz), 5.64 (1H, ddd, J=15.6, 6.3, 6.1 Hz), 4.76 (2H, d, J=6.1 Hz), 4.24 (1H, t, J=8.4 Hz), 2.91-3.05 (3H, m), 2.83 (1H, dt, J=15.6, 7.9 Hz), 2.59-2.73 (4H, m).

Analytical data of trans-(−)-enantiomer (17B): (11.4 mg) of an off-white wax: Retention time 40.6 min. LC-MS (M+H)$^+$=470.2. $^1$H NMR (500 MHz, CDCl$_3$): identical to the antipode 17A.

EXAMPLE 18

(11Z)-7-(4-chloro-1H-imidazol-1-yl)-18-(2,4-difluorophenyl)-14-methyl-10,13,14,16,17,18-hexahydro-15,2-(azeno)-8,4-(metheno)cyclopenta[h][1,6,10,12]oxatriazacycloheptadecine

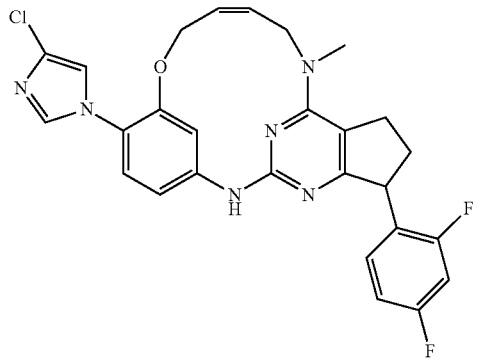

Example 18

A solution of Synthon TbA (1.2 g, 2.186 mmol) in 1,2-dicholoethane (5 L) was degassed for 1 h with nitrogen. Hoveyda-Grubbs II generation catalyst (0.200 g, 0.319 mmol) was added and the mixture was heated at 85° C. for 16 h. The solvent was removed under reduced pressure and subjected to silica gel column chromatography to remove metallic impurities. The two enantiomers were separated by SFC [Chiralcel OD-H, 30×250 mm, 5 μm column, 70 mL/min of 35% MeOH (0.1% DEA) in CO$_2$ at 150 bar and 35° C.].

EXAMPLE 18

Analytical data of cis-(+)-enantiomer (18A): (120 mg, 10.54%) of a dark brown solid. Retention time 11.2 min. LC-MS (M+H)$^+$=521.0. $^1$H NMR (400 MHz, CDCl$_3$) δ ppm 9.47 (1H, s),7.56 (1H, s), 7.26-7.00 (4H, m), 6.99-6.83 (2H, m), 6.33-6.28 (1H, m), 5.78-5.60 (2H, m), 5.28-5.21 (1H, m), 5.05-5.02 (1H, m), 4.62-4.58 (1H, m), 4.37-4.34 (1H, m), 3.47-3.46 (1H, m), 3.42 (3H, s), 3.21-3.01 (2H, m), 2.52-2.55 (1H, m), 1.94-1.91 (1H, m).

Analytical data of cis-(−)-enantiomer (18B): (100 mg, 8.78%) of a dark brown solid. Retention time 8.52 min. LC-MS (M+H)$^+$=521.0 $^1$H NMR (400 MHz, CDCl$_3$) identical to its antipode 18A.

EXAMPLE 19

7-(4-chloro-1H-imidazol-1-yl)-18-(2,4-difluorophenyl)-14-methyl-10,11,12,13,14,16,17,18-octahydro-15,2-(azeno)-8,4-(metheno)cyclopenta[h][1,6,10,12]oxatriazacycloheptadecine

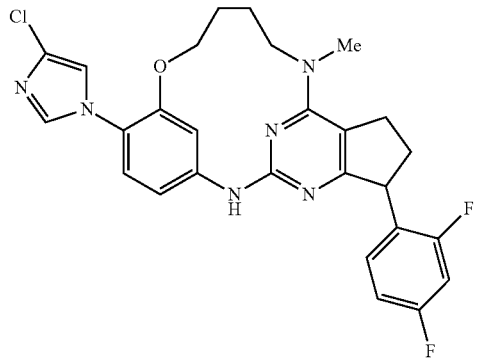

Example 19

A solution of example 18A (0.10 g, 0.154 mmol) in 5 mL of 1:1 (MeOH:THF) was hydrogenated (balloon of H$_2$) at room temperature in presence of Platinum(IV)oxide (0.008 g, 0.032 mmol) for 40 min. The reaction mixture was degassed with nitrogen and filtered through celite. Solvents were removed under reduced pressure and the residue was purified by chiral preparative HPLC [Chiralpak IC (250×4.6 mm), 5 micron, mobile Phase: 0.2% DEA in n-hexane:ethanol (70:30)] to give Example 19A. Example 19B was obtained when 18B was subjected to hydrogenation on a same scale using above conditions. In both cases, a ring opened phenolic isomer was also obtained.

EXAMPLE 19

Analytical data of (+)-enantiomer (19A): (10.4 mg, 10.4%) of off-white solid. Retention time 19.79 min. LC-MS (M+H)$^+$=523.0 $^1$H NMR (400 MHz, CDCl$_3$) δ ppm 9.20 (1H, s), 7.56 (1H, s), 7.27-7.24 (3H, m), 7.05-6.85 (3H, m), 6.37-6.35 (1H, d, J=6.4 Hz), 4.38-4.34 (3H, m), 3.31 (3H, s), 3.19-3.10 (2H, m), 2.56-2.53 (1H, m), 2.07-1.87 (5H, m), 1.60 (2H, m).

Analytical data of (−)-Enantiomer (19B): (16.4 mg, 20%) of off white solid. Retention time 14.21 min. LC-MS (M+H)⁺ =523.0 ¹H NMR (400 MHz, CDCl₃) identical to its antipode 19A.

EXAMPLE 20

7-(4-chloro-1H-imidazol-1-yl)-17-(2,4-difluorophenyl)-13-methyl-11,12,13,15,16,17-hexahydro-10H-14,2-(azeno)-8,4-(metheno)cyclopenta[g][1,5,9,11]oxatriazacyclohexadecine

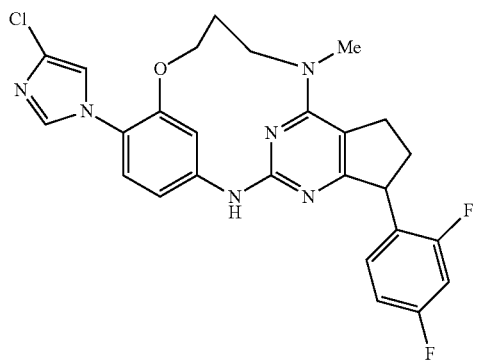

Example-20

A mixture of Synthon TfA (1.2 g, 2.200 mmol), xanthphos (0.191 g, 0.330 mmol), cesium carbonate (1.075 g, 3.30 mmol) and Pd(OAc)2 (0.049 g, 0.220 mmol) in 1,4-dioxane (60 mL) was degassed with nitrogen for 1 h, then heated at 100° C. for 4 h. The solvent was removed under reduced pressure and the residue was dissolved in ethyl acetate (500 mL) and filtered through celite. The filtrate was evaporated under reduced pressure and the crude compound was purified by column chromatography (60-120 mesh silica) using 17-20% ethyl acetate in chloroform as mobile phase to give 180 mg of racemic Example 20. The enantiomers were separated by chiral chromatography [Chiral cel AD-H (250×4.6 mm), mobile phase: A: 0.2% of DEA in n-hexane(70%) B: Ethanol (30%)] to get enantiomeric components Example 20A and Example 20B.

EXAMPLE 20

Analytical data of (+)-enantiomer (20A): (0.0115 g, 1.06%) of off-white solid. Retention time 10.15 min. LC-MS (M+H)⁺=509.2. ¹H NMR (400 MHz, CDCl₃): δ ppm 8.82 (1H, s), 7.58 (1H, s), 7.27-7.00 (3H, m), 6.99-6.81 (3H, m), 6.50-6.48 (1H, d, J=8.4 Hz), 4.37-4.28 (3H, m), 3.75-3.55 (2H, m), 3.24 (3H, s), 3.22-3.03 (2H, m), 2.57-2.53 (1H, m), 2.31-2.28 (2H, m), 1.99-1.94 (1H, m), 2.52-2.48 (3H, m), 1.94-1.91 (1H, m).

Analytical data of (−)-enantiomer (20B): (0.0135 g, 1.24%) of off-white solid. Retention time 16.34 min. LC-MS (M+H)⁺=509.2. ¹H NMR (400 MHz, CDCl₃): identical to its antipode 20A.

EXAMPLE 21 and 22

(11Z)-7-cyano-18-phenyl-10,13,14,16,17,18-hexahydro-15,2-(azeno)-8,4-(metheno)cyclopenta[h][1,6,10,12]oxatriazacycloheptadecine and (11E)-7-cyano-18-phenyl-10,13,14,16,17,18-hexahydro-15,2-(azeno)-8,4-(metheno)cyclopenta[h][1,6,10,12]oxatriazacycloheptadecine

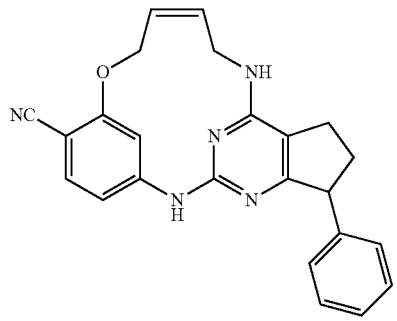

Example 21

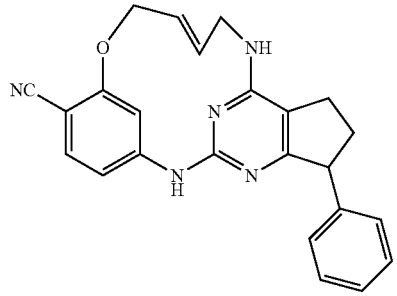

Example 22

A solution of Synthon RaD (1.4 g, 0.0.33 mmol) in 1,2-dicholoethane (1.5 L) was taken in a 3 L three-necked round bottom flask equipped with a reflux condenser and nitrogen inlet. The solution was degassed with nitrogen for 1 h and Hoveyda-Grubbs II generation catalyst (0.14 g, 0.021 mmol) was added. The mixture was heated at 100° C. for 18 h under nitrogen while monitoring by LC-MS. The solvent was evaporated under reduced pressure and the residue was subjected to flash chromatography using a Teledyne Isco instrument (40 g RediSep silica column, 50% ethyl acetate in DCM) to remove metallic and other impurities. The fractions having desired compound were concentrated and the component isomers were further separated by chiral normal phase HPLC [Chiralpak IC (250×4.6)mm 5 mm column, 1.0 mL/min of 0.2% DEA in hexane:ethanol (70:30) as mobile phase].

EXAMPLE 21

Analytical data of cis-(+)-enantiomer (21A): (50 mg, 3.96%) of off white solid. Retention time 8.61 min. LC-MS (M−H)⁺=394.2. ¹H NMR (400 MHz, DMSO-d6): δ ppm 9.70 (1H, s), 9.69 (1H, s) 7.61-7.14 (7H, m), 6.63 (1H, d, J=8 Hz), 5.62 (2H, d, J=11.2 Hz), 5.20-5.19 (1H, m), 4.72-4.69 (1H, m), 4.59 (1H, t, J=15.2 Hz), 4.16-4.11 (1H, m), 3.60-3.32 (1H, m), 2.81-2.50 (2H, m), 1.93 (1H, d, J=5.6 Hz).

Analytical data of cis-(−)-enantiomer (21B): (60 mg, 4.76%) of off white solid. Retention time 8.38 min. LC-MS (M+H)$^+$=396.2. $^1$H NMR (400 MHz, DMSO-d6): identical to its antipode 21A.

EXAMPLE 22

Analytical data of trans-(+)-enantiomer (22A): (60 mg, 4.76%) of off-white solid. Retention time 10.4 min. LC-MS (M+H)$^+$=396.2. $^1$H NMR (400 MHz, DMSO-d6): δ ppm 9.70 (1H, s), 8.43 (1H, s), 7.36 (1H, d, J=8.4 Hz), 7.31-7.16 (7H, m), 6.58 (1H, d, J=1.6 Hz), 6.01 (1H, d, J=15.6 Hz), 5.72 (1H, d, J=16 Hz), 4.7 (1H, s), 4.13 (1H, t, J=8 Hz), 3.91 (2H, m), 2.84-2.50 (3H, m), 1.94 (1H, t, J=3.6 Hz).

Analytical data of trans-(−)-Enantiomer (22B): (38 mg, 3%) of off white solid. Retention time 10.7 min. LC-MS (M+H)$^+$=396.2. $^1$H NMR (400 MHz, DMSO-d6): identical to its antipode 22A.

EXAMPLE 23

7-cyano-18-phenyl-10,11,12,13,14,16,17,18-octahydro-15,2-(azeno)-8,4-(metheno)cyclopenta[h][1,6,10,12]oxatriazacycloheptadecine

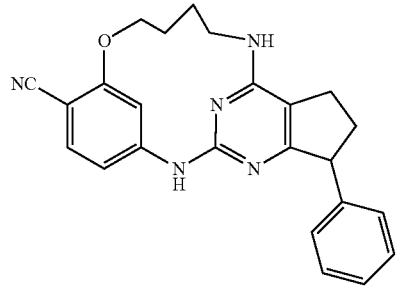

Example 23

A mixture of Synthon RkN (0.5 g, 0.1.15 mmol), xanthphos (0.100 g, 0.173 mmol), and cesium carbonate (0.560 g, 1.732 mmol) in 1,4-dioxane (25 mL) was taken in a two-necked 100 mL round bottom flask equipped with a reflux condenser and nitrogen inlet. The mixture was degassed with nitrogen for 1 h and then Pd(OAc)2 (0.025 g, 0.11 mmol) was added. The reaction mixture was heated at 110° C. for 18 h while monitoring by TLC and LC-MS. The solvent was evaporated under reduced pressure and the residue was dissolved in ethyl acetate (20 mL) and filtered through celite. The filtrate was concentrated and the crude compound was purified by flash chromatography using a Teledyne Isco instrument (12 g RediSep silica column, 10% methanol in chloroform) to give enantiomeric mixture of target compound (130 mg). The enantiomers were further separated by chiral normal phase HPLC [Chiralpak IA (250×4.6)mm 5 mm column, 1.0 mL/min of 0.2% DEA in Hexane:Ethanol (70:30)].

EXAMPLE 23

Analytical data of (+)-enantiomer (23A): (0.025 g, 5.4%), off white solid. Retention time 6.80 min. LC-MS (M+H)$^+$ =397.19. $^1$H NMR (400 MHz, CDCl$_3$): δ ppm 9.62 (1H, s), 9.35 (1H, s), 7.41-7.15 (8H, m), 6.68-6.66 (1H, d, J=8.4 Hz), 4.43 (2H, br s), 4.15-4.11 (1H, t, J=8 Hz), 3.41-3.31 (2H, br s), 2.78-2.59 (3H, m), 1.99-1.92 (5H, m).

Analytical data of (−)-enantiomer (23B): (0.025 g, 5.4%), off-white solid. Retention time 6.84 min. LC-MS and $^1$H NMR: identical to its antipode 23A.

EXAMPLE 24 and 25

(11Z)-7-cyano-18-(2,4-difluorophenyl)-10,13,14,16,17,18-hexahydro-15,2-(azeno)-8,4-(metheno)cyclopenta[h][1,6,10,12]oxatriazacycloheptadecine and
(11E)-7-cyano-18-(2,4-difluorophenyl)-10,13,14,16,17,18-hexahydro-15,2-(azeno)-8,4-(metheno)cyclopenta[h][1,6,10,12]oxatriazacycloheptadecine

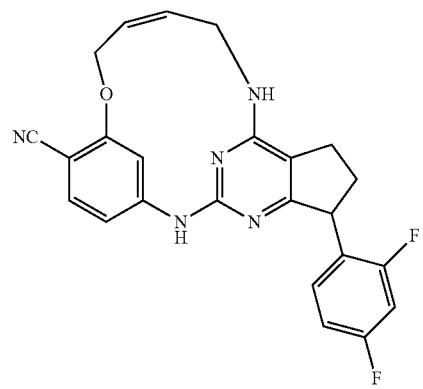

Example 24

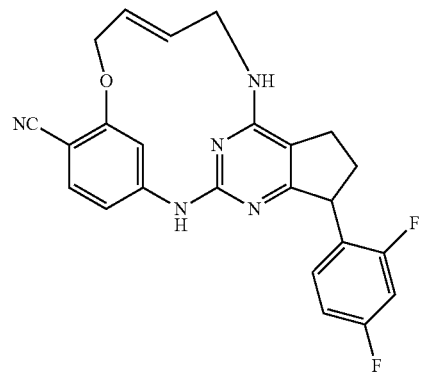

Example 25

A solution of Synthon TaD (0.520 g, 1.13 mmol) in 1,2-dicholoethane (2.5 L) was taken in a 3 L three-necked round bottom flask equipped with a reflux condenser and nitrogen inlet. The solution was degassed with nitrogen for 1 h and Hoveyda-Grubbs II generation catalyst (0.177 g, 0.282 mmol) was added. The mixture was heated at 95° C. for 18 h under nitrogen while monitoring by LC-MS. The solvent was evaporated under reduced pressure and the residue was subjected to flash chromatography using a Teledyne Isco instrument (40 g RediSep silica column, 10% MeOH/CHCl$_3$) to remove metallic and other impurities. The fractions having the desired compound were concentrated and the component isomers were further separated by chiral SFC [Chiral cel OJ H, 30×250 mm, 5 μm column, 125 mL/min of 30% MeOH (0.5% DEA) in CO$_2$ at 100 bar and 35° C.].

EXAMPLE 24

Analytical data of cis-(+)-enantiomer (24A): (35.12 mg, 7.1%) of a light brown solid. Retention time 4.98 min. LC-MS (M+H)+=432.2. $^1$H NMR (400 MHz, CDCl$_3$): δ ppm 9.81 (1H, s), 7.33-7.31 (1H, m), 7.15 (1H, s), 7.01-6.99 (1H, m), 6.83-6.79 (2H, m), 6.30-6.26 (1H, m), 5.74-5.69 (2H, m), 5.16-5.08 (2H, m), 4.79-4.73 (2H, q, J=7.6 Hz), 4.43 (1H, t, J=7.6 Hz), 3.74-3.69 (1H, m), 2.78-2.67 (3H, m), 2.01-1.99 (1H, m).

Analytical data of cis-(−)-enantiomer (24B): (38.12 mg, 7.7%) of a light brown solid. Retention time 8.53 min. LC-MS (M+H)+=432.2. $^1$H NMR (400 MHz, CDCl$_3$): identical to its antipode 24A.

EXAMPLE 25

Analytical data of trans-(+)-enantiomer (25A): (6.57 mg, 1.3%) of a light brown solid. Retention time 3.88 min. LC-MS (M+H)+=432.2. $^1$H NMR (400 MHz, CDCl$_3$): δ ppm 8.41 (1H, s), 7.34 (1H, d, J=8.4 Hz), 7.27 (1H, s), 7.05-6.99 (1H, m), 6.84-6.80 (2H, m), 6.35-6.33 (1H, d, J=8.4 Hz), 5.96 (1H, q, J=5.4 Hz) 5.84 (1H, q, J=6 Hz), 4.88 (3H, m), 4.43 (1H, t, J=6 Hz), 4.08 (2H, m), 2.78-2.62 (3H, m), 2.04-1.98 (1H, m).

Analytical data of trans-(−)-enantiomer (25B): (13.85 mg, 2.7%) of a light brown solid. Retention time 3.88 min. LC-MS (M+H)+=432.2. $^1$H NMR (400 MHz, CDCl$_3$): identical to its antipode 25A.

EXAMPLE 26

7-cyano-19-(4-fluorophenyl)-11,12,13,14,15,17,18,19-octahydro-10H-16,2-(azeno)-8,4-(metheno)cyclopenta[i][1,4,7,11,13]oxatetraazacyclooctadecine

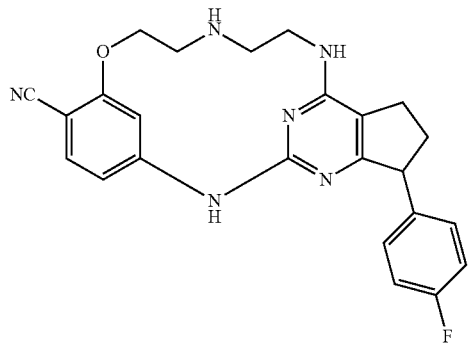

Example 26

An ice-cooled solution of Synthon SfN (0.1 g, 0.214 mmol) in NMP (1 mL) was taken in a round bottom flask and treated with 0.1 mL of conc. H$_2$SO$_4$. The mixture was heated at 100° C. for 18 h while monitoring by LC-MS. The reaction mixture was cooled to rt, diluted with ethyl acetate (10 mL) and treated with saturated sodium bicarbonate (15 mL). The ethyl acetate layer was separated and the aqueous layer was further extracted with ethyl acetate (2×10 mL). The combined organic layers were washed with brine (2×10 mL), dried over anhydrous sodium sulfate, and concentrated under reduced pressure. The crude compound was purified by flash chromatography using a Teledyne Isco instrument (12 g RediSep silica column, 10% methanol in chloroform). The enantiomers were separated via chiral HPLC [Chiral OD-H (250× 4.6 mm) 5 mm column, 1.0 mL/min of 0.2% DEA in hexane:ethanol (70:30) as a mobile phase].

EXAMPLE 26

Analytical data of enantiomer-I (26A): (0.003 g, 3.2%) off-white solid. Retention time 7.8 min. LC-MS (M+H)+ =431.2. $^1$H NMR (400 MHz, DMSO-d6): δ ppm 9.71 (1H, s), 8.44 (1H, s), 8.46 (1H, s), 7.46-7.43 (1H, d, J=8.4 Hz), 7.32-7.10 (5H, m), 6.73-6.70 (1H, d J=8.8 Hz), 4.41 (2H, m), 1.19-4.05 (1H, m) 3.67 (2H, m), 3.25-3.22 (2H, m), 3.16-3.08 (4H, m), 2.54-2.48 (1H, m), 2.01-1.93 (1H, m).

Analytical data of enantiomer-II (26B): (0.003 g,3.2%) off white solid. Retention time 16.8 min. LC-MS (M+H)+ =431.2. $^1$H NMR (400 MHz, DMSO-d6): identical to its antipode 26A.

EXAMPLE 27

7-cyano-19-(4-fluorophenyl)-12-methyl-11,12,13,14,15,17,18,19-octahydro-10H-16,2-(azeno)-8,4-(metheno)cyclopenta[i][1,4,7,11,13]oxatetraazacyclooctadecine

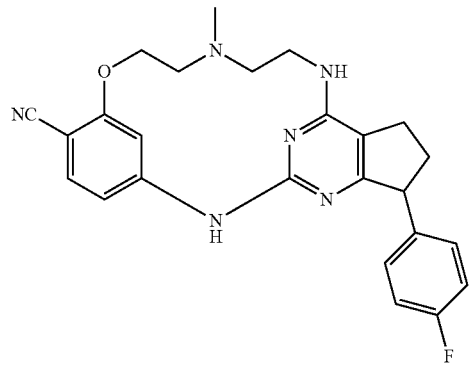

Example 27

An ice-cooled solution of Synthon SgN (0.35 g, 0.72 mmol) in NMP (5 mL) was taken in a round-bottom flask and treated with 0.35 mL of conc. H$_2$SO$_4$. The mixture was heated at 100° C. for 18 h while monitoring by LC-MS. The reaction mixture was cooled to rt, diluted with ethyl acetate (20 ml) and treated with saturated sodium bicarbonate (25 ml). Ethyl acetate layer was separated and aqueous layer was further extracted with ethyl acetate (2×10 mL). Combined organic layer was washed with brine (2×10 mL), dried over anhydrous sodium sulfate, and concentrated under reduced pressure. The crude compound was purified by flash chromatography using Teledyne Isco instrument (12 g RediSep silica column, 10% methanol in chloroform solvent system). Enantiomers were separated through chiral HPLC. [Chiralpak AD-H (250×4.6)mm 5 mm column, 1.0 mL/min of 0.2% DEA in hexane:ethanol(50:50) as mobile phase].

EXAMPLE 27

Analytical data of enantiomer-I (27A): (3 mg, 1%) off white solid. Retention time 12.63 min. LC-MS (M+H)+ =445.2 $^1$H NMR (400 MHz, CDCl$_3$): δ ppm 8.28 (1H, s), 7.37-7.35 (1H, d, J=8.4 Hz), 7.18-7.14 (2H, m), 7.02-6.98 (2H, m), 6.45-6.35 (1H, m), 4.33-4.30 (2H, m), 4.17-4.05

(1H, s), 3.75-3.60 (5H, m), 3.44 (3H, s), 3.35-3.05 (5H, m), 2.58-2.54 (1H, m), 2.05-2.02 (1H, m).

Analytical data of enantiomer-II (27B): (3 mg, 1%) off white solid. Retention time 8.55 min. LC-MS (M+H)+=445.2 1H NMR (400 MHz, CDCl3): identical to its antipode 27A.

EXAMPLE 28

(11Z)-7-cyano-18-(2,4-difluorophenyl)-14-methyl-10,13,14,16,17,18-hexahydro-15,2-(azeno)-8,4-(metheno)cyclopenta[h][1,6,10,12]oxatriazacycloheptadecine

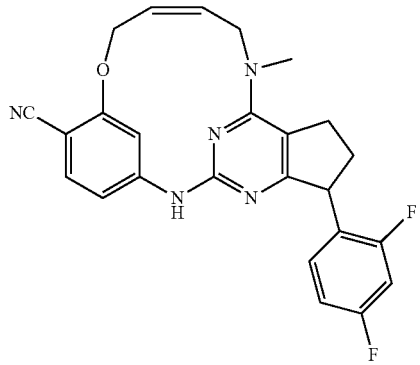

Example 28

A solution of Synthon TbD (0.400 g, 0.845 mmol) in 1,2-dicholoethane (2.5 L) was taken in a 3 L three-necked round bottom flask equipped with a reflux condenser and nitrogen inlet. The solution was degassed by nitrogen for 1 h and Hoveyda-Grubbs II generation catalyst (0.125 g, 0.199 mmol) was added. The mixture was heated at 95° C. for 18 h under nitrogen while monitoring by LC-MS. The solvent was evaporated under reduced pressure and the residue was subjected to flash chromatography using Teledyne Isco instrument (40 g RediSep silica column, 10% MeOH in CHCl3) to remove metallic and other impurities. The fractions having desired compound were concentrated and its component isomers were further separated by chiral SFC [Chiral cel-OJ-H, 30×250 mm, 5 μm column, 125 mL/min of 40% MeOH (0.5% DEA) in CO2 at 100 bar and 35° C.].

EXAMPLE 28

Analytical data of cis-(+)-enantiomer (28A): (65 mg, 17.2%) of a brown solid. Retention time 4.25 min. LC-MS (M+H)+=446.2. 1H NMR (400 MHz, CDCl3): δ ppm 9.47 (1H, s), 7.32-7.31 (1H, m), 7.10 (1H, s), 7.00-6.98 (1H, m), 6.81-6.79 (2H, m), 6.27-6.23 (1H, m), 5.81-5.76 (2H, m), 5.21-5.18 (1H, m), 5.04 (1H, t, J=10.4 Hz), 4.74 (1H, d, J=15.2 Hz), 4.37-4.34 (1H, m), 3.48 (1H, m), 3.44 (3H, s), 3.20-3.19 (2H, m), 2.58-2.54 (1H, m), 1.95-1.92 (1H, m).

Analytical data of cis-(−)-enantiomer (28B): (75 mg, 20%) of a brown solid. Retention time 8.99 min. LC-MS (M+H)+=446.2. 1H NMR (400 MHz, CDCl3): identical to its antipode 28A.

EXAMPLE 29 and 30

(11Z)-7-cyano-14-methyl-18-phenyl-10,13,14,16,17,18-hexahydro-15,2-(azeno)-8,4-(metheno)cyclopenta[h][1,6,10,12]oxatriazacycloheptadecine and (11E)-7-cyano-14-methyl-18-phenyl-10,13,14,16,17,18-hexahydro-15,2-(azeno)-8,4-(metheno)cyclopenta[h][1,6,10,12]oxatriazacycloheptadecine

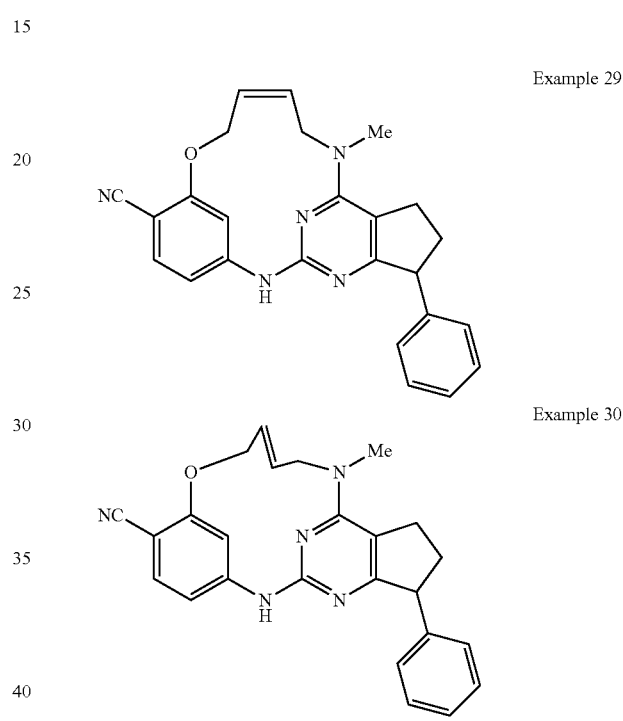

Example 29

Example 30

A solution of Synthon RbD (0.5 g, 1.143 xxmmol, in 1,2-dicholoethane (3000 xxL) was taken in a 5 L three-necked round bottom flask equipped with a reflux condenser and nitrogen inlet. The solution was degassed by nitrogen for 1 h and Hoveyda-Grubbs II generation catalyst (0.1 g, 0.159 mmol) was added. The mixture was heated at 100° C. for 18 h under nitrogen while monitoring by LC-MS. Another two batches of same reaction was performed and work up was done together. The solvent was evaporated under reduced pressure and the residue was subjected to flash chromatography using a Teledyne Isco instrument (40 g RediSep silica column, 10% of ethyl acetate in chloroform) to remove metallic and other impurities. The fractions having desired compound were concentrated and its component isomers were further separated by chiral HPLC [WELKO (250×4.6)mm 5 mm column, 1.0 mL/min of 0.2% DEA in hexane:ethanol (70:30) as a mobile phase]

EXAMPLE 29

Analytical data of cis-(+)-enantiomer (29A): (0.042 g, 3%), off-white solid. Retention time 21.24 min. LC-MS (M+H)+=410.2. 1H NMR (400 MHz, DMSO-d6): δ ppm 9.65 (1H, s), 9.47 (1H, s), 7.37-7.16 (6H, m), 6.67-6.64 (1H, d, J=8.4 Hz), 5.81-5.79 (1H, m), 5.61-5.58 (1H, m), 4.69-4.66

(1H, m), 4.12-4.06 (1H, m), 3.61-3.58 (2H, m), 3.51 (3H, s), 3.39-3.12 (2H, m), 2.52-2.48 (2H, m), 1.99-1.95 (1H, m).

Analytical data of cis-(−)-enantiomer (29B): (0.058 g, 4%), off-white solid. Retention time 26.65 min. LC-MS (M+H)+=410.2. ¹H NMR (400 MHz, DMSO-d6): identical to its antipode 29A.

EXAMPLE 30

Analytical data of trans-enantiomer-I (30A): (0.008 g, 5.3%), brown solid. Retention time 17.5 min. LC-MS (M+H)+=LC-MS (M+H)+=410.2. ¹H NMR (400 MHz, DMSO-d6): δ ppm 9.59 (1H, s), 8.06 (1H, s), 7.42-7.19 (6H, m), 6.61-6.59 (1H, d, J=8.4 Hz), 6.08-6.04 (1H, d, J=16 Hz), 5.59-5.57 (1H, d, J=16 Hz), 4.91-4.90 (2H, m), 3.61-3.58 (2H, m), 3.51 (3H, s), 3.39-3.12 (2H, m), 2.52-2.48 (2H, m), 1.99-1.95 (1H, m).

Analytical data of trans-(−)-enantiomer-II (30B): Retention time 23.1 min.

EXAMPLE 31

7-cyano-β-methyl-17-phenyl-11,12,13,15,16,17-hexahydro-10H-14,2-(azeno)-8,4-(metheno)cyclopenta[g][1,5,9,11]oxatriazacyclohexadecine

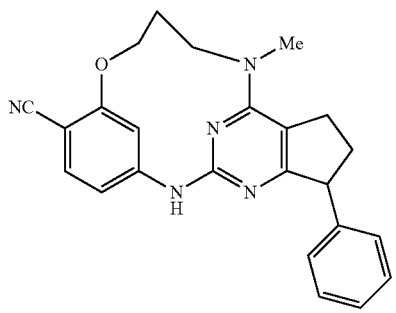

Example 31

A mixture of Synthon RjI (0.5 g, 1.152 mmol), xanthphos (0.1 g, 0.173 mmol), and cesium carbonate (0.563 g, 1.728 mmol) in 1,4-dioxane (5 mL) was taken in a two-necked 50 mL round bottom flask equipped with a refluxed condenser and nitrogen inlet. The mixture was degassed with nitrogen for 1 h and Pd(dba)₃ (0.026 g, 0.115 mmol) was added. The reaction mixture was heated at 105° C. for 5 h while monitoring by TLC and LC-MS. The solvent was evaporated under reduced pressure and the residue was dissolved in ethyl acetate (20 mL) and filtered through celite. The filtrate was concentrated and the crude compound was purified by flash chromatography using Teledyne Isco instrument (12 g RediSep silica column, using a 50% ethyl acetate in pet-ether) to give a racemic mixture of target compound (90 mg). Enantiomers were further separated by chiral HPLC [Chiralpak AD H (250×4.6)mm 5 mm column, 1.0 mL/min of 0.2% DEA in hexane:ethanol(50:50) as a mobile phase].

EXAMPLE 31

Analytical data of (+)-enantiomer (31A): (0.027 g, 6%) off-white solid. Retention time 15.56 min. LC-MS (M+H)+=398.2. ¹H NMR (400 MHz, CDCl₃): δ ppm 8.93 (1H, s), 7.34-7.22 (6H, m), 6.83 (1H, br s), 7.16 (1H, d, J=7.2 Hz), 4.44-4.43 (2H, br s), 4.13-4.09 (1H, t, J=7.6 Hz), 3.68-3.61 (2H, m), 3.23 (3H, s), 3.20-3.06 (2H, m), 2.59-2.53 (1H, m), 2.41-2.35 (2H, m), 1.99-1.98 (1H m).

Analytical data of (−)-enantiomer (31B): (0.035 g, 7.6%) off-white solid. Retention time 12.37 min. LC-MS (M+H)+=398.2. ¹H NMR (400 MHz, CDCl₃): identical to its antipode 31A.

EXAMPLE 32

7-cyano-18-(2,4-difluorophenyl)-14-methyl-10,11,12,13,14,16,17,18-octahydro-15,2-(azeno)-8,4-(metheno)cyclopenta[h][1,6,10,12]oxatriazacycloheptadecine

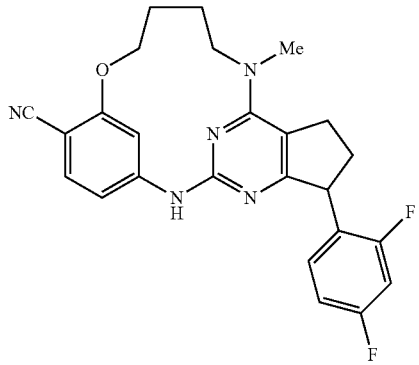

Example 32

Example 28A (0.120 g, 0.269 mmol) in 20 mL of 1:1 (MeOH:THF) was hydrogenated (balloon pressure H₂) at room temperature in presence of platinum(IV)oxide (0.012 g, 0.052 mmol) for 30 min while monitoring by LC-MS. The reaction mixture was degassed with nitrogen and filtered through celite. The filtrate was concentrated under reduced pressure and the residue was subjected to chiral preparative SFC (chiral cel-OD-H, 30×250 mm, 5 µm column, 125 mL/min of 30% MeOH (0.5% DEA) in CO₂ at 100 bar and 35° C.) to give example 32A along with a ring-opened phenolic compound.

Example 28B (0.128 g, 0.287 mmol) in 12 mL of 1:1 (MeOH:THF) was hydrogenated (balloon pressure H₂) at room temperature in presence of platinum(IV)oxide (0.012 g, 0.052 mmol) for 30 min while monitoring by LC-MS. The reaction mixture was degassed with nitrogen and filtered through celite. The filtrate was concentrated under reduced pressure and the residue was subjected to chiral preparative SFC (chiral cel-OD-H, 30×250 mm, 5 µm column, 125 mL/min of 30% MeOH (0.5% DEA) in CO₂ at 100 bar and 35° C.) to give example 32B along with a ring-opened phenolic compound.

EXAMPLE 32

Analytical data of (+)-Enantiomer (32A): (10 mg, 8.8%) light brown solid. Retention time 6.68 min. LC-MS (M+H)+=448.2. ¹H NMR (400 MHz, DMSO-d₆): δ ppm 9.60 (1H, s), 9.20 (1H, s), 7.37 (1H, d, J=8.4 Hz), 7.21-6.94 (3H, m), 6.72-6.69 (1H, dd, J=2, 8.8 Hz), 4.31 (2H, m), 3.31 (1H, t, J=8.8 Hz), 3.31 (3H, s), 3.11-3.09 (3H, m), 2.47-2.44 (2H, m), 1.91-1.82 (5H, m).

Analytical data of (−)-Enantiomer (32B) (15 mg, 12.5%) of a light brown solid. Retention time 7.14 min. LC-MS (M+H)+=448.2. $^1$H NMR (400 MHz, DMSO-d$_6$): identical to its antipode.

EXAMPLE 33

7-cyano-17-(2,4-difluorophenyl)-11,12,13,15,16,17-hexahydro-10H-14,2-(azeno)-8,4-(metheno)cyclopenta[g][1,5,9,14]oxatriazacyclohexadecine

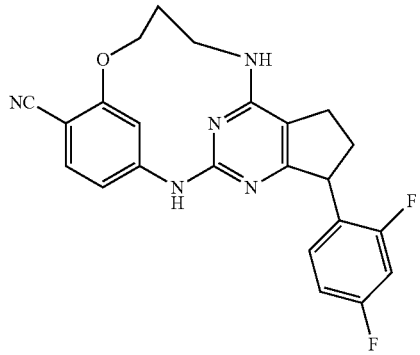

Example 33

A mixture of Synthon TcH (0.8 g, 1.755 mmol), xanthphos (0.152 g, 0.263 mmol), and cesium carbonate (0.858 g, 2.63 mmol) in 1,4-dioxane (10 mL) was taken in a two-necked 50 mL round bottom flask equipped with a refluxed condenser and nitrogen inlet. The mixture was degassed with nitrogen for 1 h and then Pd(OAc)$_2$ (0.0394 g, 0.175 mmol) was added. The reaction mixture was heated at 110° C. for 4 h while monitoring by TLC and LC-MS. The solvent was evaporated under reduced pressure and the residue was dissolved in ethyl acetate (250 ml) and filtered through celite. The filtrate was concentrated and the crude compound was purified by flash chromatography using Teledyne Isco instrument (40 g RediSep silica column, 15-25% of ethyl acetate in chloroform gradient) to give the racemic target compound (130 mg). The enantiomers were further separated by chiral HPLC [Chiralcel OJH (250×4.6)mm 5 mm column, 1.0 mL/min of 0.2% DEA in hexane:ethanol(70:30) as a mobile phase].

EXAMPLE 33

Analytical data of (+)-enantiomer (33A): (0.0428 g, 5.53%) off-white solid. Retention time 13.66 min. LC-MS (M+H)+=420.0. $^1$H NMR (400 MHz, CDCl$_3$): δ ppm 9.07 (1H, s), 7.32 (1H, d, J=8.4 Hz), 6.99-6.98 (1H, m), 6.83-6.76 (3H, m), 6.44-6.42 (1H, dd, J=2, 8.8 Hz), 4.82 (1H, m), 4.52-4.56 (3H, m), 3.63-3.59 (2H, m), 2.70-2.60 (3H, m), 2.43 (2H, m), 1.97-1.95 (1H, m).

Analytical data of (−)-enantiomer (33B): (0.0437 g, 5.66%) off-white solid. Retention time 24.3 min. LC-MS (M+H)+=420.0. $^1$H NMR (400 MHz, CDCl$_3$): identical to its antipode 33A.

EXAMPLE 34

7-cyano-14-methyl-18-phenyl-10,11,12,13,14,16,17,18-octahydro-15,2-(azeno)-8,4-(metheno)cyclopenta[h][1,6,10,12]oxatriazacycloheptadecine

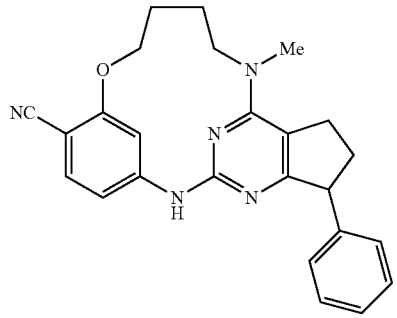

Example 34

Example 29A (0.022 g, 0.054 mmol) in 8 mL of 1:1 (MeOH:THF) was hydrogenated (balloon pressure H$_2$) at room temperature in presence of platinum(IV)oxide (0.0022 g, 0.0096 mmol) for 40 min while monitoring by LC-MS. The reaction mixture was degassed with nitrogen and filtered through celite. The filtrate was concentrated under reduced pressure and the residue was subjected to chiral reverse phase supercritical fluid chromatography [Chiralcel OD-H (30×250)mm 5 mm column, 20 mL/min of 0.5% DEA in CO2 at 101 bar pressure and 32.7° C.] to get Example 34A and a ring-opened phenolic compound. Similarly, Example 29B was reduced on 38 mg scale to get Example 34B.

EXAMPLE 34

Analytical data of enantiomer-I (34A): (0.0039 g, 16.5%), off white solid. Retention time 8.59 min. LC-MS (M+H)+=412.2. $^1$H NMR (400 MHz, CDCl$_3$): δ ppm 9.17 (1H, s), 7.33-7.15 (7H, m), 6.29 (1H, d, J=7.2 Hz), 4.45 (2H, m), 4.11 (1H, t, J=7.6 Hz), 3.27 (3H, s), 3.23-3.21 (1H, m), 3.12-3.10 (1H, m), 2.56-2.53 (1H, m), 2.05-1.98 (4H, m), 1.42-1.22 (3H, m).

Analytical data of Enantiomer-II (34B): (0.00711 g, 18.62%), off white solid. Retention time 14.62 min. LC-MS (M+H)+=412.2. $^1$H NMR (400 MHz, CDCl$_3$): δ ppm 9.17 (1H, s), 7.33-7.15 (7H, m), 6.29 (1H, d, J=7.2 Hz), 4.45 (2H, m), 4.11 (1H, t, J=7.6 Hz), 3.27 (3H, s), 3.23-3.21 (1H, m), 3.12-3.10 (1H, m), 2.56-2.53 (1H, m), 2.05-1.98 (4H, m), 1.42-1.22 (3H, m).

EXAMPLE 35

7-cyano-17-(2,4-difluorophenyl)-13-methyl-11,12,13,15,16,17-hexahydro-10H-14,2-(azeno)-8,4-(metheno)cyclopenta[g][1,5,9,11]oxatriazacyclohexadecine

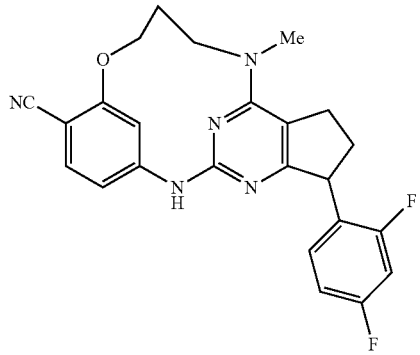

Example 35

A mixture of Synthon TdI (0.76 g, 1.67 mmol), xanthphos (0.14 g, 0.243 mmol), and cesium carbonate (0.79 g, 2.42 mmol) in 1,4-dioxane (40 mL) was taken in a two-necked 100 mL round bottom flask equipped with a refluxed condenser and nitrogen inlet. The mixture was degassed with nitrogen for 1 h and Pd(OAc)$_2$ (0.0363 g, 0.162 mmol) was added. The reaction mixture was heated at 100° C. for 4 h while monitoring by TLC and LC-MS. The solvent was evaporated under reduced pressure and the residue was dissolved in ethyl acetate (250 mL) and filtered through celite. The filtrate was concentrated and the crude compound was purified by flash chromatography using a Teledyne Isco instrument (40 g RediSep silica column, 8% ethyl acetate in chloroform) to give the racemic target compound (200 mg). Enantiomers were further separated by chiral normal phase HPLC [Chiralcel AD-H (250×4.6)mm 5 mm column, 1.0 mL/min of 0.2% DEA in hexane:ethanol(70:30) as mobile phase].

EXAMPLE 35

Analytical data of (+)-Enantiomer (35A): (0.0617 g, 8.37%), off white solid. Retention time 12.06 min. LC-MS (M+H)$^+$=434.2. $^1$H NMR (400 MHz, CDCl$_3$): δ ppm 8.90 (1H, s), 7.365-7.344 (1H, d, J=8.4 Hz), 7.06-7.00 (2H, m), 6.87-6.81 (2H, m), 6.48-6.46 (1H, m), 4.49-4.36 (3H, m), 3.85-3.505 (2H, m), 3.30 (3H, s), 3.2-3.05 (2H, m), 2.60-2.56 (1H, m), 2.43-2.36 (2H, m), 1.96-1.93 (1H, m).

Analytical data of (−)-Enantiomer (35B): (0.0522 g, 7.08%), off white solid. Retention time 17.95 min. LC-MS (M+H)$^+$=434.2. $^1$H NMR (400 MHz, CDCl$_3$): identical to its antipode 35A.

EXAMPLE 36 and 37

(11Z)-7-cyano-18-phenyl-10,13,14,16,17,18-hexahydro-15,2-(azeno)-8,4-(metheno)cyclopenta[h][1,10,12]oxadiazacycloheptadecine and (11E)-7-cyano-18-phenyl-10,13,14,16,17,18-hexahydro-15,2-(azeno)-8,4-(metheno)cyclopenta[h][1,10,12]oxadiazacycloheptadecine

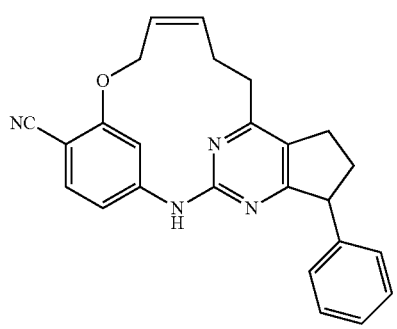

Example 36

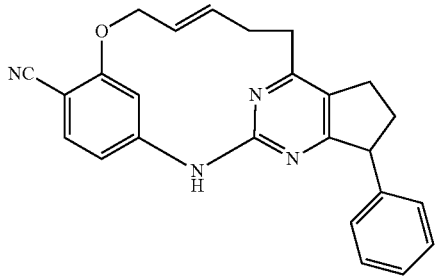

Example 37

A solution of synthon RhD (0.5 g, 1.183 mmol) in 1,2-dicholoethane (2.5 L) was taken in a 3 L three-necked round bottom flask equipped with a reflux condenser and nitrogen inlet. The solution was degassed by nitrogen for 1 h and Hoveyda-Grubbs II generation catalyst (0.05 g, 0.080 mmol) was added. The mixture was heated at 100° C. for 18 h under nitrogen while monitoring by LC-MS. Another two batches of the reaction were performed on the same scale and worked-up together. The solvent was evaporated under reduced pressure and the residue was subjected to flash chromatography using a Teledyne Isco instrument (40 g RediSep silica column, 20% ethyl acetate in chloroform) to remove metallic and other impurities. The fractions having desired compound were concentrated and its component isomers were further separated by chiral reverse phase supercritical fluid chromatography [Chiralcel OJ-H (30×250)mm 5 mm column, 15 mL/min of 0.5% DEA) in CO2 at 96 bar pressure and 32.7° C.].

EXAMPLE 36

Analytical data of cis-(+)-enantiomer (36A): (0.16 g, 12.3%), off white solid. Retention time 11.7 min. LC-MS (M−H)$^+$=395.2. $^1$H NMR (400 MHz, CDCl$_3$): δ ppm 9.62 (1H, s), 7.34-7.13 (8H, m), 6.28-6.26 (1H, d, J=8.8 Hz), 5.68-5.58 (2H, m), 5.15-5.09 (1H, m), 4.83-4.79 (1H, m), 4.26-4.25 (1H, m), 3.30-2.81 (5H, m), 2.37-2.11 (2H, m).

Analytical data of cis-(−)-enantiomer 36B (0.18 g, 13.8%), off white solid. Retention time 6.45 min. LC-MS (M−H)⁺ =395.2. ¹H NMR (400 MHz, CDCl₃): identical to its antipode 36A.

EXAMPLE 37

Analytical data of trans-(+)-enantiomer (37A): (0.09 g, 6.92%), off white solid. Retention time 9.87 min. LC-MS (M+H)⁺=395.2. ¹H NMR (400 MHz, CDCl₃): δ ppm 8.83 (1H, s), 7.35-7.14 (8H, m), 6.31-6.29 (1H, d, J=8.4 Hz), 5.98-5.94 (1H, d, J=15.6 Hz), 5.73-5.69 (1H, d, J=15.6 Hz) 4.89-4.87 (2H, m), 4.27-4.23 (1H, t, J=8.4 Hz), 3.03-2.93 (3H, m), 2.67-2.62 (3H, m), 2.11-2.09 (1H, m).

Analytical data of trans-(−)-enantiomer (37B): (0.09 g, 6.92%), off white solid. Retention time 5.18 min. LC-MS (M+H)⁺=395.2. ¹H NMR (400 MHz, CDCl₃): identical to its antipode 37A.

EXAMPLE 38

7-cyano-18-phenyl-10,11,12,13,14,16,17,18-octahydro-15,2-(azeno)-8,4-(metheno)cyclopenta[h][1,10,12]oxadiazacycloheptadecine

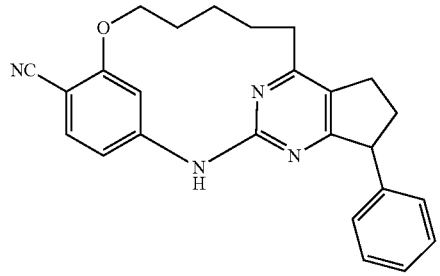

Example 38

Example 37A (0.06 g, 0.152 mmol) in 100 mL of 1:1 (MeOH:THF) was hydrogenated (balloon pressure H₂) at room temperature in presence of palladium on carbon (0.006 g, 0.056 mmol) and ammonia (10 mL) for 14 h while monitoring by LC-MS. The reaction mixture was degassed with nitrogen and filtered through celite. The filtrate was concentrated under reduced pressure and the residue was subjected to chiral normal phase supercritical fluid chromatography [Chiralcel OD-H (30×250)mm 5 mm column, 20 mL/min of 0.5% DEA in methanol) in CO2 at 100 bar pressure and 31.2° C.] to get Example 38A. Similarly, Example 37B was hydrogenated to get Example 38B.

EXAMPLE 38

Analytical data of (+)-Enantiomer (38A): (0.012 g, 20%), brown solid. Retention time 5.7 min. LC-MS (M+H)⁺=397.2. ¹H NMR (400 MHz, CDCl₃): δ ppm 7.61 (1H, s), 7.38-7.19 (7H, m), 6.89-6.87 (1H, m), 5.52-5.50 (2H, m), 4.28-4.26 (1H, t, J=8.4 Hz), 2.70-2.46 (7H, m), 2.22-2.10 (2H, m), 1.67-1.52 (4H, m).

Analytical data of (−)-Enantiomer (38B): (0.0106 g, 20.02%), brown solid. Retention time 3.76 min. LC-MS (M+H)⁺=397.2. ¹H NMR (400 MHz, CDCl₃): identical to its antipode 38A.

EXAMPLE 39 and 40

(11Z)-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine and (11E)-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine

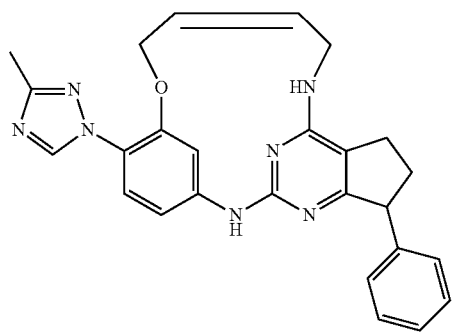

Example 39

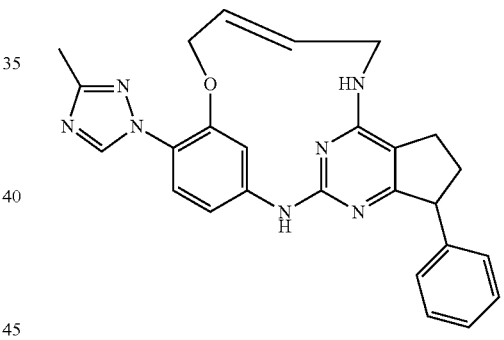

Example 40

A solution of Synthon RaB (1.2 g, 2.50 mmol) in 1,2-dicholoethane (1.2 L) was taken in a 2 L three-necked round bottom flask equipped with a reflux condenser and nitrogen inlet. The solution was degassed by nitrogen for 1 h and Hoveyda-Grubbs II generation catalyst (0.156 g, 0.25 mmol) was added. The mixture was heated at 100° C. for 18 h under nitrogen while monitoring by LC-MS. The solvent was evaporated under reduced pressure and the residue was subjected to flash chromatography using a Teledyne Isco instrument (40 g RediSep silica column) to remove metallic and other impurities. The fractions having desired compound were concentrated and its component isomers were further separated by chiral normal phase HPLC [Chiralpak IC (250× 4.6)mm 5 mm column, 1.0 mL/min of 0.2% DEA in hexane: ethanol (80:20) as mobile phase].

EXAMPLE 39

Analytical data of cis-(+)-enantiomer (39A): (0.065 g, 5.7%), off-white solid. Retention time 11.47 min. LC-MS (M+H)⁺=452.2. ¹H NMR (400 MHz, DMSO-d6): δ ppm 9.77

(1H, s), 9.44 (1H, s), 8.68 (1H, s), 7.53-7.50 (1H, m), 7.31-7.15 (6H, m), 6.67-6.63 (1H, m), 5.61-5.59 (2H, m), 5.17-5.10 (1H, m), 4.67-4.64 (2H, m), 4.13-4.11 (1H, m), 3.61-3.56 (1H, m), 2.68-2.56 (2H, m), 2.56-2.50 (1H, m), 2.32 (3H, s), 1.97-1.91 (1H, m).

Analytical data of cis-(−)-enantiomer (39B): (0.065 g, 5.7%), off-white solid. Retention time 10.97 min. LC-MS (M+H)$^+$=452.2. $^1$H NMR (400 MHz, DMSO-d6): identical to its antipode.

EXAMPLE 40

Analytical data of trans-(+)-enantiomer (40A): (0.065 g, 5.7%), off-white solid. Retention time 11.07 min. LC-MS (M+H)$^+$=452.2. $^1$H NMR (400 MHz, DMSO-d6): δ ppm 9.3 (1H, s), 8.65 (1H, s), 8.34 (1H, s), 7.32-7.17 (7H, m), 6.61-6.58 (1H, m), 6.03-5.99 (1H, d, J=16 Hz), 5.68-5.64 (1H, d, J=16 Hz), 4.84 (2H, s), 4.13-4.09 (1H, t, J=8 Hz), 3.89 (2H, s), 2.80-2.76 (1H, m), 2.68-2.62 (1H, m), 2.56-2.50 (1H, m), 2.32 (3H, s), 1.97-1.91 (1H, m).

Analytical data of trans-(−)-enantiomer (40B): (0.065 g, 5.7%) off-white solid. Retention time 13.74 min. LC-MS (M+H)$^+$=452.2. $^1$H NMR (400 MHz, DMSO-d6): identical to its antipode.

EXAMPLE 41

(11Z)-14-methyl-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine

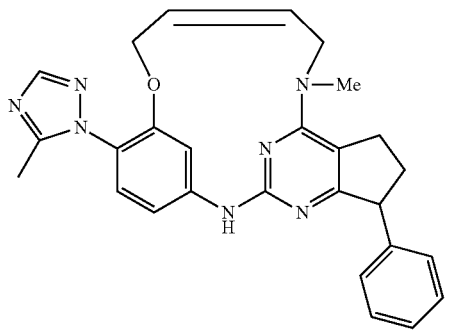

Example 41

A solution of Synthon RbC (0.600 g, 1.121 mmol) in 1,2-dicholoethane (2.5 L) was taken in a 3 L three-necked round bottom flask equipped with a reflux condenser and nitrogen inlet. The solution was degassed by nitrogen for 1 h and Hoveyda-Grubbs II generation catalyst (0.190 g, 0.319 mmol) was added. The mixture was heated at 90° C. for 18 h under nitrogen while monitoring by LC-MS. The solvent was evaporated under reduced pressure and the residue was subjected to flash chromatography using a Teledyne Isco instrument (40 g RediSep silica column, 10% MeOH/CHCl$_3$) to remove metallic and other impurities. The fractions having desired compound were concentrated and its component isomers were further separated by chiral normal phase HPLC [CHIRALPAK IA (250×4.6 mm) 5 micron, A: 0.2% DEA in n-Hexane (50) B: Ethanol (50), Flow: 1.0 mL/min.].

EXAMPLE 41

Analytical data of cis-(+)-enantiomer (41A): (65 mg, 11.6%), off-white solid. Retention time 14.5 min. LC-MS (M+H)=466.2. $^1$H NMR (400 MHz, CDCl$_3$): δ ppm 9.50 (1H, s), 7.93 (1H, s), 7.35-7.29 (3H, m), 7.26-7.10 (2H, m), 7.09-7.07 (1H, m), 6.35 (1H, t, J=7.8 Hz), 5.81-5.64 (2H, m), 5.24 (1H, m), 5.02 (1H, t, J=13.2 Hz), 4.53 (1H, d, J=14 Hz), 4.13 (1H, q, J=5.6 Hz), 3.46 (3H, s), 3.46-3.42 (1H, m), 3.27-3.12 (2H, m), 2.58-2.35 (1H, m), 2.05 (3H, s), 2.05-2.02 (1H, m).

Analytical data of cis-(−)-enantiomer (41B): (65 mg, 11.6%) of off-white solid. Retention time 8.33 min. LC-MS (M+H)$^+$=466.2. $^1$H NMR (400 MHz, CDCl$_3$): identical to its antipode 41A.

EXAMPLE 42 and 43

(11Z)-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine and (11E)-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine

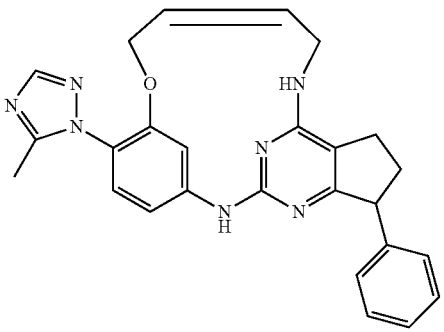

Example 42

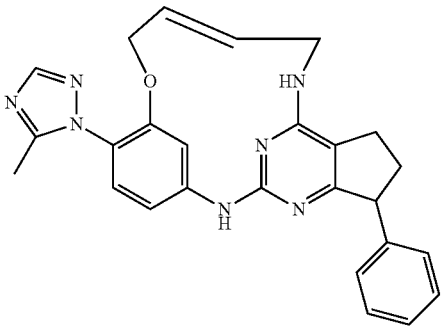

Example 43

A solution of Synthon RaC (1.4 g, 2.92 mmol) in 1,2-dicholoethane (1.5 L) was taken in a 2 L three-necked round bottom flask equipped with a reflux condenser and nitrogen inlet. The solution was degassed by nitrogen for 1 h and Hoveyda-Grubbs II generation catalyst (0.183 g, 0.292 mmol) was added. The mixture was heated at 100° C. for 18 h under nitrogen while monitoring by LC-MS. The solvent was evaporated under reduced pressure and the residue was subjected to flash chromatography using a Teledyne Isco instrument (40 g RediSep silica column) to remove metallic and other impurities. The fractions having desired compound were concentrated and its component isomers were further separated by chiral normal phase HPLC [Chiralpak IC (250×4.6)mm 5 mm column, 1.0 mL/min of 0.2% DEA in hexane: ethanol(80:20) as mobile phase].

EXAMPLE 42

Analytical data of cis-(+)-enantiomer (42A): (0.035 g, 2.6%) off-white solid. Retention time 16.63 min. LC-MS (M+H)+=452.2. ¹H NMR (400 MHz, DMSO-d6): δ ppm 9.77 (1H, s), 9.44 (1H, s), 7.91 (1H, s), 7.53 (1H, s), 7.32-7.22 (2H, m), 7.21-7.16 (3H, m), 7.06-7.03 (1H, d, J=8.4 Hz), 6.68-6.64 (1H, m), 5.76-5.4 (2H, m), 5.22-5.05 (1H, m), 4.71-4.51 (2H, m), 4.20-4.05 (1H, m), 3.65-3.55 (1H, m), 2.92-2.55 (3H, m), 2.25 (3H, s), 1.97-1.91 (1H, m).

Analytical data of cis-(−)-enantiomer (42B): (0.035 g, 2.6%) off-white solid. Retention time 16.17 min. LC-MS (M+H)+=452.2. ¹H NMR (400 MHz, DMSO-d6): identical to its antipode 42A.

EXAMPLE 43

Analytical data of trans-(+)-enantiomer (43A): (0.035 g, 2.6%) off-white solid. Retention time 17.39 min. LC-MS (M+H)+=452.2. ¹H NMR (400 MHz, DMSO-d6): δ ppm 9.33 (1H, s), 8.37 (1H, s), 7.91 (1H, s), 7.32-7.22 (2H, m), 7.20-7.17 (4H, m), 7.06-7.04 (1H, d, J=8.4 Hz), 6.62-6.60 (1H, d, J=8.4 Hz), 6.02-5.98 (1H, d, J=16 Hz), 5.65-5.61 (1H, d, J=16 Hz), 4.77 (2H, s), 4.14-4.10 (1H, t, J=8 Hz), 3.90 (2H, s), 2.80-2.50 (3H, m), 2.24 (3H, s), 1.97-1.91 (1H, m).

Analytical data of trans-(−)-enantiomer (43B): (0.025 g, 2%) off-white solid. Retention time 25.67 min. LC-MS (M+H)+=452.2. ¹H NMR (400 MHz, DMSO-d6): identical to its antipode 43A.

EXAMPLE 44

(11Z)-14-methyl-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine

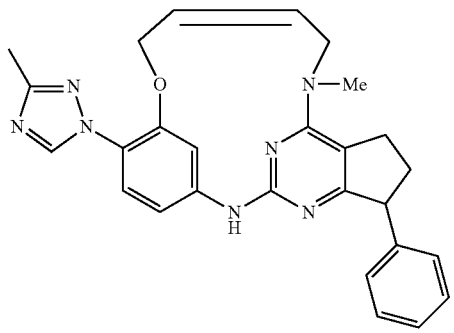

Example 44

A solution of Synthon RbB (1.6 g, 3.232 mmol) in 1,2-dicholoethane (2.5 L) was taken in a 3 L three-necked round bottom flask equipped with a reflux condenser and nitrogen inlet. The solution was degassed with nitrogen for 1 h and Hoveyda-Grubbs II generation catalyst (0.508 g, 0.811 mmol) was added. The mixture was heated at 95° C. for 18 h under nitrogen while monitoring by LC-MS. The solvent was evaporated under reduced pressure and the residue was subjected to flash chromatography using a Teledyne Isco instrument (40 g RediSep silica column, 10% MeOH in CHCl₃) to remove metallic and other impurities. The fractions having desired compound were concentrated and its component isomers were further separated by chiral normal phase HPLC [CHIRAL PAK IA (250×4.6 mm) 5 micron, A: 0.2% DEA in n-Hexane (50) B: Ethanol (50), Flow: 1.0 mL/min.].

EXAMPLE 44

Analytical data of Cis-(+)-Enantiomer (44A): (30 mg, 2%) of a light brown solid. Retention time 10.27 min. LC-MS (M+H)+=466.2. ¹H NMR (400 MHz, CDCl₃): δ ppm 9.46 (1H, s), 9.37 (1H, s), 8.66 (1H, s), 7.32-7.16 (5H, m), 6.68 (1H, d, J=2Hz), 5.79 (2H, m), 5.11-5.08 (1H, m), 4.63 (1H, d, J=14 Hz), 7.09-7.07 (1H, m), 6.35 (1H, t, J=7.8 Hz), 5.81-5.64 (2H, m), 5.24 (1H, m), 5.02 (1H, t, J=13.2 Hz), 4.53 (1H, d, J=14 Hz), 4.13 (1H, q, J=5.6 Hz), 3.45 (1H, d J=14 Hz), 3.40 (3H, s), 3.31-3.17 (1H, m), 2.50-2.48 (1H, m), 2.32 (3H, s), 1.92 (1H, m).

Analytical data of Cis-(−)-Enantiomer (44B): (30 mg, 2%) of light brown solid. Retention time 9.76 min. LC-MS (M+H)+=466.2. ¹H NMR (400 MHz, CDCl₃): identical to its antipode.

EXAMPLE 45 and 46

(11Z)-18-(4-fluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine and (11E)-18-(4-fluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine

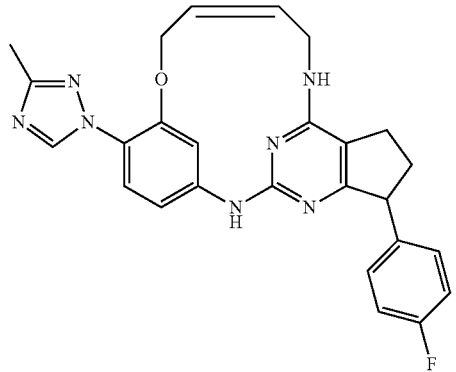

Example 45

Example 46

A solution of Synthon SaB (0.75 g, 1.50 mmol) in 1,2-dicholoethane (0.8 L) was taken in a 2 L three-necked round bottom flask equipped with a reflux condenser and nitrogen inlet. The solution was degassed with nitrogen for 1 h and Hoveyda-Grubbs II generation catalyst (0.094 g, 0.15 mmol) was added. The mixture was heated at 100° C. for 18 h under nitrogen while monitoring by LC-MS. The solvent was evaporated under reduced pressure and the residue was subjected to flash chromatography using a Teledyne Isco instrument (24 g RediSep silica column) to remove metallic and other impurities. The fractions having desired compound were concentrated and its component isomers were further separated by chiral normal phase HPLC [Chiralpak IC (250× 4.6)mm 5 mm column, 1.0 mL/min of 0.2% DEA in hexane: ethanol (80:20) as a mobile phase].

EXAMPLE 45

Analytical data of cis-(+)-enantiomer (45A): (0.07 g, 10%) off-white solid. Retention time 11.49 min. LC-MS (M+H)$^+$=470.2. $^1$H NMR (400 MHz, DMSO-d6): δ ppm 9.76 (1H, s), 9.39 (1H, s) 8.67 (1H, s), 7.53-7.50 (1H, m), 7.29-7.11 (5H, m), 6.67-6.63 (1H, m), 5.61-5.59 (2H, m), 5.17-5.10 (1H, m), 4.66-4.63 (2H, m), 4.15-4.13 (1H, m), 3.61-3.56 (1H, m), 2.78-2.53 (2H, m), 2.56-2.49 (1H, m), 2.31 (3H, s), 1.97-1.91 (1H, m).

Analytical data of Cis-(−)-Enantiomer (45B): (0.06 g, 8.5%) off-white solid. Retention time 10.60 min. LC-MS (M+H)$^+$=470.2. $^1$H NMR (400 MHz, DMSO-d6): identical to its antipode 45A.

EXAMPLE 46

Analytical data of trans-(+)-enantiomer (46A): (0.04 g, 5.7%) off-white solid. Retention time 11.26 min. LC-MS (M+H)$^+$=470.2. $^1$H NMR (400 MHz, DMSO-d6): δ ppm 9.25 (1H, s), 8.64 (1H, s), 8.32 (1H, s), 7.27-7.08 (6H, m), 6.61-6.58 (1H, d, J=8.4 Hz), 6.01-5.97 (1H, d, J=16 Hz), 5.67-5.63 (1H, d, J=16 Hz), 4.84-4.82 (2H, br s), 4.15-4.11 (1H, t, J=8 Hz), 3.89 (2H, br s), 2.79-2.74 (1H, m), 2.68-2.62 (1H, m), 2.59-2.52 (1H, m), 2.31 (3H, s), 1.97-1.91 (1H, m).

Analytical data of trans-(−)-enantiomer (46B): (0.035 g, 5%) off-white solid. Retention time 14.07 min. LC-MS (M+H)$^+$=470.2. $^1$H NMR (400 MHz, DMSO-d6): identical to its antipode 46A.

EXAMPLE 47

7-(5-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine

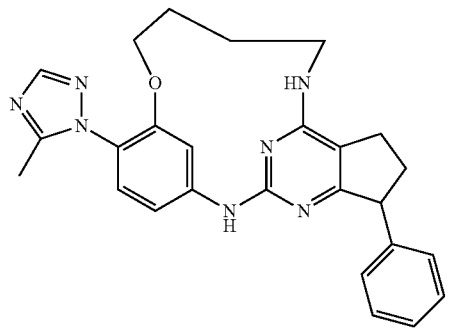

Example 47

Example 42A (0.03 g, 0.066 mmol) in 4 mL of 1:1 (MeOH: THF) was hydrogenated (balloon pressure H$_2$) at room temperature in presence of platinum(IV)oxide (0.0037 g, 0.016 mmol) for 60 min while monitoring by LC-MS. The reaction mixture was degassed with nitrogen and filtered through celite. The filtrate was concentrated under reduced pressure and the residue was subjected to chiral normal phase HPLC [Chiralpak IC (250×4.6)mm 5 mm column, 1.0 mL/min of 0.2% DEA in hexane:ethanol (80:20) as a mobile phase] to give Example 47A and a ring-opened phenolic compound. Similarly Example 42B (35 mg) was reduced to get Example 47B and the corresponding ring-opened phenolic compound.

EXAMPLE 47

Analytical data of (+)-enantiomer (47A): (0.008 g, 26%), off-white solid. Retention time 17.54 min. LC-MS (M+H)$^+$=454.2. $^1$H NMR (400 MHz, CDCl$_3$): δ ppm 9.24 (1H, s), 7.91 (1H, s), 7.33-7.10 (7H, m), 6.43-6.40 (1H, d, J=8.4 Hz), 4.87-4.80 (1H, m), 4.34-4.32 (2H, m), 4.19-4.18 (1H, m), 3.55-3.50 (2H, m), 2.75-2.65 (3H, m), 2.33 (3H, s), 2.08-2.03 (4H, m), 1.92-1.90 (1H, m).

Analytical data of (−)-enantiomer (47B): (0.01 g, 28.5%), off-white solid. Retention time 18.17 min. LC-MS (M+H)$^+$ =454.2. $^1$H NMR (400 MHz, CDCl$_3$): identical to its antipode 47A.

EXAMPLE 48

14-methyl-7-(5-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine

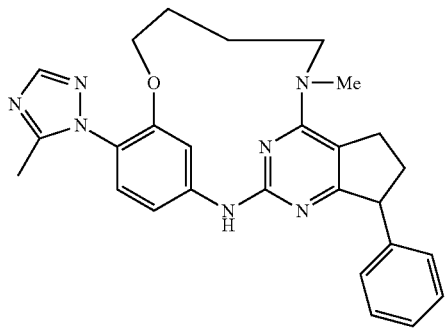

Example 48

Example 41A (0.05 g, 0.107 mmol) in 4 mL of 1:1 (MeOH:THF) was hydrogenated (balloon pressure H$_2$) at room temperature in presence of platinum(IV)oxide (0.006 g, 0.026 mmol) for 60 min while monitoring by LC-MS. The reaction mixture was degassed with nitrogen and filtered through celite. The filtrate was concentrated under reduced pressure and the residue was subjected to chiral normal phase HPLC (Chiralpak IC (250×4.6)mm 5 mm column, 1.0 mL/min of 0.2% DEA in hexane:ethanol(80:20) as a mobile phase) to give Example 48A along a ring-opened phenolic compound. Similarly, reduction of Example 41B yielded Example 48B and the corresponding ring-opened phenolic compound.

EXAMPLE 48

Analytical data of (+)-Enantiomer (48A): (0.008 g,16%) of off-white solid. Retention time 45.52 min. LC-MS (M+H)$^+$ =468.2. $^1$H NMR (400 MHz, CDCl$_3$): δ ppm 9.20 (1H, s), 7.91 (1H, s), 7.33-7.07 (7H, m), 6.39-6.36 (1H, d, J=8.4 Hz), 4.32 (2H, br s), 4.13-4.09 (1H, m), 3.81-3.62 (2H, m), 3.31 (3, s), 3.27-3.12 (2H, m), 2.60-2.51 (1H, m), 2.33 (3H, s), 2.08-2.03 (3H, m), 1.92-1.90 (2H, m).

Analytical data of (−)-Enantiomer (48B): (0.014 g, 28%) of off-white solid. Retention time 45.05 min. LC-MS (M+H)$^+$ =468.2. $^1$H NMR (400 MHz, CDCl$_3$): identical to its antipode 48A.

EXAMPLE 49

7-(3-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine

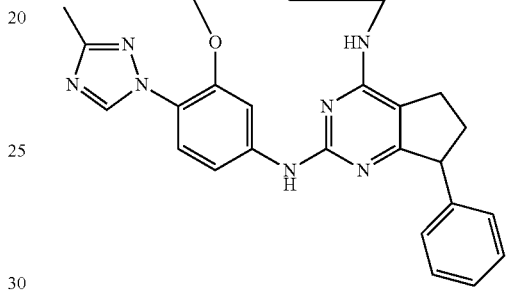

Example 49

Example 39A (0.05 g, 0.107 mmol) in 4 mL of 1:1 (MeOH:THF) was hydrogenated (balloon pressure H$_2$) at room temperature in presence of platinum(IV)oxide (0.006 g, 0.026 mmol) for 60 min while monitoring by LC-MS. The reaction mixture was degassed with nitrogen and filtered through celite. The filtrate was concentrated under reduced pressure and the residue was subjected to chiral normal phase HPLC [Chiralcel OJH (250×4.6)mm 5 mm column, 1.0 mL/min of 0.2% DEA in hexane:ethanol(80:20) as mobile phase] to give Example 49A along with a ring-opened phenolic compound. Similarly, Example 39B was reduced to get Example 49B and the corresponding ring-opened phenolic compound.

EXAMPLE 49

Analytical data of (+)-enantiomer (49A): (0.011 g, 22%) of an off-white solid. Retention time 11.3 min. LC-MS (M+H)$^+$ =454.2. $^1$H NMR (400 MHz, CDCl$_3$): δ ppm 9.28 (1H, s), 8.53 (1H, s), 7.49 (1H, d, J=8.4 Hz), 7.33-7.15 (6H, m), 6.406.38 (1H, dd, J=2.4, 8.4 Hz), 4.85 (1H, m), 4.43 (1H, t, J=5.6 Hz), 4.18 (1H, m), 3.66-3.57 (3H, m),2.75-265 (3H, m), 2.47 (3H, s), 2.10-1.97 (5H, m).

Analytical data of (−)-enantiomer (49B): (0.014 g, 28%) of an off-white solid. Retention time 10.97 min. LC-MS (M+H)+=454.2. $^1$H NMR (400 MHz, CDCl$_3$): identical to its antipode 49A.

EXAMPLE 50

14-methyl-7-(3-methyl-1H-1,2,4-triazol-1-yl)-18-phenyl-10,11,12,13,14,16,17,18-octahydro-15,2-(azeno)-8,4-(metheno)cyclopenta[h][1,6,10,12]ox-atriazacycloheptadecine

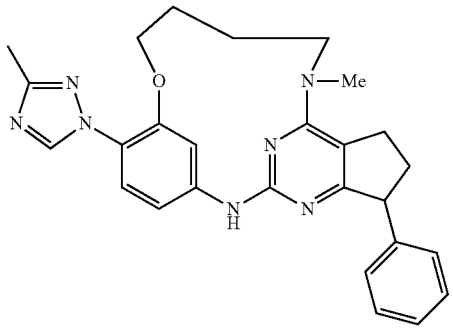

Example 50

Example 44A (0.02 g, 0.0.042 mmol) in 2 mL of 1:1 (MeOH:THF) was hydrogenated (balloon pressure H$_2$) at room temperature in presence of platinum(IV)oxide (0.0024 g, 0.001 mmol) for 30 min while monitoring by LC-MS. The reaction mixture was degassed with nitrogen and filtered through celite. The filtrate was concentrated under reduced pressure and the residue was subjected to chiral normal phase HPLC [Chiralpak IC (250×4.6)mm 5 mm column, 1.0 mL/min of 0.2% DEA in hexane:ethanol (80:20) as mobile phase] to give Example 50A along a ring-opened phenolic compound. Similarly, Example 44B was reduced to get Example 50B and the corresponding phenolic compound.

EXAMPLE 50

Analytical data of (+)-Enantiomer (50A): (0.002 g, 10%) off-white solid. Retention time 25.37 min. LC-MS (M+H)+ =468.2. $^1$H NMR (400 MHz, CDCl$_3$): δ ppm 9.22 (1H, s), 8.52 (1H, s), 7.48-7.46 (1H, m), 7.33-7.18 (5H, m), 6.98 (1H, br s), 6.41-6.38 (1H, d, J=8.4 Hz), 4.42 (2H, br s), 4.13-4.09 (1H, t, J=7.2 Hz), 3.81-3.62 (2H, m), 3.32 (3H, s), 3.27-3.12 (2H, m), 2.60-2.51 (1H, m), 2.46 (3H, s), 2.08-2.03 (3H, m), 1.92-1.90 (2H, m).

Analytical data of (−)-Enantiomer (SOB): (0.0025 g, 12.5%) off-white solid. Retention time 24.02 min. LC-MS (M+H)+=468.2. $^1$H NMR (400 MHz, CDCl$_3$): identical to its antipode 50A.

EXAMPLE 51 and 52

(11Z)-18-(2,4-difluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]ox-atriazacycloheptadecine and (11E)-18-(2,4-difluorophenyl)-7-(3-methyl-1H-1,2,4-triazol-1-yl)-10,13,14,16,17,18-hexahydro-15,2-(azeno)-8,4-(metheno)cyclopenta[h][1,6,10,12] oxatriazacycloheptadecine

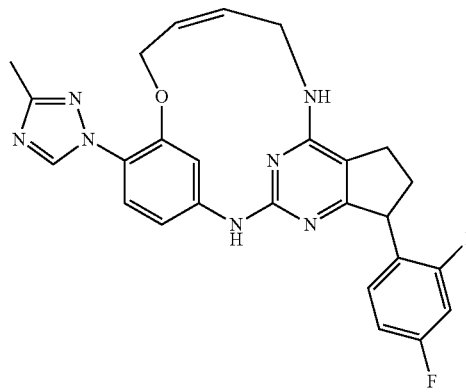

Example 51

Example 52

A solution of Synthon TaB (0.430, 0.834 mmol) in 1,2-dicholoethane (2.5 L) was taken in a 2 L three-necked round bottom flask equipped with a reflux condenser and nitrogen inlet. The solution was degassed with nitrogen for 1 h and Hoveyda-Grubbs II generation catalyst (0.130 g, 0.208 mmol) was added. The mixture was heated at 95° C. for 18 h under nitrogen while monitoring by LC-MS. The solvent was evaporated under reduced pressure and the residue was subjected to flash chromatography using a Teledyne Isco instrument (40 g RediSep silica column, 10% MeOH/CHCl$_3$) to remove metallic and other impurities. The fractions having the desired compounds were concentrated and its component isomers were further separated by chiral SFC (chiral cel-OJ-H, 30×250 mm, 5 μm column, 125 mL/min of 25% MeOH (0.5% DEA) in CO$_2$ at 100 bar and 35° C.

EXAMPLE 51

Analytical data of cis-(+)-enantiomer (51A): (24 mg, 6%) of light brown solid. Retention time 5.45 min. LC-MS (M+H)$^+$=488.2. $^1$H NMR (400 MHz, CDCl$_3$): δ ppm 9.73 (1H, s), 8.57 (1H, m), 7.51-7.49 (1H, m), 7.03-6.99 (2H, m), 6.83-6.78 (2H, m), 6.39-6.35 (1H, m), 5.73-5.68 (2H, m), 5.15-5.05 (2H, m), 4.71-4.68 (2H, m), 4.42 (1H, t, J=7.2 Hz), 3.71-3.69 (1H, m), 2.76-2.63 (3H, m), 2.48 (3H, s), 1.98-1.97 (1H, m).

Analytical data of cis-(−)-enantiomer (51B): (33 mg, 8.2%) of light brown solid. Retention time 8.04 min. LC-MS (M+H)$^+$=488.2. $^1$H NMR (400 MHz, CDCl$_3$): identical to its antipode 51A.

EXAMPLE 52

Analytical data of trans-(+)-enantiomer (52A): (3 mg, 1%) of brown solid. Retention time 4.25 min. LC-MS (M+H)$^+$=488.2. $^1$H NMR (400 MHz, CDCl$_3$): δ ppm 9.33 (1H, s), 8.64 (1H, s), 8.33 (1H, s), 7.28-7.19 (4H, m), 7.18-7.15 (1H, m), 6.59 (1H, dd, J=2, 8.8 Hz), 6.29 (1H, d, J=16 Hz), 5.66 (1H, d, J=16 Hz), 4.84-4.83 (2H, m), 4.34 (1H, t, J=8.4 Hz), 3.89 (2H, m), 2.78-2.61 (3H, m), 2.33 (3H, s), 1.91-1.87 (1H, m).

Analytical data of trans-(−)-enantiomer (52B): (6 mg, 1.5%) of brown solid. Retention time 6.43 min. LC-MS (M+H)$^+$=488.2. $^1$H NMR (400 MHz, CDCl$_3$): identical to its antipode 52A.

EXAMPLE 53 and 54

(11Z)-18-(2,4-difluorophenyl)-7-(5-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine and (11E)-18-(2,4-difluorophenyl)-7-(5-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine Example 53

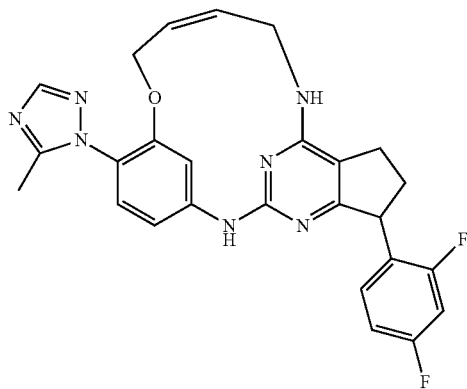

Example 54

A solution of Synthon TaC (0.450 g, 0.873 mmol) in 1,2-dicholoethane (2.5 L) was taken in a 2 L three-necked round bottom flask equipped with a reflux condenser and nitrogen inlet. The solution was degassed with nitrogen for 1 h and Hoveyda-Grubbs II generation catalyst (0.136 g, 0.218 mmol) was added. The mixture was heated at 95° C. for 18 h under nitrogen while monitoring by LC-MS. The solvent was evaporated under reduced pressure and the residue was subjected to flash chromatography using a Teledyne Isco instrument (40 g RediSep silica column, 10% MeOH/CHCl$_3$) to remove metallic and other impurities. The fractions having desired compound were concentrated and its component isomers were further separated by chiral SFC [Chiral cel-OJ-H, 30×250 mm, 5 µm column, 125 mL/min of 25% MeOH (0.5% DEA) in CO$_2$ at 100 bar and 35° C.].

EXAMPLE 53

Analytical data of cis-enantiomer-I (53A): (13.15 mg, 3.1%) of brown solid. Retention time 6.43 min. LC-MS (M+H)$^+$=488.2. $^1$H NMR (400 MHz, DMSO-d$_6$): δ ppm 9.79 (1H, s), 9.77 (1H, s), 7.92 (1H, s), 7.57 (1H, m), 7.22-7.01 (4H, m), 6.69-6.66 (1H, m), 5.61 (2H, m), 5.14 (1H, m), 4.56-4.35 (3H, m), 3.52 (1H, m), 2.79-2.66 (3H, m), 2.23 (3H, s), 1.91 (1H, m).

Analytical data of cis-enantiomer-II (53B): (18 mg, 4.2%) of light brown solid. Retention time 5.61 min. LC-MS (M+H)$^+$=488.2. $^1$H NMR (400 MHz, DMSO-d$_6$): identical to its antipode 53A.

EXAMPLE 54

Analytical data of trans-(+)-enantiomer (54A): (12 mg, 2.8%) of light brown solid. Retention time 3.3 min. LC-MS (M+H)$^+$=488.2. $^1$H NMR (400 MHz, DMSO-d$_6$): δ ppm 9.34 (1H, s), 8.36 (1H, s), 7.90 (1H, s), 7.24-7.16 (3H, m), 7.15-7.00 (2H, m), 6.63-6.30 (1H, dd, J=2, 8.8, Hz), 5.99 (1H, d, J=10 Hz), 5.63 (1H, d, J=10 Hz), 4.77 (1H, m), 4.35 (1H, t, J=8 Hz), 3.89 (1H, m), 2.79-2.76 (1H, m), 2.67-2.57 (2H, m), 2.50 (3H, s), 1.94-1.90 (1H, m).

Analytical data of trans-(−)-enantiomer (54B): (18 mg, 4.2%) of light brown solid. Retention time 4.23 min. LC-MS (M+H)⁺=488.2. ¹H NMR (400 MHz, DMSO-d₆): identical to its antipode 54A.

EXAMPLE 55

19-(4-fluorophenyl)-7-(3-methyl-1H-1,2,4-triazol-1-yl)-11,12,13,14,15,17,18,19-octahydro-10H-16,2-(azeno)-8,4-(metheno)cyclopenta[i][1,4,7,11,13]oxatetraazacyclooctadecine

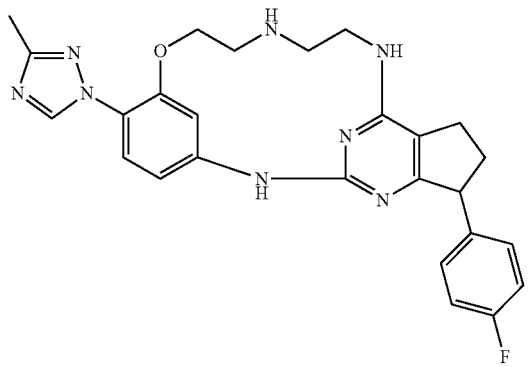

Example 55

An ice-cooled solution of Synthon ScJ (0.1 g, 0.191 mmol) in NMP (1 mL) was taken in a round bottom flask and treated with 0.1 mL of conc. $H_2SO_4$. The mixture was heated at 100° C. for 18 h while monitoring by LC-MS. The reaction mixture was cooled to rt, diluted with ethyl acetate (10 mL) and treated with saturated sodium bicarbonate (15 mL). The ethyl acetate layer was separated and the aqueous layer was further extracted with ethyl acetate (2×10 mL). The combined organic layers were washed with brine (2×10 mL), dried over anhydrous sodium sulfate, and concentrated under reduced pressure. The crude compound was purified by flash chromatography using a Teledyne Isco instrument (12 g RediSep silica column, 10% methanol in chloroform). The enantiomers were separated through chiral normal phase HPLC [Chiralpak AD-H (250×4.6)mm, 5 μm column, 1.0 mL/min of 0.2% DEA in hexane:ethanol(50:50) as mobile phase].

EXAMPLE 55

Analytical data of Enantiomer-I (55A): (0.01 g, 11%) of white solid. Retention time 17.69 min. LC-MS (M+H)⁺=487.2. ¹H NMR (400 MHz, CDCl₃): δ ppm 8.57 (1H, s), 8.47 (1H, s), 7.51-7.49 (1H, d, J=8.8 Hz), 7.16-7.12 (2H, m), 7.02-7.00 (2H, m), 6.44-6.42 (1H, d, J=8.4 Hz), 4.81 (1H, br s), 4.32-4.28 (2H, t, J=7.8 Hz), 4.18-4.15 (1H, m), 3.67-3.65 (2H, m), 3.21-3.18 (2H, m), 3.11-3.07 (2H, m), 2.65-2.62 (3H, m), 2.47 (3H, s), 2.01-1.98 (1H, m).

Analytical data of Enantiomer-II (55B): (0.011 g, 12%) of white solid. Retention time 6.00 min. LC-MS (M+H)⁺=487.2. ¹H NMR (400 MHz, CDCl₃): identical to its antipode 55A.

EXAMPLE 56

19-(4-fluorophenyl)-12-methyl-7-(3-methyl-1H-1,2,4-triazol-1-yl)-11,12,13,14,15,17,18,19-octahydro-10H-16,2-(azeno)-8,4-(metheno)cyclopenta[i][1,4,7,11,13]oxatetraazacyclooctadecine

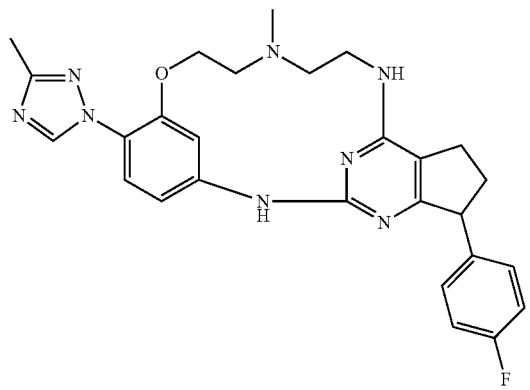

Example 56

An ice-cooled solution of Synthon SdJ (0.15 g, 0.279 mmol) in NMP (1.5 mL) was taken in a round bottom flask and treated with 0.15 mL of conc. $H_2SO_4$. The mixture was heated at 100° C. for 18 h while monitoring by LC-MS. The reaction mixture was cooled to rt, diluted with ethyl acetate (10 mL) and treated with saturated sodium bicarbonate (20 mL). The ethyl acetate layer was separated and the aqueous layer was further extracted with ethyl acetate (2×10 mL). The combined organic layers were washed with brine (2×10 mL), dried over anhydrous sodium sulfate, and concentrated under reduced pressure. The crude compound was purified by flash chromatography using a Teledyne Isco instrument (12 g RediSep silica column, with 10% MeOH in CHCl₃). The enantiomers were separated by chiral normal phase HPLC [Chiral OD-H (250×4.6)mm 5 mm column, 1.0 mL/min of 0.2% DEA in hexane:ethanol(70:30) as mobile phase].

EXAMPLE 56

Analytical data of (+)-enantiomer (56A): (0.018 g, 13%) off-white solid. Retention time 8.81 min. LC-MS (M+H)⁺=501.0. ¹H NMR (400 MHz, CDCl₃): δ ppm 8.44 (1H, s), 8.43 (1H, s), 7.49-7.47 (1H, d, J=8.4 Hz), 7.26-7.12 (2H, m), 7.03-7.00 (2H, m), 6.42-6.39 (1H, d, J=8.8 Hz), 4.3-4.26 (1H, t, J=7.2 Hz), 4.32-4.28 (2H, t, J=7.2 Hz), 4.10-4.06 (1H, t, J=8.4 Hz), 3.67 (2H, br s), 3.35 (3H, s), 3.25-3.22 (2H, m), 3.16-3.08 (4H, m), 2.54-2.48 (1H, m), 2.47 (3H, s), 2.01-1.93 (1H, m).

Analytical data of (−)-enantiomer (56B): (0.016 g, 11.5%) off-white solid. Retention time 13.11 min. LC-MS (M+H)$^+$ =501.0. $^1$H NMR (400 MHz, CDCl$_3$): identical to its antipode 56A.

EXAMPLE 57

(11Z)-18-(2,4-difluorophenyl)-14-methyl-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine

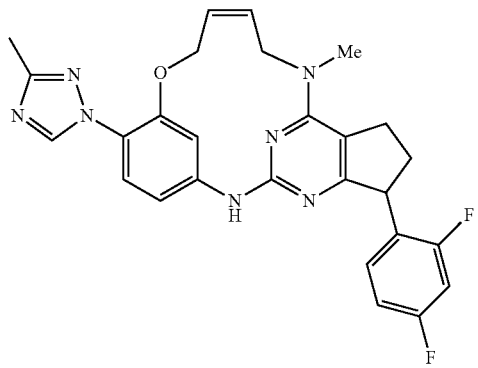

Example 57

A solution of Synthon TbB (0.500 g, 0.945 mmol) in 1,2-dicholoethane (2.5 L) was taken in a 3 L three-necked round bottom flask equipped with a reflux condenser and nitrogen inlet. The solution was degassed with nitrogen for 1 h and Hoveyda-Grubbs II generation catalyst (0.148 g, 0.236 mmol) was added. The mixture was heated at 95° C. for 18 h under nitrogen while monitoring by LC-MS. The solvent was evaporated under reduced pressure and the residue was subjected to flash chromatography using a Teledyne Isco instrument (40 g RediSep silica column, 10% MeOH/CHCl$_3$) to remove metallic and other impurities. The fractions having desired compound were concentrated and its component isomers were further separated by chiral SFC [Chiral cel-OJ-H, 30×250 mm, 5 µm column, 125 mL/min of 40% MeOH (0.5% DEA) in CO$_2$ at 100 bar and 35° C.].

EXAMPLE 57

Analytical data of cis-(+)-enantiomer (57A): (65 mg, 13.5%) of a dark ash solid. Retention time 6.19 min. LC-MS (M+H)$^+$=502.2. $^1$H NMR (400 MHz, CDCl$_3$): δ ppm 9.47 (1H, s), 8.54 (1H, s), 7.47 (1H, t, J=6.8 Hz), 7.00-6.98 (2H, m), 6.80 (2H, t, J=9.6 Hz), 6.37-6.32 (1H, m), 5.81-5.71 (2H, m), 5.22 (1H, q, J=9.2 Hz), 5.10-5.04 (1H, m), 4.65 (1H, d, J=14 Hz), 4.39 (1H, m), 3.46 (1H, m), 3.42 (3H, s), 3.25-3.07 (2H, m), 2.58-2.49 (1H, m), 2.47 (3H, s), 1.95-1.88 (1H, m).

Analytical data of cis-(−)-enantiomer (57B): (75 mg, 15%) of dark ash solid. Retention time 2.93 min. LC-MS (M+H)$^+$ =502.2. $^1$H NMR (400 MHz, CDCl$_3$): identical to its antipode 57A.

EXAMPLE 58 and 59

(11Z)-7-(3-methyl-1H-1,2,4-triazol-1-yl)-18-phenyl-10,13,14,16,17,18-hexahydro-15,2-(azeno)-8,4-(metheno)cyclopenta[h][1,10,12]oxadiazacycloheptadecine and (11E)-7-(3-methyl-1H-1,2,4-triazol-1-yl)-18-phenyl-10,13,14,16,17,18-hexahydro-15,2-(azeno)-8,4-(metheno)cyclopenta[h][1,10,12]oxadiazacycloheptadecine

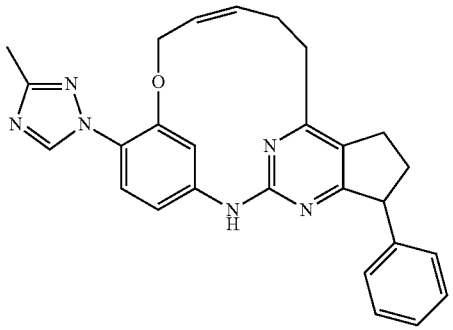

Example 58

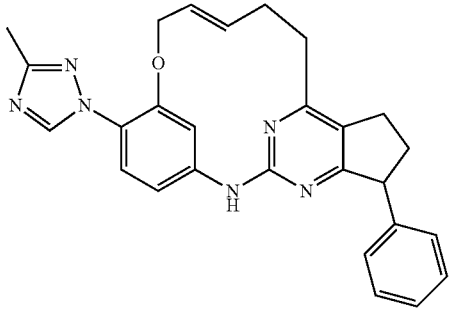

Example 59

A solution of Synthon RhB (0.45 g, 0.940 mmol in 1,2-dicholoethane (2.5 L) was taken in a 5 L three-necked round bottom flask equipped with a reflux condenser and nitrogen inlet. The solution was degassed with nitrogen for 1 h and Hoveyda-Grubbs II generation catalyst (0.045 g, 0.076 mmol) was added. The mixture was heated at 100° C. for 18 h under nitrogen while monitoring by LC-MS. Another two batches of the reaction were performed on same scale and the work-up was performed together. The solvent was evaporated under reduced pressure and the residue was subjected to flash chromatography using a Teledyne Isco instrument (40 g RediSep silica column, 50% ethyl acetate in chloroform) to remove metallic and other impurities. The fractions having desired compound were concentrated and its component isomers were further separated by chiral reverse phase supercritical fluid chromatography [Chiralcel OD-H (30×250)mm, 5 mm column, 40 mL/min of 0.5% DEA) in CO$_2$ at 101 bar pressure and 32.7° C.]

EXAMPLE 58

Analytical data of cis-(+)-enantiomer (58A): (0.21 g, 16.5%), light brown solid. Retention time 14.7 min. LC-MS (M+H)⁺=451.2. ¹H NMR (400 MHz, DMSO-d6): δ ppm 9.75 (1H, s), 9.61 (1H, s), 8.68 (1H, s), 7.33-7.18 (6H, m), 6.72-6.70 (1H, m), 5.69-5.67 (1H, m), 5.47-5.38 (1H, m), 5.12-5.05 (1H, m), 4.73-4.69 (1H, m), 4.29-4.28 (1H, m), 3.24-2.99 (4H, m), 2.86-2.60 (2H, m), 2.32 (3H, m), 2.28-2.02 (2H, m).

Analytical data of cis-(−)-enantiomer (58B): (0.20 g, 15.74%), light brown solid. Retention time 8.05 min. LC-MS (M+H)⁺=451.2. ¹H NMR (400 MHz, DMSO-d6): identical to its antipode 58A.

EXAMPLE 59

Analytical data of Trans-(+)-Enantiomer (59A): (0.12 g, 9.44%), light brown solid. Retention time 10.5 min. LC-MS (M+H)⁺=451.2. ¹H NMR (400 MHz, DMSO-d6): δ ppm 9.65 (1H, s), 8.65 (1H, s), 8.64 (1H, s), 7.33-7.20 (6H, m), 6.71-6.68 (1H, d, J=8.8 Hz), 6.05-5.02 (1H, d, J=16 Hz), 5.65-5.52 (1H, d, J=16 Hz), 4.80-4.79 (2H, m), 4.30-4.26 (1H, t, J=8.4 Hz), 3.01-2.83 (4H, m), 2.68-2.58 (3H, m), 2.33 (3H, s), 2.01-2.00 (1H, m).

Analytical data of Trans-(−)-Enantiomer (59B): (0.105 g, 8.26%), light brown solid. Retention time 6.8 min. LC-MS (M+H)⁺=451.2. ¹H NMR (400 MHz, DMSO-d6): identical to its antipode 59A.

EXAMPLE 60

13-methyl-7-(3-methyl-1H-1,2,4-triazol-1-yl)-17-phenyl-11,12,13,15,16,17-hexahydro-10H-14,2-(azeno)-8,4-(metheno)cyclopenta[g][1,5,9,11]oxatriazacyclohexadecine

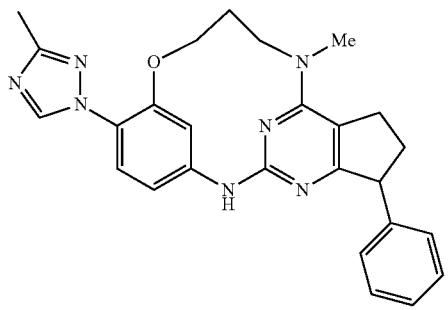

Example 60

A mixture of Synthon RiL (0.8 g, 1.633 mmol), xanthphos (0.142 g, 0.245 mmol), and cesium carbonate (0.798 g, 2.449 mmol) in 1,4-dioxane (50 mL) was taken in a two-necked 100 mL round bottom flask equipped with a reflux condenser and nitrogen inlet. The mixture was degassed with nitrogen for 1 h and Pd(dba)₃ (0.037 g, 0.163 mmol) was added. The reaction mixture was heated at 105° C. for 4 h while monitoring by TLC and LC-MS. The solvent was evaporated under reduced pressure and the residue was dissolved in ethyl acetate (20 mL) and filtered through celite. The filtrate was concentrated and the crude compound was purified by flash chromatography using a Teledyne Isco instrument (40 g RediSep silica column, with 50% ethyl acetate in pet-ether) to give a racemic mixture of the title compound (140 mg). The enantiomers were further separated by chiral normal phase HPLC [Chiralcel OJH (250×4.6)mm 5 μm column, 1.0 mL/min of 0.2% DEA in hexane:ethanol(60:40) as mobile phase].

EXAMPLE 60

Analytical data of (+)-enantiomer (60A): (0.061 g, 8%) off-white solid. Retention time 10.11 min. LC-MS (M+H)⁺=454.2. ¹H NMR (400 MHz, CDCl₃): δ ppm 8.84 (1H, s), 8.55 (1H, s), 7.50-7.48 (1H, d, J=8.4 Hz), 7.33-7.14 (5H, m), 6.62 (1H, br s), 6.51-6.49 (1H, d, J=8.8 Hz), 4.38-4.35 (2H, m), 4.13-4.09 (1H, m), 3.66-3.60 (2H, m), 3.24 (3H, s) 3.16-3.03 (2H, m), 2.54-2.52 (1H, m), 2.54 (3H, s), 2.46-2.30 (2H, m), 1.99-1.98 (1H, m).

Analytical data of (−)-enantiomer (60B): (0.058 g, 7.5%) off-white solid. Retention time 8.84 min. LC-MS (M+H)⁺=454.2. ¹H NMR (400 MHz, CDCl₃): identical to its antipode 60A.

EXAMPLE 61

18-(2,4-difluorophenyl)-14-methyl-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecine

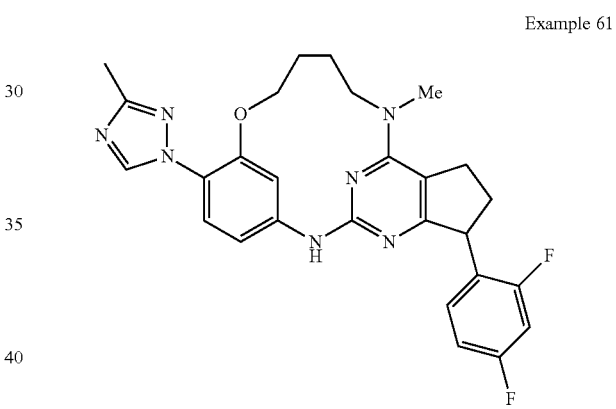

Example 61

Example 57A (0.045 g, 0.089 mmol) in 6 mL of 1:1 (MeOH:THF) was hydrogenated (balloon pressure H₂) at room temperature in presence of platinum(IV)oxide (0.005 g, 0.022 mmol) for 30 min while monitoring by LC-MS. The reaction mixture was degassed with nitrogen and filtered through celite. The filtrate was concentrated under reduced pressure and the residue was subjected to chiral preparative SFC [Chiral cel-OD-H, 30×250 mm, 5 μm column, 125 mL/min of 40% MeOH (0.5% DEA) in CO₂ at 100 bar and 35° C.] to give Example 61A along with a ring-opened phenolic compound. Similarly reduction of 55 mg of Example 57B yielded Example 61B and the corresponding ring-opened phenolic compound.

EXAMPLE 61

Analytical data of (+)-Enantiomer (61A): (7 mg, 15%) of brown solid. Retention time 5.01 min. LC-MS (M+H)⁺=504.2. ¹H NMR (400 MHz, CDCl₃): δ ppm 9.22 (1H, s), 8.53 (1H, s), 7.49-7.47 (1H, d, J=8.4 Hz), 7.01-6.95 (2H, m), 6.84-6.79 (2H, m), 6.42-6.40 (1H, m), 4.42-4.33 (3H, m), 3.81 (1H, m), 3.31 (3H, s), 3.22-3.05 (5H, m), 2.62-2.55 (1H, m), 2.47 (3H, s), 2.08-2.01 (3H, m).

Analytical data of (−)-Enantiomer (61B): (9 mg, 20%) of brown solid. Retention time 4.23 min. LC-MS (M+H)⁺ =504.2. ¹H NMR (400 MHz, CDCl₃): identical to its antipode 61A.

EXAMPLE 62

7-(3-methyl-1H-1,2,4-triazol-1-yl)-18-phenyl-10,11, 12,13,14,16,17,18-octahydro-15,2-(azeno)-8,4-(metheno)cyclopenta[h][1,10,12]oxadiazacycloheptadecine

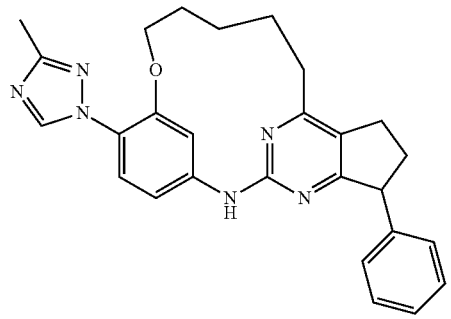

Example 62

Example 58A (0.158 g, 0.351 mmol) in 80 mL of 1:1 (MeOH:THF) was hydrogenated (balloon pressure H₂) at room temperature in the presence of platinum(IV)oxide (0.016 g, 0.070 xx mmol) for 40 min while monitoring by LC-MS. The reaction mixture was degassed with nitrogen and filtered through celite. The filtrate was concentrated under reduced pressure and the residue was subjected to chiral normal phase supercritical fluid chromatography [Chiralcel OD-H (30×250)mm 5 μm column, 30 mL/min of 0.5% DEA in methanol) in CO₂ at 100 bar pressure and 31.2° C.] to give Example 62A along with a ring-opened phenolic compound. Similarly, example 58B was reduced on the same scale to get Example 62B and the corresponding ring-opened phenolic compound.

EXAMPLE 62

Analytical data of (+)-enantiomer (62A): (0.0583 g, 34.9%), off white solid. Retention time 9.02 min. LC-MS (M+H)⁺=453.2. ¹H NMR (400 MHz, CDCl₃): δ ppm 8.93 (1H, s), 8.56 (1H, s), 7.53-7.51 (1H, d, J=8.4 Hz), 7.35-7.16 (5H, m), 6.45-6.45 (1H, m), 4.39-4.38 (2H, m), 4.27-4.23 (1H, t, J=8 Hz), 3.03-2.63 (6H, m), 2.47 (3H, s), 2.13-2.10 (1H, m), 2.02-1.91 (6H, m).

Analytical data of (−)-enantiomer (62B): (45.58 g, 27.9%), off-white solid. Retention time 9.02 min. LC-MS (M+H)⁺ =453.2. ¹H NMR (400 MHz, CDCl₃): identical to its antipode 62A.

EXAMPLE 63

17-(2,4-difluorophenyl)-7-(3-methyl-1H-1,2,4-triazol-1-yl)-11,12,13,15,16,17-hexahydro-10H-14,2-(azeno)-8,4-(metheno)cyclopenta[g][1,5,9,11]oxatriazacyclohexadecine

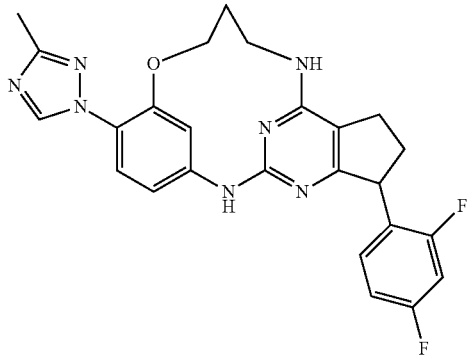

Example 63

A mixture of Synthon TeK (0.4 g, 0.781 mmol), xanthphos (0.068 g, 0.117 mmol), and cesium carbonate (0.382 g, 1.172 mmol) in 1,4-dioxane (25 mL) was taken in a two-necked 100 mL round bottom flask equipped with a reflux condenser and nitrogen inlet. The mixture was degassed with nitrogen for 1 h and Pd(dba)₃ (0.018 g, 0.078 mmol) was added. The reaction mixture was heated at 105° C. for 4 h while monitoring by TLC and LC-MS. The solvent was evaporated under reduced pressure and the residue was dissolved in ethyl acetate (20 mL) and filtered through celite. The filtrate was concentrated and the crude compound was purified by flash chromatography using a Teledyne Isco instrument (24 g RediSep silica column, with 50% ethyl acetate in pet-ether) to give a racemic mixture of the target compound (70 mg). The enantiomers were further separated by chiral normal phase HPLC [Chiralpak ADH (250×4.6)mm 5 μm column, 1.0 mL/min of 0.2% DEA in hexane:ethanol(80:20) as mobile phase].

EXAMPLE 63

Analytical data of (+)-enantiomer (63A): (0.014 g, 3.7%) off-white solid. Retention time 15.56 min. LC-MS (M+H)⁺ =476.2. ¹H NMR (400 MHz, CDCl₃): δ ppm 9.00 (1H, s), 8.57 (1H, s), 7.53-7.51 (1H, d, J=8.4 Hz), 7.05-6.98 (1H, m), 6.83-6.79 (2H, m), 6.66 (1H, br s), 6.55-6.52 (1H, d, J=8.4 Hz), 4.78-4.76 (1H, m), 4.46-4.40 (3H, m), 3.62-3.56 (2H, m), 2.69-2.60 (3H, m), 2.47 (3H, s), 2.41-2.38 (2H, m), 1.99-1.98 (1H, m).

Analytical data of (−)-enantiomer (63B): (0.012 g, 3.2%) off-white solid. Retention time 12.37 min. LC-MS (M+H)$^+$ =476.2. $^1$H NMR (400 MHz, CDCl$_3$): identical to its antipode 63A.

EXAMPLE 64

18-(2,4-difluorophenyl)-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecine

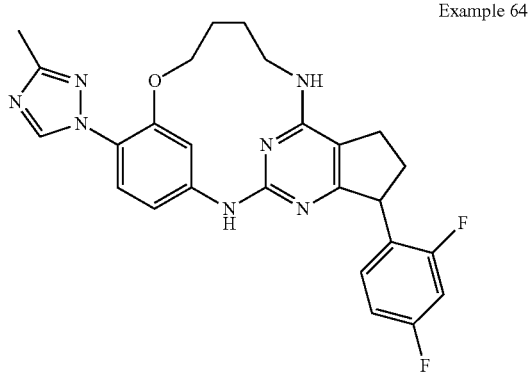 [SMILES: Cc1ncn(-c2ccc3cc2OCCCCNc2nc(nc4c2CCC4c2ccc(F)cc2F)N3)n1]

Example 64

Example 51A (0.10 g, 0.205 mmol) in 4 mL of 1:1 (MeOH:THF) was hydrogenated (balloon pressure H$_2$) at room temperature in the presence of platinum(IV)oxide (0.011 g, 0.051 mmol) for 30 min while monitoring by LC-MS. The reaction mixture was degassed with nitrogen and filtered through celite. The filtrate was concentrated under reduced pressure and the residue was subjected to chiral SFC [Chiral cel-OJ-H, 30×250 mm, 5 μm column, 125 mL/min of 20% MeOH (0.5% DEA) in CO$_2$ at 100 bar and 35° C.] to give example 64A along with a ring-opened phenolic compound. Similarly Example 51B was reduced to get Example 64B and the corresponding ring-opened phenolic compound.

EXAMPLE 64

Analytical data of (+)-Enantiomer (64A): (15 mg, 15%), brown solid. Retention time 14.93 min. LC-MS (M+H)$^+$ =490.2. $^1$H NMR (400 MHz, CDCl$_3$): δ ppm 9.28 (1H, s), 8.54 (1H, s), 7.52-7.50 (1H, d, J=8.8 Hz), 7.00-6.75 (3H, m), 6.44-6.41 (1H, m), 4.85-4.84 (1H, m), 4.42-4.40 (3H, m), 3.58-3.56 (2H, m), 2.75-2.61 (4H, m), 2.47 (3H, s), 2.08-1.94 (5H, m).

Analytical data of (−)-Enantiomer (64B): (16 mg, 16%), brown solid. Retention time 7.18 min. LC-MS (M+H)$^+$ =490.2. $^1$H NMR (400 MHz, CDCl$_3$): identical to its antipode 64A.

EXAMPLE 65

13-methyl-7-(3-methyl-1H-1,2,4-triazol-1-yl)-17-(4-fluorophenyl)-11,12,13,15,16,17-hexahydro-10H-14,2-(azeno)-8,4-(metheno)cyclopenta[g][1,5,9,11]oxatriazacyclohexadecine Example 65

A mixture of Synthon SeL (0.600 g, 1.183 mmol), xanthphos (0.099 g, 0.176 mmol), and cesium carbonate (0.776 g, 2.365 mmol) in 1,4-dioxane (50 mL) was taken in a two-necked 100 mL round bottom flask equipped with a reflux condenser and nitrogen inlet. The mixture was degassed with nitrogen for 1 h and Pd(OAc)$_2$ (0.026 g, 0.116 mmol) was added. The reaction mixture was heated at 110° C. for 16 h while monitoring by TLC and LC-MS. The solvent was evaporated under reduced pressure and the residue was dissolved in DCM (100 mL) and filtered through celite. The filtrate was concentrated and the crude compound was purified by flash chromatography using a Teledyne Isco instrument (40 g RediSep silica column, 10% MeOH in CHCl$_3$) to give a racemic mixture of the title compound (250 mg). The enantiomers were further separated by chiral SFC [Chiral cel-OD-H, 30×250 mm, 5 μm column, 125 mL/min of 30% MeOH (0.5% DEA) in CO$_2$ at 100 bar and 35° C.].

EXAMPLE 65

Analytical data of (+)-Enantiomer (65A): (58 mg, 10.3%), off-white solid. Retention time 3.8 min. LC-MS (M+H)$^+$ =472.2. $^1$H NMR (400 MHz, CDCl$_3$): δ ppm 8.82 (1H, s), 8.55 (1H, s), 7.55 (1H, d, J=8.8 Hz), 7.13-6.97 (4H, m), 6.61 (1H, s), 6.50-6.48 (1H, dd, J=2.4, 8.8 Hz), 4.38-4.34 (2H, m), 4.11-4.07 (1H, m), 3.72-3.50 (2H, m), 3.24 (3H, s), 3.14-3.02 (2H, m), 2.62-2.50 (1H, m), 2.46 (3H, s), 2.34-2.30 (2H, m), 1.95-1.90 (1H, m).

Analytical data of (−)-Enantiomer (65B): (57 mg, 10.2%), off white solid. Retention time 7.66 min. LC-MS (M+H)+ =472.2. ¹H NMR (400 MHz, CDCl₃): identical to its antipode 65A.

EXAMPLE 66

18-(2,4-difluorophenyl)-13-methyl-7-(3-methyl-1H-1,2,4-triazol-1-yl)-10,11,12,13,14,16,17,18-octahydro-3H-15,2-(azeno)-4,8-(metheno)cyclopenta[h][1,6,10,12]oxatriazacycloheptadecine

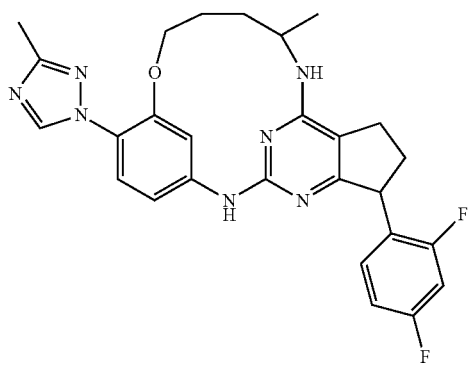

Example 66

A mixture of synthon TgP (0.5 g, 0.926 mmol), xanthphos (80 mg, 0.139 mmol), and cesium carbonate (453 mg, 1.389 mmol), in 1,4-dioxane (50 mL) was degassed with nitrogen for 1 h, and Pd(OAc)₂ (21 mg, 0.093 mmol) was added. The mixture was heated at 100° C. for 4 h while monitoring by LC-MS. The solvent was removed under reduced pressure and the residue was dissolved in ethyl acetate (300 mL) and filtered through celite. The filtrate was evaporated under reduced pressure and the crude compound was purified by a Teledyne ISCO instrument (40 g column, 2-3% of methanol in chloroform) to give 290 mg of a diastereomeric mixture of four compounds. LC-MS (M+H)+=504.2. 1H NMR: (400 MHz, CDCl₃) δ ppm 8.82 (1 H, s), 8.53 (1 H, s), 7.53-7.50 (1 H, m), 7.07-6.98 (2 H, m), 6.84-6.79 (2 H, m), 6.44-6.41 (1 H, m), 4.60 (1 H, br m), 4.42-4.39 (2 H, m), 4.14-3.93 (2 H, m), 2.72-2.62 (4 H, m), 2.48 (3 H, s), 2.17-2.16 (1 H, m), 2.05-1.95 (1H, m), 1.98-1.97 (1 H, m), 1.54-1.48 (1 H, m), 1.34-1.32 (3 H, m).

EXAMPLE 67

18-(4-fluorophenyl)-3,11,12,13,14,16,17,18-octahydro-10H-2,15-(azeno)-4,8-(metheno)cyclopenta[h][1,4,10,12]oxatriazacycloheptadecine-7-carbonitrile

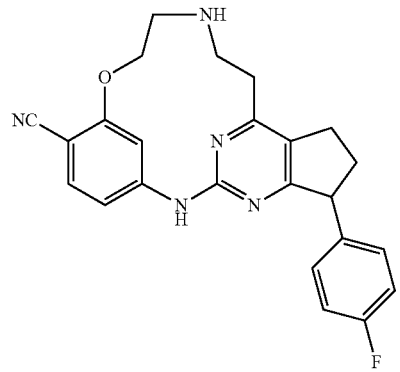 [SMILES: N#Cc1ccc2cc1OCCNCCc1nc(nc3c1CCC3c1ccc(F)cc1)N2]

To an ice-cold solution of Synthon ShQ (2 mg, 0.0038 mmol) in DCM (2 mL) was added TFA (0.2 mL). The reaction mixture was stirred at room temperature for 30 min. The solvent was removed under reduced pressure and treated with saturated sodium bicarbonate solution (1 mL), which was extracted with ethyl acetate (2×2 mL). The organic layer was dried over anhydrous sodium sulphate and concentrated under reduced pressure to get Example 67 as a racemic mixture. LC-MS (M+H)+=416.2

EXAMPLE 68 and 69

(11E)-7-cyano-18-(4-fluorophenyl)-18-methyl-10,13,14,16,17,18-hexahydro-15,2-(azeno)-8,4-(metheno)cyclopenta[h][1,6,10,12]oxatriazacycloheptadecine, TFA salt and (11Z)-7-cyano-18-(4-fluorophenyl)-18-methyl-10,13,14,16,17,18-hexahydro-15,2-(azeno)-8,4-(metheno)cyclopenta[h][1,6,10,12]oxatriazacycloheptadecine, TFA salt

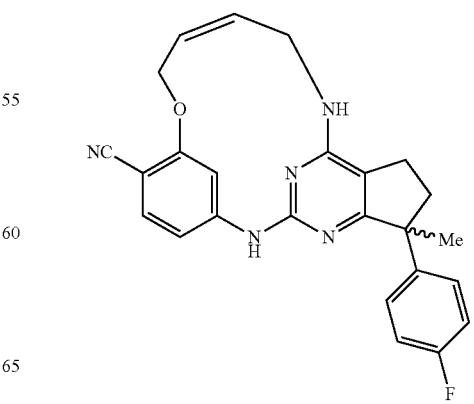

Example 68

-continued

Example 69

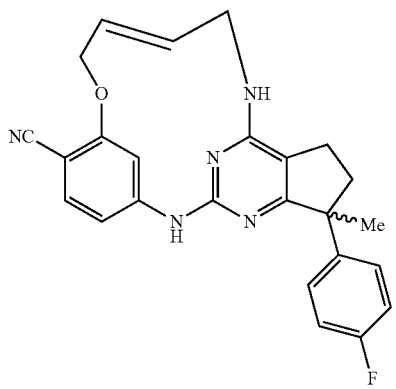

To a solution of Synthon UaD (74 mg, 0.162 mmol) in 1,2-dichloroethane (3249 µL) was added Hoyveda-Grubbs II catalyst (6.90 mg, 8.12 µmol). The resulting solution was stirred at 90° C. overnight. The reaction mixture was purified by PREP HPLC (30×150 mm HPLC XTerra C18 0 to 100% A:B over 26 min, 4 min at 100% B (A is 90:10:0.1 water: MeOH:TFA; B is 90:10:0.1 MeOH:water:TFA)). The appropriate fractions were concentrated in vacuo. Example 68 (cis): LC-MS (M+H)$^+$=428.1. $^1$H NMR (500 MHz, CDCl$_3$) δ ppm 11.97 (1 H, s), 7.86 (1 H, d, J=1.83 Hz), 7.42 (1 H, d, J=8.55 Hz), 7.23-7.31 (3 H, m), 6.98-7.07 (2 H, m), 6.81 (1 H, dd, J=8.24, 1.83 Hz), 5.94 (1 H, dt, J=15.87, 5.65 Hz), 5.74-5.84 (2 H, m), 4.90 (2 H, br. s.), 4.13 (2 H, app. br t), 2.76-2.85 (2 H, m), 2.60 (1 H, ddd, J=13.28, 8.24, 4.73 Hz), 2.33-2.42 (1 H, m), 1.84 (3 H, s).

EXAMPLE 69

(trans, atropisomers): LC-MS (M+H)$^+$=428.1. $^1$H NMR (500 MHz, CDCl$_3$) δ ppm 11.72-11.83 (1 H, d, J=23.2 Hz), 9.34 (1 H, dd, J=14.95, 1.83 Hz), 7.38 (1H, dd, J=8.39, 2.90 Hz), 7.21-7.25 (3 H, m), 6.96-7.05 (2 H, m), 6.81 (1 H, ddd, J=8.32, 4.65, 1.98 Hz), 6.23 (1 H, t, J=5.34 Hz), 5.77 (1 H, q, J=10.88 Hz), 5.59-5.68 (1 H, m), 5.04 (1 H, ddd, J=14.34, 10.99, 3.97 Hz), 4.69-4.80 (2 H, m), 3.82-3.91 (1 H, m), 2.78-2.87 (2 H, m), 2.53-2.62 (1 H, m), 2.33-2.42 (1 H, m), 1.82 (3 H, d, J=7.32 Hz).

EXAMPLE 70

19-(4-fluorophenyl)-17-methyl-7-(3-methyl-1H-1,2,4-triazol-1-yl)-11,12,13,14,16,17,18,19-octahydro-10H-15,2-(azeno)-8,4-(metheno)pyrido[3,4-h][1,6,10,12]oxatriazacycloheptadecine (+/−), TFA salt

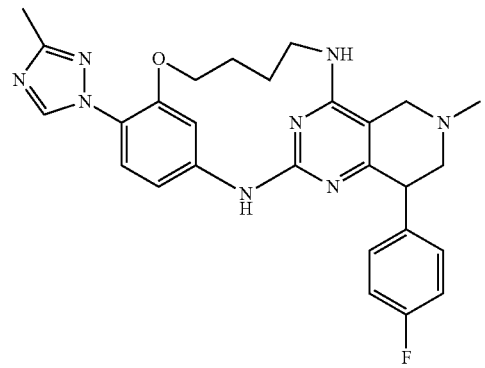 [SMILES: Cc1ncn(-c2ccc3cc2OCCCCNc2nc(nc4c2CN(C)CC4c2ccc(F)cc2)N3)n1]

A solution of N-(4-(5-amino-2-(3-methyl-1H-1,2,4-triazol-1-yl)phenoxy)butyl)-2-chloro-8-(4-fluorophenyl)-6-methyl-5,6,7,8-tetrahydropyrido[4,3-d]pyrimidin-4-amine (35 mg, 0.065 mmol) in NMP (915 µL) was treated with H$_2$SO$_4$ (8.0 µL, 0.150 mmol). The mixture was heated at 90° C. for 24 h. The crude product was purified by Prep-HPLC to obtain the title compound as a TFA salt (8.0 mg, 20% yield). LC-MS (M+H)$^+$=501.2. $^1$H NMR (500 MHz, methanol-d$_4$) δ 8.95 (s, 1H), 8.83 (br. s., 1H), 7.66-7.60 (m, 1H), 7.46-7.33 (m, 2H), 7.27-7.18 (m, 2H), 6.75 (dd, J=8.7, 2.3 Hz, 1H), 4.64 (dd, J=10.1, 6.2 Hz, 1H), 4.52 (br. s., 2H), 4.33 (d, J=15.0 Hz, 1H), 4.29-4.21 (m, 1H), 3.93 (dd, J=12.4, 5.8 Hz, 1H), 3.67-3.53 (m, 3H), 3.12 (s, 3H), 2.51-2.37 (m, 3H), 2.09 (br. s., 2H), 2.00 (br. s., 2H).

Example 70 (+/−), TFA salt (48 mg, 0.078 mmol) was separated by chiral SFC chromatography [Chiralpak AD-H, preparative column, 30×250 mm, 5 µm column, 70 mL/min of 40% MeOH (0.1% DEA) in CO$_2$ at 150 bar and 35° C.] to get the enantiomers Example 70A (5.8 mg, 13.35% yield) and Example 70B (5.6 mg, 12.89% yield).

EXAMPLE 70A

LC-MS (M+H)$^+$=501.2. $^1$H NMR (500 MHz, methanol-d$_4$) δ 9.34 (s, 1H), 8.66 (s, 1H), 7.39 (d, J=8.5 Hz, 1H), 7.29-7.16 (m, 2H), 7.06-6.97 (m, 2H), 6.55 (dd, J=8.5, 2.3 Hz, 1H), 4.46 (br. s., 2H), 4.09 (t, J=6.7 Hz, 1H), 3.55 (br. s., 2H), 3.50-3.41 (m, 1H), 3.41-3.34 (m, 1H), 3.08 (dd, J=11.4, 6.0 Hz, 1H), 2.68 (dd, J=11.7, 7.9 Hz, 1H), 2.49 (s, 3H), 2.42 (s, 3H), 2.05 (br. s., 2H), 2.02-1.85 (m, 2H).

EXAMPLE 70B

LC-MS (M+H)$^+$=501.3. $^1$H NMR (500 MHz, methanol-d$_4$) δ 9.34 (br. s., 1H), 8.66 (s, 1H), 7.39 (d, J=8.5 Hz, 1H), 7.30-7.18 (m, 2H), 7.11-6.96 (m, 2H), 6.55 (dd, J=8.5, 2.3 Hz, 1H), 4.46 (br. s., 2H), 4.09 (t, J=6.7 Hz, 1H), 3.55 (br. s., 2H), 3.50-3.42 (m, 1H), 3.42-3.34 (m, 1H), 3.08 (dd, J=11.8, 5.9

Hz, 1H), 2.68 (dd, J=11.7, 8.1 Hz, 1H), 2.49 (s, 3H), 2.42 (s, 3H), 2.04 (d, J=12.7 Hz, 2H), 2.00-1.82 (m, 2H).

EXAMPLE 71

7-cyano-19-(4-fluorophenyl)-17-methyl-11, 12, 13,14,16,17,18,19-octahydro-10H-15,2-(azeno)-8,4-(metheno)pyrido[3,4-h][1,6,10,12]oxatriazacycloheptadecine (+/−), TFA salt

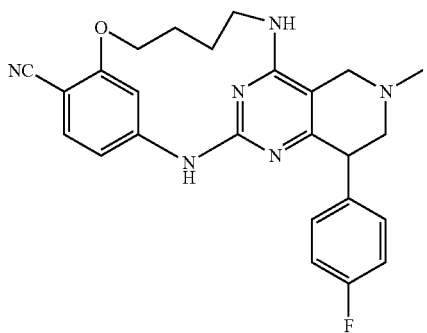 [SMILES: CN1Cc2c3nc(nc2C(c2ccc(F)cc2)C1)Nc1ccc(C#N)c(c1)OCCCCN3]

4-amino-2-(4-((2-chloro-8-(4-fluorophenyl)-6-methyl-5,6,7,8-tetrahydropyrido[4,3-d]pyrimidin-4-yl)amino)butoxy)benzonitrile was reacted as described in Example 70 with $H_2SO_4$ in NMP to get the title compound as a bis-TFA salt (33% yield). LC-MS (M+H)$^+$=445.2. $^1$H NMR (500 MHz, methanol-d$_4$) δ 8.87 (br. s., 1H), 7.47 (d, J=8.4 Hz, 1H), 7.42-7.35 (m, 2H), 7.23-7.14 (m, 2H), 6.65 (dd, J=8.4, 2.0 Hz, 1H), 4.62 (dd, J=10.4, 6.6 Hz, 1H), 4.51 (br. s., 2H), 4.34 (d, J=14.8 Hz, 1H), 4.26 (dd, J=15.0, 1.7 Hz, 1H), 3.93 (dd, J=12.1, 5.9 Hz, 1H), 3.68-3.54 (m, 3H), 3.12 (s, 3H), 2.14-1.90 (m, 4H).

EXAMPLES 72A-D 18-(4-fluorophenyl)-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecin-11(3H)-ol (diastereomeric mixture of 4 compounds), TFA salt

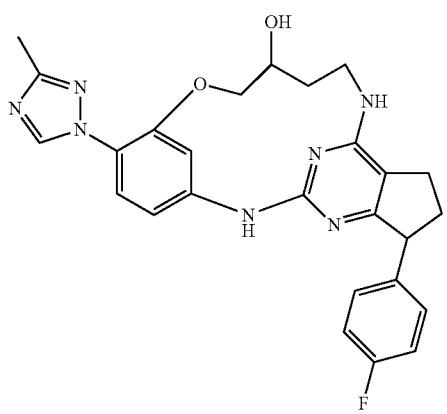 [SMILES: Cc1ncn(-c2ccc3cc2OCC(O)CCNc2nc(nc4c2CCC4c2ccc(F)cc2)N3)n1]

The mixture of 1-(5-amino-2-(3-methyl-1H-1,2,4-triazol-1-yl)phenoxy)-4-(2-chloro-7-(4-fluorophenyl)-6,7-dihydro-5H-cyclopenta[d]pyrimidin-4-ylamino)butan-2-ol (250 mg, 0.477 mmol), PdOAc$_2$ (5.36 mg, 0.024 mmol), Cs$_2$CO$_3$ (311 mg, 0.954 mmol) and xantphos (27.6 mg, 0.048 mmol) in dioxane (4771 µl) was heated at 100° C. for 6 h. The crude product was purified by Prep-HPLC to obtain 18-(4-fluorophenyl)-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecin-11(3H)-ol (diastereomeric mixture of 4 compounds), TFA salt (170 mg, 24.42% yield). LC-MS (M+H)$^+$=488.3 $^1$H NMR (500 MHz, methanol-d$_4$) δ 9.03 (d, J=4.0 Hz, 1H), 7.70-7.63 (m, 1H), 7.34-7.26 (m, 2H), 7.18-7.07 (m, 2H), 6.85-6.77 (m, 1H), 4.65 (d, J=13.4 Hz, 1H), 4.56-4.46 (m, 1H), 4.39-4.23 (m, 2H), 3.84-3.72 (m, 1H), 3.65-3.52 (m, 1H), 2.99-2.88 (m, 1H), 2.88-2.72 (m, 2H), 2.51-2.43 (m, 3H), 2.22-2.07 (m, 3H). 18-(4-fluorophenyl)-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecin-11(3H)-ol (diastereomeric mixture of 4 compounds), TFA salt (170 mg, 0.283 mmol) was separated by chiral SFC chromatography [Chiralpak AD-H preparative column, 20×250 mm, 5 µm, 45 mL/min of 35% MeOH (0.1% DEA) in CO$_2$ at 150 bar and 35° C.] to get Example 72A (29 mg, 18.94% yield), Example 72B (27 mg, 17.64% yield), Example 72C (33 mg, 21.56% yield) and Example 72D (28 mg, 18.29% yield).

EXAMPLE 72A

LC-MS (M+H)$^+$=488.3 $^1$H NMR (400 MHz, methanol-d$_4$) δ 9.21 (br. s., 1H), 8.77-8.72 (m, 1H), 7.42 (d, J=8.5 Hz, 1H), 7.19-7.12 (m, 2H), 7.05-6.96 (m, 2H), 6.59 (dd, J=8.5, 2.3 Hz, 1H), 4.56 (d, J=13.1 Hz, 1H), 4.36 (br. s., 1H), 4.26-4.16 (m, 1H), 4.10 (t, J=7.9 Hz, 1H), 3.71 (br. s., 1H), 3.50-3.39 (m, 1H), 2.82-2.52 (m, 3H), 2.47-2.36 (m, 3H), 2.20-1.90 (m, 3H).

EXAMPLE 72B

LC-MS (M+H)$^+$=488.3 $^1$H NMR (500 MHz, methanol-d$_4$) δ 9.15 (br. s., 1H), 8.74 (s, 1H), 7.43 (d, J=8.9 Hz, 1H), 7.23-7.11 (m, 2H), 7.08-6.98 (m, 2H), 6.61 (dd, J=8.5, 2.1 Hz, 1H), 4.60 (d, J=12.5 Hz, 1H), 4.41 (br. s., 1H), 4.32-4.20 (m, 1H), 4.16 (t, J=7.9 Hz, 1H), 3.75 (br. s., 1H), 3.59-3.45 (m, 1H), 2.88-2.74 (m, 1H), 2.74-2.53 (m, 2H), 2.43 (s, 3H), 2.14 (br. s., 1H), 2.11-2.04 (m, 1H), 2.04-1.90 (m, 1H).

EXAMPLE 72C

LC-MS (M+H)$^+$=488.3 $^1$H NMR (400 MHz, methanol-d$_4$) δ 9.14 (br. s., 1H), 8.75 (s, 1H), 7.43 (d, J=8.5 Hz, 1H), 7.22-7.13 (m, 2H), 7.08-6.95 (m, 2H), 6.61 (dd, J=8.7, 2.1 Hz, 1H), 4.60 (d, J=12.3 Hz, 1H), 4.41 (br. s., 1H), 4.27-4.19 (m, 1H), 4.16-4.07 (m, 1H), 3.77-3.68 (m, 1H), 3.57-3.43 (m, 1H), 2.84-2.55 (m, 3H), 2.43 (s, 3H), 2.16-1.89 (m, 3H).

EXAMPLE 72D

LC-MS (M+H)$^+$=488.3 $^1$H NMR (400 MHz, methanol-d$_4$) δ 9.24 (br. s., 1H), 8.76 (s, 1H), 7.44 (d, J=8.5 Hz, 1H), 7.25-7.13 (m, 2H), 7.10-6.98 (m, 2H), 6.62 (dd, J=8.7, 2.1 Hz, 1H), 4.70-4.55 (m, 1H), 4.40 (d, J=7.0 Hz, 1H), 4.30-4.19 (m, 1H), 4.16-4.07 (m, 1H), 3.82-3.68 (m, 1H), 3.53-3.43 (m, 1H), 2.87-2.73 (m, 1H), 2.73-2.52 (m, 2H), 2.43 (s, 3H), 2.23-1.93 (m, 3H).

EXAMPLES 73A-D 7-cyano-18-(4-fluorophenyl)-10,11,12,13,14,16,17,18-octahydro-15,2-(azeno)-8,4-(metheno)cyclopenta[h][1,6,10,12]oxatriazacycloheptadecin-11(3H)-ol (diastereomer mixture of 4 compounds), TFA salt

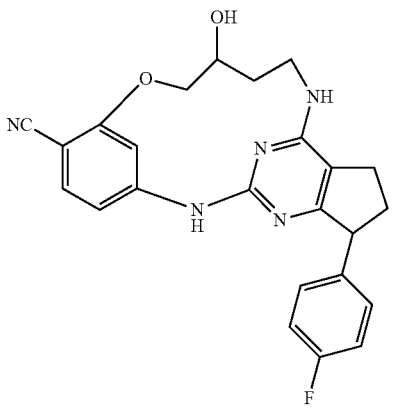 [SMILES: N#Cc1ccc2cc1OCC(O)CCNc1nc(nc3c1CCC3c1ccc(F)cc1)N2]

4-amino-2-(4-(2-chloro-7-(4-fluorophenyl)-6,7-dihydro-5H-cyclopenta[d]pyrimidin-4-ylamino)-2-hydroxybutoxy)benzonitrile, TFA salt was reacted as described in Example 72 with Pd(OAc)$_2$, Cs$_2$CO$_3$ and xantphos in dioxane to get 7-cyano-18-(4-fluorophenyl)-10,11,12,13,14,16,17,18-octahydro-15,2-(azeno)-8,4-(metheno)cyclopenta[h][1,6,10,12]oxatriazacycloheptadecin-11(3H)-ol, TFA salt (diastereomeric mixture of 4 compounds). LC-MS (M+H)$^+$=432.2. $^1$H NMR (400 MHz, methanol-d$_4$) δ 8.47 (br. s., 1H), 7.55 (d, J=8.5 Hz, 1H), 7.36-7.24 (m, 2H), 7.19-7.07 (m, 2H), 6.81-6.69 (m, 1H), 4.64 (d, J=10.8 Hz, 1H), 4.56-4.43 (m, 1H), 4.43-4.30 (m, 1H), 4.24 (br. s., 1H), 3.78 (d, J=12.5 Hz, 1H), 3.65-3.50 (m, 1H), 2.99-2.86 (m, 1H), 2.86-2.69 (m, 2H), 2.30-2.04 (m, 3H). 7-cyano-18-(4-fluorophenyl)-10,11,12,13,14,16,17,18-octahydro-15,2-(azeno)-8,4-(metheno)cyclopenta[h][1,6,10,12]oxatriazacycloheptadecin-11(3H)-ol (diastereomer mixture of 4 compounds), TFA salt (100 mg, 0.232 mmol) was separated by chiral HPLC [Chiralpak AD-H preparative column, 30×250 mm, 5 μm, 70 mL/min of 35% MeOH (0.1% DEA) in CO$_2$ at 130 bar and 35° C.] to get Example 73A (16 mg, 14.40% yield), the mixture of Example 73B and Example 73C and Example 73D (17 mg, 13.50% yield). The mixture of Example 73B and Example 73C was separated by chiral HPLC [Chiralcel OJ-H preparative column, 30×250 mm, 5 μm, 70 mL/min of 35% MeOH (0.1% DEA) in CO$_2$ at 150 bar and 35° C.] to get Example 73B (17 mg, 15.30% yield), and Example 73C (14 mg, 12.60% yield).

EXAMPLE 73A

LC-MS (M+H)$^+$=432.2. $^1$H NMR (500 MHz, methanol-d$_4$) δ 9.23 (br. s., 1H), 7.42-7.31 (m, 1H), 7.22-7.09 (m, 2H), 7.09-6.94 (m, 2H), 6.56 (dd, J=8.5, 1.8 Hz, 1H), 4.61 (d, J=11.6 Hz, 1H), 4.44-4.22 (m, 2H), 4.22-4.09 (m, 1H), 3.85-3.68 (m, 1H), 3.57-3.42 (m, 1H), 2.83-2.59 (m, 3H), 2.11 (d, J=14.3 Hz, 2H), 2.07-1.91 (m, 1H).

EXAMPLE 73B

LC-MS (M+H)$^+$=432.2. $^1$H NMR (500 MHz, methanol-d$_4$) δ 9.11 (br. s., 1H), 7.39-7.32 (m, 1H), 7.22-7.14 (m, 2H), 7.06-6.91 (m, 2H), 6.54 (dd, J=8.2, 1.8 Hz, 1H), 4.59 (d, J=11.3 Hz, 1H), 4.34 (br. s., 1H), 4.30-4.13 (m, 2H), 3.74 (br. s., 1H), 3.55-3.43 (m, 1H), 2.83-2.76 (m, 1H), 2.75-2.58 (m, 2H), 2.13 (br. s., 2H), 2.08-1.87 (m, 1H).

EXAMPLE 73C

LC-MS (M+H)$^+$=432.1. $^1$H NMR (500 MHz, methanol-d$_4$) δ 9.11 (br. s., 1H), 7.36 (d, J=8.5 Hz, 1H), 7.24-7.12 (m, 2H), 7.08-6.93 (m, 2H), 6.55 (dd, J=8.5, 1.8 Hz, 1H), 4.60 (d, J=11.9 Hz, 1H), 4.35 (br. s., 1H), 4.27 (d, J=13.1 Hz, 1H), 4.17 (t, J=7.9 Hz, 1H), 3.74 (br. s., 1H), 3.58-3.42 (m, 1H), 2.90-2.76 (m, 1H), 2.76-2.55 (m, 2H), 2.13 (br. s., 2H), 2.07-1.93 (m, 1H).

EXAMPLE 73D

LC-MS (M+H)$^+$=432.2. $^1$H NMR (500 MHz, methanol-d$_4$) δ 9.22 (br. s., 1H), 7.36 (d, J=8.2 Hz, 1H), 7.24-7.11 (m, 2H), 7.10-6.92 (m, 2H), 6.56 (dd, J=8.2, 1.8 Hz, 1H), 4.61 (d, J=12.2 Hz, 1H), 4.44-4.23 (m, 2H), 4.16 (t, J=7.8 Hz, 1H), 3.76 (br. s., 1H), 3.52-3.45 (m, 1H), 2.83-2.76 (m, 1H), 2.75-2.58 (m, 2H), 2.11 (d, J=14.6 Hz, 2H), 2.04-1.93 (m, 1H).

EXAMPLE 74

(11Z)-14,17-dimethyl-7-cyano-19-(4-fluorophenyl)-13,14,16,17,18,19-hexahydro-10H-15,2-(azeno)-8,4-(metheno)pyrido[3,4-h][1,6,10,12]oxatriazacycloheptadecine (+/−)

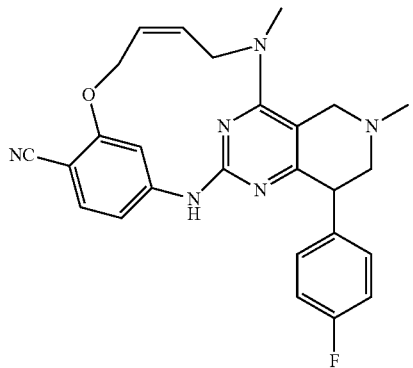 [SMILES: CN1Cc2c(nc3nc2N(C)C/C=C\COc2cc(ccc2C#N)N3)C(c2ccc(F)cc2)C1]

The mixture of 4-((4-(allyl(methyl)amino)-8-(4-fluorophenyl)-6-methyl-5,6,7,8-tetrahydropyrido[4,3-d]pyrimidin-2-yl)amino)-2-(allyloxy)benzonitrile, TFA (135 mg, 0.226 mmol) and Hoveyda-Grubbs catalyst 2nd generation (42.5 mg, 0.068 mmol) in DCE (75.3 ml) was heated at 90° C. overnight. The crude product was purified by Prep-HPLC to get (11Z)-14,17-dimethyl-7-cyano-19-(4-fluorophenyl)-13,14,16,17,18,19-hexahydro-10H-15,2-(azeno)-8,4-(metheno)pyrido[3,4-h][1,6,10,12]oxatriazacycloheptadecine (+/−) (6 mg, 4.95% yield). LC-MS (M+H)$^+$=457.6. $^1$H NMR (500 MHz, chloroform-d) δ 9.39 (d, J=1.8 Hz, 1H), 7.34-7.25 (m, 2H), 7.24-7.15 (m, 1H), 7.15-7.08 (m, 2H), 7.07-6.92 (m, 2H), 6.25 (d, J=8.2 Hz, 1H), 5.97-5.84 (m, 1H), 5.84-5.62 (m, 1H), 5.14-4.95 (m, 2H), 4.84-4.69 (m, 1H), 4.51 (m, 0.5H), 4.20-4.13 (m, 0.5H), 3.71-3.49 (m, 2H), 3.31 (d, J=4.0 Hz, 3H), 3.17 (ddd, J=11.8, 7.0, 2.1 Hz, 1H), 2.90 (m, 0.5H), 2.71 (m, 0.5H), 2.40 (s, 3H).

Biological Methods

Cellular Assays for Inhibition of Aβ1-40 and Aβ1-42 Production

H4 cells stably transfected with APP751 containing the Swedish mutation (H4 APP751 SWE clone 8.20, developed at BMS) were maintained in log phase through twice weekly passage at a 1:20 split. For $IC_{50}$ determinations, 30 µl cells ($1.5 \times 10^4$ cells/well) in DMEM media containing 0.0125% BSA (Sigma A8412) were plated directly into 384-well compound plates (Costar 3709) containing 0.1 µl serially diluted compound in DMSO. Following incubation for 19 h in 5% $CO_2$ at 37° C., plates were briefly centrifuged (1000 rpm, 5 min). A 10 µl aliquot from each well was transferred to a second assay plate (Costar 3709) for Aβ40 measurements. Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at BMS; conjugated to the Wallac reagent (Perkin Elmer)) and the N-terminal sequence of Aβ peptide (26D6, developed at SIBIA; conjugated to APC (Perkin Elmer)) were mixed and 20 µl of the mixture was added to each well of the incubated cell plate yielding a final concentration of 0.8 ng/well 565 and 75 ng/well 26D6. For the Aβ40 measurements, antibodies specific for the Aβ40 neoepitope (TSD, developed at BMS; conjugated to the Wallac reagent (Perkin Elmer)) and 26D6 as described above were mixed and 20 µl of the mixture was added to the 10 µl aliquots which had been removed previously from the cell plate yielding a final concentration of 1.6 ng/well TSD and 17.5 ng/well 26D6. Assay plates containing antibodies were sealed with aluminum foil and incubated overnight at 4° C. Signal was determined using a Viewlux counter (Perkin Elmer) and $IC_{50}$ values determined using curve fitting in CurveMaster (Excel Fit based).

The activity of representative compounds of the present invention, based on Aβ42 cellular $IC_{50}$ values in H4 APP751 SWE clone 8.20, are illustrated in Table 1 (below).

TABLE 1

| Compound of Example | Activity Rating[a] |
|---|---|
| 1A | 3.9 |
| 2A | ++ |
| 3A | +++ |
| 4A | +++ |
| 5A | +++ |
| 6A | 3.6 |
| 7A | 8.8 |
| 8A | +++ |
| 9A | +++ |
| 10A | ++ |
| 11A | 3.8 |
| 12A | +++ |
| 13A | +++ |
| 14A | +++ |
| 15A | +++ |
| 16A | +++ |
| 17A | 5.6 |
| 18A | +++ |
| 19A | +++ |
| 20A | +++ |
| 21A | 7.8 |
| 22A | ++ |

TABLE 1-continued

| Compound of Example | Activity Rating[a] |
|---|---|
| 23A | ++ |
| 24A | +++ |
| 25A | ++ |
| 26A | ++ |
| 27A | ++ |
| 28A | 13 |
| 29A | +++ |
| 30A | ++ |
| 31A | ++ |
| 32A | ++ |
| 33A | ++ |
| 34A | 21 |
| 35A | ++ |
| 36A | + |
| 38A | + |
| 39A | 4.0 |
| 40A | +++ |
| 41A | ++ |
| 42A | 6.6 |
| 43A | +++ |
| 44A | +++ |
| 45A | ++ |
| 46A | + |
| 47A | 5.6 |
| 48A | +++ |
| 49A | +++ |
| 50A | +++ |
| 51A | +++ |
| 52A | 11 |
| 53A | +++ |
| 54A | +++ |
| 55A | ++ |
| 56A | ++ |
| 57A | 5.5 |
| 58A | +++ |
| 59A | +++ |
| 60A | ++ |
| 61A | 4.1 |
| 62A | +++ |
| 63A | +++ |
| 64A | 5.3 |
| 65A | ++ |
| 68 | 160 |
| 70A | ++ |
| 71 | ++ |
| 72A | +++ |
| 72C | +++ |
| 73A | ++ |
| 73C | ++ |
| 1B | ++ |
| 2B | 15 |
| 3B | ++ |
| 4B | ++ |
| 5B | ++ |
| 6B | ++ |
| 7B | + |
| 8B | +++ |
| 9B | 17 |
| 10B | ++ |
| 11B | ++ |
| 12B | ++ |
| 13B | 26 |
| 14B | ++ |
| 15B | 23 |
| 16B | ++ |
| 17B | ++ |
| 18B | 47 |
| 19B | ++ |
| 20B | 11 |
| 21B | ++ |
| 22B | ++ |
| 23B | ++ |
| 24B | 43 |
| 25B | 53 |
| 26B | + |
| 27B | + |
| 28B | + |

TABLE 1-continued

| Compound of Example | Activity Rating[a] |
|---|---|
| 29B | + |
| 30B | ++ |
| 31B | 31 |
| 32B | + |
| 33B | 37 |
| 34B | 160 |
| 35B | 140 |
| 37B | ++ |
| 38B | + |
| 39B | ++ |
| 40B | 25 |
| 41B | ++ |
| 42B | ++ |
| 43B | 53 |
| 44B | 30 |
| 45B | ++ |
| 46B | + |
| 47B | ++ |
| 48B | 88 |
| 49B | ++ |
| 50B | ++ |
| 51B | ++ |
| 52B | ++ |
| 53B | 17 |
| 54B | ++ |
| 55B | ++ |
| 56B | ++ |
| 57B | ++ |
| 58B | 24 |
| 59B | 32 |
| 60B | ++ |
| 61B | ++ |
| 62B | 22 |
| 63B | 25 |
| 64B | ++ |
| 65B | ++ |
| 69 | 120 |
| 70B | +++ |
| 74 | ++ |
| 72B | +++ |
| 72D | +++ |
| 74B | 10 |
| 74D | +++ |

[a]Activity based on Aβ42 cellular IC$_{50}$ values in H4 APP751 SWE clone 8.20.
+++ = <0.010 μM
++ = 0.010-0.100 μM
+ = 0.100-1.0 μM It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

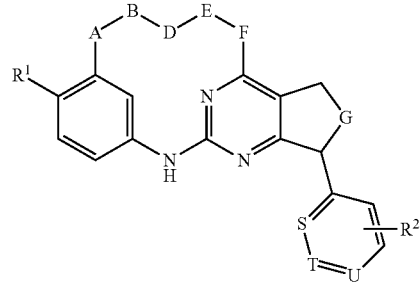

including pharmaceutically acceptable salts thereof, wherein
$R^1$ is a nitrile group, or is a five- or six-membered heteroaromatic ring containing from one to three heteroatoms independently selected from nitrogen, oxygen, and sulfur; wherein said heteroaromatic ring is optionally substituted with one or two groups selected from halo, halo$C_{1-6}$alkyl, hydroxyl, amino, $C_{1-6}$alkoxy, and $C_{1-6}$alkyl;
A is selected from O and $CH_2$, or is a bond;
B-D-E is —$CH_2$—CH=CH—$CH_2$— (cis), —$CH_2$—CH=CH—$CH_2$— (trans), —$(CH_2)_3$—, —$(CH_2)_4$—, —$CH_2$—CH(OH)—$CH_2$—$CH_2$—, —$CH_2$—$CH_2$—CH(OH)—$CH_2$—, —$CH_2$—$CH_2$—N($R^3$)—$CH_2$—$CH_2$—, or —$CH_2$—$CH_2$—O—$CH_2$—$CH_2$—;
F is selected from O and $NR^3$, or is a bond;
G is selected from —$CH_2$—, —$CH_2$—$CH_2$—, $NR^3$, and —N($R^3$)—$CH_2$—;
S, T, and U are independently selected from carbon and nitrogen, with the proviso that no more than one of S, T, and U is nitrogen;
$R^2$ is optionally one, two, or three of the following: halogen, $C_{1-4}$alkoxy, $OCF_3$, $C_{1-4}$alkyl, CN;
$R^3$ is independently $C_{1-4}$ alkyl or hydrogen.

2. A compound of claim 1, wherein $R^1$ is a five-membered heteroaromatic ring containing two nitrogen atoms wherein the ring is substituted with a halo group.

3. A compound of claim 1, wherein $R^1$ is a five-membered heteroaromatic ring containing three nitrogen atoms wherein the ring is substituted with a methyl group.

4. A compound of claim 1, wherein $R^1$ is —CN.

5. A compound of claim 1, wherein A is oxygen.

6. A compound of claim 1, wherein F is NH, NMe, or NEt.

7. A compound of claim 1, wherein B-D-E is —$CH_2$—CH=CH—$CH_2$—(cis), —$CH_2$—CH=CH—$CH_2$— (trans), —$(CH_2)_3$— or —$(CH_2)_4$—.

8. A compound of claim 1, wherein B-D-E is —$CH_2$—CH(OH)—$CH_2$—$CH_2$—, —$CH_2$—$CH_2$—CH(OH)—$CH_2$—, —$CH_2$—$CH_2$—N($R^3$)—$CH_2$—$CH_2$—, or —$CH_2$—$CH_2$—O—$CH_2$—$CH_2$—.

9. A compound of claim 1, wherein G is —$CH_2$—, —$CH_2$—$CH_2$—, or —N($R^3$)—$CH_2$—.

10. A compound which is selected from the group consisting of:
(11Z)-7-(4-chloro-1H-imidazol-1-yl)-18-phenyl-10,13,14,16,17,18-hexahydro-15,2-(azeno)-8,4-(metheno)cyclopenta[h][1,6,10,12]oxatriazacycloheptadecine;
(11E)-7-(4-chloro-1H-imidazol-1-yl)-18-phenyl-10,13,14,16,17,18-hexahydro-15,2-(azeno)-8,4-(metheno)cyclopenta[h][1,6,10,12]oxatriazacycloheptadecine;
(11Z)-7-(4-chloro-1H-imidazol-1-yl)-14-methyl-18-phenyl-10,13,14,16,17,18-hexahydro-15,2-(azeno)-8,4-(metheno)cyclopenta[h][1,6,10,12]oxatriazacycloheptadecine;

(11E)-7-(4-chloro-1H-imidazol-1-yl)-14-methyl-18-phenyl-10,13,14,16,17,18-hexahydro-15,2-(azeno)-8,4-(metheno)cyclopenta[h][1,6,10,12]oxatriazacycloheptadecine;

(11E)-7-(4-chloro-1H-imidazol-1-yl)-19-phenyl-3,10,13,14,15,17,18,19-octahydro-2,16-(azeno)-8,4-(metheno)cyclopenta[j][1,7,9,13]oxatriazacyclooctadecine;

(11Z)-7-(4-chloro-1H-imidazol-1-yl)-14-methyl-19-phenyl-3,10,13,14,15,17,18,19-octahydro-2,16-(azeno)-8,4-(metheno)cyclopenta[j][1,7,9,13]oxatriazacyclooctadecine;

(11E)-7-(4-chloro-1H-imidazol-1-yl)-14-methyl-19-phenyl-3,10,13,14,15,17,18,19-octahydro-2,16-(azeno)-8,4-(metheno)cyclopenta[j][1,7,9,13]oxatriazacyclooctadecine;

7-(4-chloro-1H-imidazol-1-yl)-19-phenyl-10,11,13,14,15,17,18,19-octahydro-16,2-(azeno)-8,4-(metheno)cyclopenta[i][1,4,7,11,13]dioxatriazacyclooctadecine;

7-(4-chloro-1H-imidazol-1-yl)-17-phenyl-11,12,13,15,16,17-hexahydro-10H-14,2-(azeno)-8,4-(metheno)cyclopenta[g][1,5,9,11]oxatriazacyclohexadecine;

7-(4-chloro-1H-imidazol-1-yl)-13-methyl-17-phenyl-11,12,13,15,16,17-hexahydro-10H-14,2-(azeno)-8,4-(metheno)cyclopenta[g][1,5,9,11]oxatriazacyclohexadecine;

7-(4-chloro-1H-imidazol-1-yl)-19-phenyl-3,10,11,12,13,14,15,17,18,19-decahydro-2,16-(azeno)-8,4-(metheno)cyclopenta[j][1,7,9,13]oxatriazacyclooctadecine;

7-(4-chloro-1H-imidazol-1-yl)-18-phenyl-10,11,12,13,14,16,17,18-octahydro-15,2-(azeno)-8,4-(metheno)cyclopenta[h][1,6,10,12]oxatriazacycloheptadecine;

7-(4-chloro-1H-imidazol-1-yl)-14-methyl-18-phenyl-10,11,12,13,14,16,17,18-octahydro-15,2-(azeno)-8,4-(metheno)cyclopenta[h][1,6,10,12]oxatriazacycloheptadecine;

(11Z)-7-(4-chloro-1H-imidazol-1-yl)-18-(2,4-difluorophenyl)-10,13,14,16,17,18-hexahydro-15,2-(azeno)-8,4-(metheno)cyclopenta[h][1,6,10,12]oxatriazacycloheptadecine;

(11E)-7-(4-chloro-1H-imidazol-1-yl)-18-(2,4-difluorophenyl)-10,13,14,16,17,18-hexahydro-15,2-(azeno)-8,4-(metheno)cyclopenta[h][1,6,10,12]oxatriazacycloheptadecine;

(11Z)-7-(4-chloro-1H-imidazol-1-yl)-18-phenyl-10,13,14,16,17,18-hexahydro-15,2-(azeno)-8,4-(metheno)cyclopenta[h][1,10,12]oxadiazacycloheptadecine;

(11E)-7-(4-chloro-1H-imidazol-1-yl)-18-phenyl-10,13,14,16,17,18-hexahydro-15,2-(azeno)-8,4-(metheno)cyclopenta[h][1,10,12]oxadiazacycloheptadecine;

(11Z)-7-(4-chloro-1H-imidazol-1-yl)-18-(2,4-difluorophenyl)-14-methyl-10,13,14,16,17,18-hexahydro-15,2-(azeno)-8,4-(metheno)cyclopenta[h][1,6,10,12]oxatriazacycloheptadecine;

7-(4-chloro-1H-imidazol-1-yl)-18-(2,4-difluorophenyl)-14-methyl-10,11,12,13,14,16,17,18-octahydro-15,2-(azeno)-8,4-(metheno)cyclopenta[h][1,6,10,12]oxatriazacycloheptadecine;

7-(4-chloro-1H-imidazol-1-yl)-17-(2,4-difluorophenyl)-13-methyl-11,12,13,15,16,17-hexahydro-10H-14,2-(azeno)-8,4-(metheno)cyclopenta[g][1,5,9,11]oxatriazacyclohexadecine;

(11Z)-7-cyano-18-phenyl-10,13,14,16,17,18-hexahydro-15,2-(azeno)-8,4-(metheno)cyclopenta[h][1,6,10,12]oxatriazacycloheptadecine;

(11E)-7-cyano-18-phenyl-10,13,14,16,17,18-hexahydro-15,2-(azeno)-8,4-(metheno)cyclopenta[h][1,6,10,12]oxatriazacycloheptadecine;

7-cyano-18-phenyl-10,11,12,13,14,16,17,18-octahydro-15,2-(azeno)-8,4-(metheno)cyclopenta[h][1,6,10,12]oxatriazacycloheptadecine;

(11Z)-7-cyano-18-(2,4-difluorophenyl)-10,13,14,16,17,18-hexahydro-15,2-(azeno)-8,4-(metheno)cyclopenta[h][1,6,10,12]oxatriazacycloheptadecine;

(11E)-7-cyano-18-(2,4-difluorophenyl)-10,13,14,16,17,18-hexahydro-15,2-(azeno)-8,4-(metheno)cyclopenta[h][1,6,10,12]oxatriazacycloheptadecine;

7-cyano-19-(4-fluorophenyl)-11,12,13,14,15,17,18,19-octahydro-10H-16,2-(azeno)-8,4-(metheno)cyclopenta[i][1,4,7,11,13]oxatetraazacyclooctadecine;

7-cyano-19-(4-fluorophenyl)-12-methyl-11,12,13,14,15,17,18,19-octahydro-10H-16,2-(azeno)-8,4-(metheno)cyclopenta[i][1,4,7,11,13]oxatetraazacyclooctadecine;

(11Z)-7-cyano-18-(2,4-difluorophenyl)-14-methyl-10,13,14,16,17,18-hexahydro-15,2-(azeno)-8,4-(metheno)cyclopenta[h][1,6,10,12]oxatriazacycloheptadecine;

(11Z)-7-cyano-14-methyl-18-phenyl-10,13,14,16,17,18-hexahydro-15,2-(azeno)-8,4-(metheno)cyclopenta[h][1,6,10,12]oxatriazacycloheptadecine;

(11E)-7-cyano-14-methyl-18-phenyl-10,13,14,16,17,18-hexahydro-15,2-(azeno)-8,4-(metheno)cyclopenta[h][1,6,10,12]oxatriazacycloheptadecine;

7-cyano-13-methyl-17-phenyl-11,12,13,15,16,17-hexahydro-10H-14,2-(azeno)-8,4-(metheno)cyclopenta[g][1,5,9,11]oxatriazacyclohexadecine;

7-cyano-18-(2,4-difluorophenyl)-14-methyl-10,11,12,13,14,16,17,18-octahydro-15,2-(azeno)-8,4-(metheno)cyclopenta[h][1,6,10,12]oxatriazacycloheptadecine;

7-cyano-17-(2,4-difluorophenyl)-11,12,13,15,16,17-hexahydro-10H-14,2-(azeno)-8,4-(metheno)cyclopenta[g][1,5,9,11]oxatriazacyclohexadecine;

7-cyano-14-methyl-18-phenyl-10,11,12,13,14,16,17,18-octahydro-15,2-(azeno)-8,4-(metheno)cyclopenta[h][1,6,10,12]oxatriazacycloheptadecine;

7-cyano-17-(2,4-difluorophenyl)-13-methyl-11,12,13,15,16,17-hexahydro-10H-14,2-(azeno)-8,4-(metheno)cyclopenta[g][1,5,9,11]oxatriazacyclohexadecine;

(11Z)-7-cyano-18-phenyl-10,13,14,16,17,18-hexahydro-15,2-(azeno)-8,4-(metheno)cyclopenta[h][1,10,12]oxadiazacycloheptadecine;

(11E)-7-cyano-18-phenyl-10,13,14,16,17,18-hexahydro-15,2-(azeno)-8,4-(metheno)cyclopenta[h][1,10,12]oxadiazacycloheptadecine;

7-cyano-18-phenyl-10,11,12,13,14,16,17,18-octahydro-15,2-(azeno)-8,4-(metheno)cyclopenta[h][1,10,12]oxadiazacycloheptadecine;

(11Z)-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11E)-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11Z)-14-methyl-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11E)-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11Z)-7-(5-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11Z)-14-methyl-7-(3-methyl-1H-1,2,4-triazol-1-yl)-18-phenyl-10,13,14,16,17,18-hexahydro-15,2-(azeno)-8,4-(metheno)cyclopenta[h][1,6,10,12]oxatriazacycloheptadecine;

(11Z)-18-(4-fluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11E)-18-(4-fluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

7-(5-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine;

14-methyl-7-(5-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine;

7-(3-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine;

14-methyl-7-(3-methyl-1H-1,2,4-triazol-1-yl)-18-phenyl-10,11,12,13,14,16,17,18-octahydro-15,2-(azeno)-8,4-(metheno)cyclopenta[h][1,6,10,12]oxatriazacycloheptadecine;

(11Z)-18-(2,4-difluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11E)-18-(2,4-difluorophenyl)-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11Z)-18-(2,4-difluorophenyl)-7-(5-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11E)-18-(2,4-difluorophenyl)-7-(5-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

19-(4-fluorophenyl)-7-(3-methyl-1H-1,2,4-triazol-1-yl)-11,12,13,14,15,17,18,19-octahydro-10H-16,2-(azeno)-8,4-(metheno)cyclopenta[i][1,4,7,11,13]oxatetraazacyclooctadecine;

19-(4-fluorophenyl)-12-methyl-7-(3-methyl-1H-1,2,4-triazol-1-yl)-11,12,13,14,15,17,18,19-octahydro-10H-16,2-(azeno)-8,4-(metheno)cyclopenta[i][1,4,7,11,13]oxatetraazacyclooctadecine;

(11Z)-18-(2,4-difluorophenyl)-14-methyl-7-(3-methyl-1H-1,2,4-triazol-1-yl)-10,13,14,16,17,18-hexahydro-15,2-(azeno)-8,4-(metheno)cyclopenta[h][1,6,10,12]oxatriazacycloheptadecine;

(11Z)-7-(3-methyl-1H-1,2,4-triazol-1-yl)-18-phenyl-10,13,14,16,17,18-hexahydro-15,2-(azeno)-8,4-(metheno)cyclopenta[h][1,10,12]oxadiazacycloheptadecine;

(11E)-7-(3-methyl-1H-1,2,4-triazol-1-yl)-18-phenyl-10,13,14,16,17,18-hexahydro-15,2-(azeno)-8,4-(metheno)cyclopenta[h][1,10,12]oxadiazacycloheptadecine;

13-methyl-7-(3-methyl-1H-1,2,4-triazol-1-yl)-17-phenyl-11,12,13,15,16,17-hexahydro-10H-14,2-(azeno)-8,4-(metheno)cyclopenta[g][1,5,9,11]oxatriazacyclohexadecine;

18-(2,4-difluorophenyl)-14-methyl-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecine;

7-(3-methyl-1H-1,2,4-triazol-1-yl)-18-phenyl-10,11,12,13,14,16,17,18-octahydro-15,2-(azeno)-8,4-(metheno)cyclopenta[h][1,10,12]oxadiazacycloheptadecine;

17-(2,4-difluorophenyl)-7-(3-methyl-1H-1,2,4-triazol-1-yl)-11,12,13,15,16,17-hexahydro-10H-14,2-(azeno)-8,4-(metheno)cyclopenta[g][1,5,9,11]oxatriazacyclohexadecine;

18-(2,4-difluorophenyl)-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecine;

13-methyl-7-(3-methyl-1H-1,2,4-triazol-1-yl)-17-(4-fluorophenyl)-11,12,13,15,16,17-hexahydro-10H-14,2-(azeno)-8,4-(metheno)cyclopenta[g][1,5,9,11]oxatriazacyclohexadecine;

18-(2,4-difluorophenyl)-13-methyl-7-(3-methyl-1H-1,2,4-triazol-1-yl)-10,11,12,13,14,16,17,18-octahydro-3H-15,2-(azeno)-4,8-(metheno)cyclopenta[h][1,6,10,12]oxatriazacycloheptadecine;

18-(4-fluorophenyl)-3,11,12,13,14,16,17,18-octahydro-10H-2,15-(azeno)-4,8-(metheno)cyclopenta[h][1,4,10,12]oxatriazacycloheptadecine-7-carbonitrile;

(11E)-7-cyano-18-(4-fluorophenyl)-18-methyl-10,13,14,16,17,18-hexahydro-15,2-(azeno)-8,4-(metheno)cyclopenta[h][1,6,10,12]oxatriazacycloheptadecine;

(11Z)-7-cyano-18-(4-fluorophenyl)-18-methyl-10,13,14,16,17,18-hexahydro-15,2-(azeno)-8,4-(metheno)cyclopenta[h][1,6,10,12]oxatriazacycloheptadecine;

19-(4-fluorophenyl)-17-methyl-7-(3-methyl-1H-1,2,4-triazol-1-yl)-11,12,13,14,17,18,19-octahydro-10H-15,2-(azeno)-8,4-(metheno)pyrido[3,4-h][1,6,10,12]oxatriazacycloheptadecine;

7-cyano-19-(4-fluorophenyl)-17-methyl-11,12,13,14,16,17,18,19-octahydro-10H-15,2-(azeno)-8,4-(metheno)pyrido[3,4-h][1,6,10,12]oxatriazacycloheptadecine;

18-(4-fluorophenyl)-7-(3-methyl-1H-1,2,4-triazol-1-yl)-10,11,12,13,14,16,17,18-octahydro-15,2-(azeno)-8,4-(metheno)cyclopenta[h][1,6,10,12]oxatriazacycloheptadecin-11(3H)-ol;

7-cyano-18-(4-fluorophenyl)-10,11,12,13,14,16,17,18-octahydro-15,2-(azeno)-8,4-(metheno)cyclopenta[h][1,6,10,12]oxatriazacycloheptadecin-11(3H)-ol, and (11Z)-14,17-dimethyl-7-cyano-19-(4-fluorophenyl)-13,14,16,17,18,19-hexahydro-10H-15,2-(azeno)-8,4-(metheno)pyrido[3,4-h][1,6,10,12]oxatriazacycloheptadecine; or a pharmaceutically acceptable salt thereof.

11. A pharmaceutical composition comprising a compound of claim 1 in association with a pharmaceutically acceptable carrier or diluent.

12. A pharmaceutical composition comprising a compound of claim 10 in association with a pharmaceutically acceptable carrier or diluent.

* * * * *